US012679878B2

(12) United States Patent
Illiano et al.

(10) Patent No.: US 12,679,878 B2

(45) Date of Patent: Jul. 14, 2026

(54) CRF2 RECEPTOR AGONISTS AND THEIR USE IN THERAPY

(71) Applicant: SANOFI, Paris (FR)

(72) Inventors: Stephane Illiano, Paris (FR); Laurence Lucats, Paris (FR); Laetitia Ledein, Paris (FR); Philippe Beauverger, Paris (FR); Philip Janiak, Paris (FR); Marie-Laure Ozoux, Paris (FR); Nis Halland, Frankfurt am Main (DE); Ziyu Li, Frankfurt am Main (DE); Ralf Elvert, Frankfurt am Main (DE); Andreas Evers, Frankfurt am Main (DE); Elisabetta Bianchi, Pomezia (IT); Alessia Santorprete, Pomezia (IT); Daniela Roversi, Pomezia (IT); Martina Tripepi, Pomezia (IT)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 18/021,712

(22) PCT Filed: Aug. 18, 2021

(86) PCT No.: PCT/EP2021/072923

§ 371 (c)(1),
(2) Date: Feb. 16, 2023

(87) PCT Pub. No.: WO2022/038179

PCT Pub. Date: Feb. 24, 2022

(65) Prior Publication Data

US 2025/0243255 A1 Jul. 31, 2025

(30) Foreign Application Priority Data

Aug. 19, 2020 (EP) .................................... 20315387

(51) Int. Cl.
*C07K 14/575* (2006.01)
*A61K 38/22* (2006.01)
*A61P 3/04* (2006.01)

(52) U.S. Cl.
CPC .... *C07K 14/57509* (2013.01); *A61K 38/2228* (2013.01); *A61P 3/04* (2018.01)

(58) Field of Classification Search
CPC .......... C07K 14/57509; A61K 38/2228; A61K 38/16
See application file for complete search history.

(56) References Cited

FOREIGN PATENT DOCUMENTS

| | | | |
|---|---|---|---|
| CN | 104356224 | A | 2/2015 |
| WO | 2008047241 | A2 | 4/2008 |
| WO | 2008047241 | A3 | 4/2008 |
| WO | 2009022006 | A1 | 2/2009 |
| WO | 2009115469 | A1 | 9/2009 |
| WO | 2015028966 | A2 | 3/2015 |
| WO | 2018013803 | A1 | 1/2018 |
| WO | 2019140030 | A1 | 7/2019 |

OTHER PUBLICATIONS

Waser, et al., CRF receptors in the rodent and human cardiovascular systems: Species differences, Science Direct, Peprides, vol. 27, pp. 3029-3038, 2006.
Biancalana, et al., "Molecular Mechanism of Thioflavin-T Binding to Amyloid Fibrils", Biochim. Biophys. Acta., vol. 7, pp. 1405-1412, 2010.
Chan, et al., "Urocorlin-2 Infusion in Acute Decompensated Hearl Failure", JACC: Heart Failure, vol. 1, No. 5, pp. 433-441, 2013.
Davis, et al., "Urocortin 2 Infusion in Healthy Humans", Journal of the American College of Cardiology, vol. 49, No. 4, pp. 461-471, 2007.
Vojkovsky, "Detection of secondary amines on solid phase", Pept. Res., one page, vol. 8, No. 4, 1995.
International Search Report mailed Jan. 4, 2022 in reference to co-pending European Application No. PCT/EP2021/072923 filed Aug. 18, 2021.
Written Opinion mailed Jan. 4, 2022 in reference to co-pending European Application No. PCT/EP2021/072923 filed Aug. 18, 2021.
Borg, et al., "Modified UCN2 Peptide Acts as an Insulin Sensitizer in Skeletal Muscle of Obese Mice", Diabetes, vol. 68, pp. 1403-1414, Jul. 2019.
Chhabra, et al., "Versatile Dde-based primary amine linkers for solid phase synthesis", Tetrahedron Letters, vol. 39, pp. 3585-3588, 1998.
Connolly, et al., "Weak Interactions Govern the Viscosity of Concentrated Antibody Solutions: High-Throughput Analysis Using the Diffusion Interaction Parameter", Biophysical Journal, vol. 103, pp. 69-78, Jul. 2012.
Dubowchik, et al., "Monomethoxytrityl (MMT) as a Versatile Amino Protecting Group for Complex Prodrugs of Anticancer Compounds Sensitive to Strong Acids, Bases and Nucleophiles", Tetrahedron Letters, vol. 38, No. 30, pp. 5257-5260, 1997.

(Continued)

*Primary Examiner* — Gyan Chandra
(74) *Attorney, Agent, or Firm* — DINSMORE & SHOHL LLP

(57) ABSTRACT

The present disclosure provides compounds which are peptides comprising the amino acid sequence of the formula (I) disclosed herein or pharmaceutically acceptable salts thereof. The compounds act as agonists of the corticotropin-releasing factor receptor 2 (CRF2) and are useful in therapy, especially in the treatment or prevention of cardiovascular diseases, obesity and diabetes.

12 Claims, 3 Drawing Sheets

Specification includes a Sequence Listing.

(56) References Cited

OTHER PUBLICATIONS

Gheorghiade, et al., "Haemodynamic effects, safety, and pharmacokinetics of human stresscopin in heart failure with reduced ejection fraction", European Journal of Heart Failure, vol. 15, pp. 679-689, 2013.
Giamouridis, et al., "Effects of Urocortin 2 Versus Urocortin 3 Gene Transfer on Left Ventricular Function and Glucose Disposal", Preclinical Research, vol. 3, No. 2, pp. 249-264, 2018.
King, et al., "A cleavage method which minimizes side reactions following Fmoc solid phase peptide synthesis", Int. Journal Peptide Protein Res., vol. 36, pp. 255-266, 1990.
Naikia, et al., "Fluorometric Determination of Amyloid Fibrils in Vitro Using the Fluorescent Dye, Thioflavine $T_1$,", Analytical Biochemistry, vol. 177, pp. 244-249, 1989.
Stirrat, et al., "Cardiovascular effects of urocortin 2 and urocortin 3 in patients with chronic heart failure, British Journal of Clinical Pharmacology", vol. 82, pp. 974-982, 2016.
Grieco, et al., "Ntural and synthetic peptides in the cardiovascular diseases: An update on diagnostic and therapeutic potentials", Archives of Biochemistry and Biophysics, vol. 662, pp. 15-32, 2019.
Yadav, et al., "Specific Interactions in High Concentration Antibody Solutions Resulting in High Viscosity", Biotechnology, vol. 99, No. 3, pp. 1152-1168, Mar. 2010.
Levine, "Quantification of B-Sheet Amyloid Fibril Structures with Thioflavin T", Methods in Enzymology, vol. 309, pp. 274-284, 1999.
Kaiser, et al., "Color Test for Detection of Free Terminal Amino Groups in the Solid-Phase Synthesis of Peptides", Short Communications, pp. 595-598, 1970.

| Peptide Seq. | Patent Sequence N° | N-term | 1 | 2 | 3 | 4 | 5 | 6 | 7 | 8 | 9 | 10 | 11 | 12 |
|---|---|---|---|---|---|---|---|---|---|---|---|---|---|---|
| 1 | 130 | H2N | I | V | L | S | L | D | dv | P | I | K | L | K[sema] |
| | 171 | | | | | | | | | | | | | K[(AEEA)2-(gGlu)2-C18OH] |
| | 172 | | | | | | | | | | | | | K[(AEEA)2-(gGlu)2-C20OH] |
| | 173 | | | | | | | | | | | | | K[(AEEA)2-(gGlu)-C20OH] |
| 2 | 83 | H2N | I | V | L | S | L | D | dv | P | I | G | L | K[sema] |
| 3 | 135 | H2N | I | V | L | S | L | D | dv | P | I | K | L | K[sema] |
| 4 | 136 | H2N | I | V | L | S | L | D | dv | P | I | K | L | K[sema] |
| 5 | 137 | H2N | I | V | L | S | L | D | dv | P | I | K | L | K[sema] |
| 6 | 138 | H2N | I | V | L | S | L | D | dv | P | I | K | L | K[sema] |
| 7 | 139 | H2N | I | V | L | S | L | D | dv | P | I | K | L | K[sema] |
| 8 | 147 | H2N | I | V | L | S | L | D | dv | P | I | G | L | K[sema] |
| 9 | 151 | H2N | I | V | L | S | L | D | dv | P | I | G | L | K[sema] |
| 10 | 174 | H2N | I | V | L | S | L | D | dv | P | I | K | L | K[(AEEA)2-(gGlu)2-C18OH] |

| Peptide Seq. | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | C-term | EC50 [nM] CRF2R | EC50 [nM] CRF2R | hCRF2R Emax | hCRF1 EC50 [nM] | hCRF1 Emax |
|---|---|---|---|---|---|---|---|---|---|---|---|---|---|---|---|---|---|---|---|---|---|---|---|---|---|---|---|---|---|---|---|---|
| 1 | Q | I | L | L | K | Q | E | R | Q | K | Aib | Q | R | E | Q | A | E | K | N | K | Q | I | L | A | Q | V | NH2 | 0.05 | 0.05 | 101.19 | .NoVal | 20.3 |
| | | | | | | | | | | | | | | | | | | | | | | | | | | | | 0.17 | 0.17 | 94.07 | .NoVal | 7.54 |
| | | | | | | | | | | | | | | | | | | | | | | | | | | | | 0.04 | 0.04 | 92.98 | .NoVal | 25.56 |
| | | | | | | | | | | | | | | | | | | | | | | | | | | | | 0.03 | 0.03 | 100.54 | 79.3 | 53.33 |
| 2 | Q | I | L | L | K | Q | E | R | Q | K | K | Aib | R | E | Q | A | E | T | N | K | R | I | L | E | R | V | NH2 | 0.07 | 0.07 | 100.75 | .NoVal | 7.51 |
| 3 | Q | I | L | L | K | Q | E | R | Q | K | Aib | Q | R | Q | Q | A | E | K | N | K | Q | I | L | A | Q | V | NH2 | 0.04 | 0.04 | 101.13 | .NoVal | 28.4 |
| 4 | Q | I | L | L | K | Q | E | R | Q | K | K | Aib | R | Q | K | A | E | K | N | K | Q | I | L | A | Q | V | NH2 | 0.05 | 0.05 | 100.47 | .NoVal | 21.75 |
| 5 | Q | I | L | L | K | Q | E | R | Q | K | K | Q | R | E | Q | A | E | K | N | K | Q | I | L | E | Q | V | NH2 | 0.04 | 0.04 | 100.95 | .NoVal | 22.5 |
| 6 | Q | I | L | L | K | Q | E | R | Q | K | K | Q | R | E | K | A | E | K | N | K | Q | I | L | A | Q | V | NH2 | 0.06 | 0.06 | 100.02 | .NoVal | 4.38 |
| 7 | Q | I | L | L | K | Q | E | R | Q | K | K | Q | R | Q | Q | A | E | K | N | K | Q | I | L | A | Q | V | NH2 | 0.03 | 0.03 | 101.13 | .NoVal | 37.61 |
| 8 | Q | I | L | L | K | Q | E | R | Q | K | K | Aib | R | E | Q | A | E | T | N | K | Q | I | L | A | Q | V | NH2 | 0.18 | 0.18 | 97.98 | .NoVal | 4.54 |
| 9 | Q | I | L | L | K | Q | E | R | Q | K | K | Aib | R | E | Q | A | E | K | N | K | R | I | L | E | R | V | NH2 | 0.08 | 0.08 | 102.79 | .NoVal | 9.07 |
| 10 | Q | I | L | L | K | Q | A | R | Q | K | Aib | Q | R | A | Q | A | E | K | N | K | R | I | L | E | R | V | NH2 | 0.07 | 0.07 | 101.19 | 91 | 42.06 |

Fig. 3

CRF2 RECEPTOR AGONISTS AND THEIR USE IN THERAPY

CROSS REFERENCES TO RELATED APPLICATIONS

This application is a national-stage application under 35 U.S.C. § 371 of International Application No. PCT/EP2021/072923, filed Aug. 18, 2021, which International Application claims benefit of priority to European Patent Application No. 20315387.9, filed Aug. 19, 2020.

SEQUENCE LISTING

A computer readable form (CRF) sequence listing in ASCII format having file name "CRP-001 211126 Sequence Listing.txt" (179,497 bytes), created on Nov. 21, 2025, is incorporated herein by reference.

FIELD

The present disclosure relates to compounds which are agonists of the corticotropin-releasing factor receptor 2 (CRF2) and their use in therapy, especially in the treatment or prevention of cardiovascular diseases, obesity and diabetes.

BACKGROUND

Urocortins (UCNs) are endogenous peptides which act through corticotropin-releasing factor (CRF) receptors, which are type 2 G protein-coupled receptors (GPCRs). The CRF receptor family comprises CRF1 receptors, which are encoded by the CRHR1 gene, and CRF2 receptors, which are encoded by the CRHR2 gene.

There are three known endogenous urocortins found in mammals: UCN1, UCN2 and UCN3. Despite a high degree of sequence homology, the binding of these peptides to CRF1 and CRF2 is different. CRF1 and CRF2 are activated non-selectively by CRH and UCN1, whereas UCN2 and UCN3 are CRF2-selective agonists. In particular, UCN2 is a thirty-eight amino acid peptide which selectively activates the CRF2 receptor, including the known isoforms CRF2-alpha (α), -beta (β) and -gamma (γ).

Urocortins and their receptors are involved in neurohumoral responses to various stress and pathological situations. In particular, urocortins evoke positive hemodynamic effects in both preclinical models and patients with heart failure or hypertension. Urocortins and CRF receptors are expressed in the heart and in vessels, with CRF2 expressed robustly and CRF1 expressed minimally if at all (see Waser et al., Peptides, 2006, 27, 3029-3038). In experimental models, urocortins acting via CRF2 activation have been shown to improve cardiovascular function via the alleviation of vascular resistance and via cardiac inotropic and lusitropic actions. In clinical studies, UCN2 and UCN3 have been shown to have direct vasodilator actions in healthy volunteers and in patients with heart failure (see Stirrat et al., Br. J. Clin. Pharmacol., 2016, 82, 974-982), while UCN2 has also been shown to increase cardiac output and reduce vascular resistance in patients with heart failure (see Davis et al., Eur. Heart J., 2007, 28, 2589-2597; and Chan et al., JACC: Heart Failure, 2013, 1, 433-441). A recombinant acetate salt of UCN3 has been shown to improve cardiac output and reduce vascular resistance in a multicentre study of patients with chronic stable heart failure (see Gheorghiade et al., Eur. J. Heart Fail., 2013, 15, 679-89).

Recent studies have demonstrated that UCN2 and/or UCN3 gene transfer in mice improves not only cardiac function but also glucose disposal (see Giamouridis et al., JACC: Basic to Translational Science, 2018, 3, 2). In addition, subcutaneous delivery of pegylated UCN2 has been shown to improve glucose tolerance and increase glucose uptake in skeletal muscle while reducing body weight via limitation of food intake (see Borg et al., Diabetes, 2019, 1403-1414). These findings suggest that urocortins may be useful not only in the treatment of cardiovascular diseases but also in the treatment of diseases such as diabetes and obesity.

Nevertheless, the extremely short half-life of urocortins remains a major limitation to their therapeutic use (see Davies et al., JACC, 2007, 49, 461-471). To date, treatment with urocortins cannot be sustained without chronic intravenous infusion. However, the management of chronic diabetic or heart failure patients requires treatment suitable for long-standing and home self-administration.

In an attempt to overcome such limitations, various analogs of urocortins have been proposed. For instance, WO2018013803 (Alsina-Fernandez; Eli Lilly and Company) discloses analogs of UCN2 which are taught as having utility in the treatment of diseases such as chronic kidney disease and type II diabetes.

However, there remains a need for improved CRF2 receptor agonists which are useful as therapeutic agents, especially in the treatment and prevention of cardiovascular diseases, obesity and diabetes. In particular, there is a need for CRF2 agonists having desirable efficacy, pharmacokinetic properties (e.g., improved half-life) and/or physicochemical properties (e.g., improved stability and/or solubility).

SUMMARY

In a first aspect, the present disclosure provides a compound which is a peptide comprising the amino acid sequence of formula (I) (SEQ ID NO: 186):

X1-X2-X3-X4-X5-X6-X7-X8-X9-X10-X11-X12-X13-X14-X15-X16-X17-X18-X19-X20-X21-X22-X23-X24-X25-X26-X27-X28-X29-X30-X31-X32-X33-X34-X35-X36-X37-X38 (I)

wherein

X1 is isoleucine (I) or phenylalanine (F);
X2 is valine (V) or threonine (T);
X3 is leucine (L);
X4 is serine(S);
X5 is leucine (L);
X6 is aspartate (D);
X7 is valine (V) or D-valine (v);
X8 is proline (P);
X9 is isoleucine (I) or threonine (T);
X10 is lysine (K), glutamate (E), histidine (H) or glycine (G);
X11 is isoleucine (I) or leucine (L);
X12 is lysine (K), wherein the epsilon-amino group of the lysine side chain is covalently bound to an albumin-binding moiety;
X13 is glutamine (Q) or lysine (K);
X14 is isoleucine (I), lysine (K) or 2-aminoisobutyric acid (Aib);
X15 is leucine (L);
X16 is leucine (L) or phenylalanine (F);
X17 is glutamate (E) or lysine (K);
X18 is glutamine (Q);
X19 is alanine (A), glutamate (E) or glutamine (Q);

X20 is lysine (K) or arginine (R);
X21 is glutamine (Q) or lysine (K);
X22 is lysine (K), arginine (R) or glutamate (E);
X23 is lysine (K) or 2-aminoisobutyric acid (Aib);
X24 is glutamine (Q), 2-aminoisobutyric acid (Aib), leucine (L) or glutamate (E);
X25 is arginine (R), lysine (K) or 2-aminoisobutyric acid (Aib);
X26 is alanine (A), glutamate (E), 2-aminoisobutyric acid (Aib) or glutamine (Q);
X27 is glutamine (Q), 2-aminoisobutyric acid (Aib) or lysine (K);
X28 is alanine (A);
X29 is glutamate (E) or lysine (K);
X30 is lysine (K) or threonine (T);
X31 is asparagine (N) or alanine (A);
X32 is lysine (K), alanine (A), valine (V), threonine (T), glutamate (E) or 2-aminoisobutyric acid (Aib);
X33 is arginine (R), lysine (K) or glutamine (Q);
X34 is isoleucine (I) or leucine (L);
X35 is leucine (L);
X36 is alanine (A) or glutamate (E);
X37 is glutamine (Q) or arginine (R); and
X38 is isoleucine (I) or valine (V);
or a pharmaceutically acceptable salt thereof.

In a second aspect of the disclosure, there is provided a pharmaceutical composition comprising a compound of the disclosure and a pharmaceutically acceptable excipient, diluent or carrier.

The compounds and pharmaceutical compositions disclosed herein are useful in therapy and may be used in the treatment or prevention of various diseases through agonism of the CRF2 receptor. Thus, in other aspects, the disclosure is directed to the use of the compounds and pharmaceutical compositions in therapy, especially in the treatment or prevention of cardiovascular diseases, obesity, diabetes, sarcopenia, muscular dystrophy, kidney disease, Pulmonary hypertension, peripheral arterial disease, inflammation, allergy, and tissue ischemia; in particular in the treatment or prevention of cardiovascular diseases including especially heart failure, obesity, and diabetes.

BRIEF DESCRIPTION OF THE DRAWINGS

FIG. 3: Representative sequences from peptides according to the invention with an optimized stability profile, wherein K[sema] stands for K[gGlu-$C(O)(CH_2)_{14}CH_3$]

DETAILED DESCRIPTION

Figure 1:
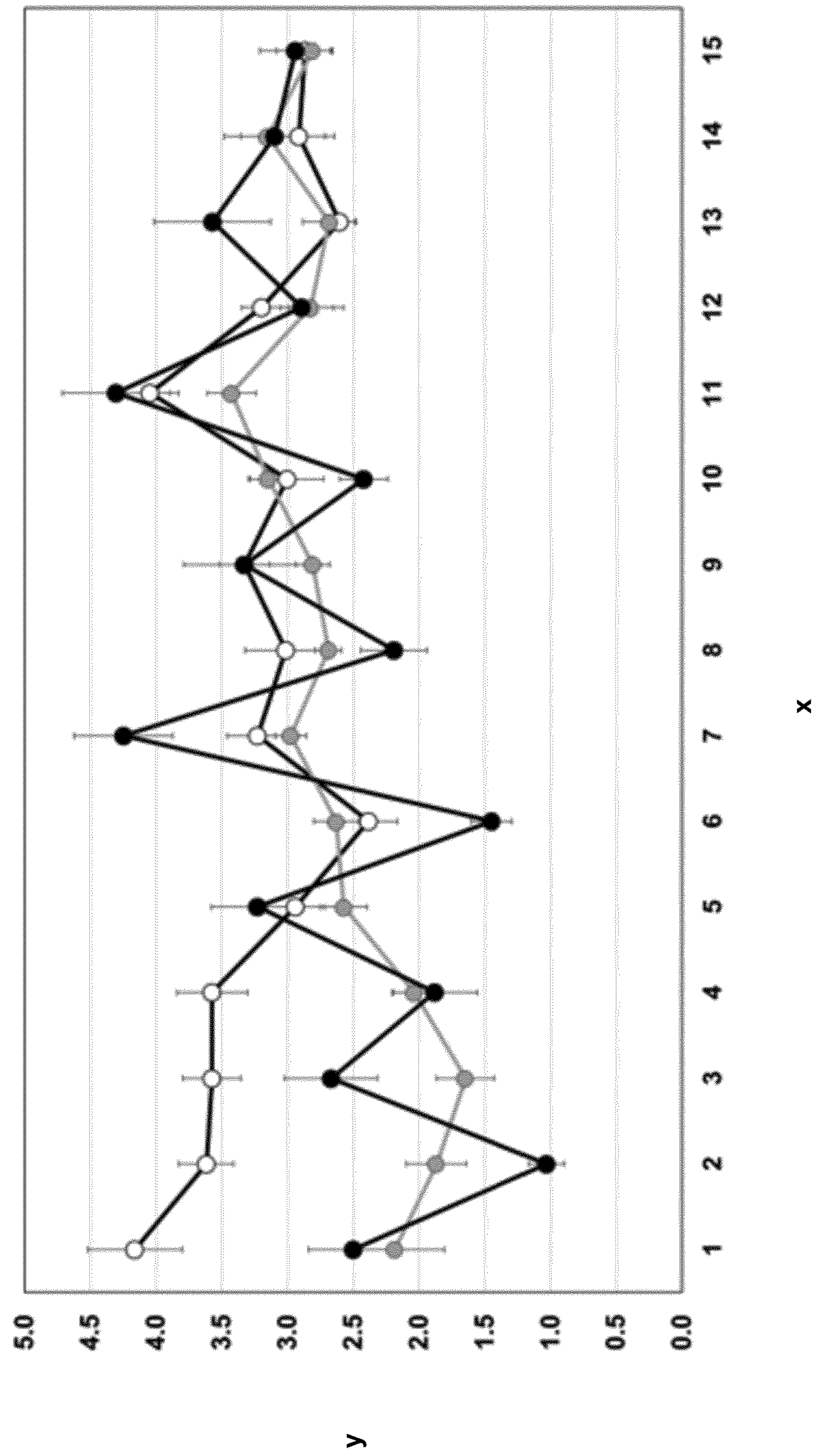
FIG. 1 is a graph depicting food intake throughout the dosing period of high-fat diet fed C57BL/6N mice (DIO), treated subcutaneously every second day with the compound of SEQ ID NO: 35 (black circles), a reference compound (grey circles) or vehicle (white circles). The x-axis indicates the study day and the y-axis indicates the food intake (in grams). Values are expressed as mean±standard error of the mean (SEM).

The present disclosure relates to compounds which are derivatives of UCN2 and which are useful as CRF2 receptor agonists. The compounds exhibit desirable activity and selectivity at the CRF2 receptor, in particular with respect to the CRF1 receptor, as well as improved pharmacokinetic properties and beneficial in vivo effects in relevant animal models. In addition, the compounds exhibit desirable physicochemical properties, such as desirable solubility and stability, making them excellent candidates for solution formulations for subcutaneous delivery. The compounds are useful in therapy, especially in the treatment or prevention of cardiovascular diseases, obesity, diabetes, sarcopenia, muscular dystrophy, kidney disease, Pulmonary hypertension, peripheral arterial disease, inflammation, allergy, and tissue ischemia; in particular in the treatment or prevention of cardiovascular diseases including especially heart failure, obesity, and diabetes.

Compounds

The compounds of the disclosure are peptides comprising the amino acid sequence of the formula (I) recited above or pharmaceutically acceptable salts of said peptides.

In the present disclosure, amino acids are referred to by their name, their commonly known three-letter symbols or by the one-letter symbols recommended by the IUPAC-IUB Biochemical Nomenclature Commission. Generally accepted three-letter codes for other amino acids, such as Aib for 2-aminoisobutyric acid, may also be used. Unless otherwise indicated, all amino acids employed in the compounds of the disclosure are L-amino acids. Thus, for example, L-valine is referred to as "valine", "V" or "Val", whereas D-valine is specifically identified as such.

In an embodiment, X1 is isoleucine (I).
In an embodiment, X2 is valine (V).
In an embodiment, X9 is isoleucine (I).
In an embodiment, X10 is lysine (K) or glycine (G).
In an embodiment, X11 is leucine (L).
In an embodiment, X14 is isoleucine (I).
In an embodiment, X16 is leucine (L).
In an embodiment, X19 is alanine (A) or glutamate (E).
In an embodiment, X21 is glutamine (Q).
In an embodiment, X22 is lysine (K).
In an embodiment, X24 is glutamine (Q) or 2-aminoisobutyric acid (Aib).
In an embodiment, X25 is arginine (R).
In an embodiment, X26 is alanine (A), glutamate (E) or glutamine (Q).
In an embodiment, X27 is glutamine (Q).
In an embodiment, X29 is glutamate (E).
In an embodiment, X31 is asparagine (N).
In an embodiment, X32 is lysine (K).
In an embodiment, X33 is arginine (R) or glutamine (Q).
In an embodiment, X34 is isoleucine (I).
In an embodiment, X35 is leucine (L).
In an embodiment, X38 is valine (V).

In an embodiment, the amino acid residue at X38 is amidated.

In an embodiment, the amino acid residue at X1 is acetylated.

In an embodiment:
X1 is isoleucine (I);
X2 is valine (V);
X9 is isoleucine (I);
X10 is lysine (K) or glycine (G);
X11 is leucine (L);
X14 is isoleucine (I);
X16 is leucine (L);
X19 is alanine (A) or glutamate (E);
X21 is glutamine (Q);
X22 is lysine (K);

X24 is glutamine (Q) or 2-aminoisobutyric acid (Aib);
X25 is arginine (R);
X26 is alanine (A), glutamate (E) or glutamine (Q);
X27 is glutamine (Q);
X29 is glutamate (E);
X31 is asparagine (N);
X32 is lysine (K);
X33 is arginine (R) or glutamine (Q);
X34 is isoleucine (I);
X35 is leucine (L); and
X38 is valine (V).

In an embodiment:
X10 is lysine (K);
X19 is glutamate (E);
X24 is glutamine (Q); and
X26 is glutamate (E).

In an embodiment:
X33 is glutamine (Q); and
X37 is glutamine (Q).

In an embodiment:
X1 is isoleucine (I);
X2 is valine (V);
X9 is isoleucine (I);
X10 is lysine (K);
X11 is leucine (L);
X14 is isoleucine (I);
X16 is leucine (L);
X19 is glutamate (E);
X21 is glutamine (Q);
X22 is lysine (K);
X24 is glutamine (Q);
X25 is arginine (R);
X26 is glutamate (E);
X27 is glutamine (Q);
X29 is glutamate (E);
X31 is asparagine (N);
X32 is lysine (K);
X33 is glutamine (Q);
X34 is isoleucine (I);
X35 is leucine (L);
X37 is glutamine (Q); and
X38 is valine (V).

As indicated above, the compounds of the disclosure comprise a modified lysine (K) residue at the position denoted by X12 in formula (I), in which an albumin-binding moiety is covalently bound to the epsilon-amino group of the lysine side chain.

The term "albumin-binding moiety" as used herein refers to a moiety which is capable of binding to albumin by covalent or non-covalent binding. In embodiments, the albumin-binding moiety is capable of binding to albumin by non-covalent binding. The albumin-binding moiety may comprise or consist of a group selected from fatty acids, phthalocyanines, coumarins, flavonoids, tetracyclines, naphthalenes, arylcarboxylic acids, heteroarylcarboxylic acids, lipids, alkyl amines, cyclic or linear tetrapyrroles and organometallic compounds thereof, halo-substituted aromatic acid derivatives, organic dyes, and derivatives of tryptophan and thyroxine.

In a particular embodiment, the albumin-binding moiety comprises a C14-C24 fatty acid group which is conjugated to the epsilon-amino group of the lysine side chain either by a direct bond or by a linker. The term "C14-C24 fatty acid" as used herein means a carboxylic acid having from 14 to 24 carbon atoms. The C14-C24 fatty acid can be a saturated monoacid or a saturated diacid. By "saturated" is meant that the fatty acid contains no carbon-carbon double or carbon-carbon triple bonds.

Examples of saturated C14-C24 fatty acids include myristic acid (tetradecanoic acid; a C14 monoacid), tetradecanedioic acid (a C14 diacid), pentadecylic acid (pentadecanoic acid; a C15 monoacid), pentadecanoic acid (a C15 diacid), palmitic acid (hexadecanoic acid; a C16 monoacid), hexadecanedioic acid (a C16 diacid), margaric acid (heptadecanoic acid; a C17 monoacid), heptadecanedioic acid (a C17 diacid), stearic acid (octadecanoic acid; a C18 monoacid), octadecanedioic acid (a C18 diacid), nonadecylic acid (nonadecanoic acid; a C19 monoacid), nonadecanedioic acid (a C19 diacid), arachadic acid (eicosanoic acid; a C20 monoacid), eicosanedioic acid (a C20 diacid), heneicosylic acid (heneicosanoic acid; a C21 monoacid), heneicosanedioic acid (a C21 diacid), behenic acid (docosanoic acid; a C22 monoacid), docosanedioic acid (a C22 diacid), lignoceric acid (tetracosanoic acid; a C24 monoacid), tricosanoic acid (a C23 monoacid), tricosanoic acid (a C23 diacid) and tetracosanedioic acid (a C24 diacid).

In an embodiment, the C14-C24 fatty acid group is selected from the group consisting of palmitic acid (hexadecanoic acid; a C16 monoacid), hexadecanedioic acid (a C16 diacid), stearic acid (octadecanoic acid; a C18 monoacid), octadecanedioic acid (a C18 diacid), arachadic acid (eicosanoic acid; a C20 monoacid) and eicosanedioic acid (a C20 diacid).

The C14-C24 fatty acid may be bound directly to the epsilon-amino group of the lysine side chain. Alternatively, the C14-C24 fatty acid may be bound to the epsilon-amino group of the lysine side chain through a linker. The linker may comprise one or more groups selected from [2-(2-aminoethoxy) ethoxy]acetyl (referred to herein as "AEEA"), glycine (Gly), N-methylglycine (N-MeGly), 3-[2-[2-[2-(2-Aminoethoxy)-ethoxy]-ethoxy]-ethoxy]-propionic acid (CAS N° 663921-15-1, also known as amino-PEG4-acid or $(PEO)_4$-Aminopropionic acid), amino-PEG6-acid (CAS N° 905954-28-1), amino-PEG8-acid (CAS N° 756526-04-2) and gamma-glutamate (gGlu); in particular selected from AEEA, Gly, N-MeGly, and gGlu; more in particular selected from AEEA, and gGlu.

In an embodiment, the albumin-binding moiety is a group of the formula (II):

$$—Z_1—Y—Z_2—C(O)R^1 \quad \text{(II)}$$

wherein

Y is AEEA, {AEEA}, $\{AEEA\}_3$, Gly, $\{Gly\}_2$, $\{Gly\}_3$, N-MeGly, $\{N\text{-}MeGly\}_2$, $\{N\text{-}MeGly\}_3$ or absent;

$Z^1$ and $Z^2$ are each independently selected from gGlu, $\{gGlu\}_2$, {gGlu}, $\{gGlu\}_4$ or absent; and $R^1$ is $—(CH_2)_xCOOH$ or $—H_2)_xCH_3$; in particular $—(CH_2)_xCOOH$ wherein x is an integer from 12 to 22.

In an embodiment, $Z^1$ is absent, Y is $\{AEEA\}_2$ and $Z^2$ is gGlu or $\{gGlu\}_2$.

In an embodiment $Z^1$ is gGlu or $\{gGlu\}_2$, Y is $\{AEEA\}_2$ and $Z^2$ is gGlu or $\{gGlu\}_2$.

In an embodiment, $Z^1$ is absent, Y is absent and $Z^2$ is gGlu or $\{gGlu\}_2$.

In an embodiment, Y and $Z^1$ and $Z^2$ are all absent.

It has surprisingly been found and as apparent from the examples hereinafter that albumin binding moieties comprising a free carboxylic acid have an improved CRF2 selectivity. Hence, in a particular embodiment, $R^1$ is —$(CH_2)_xCOOH$, wherein x is 14, 16 or 18; in particular 16 or 18; more in particular 14 or 16; even more in particular 14.

In an embodiment, $R^1$ is —$(CH_2)_xCH_3$, wherein x is 14, 16 or 18; in particular 14 and 16.

In an embodiment, the albumin-binding moiety is selected from the following groups:

-$(gGlu)_{n=1-4}$-$C(O)(CH_2)_{14}CH_3$

-$(gGlu)_{n=1-4}$-$C(O)(CH_2)_{14}COOH$

-$(gGlu)_{n=1-4}$-$C(O)(CH_2)_{16}CH_3$

-$(gGlu)_{n=1-4}$-$C(O)(CH_2)_{16}COOH$

-$(gGlu)_{n=1-4}$-$C(O)(CH_2)_{18}CH_3$

-$(gGlu)_{n=1-4}$-$C(O)(CH_2)_{18}COOH$

-$(AEEA)_{n=1,2}$-$(gGlu)_{n=1-4}$-$C(O)(CH_2)_{14}CH_3$

-$(AEEA)_{n=1,2}$-$(gGlu)_{n=1-4}$-$C(O)(CH_2)_{14}COOH$

-$(AEEA)_{n=1,2}$-$(gGlu)_{n=1-4}$-$C(O)(CH_2)_{16}CH_3$

-$(AEEA)_{n=1,2}$-$(gGlu)_{n=1-4}$-$C(O)(CH_2)_{16}COOH$

-$(AEEA)_{n=1,2}$-$(gGlu)_{n=1-4}$-$C(O)(CH_2)_{18}CH_3$

-$(AEEA)_{n=1,2}$-$(gGlu)_{n=1-4}$-$C(O)(CH_2)_{18}COOH$

-$(gGlu)_{n=1-4}$-$(AEEA)_{n=1,2}$-$(gGlu)_{n=1-4}$-$C(O)(CH_2)_{14}CH_3$

-$(gGlu)_{n=1-4}$-$(AEEA)_{n=1,2}$-$(gGlu)_{n=1-4}$-$C(O)(CH_2)_{14}COOH$

-(gGlu) n=1-4 $(AEEA)_{n=1,2}$-$(gGlu)_{n=1-4}$-$C(O)(CH_2)_{16}CH_3$

-$(gGlu)_{n=1-4}$-$(AEEA)_{n=1,2}$-$(gGlu)_{n=1-4}$-$C(O)(CH_2)_{16}COOH$

-$(gGlu)_{n=1-4}$-$(AEEA)_{n=1,2}$-$(gGlu)_{n=1-4}$-$C(O)(CH_2)_{18}CH_3$

-$(gGlu)_{n=1-4}$-$(AEEA)_{n=1,2}$-$(gGlu)_{n=1-4}$-$C(O)(CH_2)_{18}COOH$

In an embodiment, the albumin-binding moiety is selected from the following groups:

-$(gGlu)_{n=1-4}$-$C(O)(CH_2)_{14}COOH$

-$(gGlu)_{n=1-4}$-$C(O)(CH_2)_{16}COOH$

-$(gGlu)_{n=1-4}$-$C(O)(CH_2)_{18}COOH$

-$(AEEA)_{n=1,2}$-$(gGlu)_{n=1-4}$-$C(O)(CH_2)_{14}COOH$

-$(AEEA)_{n=1,2}$-$(gGlu)_{n=1-4}$-$C(O)(CH_2)_{16}COOH$

-$(AEEA)_{n=1,2}$-$(gGlu)_{n=1-4}$-$C(O)(CH_2)_{18}COOH$

-$(gGlu)_{n=1-4}$-$(AEEA)_{n=1,2}$-$(gGlu)_{n=1-4}$-$C(O)(CH_2)_{14}COOH$

-$(gGlu)_{n=1-4}$-$(AEEA)_{n=1,2}$-$(gGlu)_{n=1-4}$-$C(O)(CH_2)_{16}COOH$

-$(gGlu)_{n=1-4}$-$(AEEA)_{n=1,2}$-$(gGlu)_{n=1-4}$-$C(O)(CH_2)_{18}COOH$

In an embodiment, the albumin-binding moiety is selected from the following groups:

-$\{AEEA\}_2$-gGlu-$C(O)(CH_2)_{16}COOH$;

-$\{AEEA\}_2$-gGlu-$C(O)(CH_2)_{18}COOH$;

-$\{AEEA\}_2$-$\{gGlu\}_2$-$C(O)(CH_2)_{16}COOH$;

-$\{AEEA\}_2$-$\{gGlu\}_2$-$C(O)(CH_2)_{18}COOH$;

—$C(O)(CH_2)_{16}COOH$;

-gGlu-$C(O)(CH_2)_{16}COOH$;

-gGlu-$C(O)(CH_2)_{14}CH_3$;

-gGlu-$C(O)(CH_2)_{14}COOH$;

-$\{AEEA\}_2$-gGlu-$C(O)(CH_2)_{14}COOH$;

-$\{AEEA\}_2$-$\{gGlu\}_2$-$C(O)(CH_2)_{14}COOH$;

-$\{AEEA\}_2$-gGlu-$C(O)(CH_2)_{14}CH_3$; and

-$\{AEEA\}_2$-$\{gGlu\}_2$-$C(O)(CH_2)_{14}CH_3$.

In an embodiment, the albumin-binding moiety is selected from the following groups:

-$\{AEEA\}_2$-gGlu-$C(O)(CH_2)_{16}COOH$;

-$\{AEEA\}_2$-gGlu-$C(O)(CH_2)_{18}COOH$;

-$\{AEEA\}_2$-$\{gGlu\}_2$-$C(O)(CH_2)_{16}COOH$;

-$\{AEEA\}_2$-$\{gGlu\}_2$-$C(O)(CH_2)_{18}COOH$;

—$C(O)(CH_2)_{16}COOH$;

-gGlu-$C(O)(CH_2)_{16}COOH$;

-gGlu-$C(O)(CH_2)_{14}COOH$;

-$\{AEEA\}_2$-gGlu-$C(O)(CH_2)_{14}COOH$; and

-$\{AEEA\}_2$-$\{gGlu\}_2$-$C(O)(CH_2)_{14}COOH$.

In an embodiment, the albumin-binding moiety is selected from the following groups:

-$(gGlu)_{n=1-4}$-$C(O)(CH_2)_{14}COOH$;

-$(gGlu)_{n=1-4}$-$C(O)(CH_2)_{16}COOH$;

-$(AEEA)_{n=1,2}$-$(gGlu)_{n=1-4}$-$C(O)(CH_2)_{14}COOH$;

-$(AEEA)_{n=1,2}$-$(gGlu)_{n=1-4}$-$C(O)(CH_2)_{16}COOH$;

-$(gGlu)_{n=1-4}$-$(AEEA)_{n=1,2}$-$(gGlu)_{n=1-4}$-$C(O)(CH_2)_{14}COOH$; and

-$(gGlu)_{n=1-4}$-$(AEEA)_{n=1,2}$-$(gGlu)_{n=1-4}$-$C(O)(CH_2)_{16}COOH$.

In an embodiment, the albumin-binding moiety is selected from the following groups:

-$\{AEEA\}_2$-gGlu-$C(O)(CH_2)_{16}COOH$;

-$\{AEEA\}_2$-gGlu-$C(O)(CH_2)_{14}COOH$;

-$\{AEEA\}_2$-$\{gGlu\}_2$-$C(O)(CH_2)_{16}COOH$;

-$\{AEEA\}_2$-$\{gGlu\}_2$-$C(O)(CH_2)_{14}COOH$;

—$C(O)(CH_2)_{16}COOH$; —$C(O)(CH_2)_{14}COOH$;

-gGlu-$C(O)(CH_2)_{16}COOH$; and

-gGlu-$C(O)(CH_2)_{14}COOH$.

In an embodiment, the albumin-binding moiety is selected from the following groups:

-$(gGlu)_{n=1-4}$-$C(O)(CH_2)_{14}COOH$;

-$(AEEA)_{n=1,2}$-$(gGlu)_{n=1-4}$-$C(O)(CH_2)_{14}COOH$; and

-$(gGlu)_{n=1-4}$-$(AEEA)_{n=1,2}$-$(gGlu)_{n=1-4}$-$C(O)(CH_2)_{14}COOH$.

In an embodiment, the albumin-binding moiety is selected from the following groups:

-$\{AEEA\}_2$-gGlu-$C(O)(CH_2)_{14}COOH$;

-$\{AEEA\}_2$-$\{gGlu\}_2$-$C(O)(CH_2)_{14}COOH$;

—$C(O)(CH_2)_{14}COOH$; and

-gGlu-$C(O)(CH_2)_{14}COOH$.

In an embodiment, the albumin-binding moiety is -$\{AEEA\}_2$-gGlu-$C(O)(CH_2)_{14}COOH$; or -$\{AEEA\}_2$-gGlu-$C(O)(CH_2)_6COOH$.

The chemical structures and IUPAC names of these groups are shown in Table 1 below, in which R denotes the point of attachment of each group to the epsilon-amino group of the lysine residue at X12:

TABLE 1

| Group | Chemical structure and IUPAC name |
| --- | --- |
| -{AEEA}$_2$-gGlu-C(O)(CH$_2$)$_{16}$COOH | 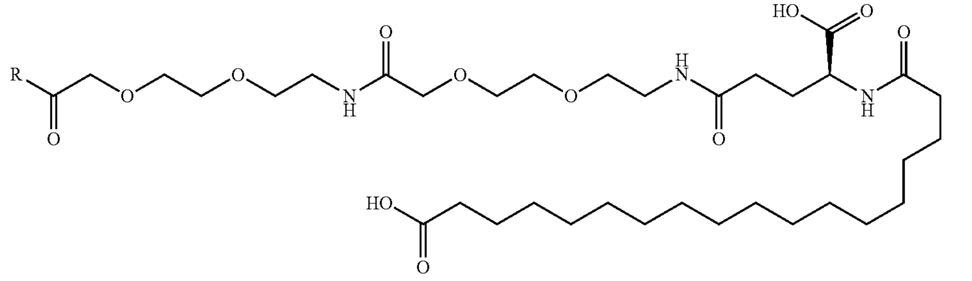 [2-[2-[2-[[2-[2-[2-[[(4S)-4-carboxy-4-(17-carboxyheptadecanoylamino)butanol]amino]ethoxy]ethoxy]-acetyl]amino]ethoxy]ethoxy]acetyl- |
| -{AEEA}$_2$-gGlu-C(O)(CH$_2$)$_{18}$COOH | 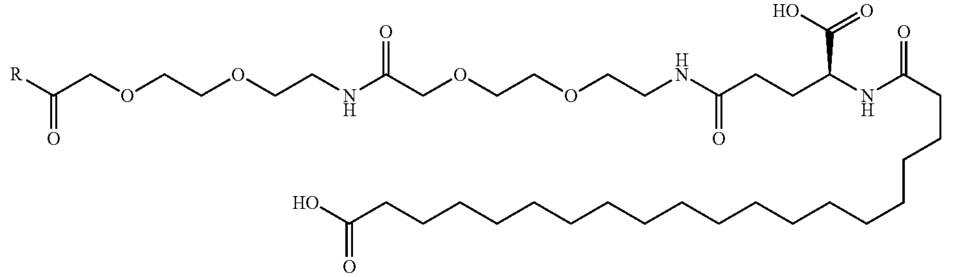 [2-[2-[2-[[2-[2-[2-[[(4S)-4-carboxy-4-(19-carboxynondecanoylamino)butanol]amino]ethoxy]ethoxy]-acetyl]amino]ethoxy]ethoxy]acetyl- |
| {AEEA}$_2$-{gGlu}$_2$-C(O)(CH$_2$)$_{16}$COOH | 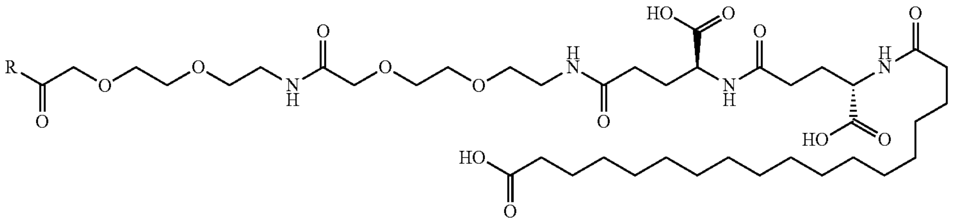 [2-[2-[2-[[2-[2-[2-[[(4S)-4-carboxy-4-[[(4S)-4-carboxy-4-(17-carboxyheptadecanoylamino)butanoyl]amino]butanoyl]amino] ethoxy]-ethoxy]acetyl]amino]ethoxy]ethoxy]acetyl- |
| -{AEEA}$_2$-{gGlu}$_2$-C(O)(CH$_2$)$_{18}$COOH | 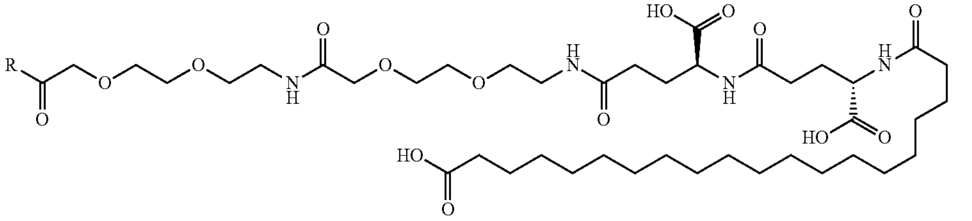 [2-[2-[2-[[2-[2-[2-[[(4S)-4-carboxy-4-[[(4S)-4-carboxy-4-(19-carboxynonadecanoylamino)butanoyl]amino]butanol]amino] ethoxy]-ethoxy]acetylamino]ethoxy]ethoxy]acetyl- |
| -C(O)(CH$_2$)$_{16}$COOH | 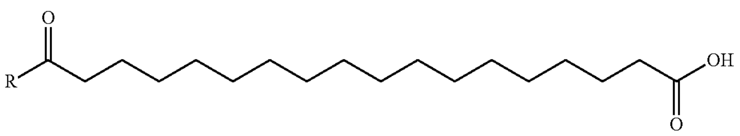 18-oxooctadecanoic acid |

TABLE 1-continued
| Group | Chemical structure and IUPAC name |
| --- | --- |
| -gGlu-$C(O)(CH_2)_{16}$ COOH | 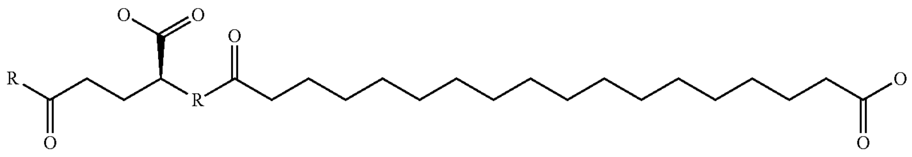 18-[[(1S)-1-carboxy-4-oxo-butyl]amino]-18-oxo-octadecanoic acid |
| -gGlu-$C(O)(CH_2)_{14}$ $CH_3$ | 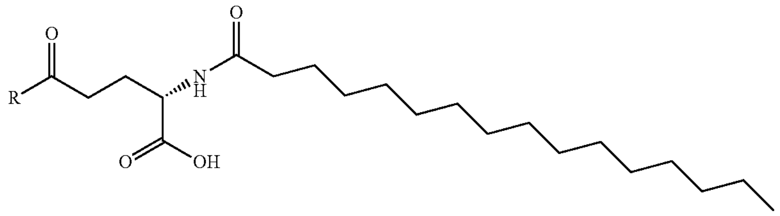 (2S)-2-(hexadecanoylamino)-5-oxo-pentanoic acid |
| -gGlu-$C(O)(CH_2)_{14}$ COOH | 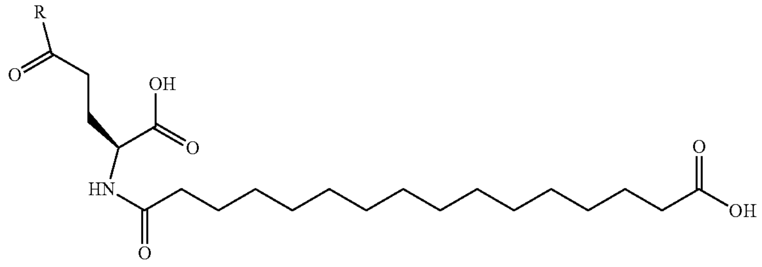 |
| -{AEEA}$_2$-gGlu-$C(O)(CH_2)_{14}COOH$ | 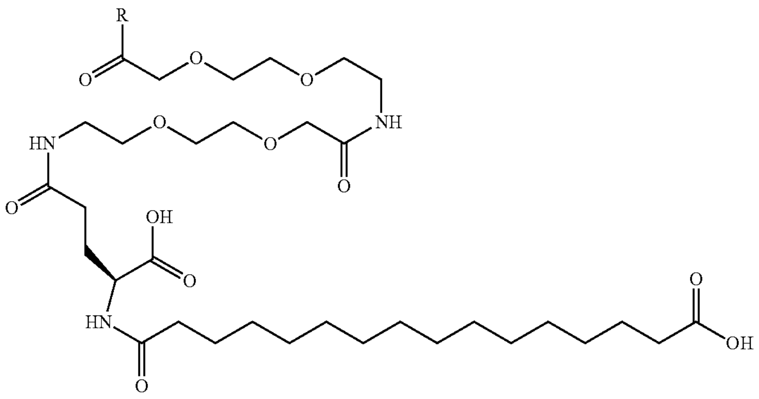 |

TABLE 1-continued
| Group | Chemical structure and IUPAC name |
|---|---|
| -{AEEA}$_2$-{gGlu}$_2$-C(O)(CH$_2$)$_{14}$COOH | 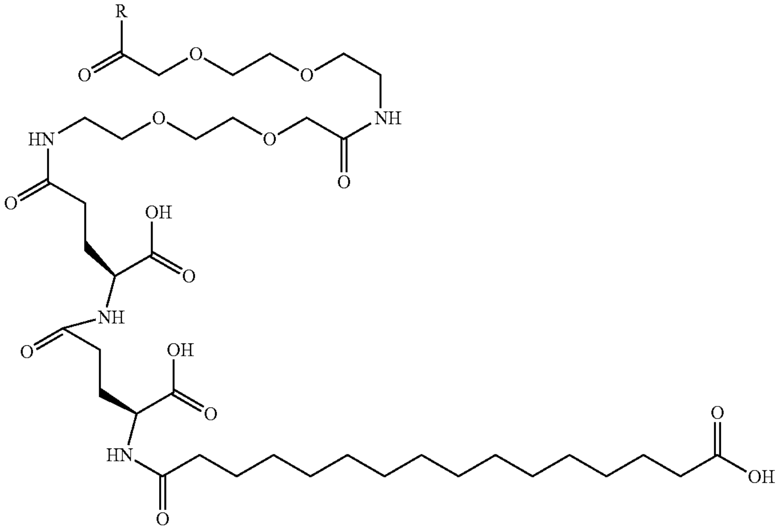 |
| -{AEEA}$_2$-{gGlu}-C(O)(CH$_2$)$_{14}$CH$_3$ | 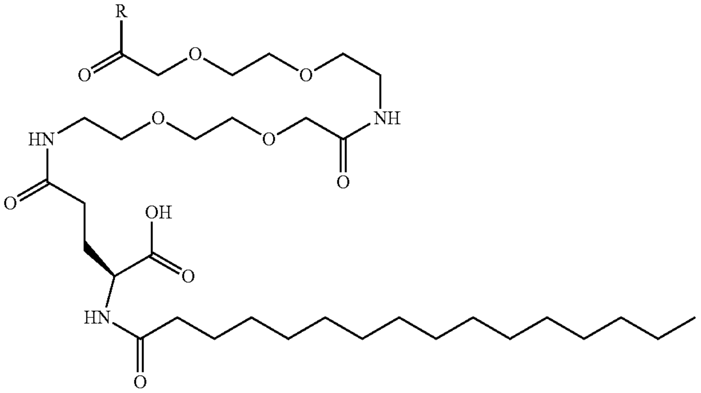 |
| -{AEEA}$_2$-{gGlu}$_2$-C(O)(CH$_2$)$_{14}$CH$_3$ | 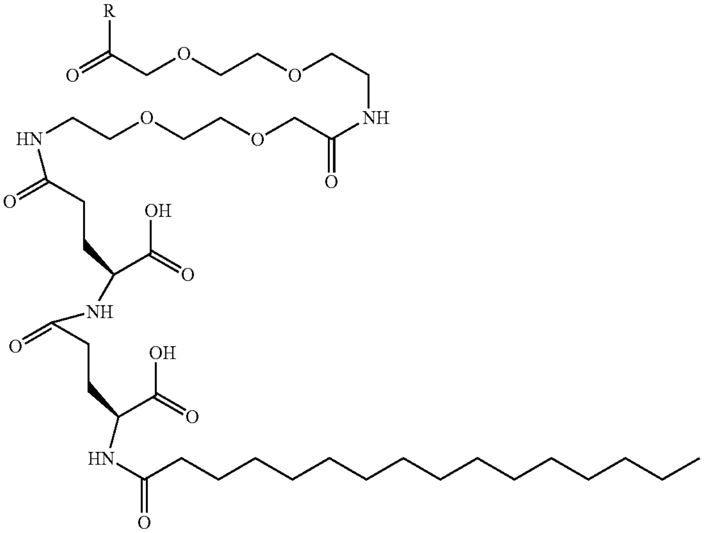 |

In a particular embodiment, the albumin-binding moiety is -{AEEA}$_2$-gGlu-C(O)$(CH_2)_{16}$COOH; -{AEEA}$_2$-gGlu-C(O)$(CH_2)_{14}$COOH; or -{AEEA}$_2$-{gGlu}$_2$-C(O)$(CH_2)_{14}$COOH. In a more particular embodiment, the albumin-binding moiety is -{AEEA}$_2$-gGlu-C(O)$(CH_2)_{16}$COOH.

In an embodiment, the compound is a peptide comprising the amino acid sequence of any one of SEQ ID NOs 1 to 227 or a pharmaceutically acceptable salt thereof.

In an embodiment, the compound is a peptide comprising the amino acid sequence of any one of SEQ ID Nos 3, 7, 35, 83, 130, 135, 136, 137, 138, 139,140, 141, 142, 147, 149, 151, 152, 171, 172, 173 and 174 or a pharmaceutically acceptable salt thereof. In another embodiment, the compound is a peptide comprising the amino acid sequence of any one of SEQ ID NOs 35, 130, 135, 137, 140, 142, 149, 151 and 152. In one embodiment, the compound is a peptide comprising the amino acid sequence of any one of SEQ ID NOs 35, 130, 83, 135, 136, 137, 138, 139, 147, 151, 174. In an even further embodiment the the compound is a peptide comprising the amino acid sequence of any one of SEQ ID Nos 35, 130, 135, 137, 138, 139, 140, 141, 142, 149, 151, and 152 or a pharmaceutically acceptable salt thereof.

In an embodiment, the compound is a peptide of the amino acid sequence of formula (I), optionally wherein the amino acid residue at X1 is acetylated and optionally wherein the amino acid residue at X38 is amidated; or a pharmaceutically acceptable salt thereof.

In an embodiment, the compound is a peptide of the amino acid sequence of formula (I) or a pharmaceutically acceptable salt thereof; wherein:

X1 is isoleucine (I);
X2 is valine (V);
X7 is valine (V) or D-valine (v)
X9 is isoleucine (I) or threonine (T); in particular isoleucine (I);
X10 is lysine (K) or glycine (G);
X11 is leucine (L);
X13 is lysine (K) or glutamine (Q);
X14 is lysine (K) or isoleucine (I); in particular isoleucine (I)
X16 is leucine (L);
X19 is alanine (A) or glutamate (E);
X21 is glutamine (Q);
X22 is glutamate (E) or arginine (R) or lysine (K); in particular arginine (R) or lysine (K); more in particular lysine (K);
X23 is lysine (K) or 2-aminoisobutyric acid (Aib); in particular lysine (K)
X24 is glutamate (E) or glutamine (Q) or 2-aminoisobutyric acid (Aib); in particular glutamine (Q) or 2-aminoisobutyric acid (Aib);
X25 is lysine (K) or arginine (R); in particular arginine (R);
X26 is alanine (A), glutamate (E) or glutamine (Q); in particular glutamate (E) or glutamine (Q);
X27 is lysine (K) or glutamine (Q); in particular lysine (K) or glutamine (Q); more in particular glutamine (Q);
X29 is glutamate (E);
X30 is lysine (K) or threonine (T); in particular lysine (K);
X31 is asparagine (N);
X32 is lysine (K) or alanine (A); in particular lysine (K)
X33 is arginine (R) or glutamine (Q)
X34 is isoleucine (I);
X35 is leucine (L);
X36 is alanine (A) or glutamate (E); in particular glutamate (E);
X37 is arginine (R) or glutamine (Q); in particular glutamine (Q); and
X38 is valine (V);

and optionally wherein the amino acid residue at X1 is acetylated and optionally wherein the amino acid residue at X38 is amidated.

In an embodiment, the compound is a peptide of the amino acid sequence of formula (I) or a pharmaceutically acceptable salt thereof; wherein:

X1 is isoleucine (I);
X2 is valine (V);
X7 is D-valine (v);
X9 is isoleucine (I);
X10 is lysine (K) or glycine (G);
X11 is leucine (L);
X13 is glutamine (Q);
X14 is isoleucine (I);
X16 is leucine (L);
X19 is alanine (A) or glutamate (E);
X21 is glutamine (Q);
X22 is lysine (K);
X23 is lysine (K) or 2-aminoisobutyric acid (Aib)
X24 is glutamine (Q) or 2-aminoisobutyric acid (Aib);
X25 is arginine (R);
X26 is glutamate (E) or glutamine (Q) or Alanine (A);
X27 is lysine (K) or glutamine (Q); in particular glutamine (Q)
X29 is glutamate (E);
X30 is lysine (K) or threonine (T);
X31 is asparagine (N);
X32 is lysine (K);
X33 is arginine (R) or glutamine (Q);
X34 is isoleucine (I);
X35 is leucine (L);
X36 is glutamate (E) or alanine (A);
X37 is glutamine (Q) or arginine (R);
X38 is valine (V);

and optionally wherein the amino acid residue at X1 is acetylated and optionally wherein the amino acid residue at X38 is amidated.

In an embodiment, the compound is a peptide of the amino acid sequence of formula (I) or a pharmaceutically acceptable salt thereof; wherein:

X1 is isoleucine (I);
X2 is valine (V);
X9 is isoleucine (I);
X10 is lysine (K);
X11 is leucine (L);
X14 is isoleucine (I);
X16 is leucine (L);
X19 is glutamate (E);
X21 is glutamine (Q);
X22 is lysine (K);
X24 is glutamine (Q);
X25 is arginine (R);
X26 is glutamate (E);
X27 is glutamine (Q);
X29 is glutamate (E);
X31 is asparagine (N);
X32 is lysine (K);
X33 is glutamine (Q);
X34 is isoleucine (I);
X35 is leucine (L);
X37 is glutamine (Q); and
X38 is valine (V);

and optionally wherein the amino acid residue at X1 is acetylated and optionally wherein the amino acid residue at X38 is amidated.

In an embodiment, the compound is a peptide of the amino acid sequence of formula (I) or a pharmaceutically acceptable salt thereof; wherein:

X7 is D-valine (V);
X10 is lysine;
X19 is glutamate (E);
X24 is glutamine (Q);
X25 is arginine (R);
X26 is glutamate (E);
X27 is glutamine (Q).
X30 is lysine (K);
X33 is glutamine (Q);
X36 is alanine (A);
X37 is glutamine (Q);
and optionally wherein the amino acid residue at X1 is acetylated and optionally wherein the amino acid residue at X38 is amidated.

In an embodiment, the compound is a peptide of the amino acid sequence of formula (I) or a pharmaceutically acceptable salt thereof; wherein the amino acid residue at X38 is amidated as a primary amide.

In an embodiment, the compound is a peptide of the amino acid sequence of formula (I) or a pharmaceutically acceptable salt thereof; wherein:

X1 is isoleucine (I);
X2 is valine (V);
X9 is isoleucine (I);
X10 is lysine (K) or glycine (G);
X11 is leucine (L);
X14 is isoleucine (I);
X16 is leucine (L);
X19 is alanine (A) or glutamate (E);
X21 is glutamine (Q);
X22 is lysine (K);
X24 is glutamine (Q) or 2-aminoisobutyric acid (Aib);
X25 is arginine (R);
X26 is alanine (A), glutamate (E) or glutamine (Q);
X27 is glutamine (Q);
X29 is glutamate (E);
X31 is asparagine (N);
X32 is lysine (K);
X33 is arginine (R) or glutamine (Q);
X34 is isoleucine (I);
X35 is leucine (L); and
X38 is valine (V);
and wherein the amino acid residue at X38 is amidated as a primary amide.

In an embodiment, the compound is a peptide of the amino acid sequence of formula (I) or a pharmaceutically acceptable salt thereof; wherein:

X1 is isoleucine (I);
X2 is valine (V);
X9 is isoleucine (I);
X10 is lysine (K), glutamate (E) or glycine (G);
X11 is leucine (L);
X14 is isoleucine (I);
X15 is leucine (L)
X16 is leucine (L);
X19 is alanine (A) or glutamate (E); in particular glutamate (E);
X21 is glutamine (Q);
X22 is lysine (K) or glutamate (E);
X23 is 2-aminoisobutyric acid (Aib);
X24 is glutamine (Q);
X25 is arginine (R);
X26 is glutamate (E);
X27 is glutamine (Q);
X29 is glutamate (E);
X31 is asparagine (N);
X32 is lysine (K) or glutamate (E); in particular glutamate (E);
X33 is glutamine (Q);
X34 is isoleucine (I);
X35 is leucine (L); and
X38 is valine (V);
and wherein the amino acid residue at X1 is acetylated and the amino acid residue at X38 is amidated as a primary amide.

In an embodiment, the compound is a peptide of the amino acid sequence of formula (I) or a pharmaceutically acceptable salt thereof; wherein:

X1 is isoleucine (I);
X2 is valine (V);
X9 is isoleucine (I);
X10 is lysine (K);
X11 is leucine (L);
X14 is isoleucine (I);
X16 is leucine (L);
X19 is glutamate (E);
X21 is glutamine (Q);
X22 is lysine (K);
X24 is glutamine (Q);
X25 is arginine (R);
X26 is glutamate (E);
X27 is glutamine (Q);
X29 is glutamate (E);
X31 is asparagine (N);
X32 is lysine (K);
X33 is glutamine (Q);
X34 is isoleucine (I);
X35 is leucine (L);
X37 is glutamine (Q); and
X38 is valine (V);
and wherein the amino acid residue at X38 is amidated as a primary amide.

In an embodiment, the compound is a peptide of any one of SEQ ID NOs 1 to 227 or a pharmaceutically acceptable salt thereof. These peptides are listed in Table 2 below, in which K* denotes the modified lysine residue at X12, Ra denotes the albumin-binding moiety, Ac-denotes that the N-terminal is acetylated, and —$NH_2$ denotes that the C-terminal amino acid residue is amidated as a primary amide:

TABLE 2

| SEQ ID NO. | Amino acid sequence | $R^a$ |
|---|---|---|
| 1 | IVLSLDVPIGLK*QILLEQEKQEKEKQQAETNAQILAQV-NH2 | -gGlu-C(O)$(CH_2)_{14}CH_3$ |
| 2 | IVLSLDVPIKLK*KILLEQEKQEKEKQQAETNAQILAQV-NH2 | -gGlu-C(O)$(CH_2)_{14}CH_3$ |

TABLE 2-continued

| SEQ ID NO. | Amino acid sequence | $R^a$ |
|---|---|---|
| 3 | IVLSLDVPIKLK*KILLEQEKQEKEKQQAEKNAQILAQV-NH2 | -gGlu-C(O)$(CH_2)_{14}CH_3$ |
| 4 | IVLSLDVPIGLK*QKLLKQEKQEKEKQQAETNAKILAQV-NH2 | -gGlu-C(O)$(CH_2)_{14}CH_3$ |
| 5 | IVLSLDVPIGLK*QKLLKQQRQRKERQQAETNARILARV-NH2 | -gGlu-C(O)$(CH_2)_{14}CH_3$ |
| 6 | IVLSLDVPIGLK*QKLLKQQRQRKERQQAEKNARILARV-NH2 | -gGlu-C(O)$(CH_2)_{14}CH_3$ |
| 7 | IVLSLDvPTKLK*QKLLKQERQRKEREQAEKNARILARV-NH2 | -gGlu-C(O)$(CH_2)_{14}CH_3$ |
| 8 | FTLSLDVPTKIK*QKLLKQEKQKKQRQKAKTAAQILAQV-NH2 | -gGlu-C(O)$(CH_2)_{14}CH_3$ |
| 9 | FTLSLDVPTKIK*QKLLKQEKQKKQRQKAKTAKQILEQV-NH2 | -gGlu-C(O)$(CH_2)_{14}CH_3$ |
| 10 | FTLSLDVPTKIK*QKLLKQEKQKKQRQKAKTNKQILEQV-NH2 | -gGlu-C(O)$(CH_2)_{14}CH_3$ |
| 11 | FTLSLDVPTKIK*QKLLKQEKQKKQRQKAKTNAQILAQV-NH2 | -gGlu-C(O)$(CH_2)_{14}CH_3$ |
| 12 | FTLSLDVPTKIK*QKLLKQEKQRKQKQQAKTNAKILARV-NH2 | -gGlu-C(O)$(CH_2)_{14}CH_3$ |
| 13 | FTLSLDVPTKIK*QILFKQQKQKKERQQAEKNKQLLEQI-NH2 | -$\{AEEA\}_2$-gGlu-C(O)$(CH_2)_{16}$COOH |
| 14 | FTLSLDVPTKIK*QKLLKQEKQRKQKQKAKTNAKILARV-NH2 | -gGlu-C(O)$(CH_2)_{14}CH_3$ |
| 15 | FTLSLDVPTKIK*QKLFKQAKQKKQRQKAKTNAQILARV-NH2 | -gGlu-C(O)$(CH_2)_{14}CH_3$ |
| 16 | IVLSLDVPIGLK*QKLLKQQRQRKERQQAEKNARILARV-NH2 | -$\{AEEA\}_2$-gGlu-C(O)$(CH_2)_{16}$COOH |
| 17 | IVLSLDVPIKLK*KILLEQEKQKKQREQAETNKQILAQV-NH2 | -gGlu-C(O)$(CH_2)_{14}CH_3$ |
| 18 | IVLSLDvPTKLK*QKLLKQERQRKEREQAEKNKRILERV-NH2 | -gGlu-C(O)$(CH_2)_{14}CH_3$ |
| 19 | IVLSLDvPTKLK*QKLLKQERQRAibEREQAEKNKRILERV-NH2 | -gGlu-C(O)$(CH_2)_{14}CH_3$ |
| 20 | IVLSLDvPTKLK*QKLLKQERQRKAibREQAEKNKRILERV-NH2 | -gGlu-C(O)$(CH_2)_{14}CH_3$ |
| 21 | IVLSLDvPTKLK*QKLLKQERQRKEAibEQAEKNKRILERV-NH2 | -gGlu-C(O)$(CH_2)_{14}CH_3$ |
| 22 | IVLSLDVPIKLK*QILLKQERQKAibQRQKAEKNKQILAQV-NH2 | -$\{AEEA\}_2$-gGlu-C(O)$(CH_2)_{16}$COOH |
| 23 | IVLSLDvPTKLK*QKLLKQERQRKERAibQAEKNKRILERV-NH2 | -gGlu-C(O)$(CH_2)_{14}CH_3$ |
| 24 | IVLSLDvPTKLK*QKLLKQERQRKEREQAEKNKRILERV-NH2 | -$\{AEEA\}_2$-gGlu-C(O)$(CH_2)_{16}$COOH |
| 25 | IVLSLDvPTKLK*KKLLKQERKRKEREKAEKNARILERV-NH2 | -gGlu-C(O)$(CH_2)_{14}CH_3$ |
| 26 | IVLSLDvPTKLK*KKLLKQERKRKEREAibAEKNARILERV-NH2 | -gGlu-C(O)$(CH_2)_{14}CH_3$ |
| 27 | IVLSLDvPTKLK*KKLLKQERKRKEREQAEKNARILERV-NH2 | -gGlu-C(O)$(CH_2)_{14}CH_3$ |
| 28 | IVLSLDvPTKLK*KKLLKQERKRKEREKAEKAARILERV-NH2 | -gGlu-C(O)$(CH_2)_{14}CH_3$ |
| 29 | IVLSLDvPTKLK*KKLLKQERKRKEREAibAEKAARILERV-NH2 | -gGlu-C(O)$(CH_2)_{14}CH_3$ |
| 30 | IVLSLDvPTKLK*KKLLKQERKRKEREQAEKAARILERV-NH2 | -gGlu-C(O)$(CH_2)_{14}CH_3$ |
| 31 | IVLSLDvPTKLK*QKLLKQERQRKEREQAEKNAibRILERV-NH2 | -gGlu-C(O)$(CH_2)_{14}CH_3$ |
| 32 | IVLSLDvPTKLK*QKLLKQERQRKEREQAEKNVRILERV-NH2 | -gGlu-C(O)$(CH_2)_{14}CH_3$ |
| 33 | IVLSLDvPTKLK*QKLLKQERQRKEREQAEKNTRILERV-NH2 | -gGlu-C(O)$(CH_2)_{14}CH_3$ |
| 34 | FTLSLDVPTKIK*QKLLKQEKQKKQRQKAKTNKQILEQV-NH2 | -$\{AEEA\}_2$-gGlu-C(O)$(CH_2)_{16}$COOH |
| 35 | IVLSLDVPIKLK*KILLEQEKQKKQREQAETNKQILAQV-NH2 | -$\{AEEA\}_2$-gGlu-C(O)$(CH_2)_{16}$COOH |
| 36 | IVLSLDvPTKLK*QKLLKQERQRKAibREQAEKNKRILERV-NH2 | -$\{AEEA\}_2$-gGlu-C(O)$(CH_2)_{16}$COOH |
| 37 | IVLSLDVPTKLK*QKLLKQERQRKERQQAETNKRILERV-NH2 | -$\{AEEA\}_2$-gGlu-C(O)$(CH_2)_{16}$COOH |
| 38 | IVLSLDVPTKLK*QKLLKQERQRAibERQQAETNKRILERV-NH2 | -$\{AEEA\}_2$-gGlu-C(O)$(CH_2)_{16}$COOH |
| 39 | IVLSLDVPIKLK*QILLEQERQRKERQQAETNAQILAQV-NH2 | -$\{AEEA\}_2$-gGlu-C(O)$(CH_2)_{16}$COOH |
| 40 | IVLSLDVPIKLK*QILLEQERQRKERQQAETNVQILAQV-NH2 | -$\{AEEA\}_2$-gGlu-C(O)$(CH_2)_{16}$COOH |

TABLE 2-continued

| SEQ ID NO. | Amino acid sequence | $R^a$ |
|---|---|---|
| 41 | IVLSLDVPIKLK*QILLEQERQRKERQQAEKNVRILERV-NH2 | $-\{AEEA\}_2$-gGlu-C(O)$(CH_2)_{16}$COOH |
| 42 | IVLSLDVPIKLK*QILLEQERQRAibERQQAEKNVRILERV-NH2 | $-\{AEEA\}_2$-gGlu-C(O)$(CH_2)_{16}$COOH |
| 43 | IVLSLDVPIKLK*QILLEQAKQKKLRAQAETNVRILERV-NH2 | $-\{AEEA\}_2$-gGlu-C(O)$(CH_2)_{16}$COOH |
| 44 | IVLSLDVPIKLK*QILLEQAKQKKERAQAETNVRILERV-NH2 | $-\{AEEA\}_2$-gGlu-C(O)$(CH_2)_{16}$COOH |
| 45 | IVLSLDVPIKLK*QILLEQAKQKAibLKAQAETNVRILERV-NH2 | $-\{AEEA\}_2$-gGlu-C(O)$(CH_2)_{16}$COOH |
| 46 | IVLSLDVPIKLK*QILLEQAKQKAibLRAQAETNVRILERV-NH2 | $-\{AEEA\}_2$-gGlu-C(O)$(CH_2)_{16}$COOH |
| 47 | IVLSLDvPTKLK*KKLLKQERKRAibEREKAEKAARILERV-NH2 | $-\{AEEA\}_2$-gGlu-C(O)$(CH_2)_{16}$COOH |
| 48 | IVLSLDVPIKLK*QILLEQERQRAibERQQAETNVQILAQV-NH2 | $-\{AEEA\}_2$-gGlu-C(O)$(CH_2)_{16}$COOH |
| 49 | IVLSLDVPIKLK*QILLEQERQRAibERQQAETNVRILERV-NH2 | $-\{AEEA\}_2$-gGlu-C(O)$(CH_2)_{16}$COOH |
| 50 | IVLSLDVPTKLK*QILLKQERQRAibERQQAETNVRILERV-NH2 | $-\{AEEA\}_2$-gGlu-C(O)$(CH_2)_{16}$COOH |
| 51 | FTLSLDVPTKIK*QILLKQQKQKKERQQAEKNKQLLEQI-NH2 | $-\{AEEA\}_2$-gGlu-C(O)$(CH_2)_{16}$COOH |
| 52 | FTLSLDVPTKIK*QILLKQQKQKKERQQAEKNKQLLERV-NH2 | $-\{AEEA\}_2$-gGlu-C(O)$(CH_2)_{16}$COOH |
| 53 | FTLSLDVPTKIK*QILLKQQKQKKERQQAETNKQLLERV-NH2 | $-\{AEEA\}_2$-gGlu-C(O)$(CH_2)_{16}$COOH |
| 54 | FTLSLDVPIKLK*QILLKQQKQKKERQQAETNVQLLERV-NH2 | $-\{AEEA\}_2$-gGlu-C(O)$(CH_2)_{16}$COOH |
| 55 | FTLSLDVPTKIK*QILLKQQKQKKERQKAETNVQLLERV-NH2 | $-\{AEEA\}_2$-gGlu-C(O)$(CH_2)_{16}$COOH |
| 56 | FTLSLDVPIGLK*QILLKQQKQKKERQQAETNVQLLERV-NH2 | $-\{AEEA\}_2$-gGlu-C(O)$(CH_2)_{16}$COOH |
| 57 | FTLSLDVPIGLK*QILLKQQKQKKERQKAETNVQLLERV-NH2 | $-\{AEEA\}_2$-gGlu-C(O)$(CH_2)_{16}$COOH |
| 58 | FTLSLDVPTKIK*QILFKQQKQKKERQQAEKNKQLLEQI-NH2 | $-\{AEEA\}_2$-gGlu-C(O)$(CH_2)_{18}$COOH |
| 59 | FTLSLDVPTKIK*QILLKQQKQKKERQQAEKNKQLLEQI-NH2 | $-\{AEEA\}_2$-gGlu-C(O)$(CH_2)_{18}$COOH |
| 60 | FTLSLDVPTKIK*QILLKQQKQKKERQQAEKNKQLLERV-NH2 | $-\{AEEA\}_2$-gGlu-C(O)$(CH_2)_{18}$COOH |
| 61 | FTLSLDVPTKIK*QILLKQQKQKKERQQAETNKQLLERV-NH2 | $-\{AEEA\}_2$-gGlu-C(O)$(CH_2)_{18}$COOH |
| 62 | FTLSLDVPIKLK*QILLKQQKQKKERQQAETNVQLLERV-NH2 | $-\{AEEA\}_2$-gGlu-C(O)$(CH_2)_{18}$COOH |
| 63 | FTLSLDVPIKLK*QILLEQQKQKKERQQAETNVQLLERV-NH2 | $-\{AEEA\}_2$-gGlu-C(O)$(CH_2)_{18}$COOH |
| 64 | FTLSLDVPTKIK*QILLKQQKQKKERQKAETNVQLLERV-NH2 | $-\{AEEA\}_2$-gGlu-C(O)$(CH_2)_{18}$COOH |
| 65 | FTLSLDVPIGLK*QILLKQQKQKKERQQAETNVQLLERV-NH2 | $-\{AEEA\}_2$-gGlu-C(O)$(CH_2)_{18}$COOH |
| 66 | FTLSLDVPIGLK*QILLKQQKQKKERQKAETNVQLLERV-NH2 | $-\{AEEA\}_2$-gGlu-C(O)$(CH_2)_{18}$COOH |
| 67 | IVLSLDVPIKLK*QILLEQEKQKKQREQAETNKQILAQV-NH2 | $-\{AEEA\}_2$-gGlu-C(O)$(CH_2)_{16}$COOH |
| 68 | IVLSLDVPIKLK*QILLEQERQKKQREQAETNKQILAQV-NH2 | $-\{AEEA\}_2$-gGlu-C(O)$(CH_2)_{16}$COOH |
| 69 | IVLSLDVPIKLK*KAibLLEQERQKKQREQAETNKQILAQV-NH2 | $-\{AEEA\}_2$-gGlu-C(O)$(CH_2)_{16}$COOH |
| 70 | IVLSLDVPIKLK*QILLEQERQKKQREQAETNAibQILAQV-NH2 | $-\{AEEA\}_2$-gGlu-C(O)$(CH_2)_{16}$COOH |
| 71 | IVLSLDVPIKLK*KAibLLEQERQKKQREQAETNAibQILAQV-NH2 | $-\{AEEA\}_2$-gGlu-C(O)$(CH_2)_{16}$COOH |
| 72 | IVLSLDVPIKLK*QILLEQERQKKQRQQAETNAibQILAQV-NH2 | $-\{AEEA\}_2$-gGlu-C(O)$(CH_2)_{16}$COOH |
| 73 | IVLSLDVPIKLK*QILLEQERQKKQRQKAETNAibQILAQV-NH2 | $-\{AEEA\}_2$-gGlu-C(O)$(CH_2)_{16}$COOH |
| 74 | IVLSLDVPIKLK*QILLEQERQKKQREQAETNAibQILERV-NH2 | $-\{AEEA\}_2$-gGlu-C(O)$(CH_2)_{16}$COOH |
| 75 | IVLSLDVPIKLK*QILLKQERQKKQRQQAETNAibQILAQV-NH2 | $-\{AEEA\}_2$-gGlu-C(O)$(CH_2)_{16}$COOH |
| 76 | IVLSLDVPIGLK*QILLEQERQKKQRQQAETNAibQILAQV-NH2 | $-\{AEEA\}_2$-gGlu-C(O)$(CH_2)_{16}$COOH |
| 77 | IVLSLDVPIKLK*QILLKQERQKKQRQKAETNKQILAQV-NH2 | $-\{AEEA\}_2$-gGlu-C(O)$(CH_2)_{16}$COOH |
| 78 | IVLSLDVPTKLK*QILLEQERQKKQREQAETNAibQILAQV-NH2 | $-\{AEEA\}_2$-gGlu-C(O)$(CH_2)_{16}$COOH |

TABLE 2-continued

| SEQ ID NO. | Amino acid sequence | $R^a$ |
|---|---|---|
| 79 | IVLSLDVPIKLK*QILLEQEKQKAibQREQAETNKQILAQV-NH2 | $-\{AEEA\}_2$-gGlu-C(O)$(CH_2)_{16}$COOH |
| 80 | IVLSLDVPTKLK*QILLEQERQKKQREQAETNAibQILAQV-NH2 | $-\{AEEA\}_2$-gGlu-C(O)$(CH_2)_{18}$COOH |
| 81 | IVLSLDVPIKLK*QILLEQEKQKAibQREQAETNKQILAQV-NH2 | $-\{AEEA\}_2$-gGlu-C(O)$(CH_2)_{18}$COOH |
| 82 | IVLSLDVPTKLK*QILLKQERQKKAibREQAETNVRILERV-NH2 | $-\{AEEA\}_2$-gGlu-C(O)$(CH_2)_{16}$COOH |
| 83 | IVLSLDvPIGLK*QILLKQERQKKAibREQAETNKRILERV-NH2 | $-\{AEEA\}_2$-gGlu-C(O)$(CH_2)_{16}$COOH |
| 84 | IVLSLDVPIKLK*QKLLEQEKQKKQREQAETNKQILAQV-NH2 | $-\{AEEA\}_2$-gGlu-C(O)$(CH_2)_{16}$COOH |
| 85 | IVLSLDVPIKLK*QILLKQERQKKQREQAETNKQILAQV-NH2 | $-\{AEEA\}_2$-gGlu-C(O)$(CH_2)_{16}$COOH |
| 86 | IVLSLDVPIKLK*QILLKQERQKKQREQAKTNKQILAQV-NH2 | $-\{AEEA\}_2$-gGlu-C(O)$(CH_2)_{16}$COOH |
| 87 | IVLSLDVPIKLK*QILLKQERQKKQREKAKTNKQILAQV-NH2 | $-\{AEEA\}_2$-gGlu-C(O)$(CH_2)_{16}$COOH |
| 88 | IVLSLDVPIKLK*QILLKQERQKKQREKAKTNAibQILAQV-NH2 | $-\{AEEA\}_2$-gGlu-C(O)$(CH_2)_{16}$COOH |
| 89 | IVLSLDVPIKLK*QILLKQERQKKQREQAKTNAibQILAQV-NH2 | $-\{AEEA\}_2$-gGlu-C(O)$(CH_2)_{16}$COOH |
| 90 | IVLSLDVPIKLK*QILLKQERQKKQREKAKTNVQILAQV-NH2 | $-\{AEEA\}_2$-gGlu-C(O)$(CH_2)_{16}$COOH |
| 91 | IVLSLDVPIKLK*QKLLKQERQKKQREKAKTNAibQILAQV-NH2 | $-\{AEEA\}_2$-gGlu-C(O)$(CH_2)_{16}$COOH |
| 92 | IVLSLDVPIKLK*QKLLEQERQKKQREQAETNAibQILAQV-NH2 | $-\{AEEA\}_2$-gGlu-C(O)$(CH_2)_{16}$COOH |
| 93 | IVLSLDVPIKLK*QKLLKQERQKKQREKAKTNVQILAQV-NH2 | $-\{AEEA\}_2$-gGlu-C(O)$(CH_2)_{16}$COOH |
| 94 | IVLSLDVPIKLK*KILLKQERQKKEREQAETNKQILAQV-NH2 | $-\{AEEA\}_2$-gGlu-C(O)$(CH_2)_{16}$COOH |
| 95 | IVLSLDVPIKLK*QKLLKQERQKKEREQAETNKQILAQV-NH2 | $-\{AEEA\}_2$-gGlu-C(O)$(CH_2)_{16}$COOH |
| 96 | IVLSLDVPIKLK*QILLKQERQKKEREQAETNKQILAQV-NH2 | $-\{AEEA\}_2$-gGlu-C(O)$(CH_2)_{16}$COOH |
| 97 | IVLSLDVPIKLK*QKLLKQERQKKQREQAETNKQILAQV-NH2 | $-\{AEEA\}_2$-gGlu-C(O)$(CH_2)_{16}$COOH |
| 98 | IVLSLDVPIKLK*QKLLKQERQKKAibREQAETNKQILAQV-NH2 | $-\{AEEA\}_2$-gGlu-C(O)$(CH_2)_{16}$COOH |
| 99 | IVLSLDVPIKLK*KILLKQERQKKAibREQAEKNKQILAQV-NH2 | $-\{AEEA\}_2$-gGlu-C(O)$(CH_2)_{16}$COOH |
| 100 | IVLSLDVPIKLK*KILLKQERQKKAibREQAETNAibQILAQV-NH2 | $-\{AEEA\}_2$-gGlu-C(O)$(CH_2)_{16}$COOH |
| 101 | IVLSLDVPIKLK*KILLKQERQKKAibREQAETNKQILERV-NH2 | $-\{AEEA\}_2$-gGlu-C(O)$(CH_2)_{16}$COOH |
| 102 | IVLSLDvPIKLK*QILLKQERQKKQREQAETNKQILAQV-NH2 | $-\{AEEA\}_2$-gGlu-C(O)$(CH_2)_{16}$COOH |
| 103 | IVLSLDVPIKLK*QILLEQERQKAibQREQAETNKQILAQV-NH2 | $-\{AEEA\}_2$-gGlu-C(O)$(CH_2)_{16}$COOH |
| 104 | IVLSLDVPIKLK*QILLKQERQKAibQREQAETNKQILAQV-NH2 | $-\{AEEA\}_2$-gGlu-C(O)$(CH_2)_{16}$COOH |
| 105 | IVLSLDVPIKLK*QILLEQERQKAibQRQQAETNKQILAQV-NH2 | $-\{AEEA\}_2$-gGlu-C(O)$(CH_2)_{16}$COOH |
| 106 | IVLSLDVPIKLK*QILLEQERQKAibQREQAETNKQILERV-NH2 | $-\{AEEA\}_2$-gGlu-C(O)$(CH_2)_{16}$COOH |
| 107 | IVLSLDVPIKLK*QILLKQERQKAibQREQAETNKQILERV-NH2 | $-\{AEEA\}_2$-gGlu-C(O)$(CH_2)_{16}$COOH |
| 108 | IVLSLDVPIKLK*QILLKQERQKAibQRQKAETNKQILAQV-NH2 | $-\{AEEA\}_2$-gGlu-C(O)$(CH_2)_{16}$COOH |
| 109 | IVLSLDVPIKLK*QILLKQERQKAibQREKAETNKQILAQV-NH2 | $-\{AEEA\}_2$-gGlu-C(O)$(CH_2)_{16}$COOH |
| 110 | IVLSLDVPIKLK*QILLKQERQKAibQRQQAETNKQILAQV-NH2 | $-\{AEEA\}_2$-gGlu-C(O)$(CH_2)_{16}$COOH |
| 111 | IVLSLDVPIKLK*QILLKQERQKKQREQAETNKQILEQV-NH2 | $-\{AEEA\}_2$-gGlu-C(O)$(CH_2)_{16}$COOH |
| 112 | IVLSLDVPIKLK*QILLKQERQKKQREKAETNKQILAQV-NH2 | $-\{AEEA\}_2$-gGlu-C(O)$(CH_2)_{16}$COOH |
| 113 | IVLSLDVPIKLK*QILLKQERQKKQRQQAETNKQILAQV-NH2 | $-\{AEEA\}_2$-gGlu-C(O)$(CH_2)_{16}$COOH |
| 114 | IVLSLDVPIKLK*QILLEQARQKAibQRAQAETNKRILERV-NH2 | $-\{AEEA\}_2$-gGlu-C(O)$(CH_2)_{16}$COOH |
| 115 | IVLSLDVPIKLK*QILLKQERQKAibQREQAEKNKQILERV-NH2 | $-\{AEEA\}_2$-gGlu-C(O)$(CH_2)_{16}$COOH |
| 116 | IVLSLDVPIKLK*QILLKQERQKAibQREKAEKNKQILAQV-NH2 | $-\{AEEA\}_2$-gGlu-C(O)$(CH_2)_{16}$COOH |

TABLE 2-continued

| SEQ ID NO. | Amino acid sequence | $R^a$ |
|---|---|---|
| 117 | IVLSLDVPIKLK*QILLKQERQKAibQRQQAEKNKQILAQV-NH2 | -{AEEA}$_2$-gGlu-C(O)(CH$_2$)$_{16}$COOH |
| 118 | IVLSLDvPIKLK*QILLKQERQKAibQRQKAEKNKQILAQV-NH2 | -{AEEA}$_2$-gGlu-C(O)(CH$_2$)$_{16}$COOH |
| 119 | IVLSLDVPIKLK*QILLKQERQKKAibRQKAEKNKQILAQV-NH2 | -{AEEA}$_2$-gGlu-C(O)(CH$_2$)$_{16}$COOH |
| 120 | IVLSLDVPIKLK*QILLKQERQKKQREQAEKNKQILEQV-NH2 | -{AEEA}$_2$-gGlu-C(O)(CH$_2$)$_{16}$COOH |
| 121 | IVLSLDVPIKLK*QILLKQERQKKQREKAEKNKQILAQV-NH2 | -{AEEA}$_2$-gGlu-C(O)(CH$_2$)$_{16}$COOH |
| 122 | IVLSLDVPIKLK*QILLKQERQKKQRQQAEKNKQILAQV-NH2 | -{AEEA}$_2$-gGlu-C(O)(CH$_2$)$_{16}$COOH |
| 123 | IVLSLDVPIKLK*QILLEQARQKAibQRAQAEKNKRILERV-NH2 | -{AEEA}$_2$-gGlu-C(O)(CH$_2$)$_{16}$COOH |
| 124 | IVLSLDVPIKLK*QILLKQARQKAibQRAQAEKNKRILERV-NH2 | -{AEEA}$_2$-gGlu-C(O)(CH$_2$)$_{16}$COOH |
| 125 | IVLSLDVPIKLK*QILLEQARQKAibQREQAEKNKRILERV-NH2 | -{AEEA}$_2$-gGlu-C(O)(CH$_2$)$_{16}$COOH |
| 126 | IVLSLDvPIKLK*QILLEQAKQKAibQRAQAEKNKRILERV-NH2 | -{AEEA}$_2$-gGlu-C(O)(CH$_2$)$_{16}$COOH |
| 127 | IVLSLDvPIKLK*QILLEQAKQKAibQREQAEKNKRILERV-NH2 | -{AEEA}$_2$-gGlu-C(O)(CH$_2$)$_{16}$COOH |
| 128 | IVLSLDvPIKLK*QILLKQARQKAibQREQAEKNKRILERV-NH2 | -{AEEA}$_2$-gGlu-C(O)(CH$_2$)$_{16}$COOH |
| 129 | IVLSLDvPIKLK*QILLEQERQKAibQREQAEKNKQILAQV-NH2 | -{AEEA}$_2$-gGlu-C(O)(CH$_2$)$_{16}$COOH |
| 130 | IVLSLDvPIKLK*QILLKQERQKAibQREQAEKNKQILAQV-NH2 | -{AEEA}$_2$-gGlu-C(O)(CH$_2$)$_{16}$COOH |
| 131 | IVLSLDvPIKLK*QILLEQERQKAibQRQQAEKNKQILAQV-NH2 | -{AEEA}$_2$-gGlu-C(O)(CH$_2$)$_{16}$COOH |
| 132 | IVLSLDvPIKLK*QILLEQERQKAibQREQAEKNKQILERV-NH2 | -{AEEA}$_2$-gGlu-C(O)(CH$_2$)$_{16}$COOH |
| 133 | IVLSLDvPIKLK*QILLKQERQKAibQREQAEKNKQILERV-NH2 | -{AEEA}$_2$-gGlu-C(O)(CH$_2$)$_{16}$COOH |
| 134 | IVLSLDvPIKLK*QILLKQERQKAibQREKAEKNKQILAQV-NH2 | -{AEEA}$_2$-gGlu-C(O)(CH$_2$)$_{16}$COOH |
| 135 | IVLSLDvPIKLK*QILLKQERQKAibQRQQAEKNKQILAQV-NH2 | -{AEEA}$_2$-gGlu-C(O)(CH$_2$)$_{16}$COOH |
| 136 | IVLSLDvPIKLK*QILLKQERQKKAibRQKAEKNKQILAQV-NH2 | -{AEEA}$_2$-gGlu-C(O)(CH$_2$)$_{16}$COOH |
| 137 | IVLSLDvPIKLK*QILLKQERQKKQREQAEKNKQILEQV-NH2 | -{AEEA}$_2$-gGlu-C(O)(CH$_2$)$_{16}$COOH |
| 138 | IVLSLDvPIKLK*QILLKQERQKKQREKAEKNKQILAQV-NH2 | -{AEEA}$_2$-gGlu-C(O)(CH$_2$)$_{16}$COOH |
| 139 | IVLSLDvPIKLK*QILLKQERQKKQRQQAEKNKQILAQV-NH2 | -{AEEA}$_2$-gGlu-C(O)(CH$_2$)$_{16}$COOH |
| 140 | IVLSLDvPIKLK*QILLEQARQKAibQRAQAEKNKRILERV-NH2 | -{AEEA}$_2$-gGlu-C(O)(CH$_2$)$_{16}$COOH |
| 141 | IVLSLDvPIKLK*QILLKQARQKAibQRAQAEKNKRILERV-NH2 | -{AEEA}$_2$-gGlu-C(O)(CH$_2$)$_{16}$COOH |
| 142 | IVLSLDvPIKLK*QILLEQARQKAibQREQAEKNKRILERV-NH2 | -{AEEA}$_2$-gGlu-C(O)(CH$_2$)$_{16}$COOH |
| 143 | FTLSLDVPTKIK*QILLKQEKQKKQRQKAKTNKQILERV-NH2 | -{AEEA}$_2$-gGlu-C(O)(CH$_2$)$_{16}$COOH |
| 144 | FTLSLDVPTKIK*QILLKQERQKKQRQKAKTNKQILERV-NH2 | -{AEEA}$_2$-gGlu-C(O)(CH$_2$)$_{16}$COOH |
| 145 | FTLSLDVPTKIK*QILLKQERQKKQRQKAKKNKQILERV-NH2 | -{AEEA}$_2$-gGlu-C(O)(CH$_2$)$_{16}$COOH |
| 146 | FTLSLDVPIKLK*QILLKQERQKKQRQKAKKNKQILERV-NH2 | -{AEEA}$_2$-gGlu-C(O)(CH$_2$)$_{16}$COOH |
| 147 | IVLSLDvPIGLK*QILLKQERQKKAibREQAETNKQILAQV-NH2 | -{AEEA}$_2$-gGlu-C(O)(CH$_2$)$_{16}$COOH |
| 148 | IVLSLDVPIGLK*QILLKQERQKKAibREQAETNKRILERV-NH2 | -{AEEA}$_2$-gGlu-C(O)(CH$_2$)$_{16}$COOH |
| 149 | IVLSLDvPIKLK*QILLKQERQKKAibREQAETNKRILERV-NH2 | -{AEEA}$_2$-gGlu-C(O)(CH$_2$)$_{16}$COOH |
| 150 | IVLSLDvPIGLK*QILLKQERQKKAibRQQAETNKRILERV-NH2 | -{AEEA}$_2$-gGlu-C(O)(CH$_2$)$_{16}$COOH |
| 151 | IVLSLDvPIGLK*QILLKQERQKKAibREQAEKNKRILERV-NH2 | -{AEEA}$_2$-gGlu-C(O)(CH$_2$)$_{16}$COOH |
| 152 | IVLSLDVPIKLK*QILLKQERQKKAibREQAETNKRILERV-NH2 | -{AEEA}$_2$-gGlu-C(O)(CH$_2$)$_{16}$COOH |
| 153 | Ac-IVLSLDVPIGLK*QILLEQEKQEKEKQQAETNAQILAQV-NH2 | -{AEEA}$_2$-gGlu-C(O)(CH$_2$)$_{16}$COOH |
| 154 | IVLSLDVPIGLK*QILLEQEKQEKEKQQAETNKRILERV-NH2 | -{AEEA}$_2$-gGlu-C(O)(CH$_2$)$_{16}$COOH |

TABLE 2-continued

| SEQ ID NO. | Amino acid sequence | $R^a$ |
|---|---|---|
| 155 | IVLSLDVPIGLK*QILLEQEKQEKEKQQAEKNKRILERV-NH2 | $-\{AEEA\}_2$-gGlu-C(O)$(CH_2)_{16}$COOH |
| 156 | IVLSLDVPIGLK*QILLKQERQKKAibREQAETNAQILAQV-NH2 | $-\{AEEA\}_2$-gGlu-C(O)$(CH_2)_{16}$COOH |
| 157 | Ac-IVLSLDvPIKLK*QILLEQARQKAibQREQAEKNKQILEQV-NH2 | $-\{AEEA\}_2$-gGlu-C(O)$(CH_2)_{16}$COOH |
| 158 | Ac-IVLSLDvPIKLK*QILLEQERQKAibQREQAEKNKQILEQV-NH2 | $-\{AEEA\}_2$-gGlu-C(O)$(CH_2)_{16}$COOH |
| 159 | Ac-IVLSLDvPIKLK*QILLEQERQEAibQREQAEKNKQILEQV-NH2 | $-\{AEEA\}_2$-gGlu-C(O)$(CH_2)_{16}$COOH |
| 160 | Ac-IVLSLDvPIKLK*QILLEQERQEAibEREQAETNKQILEQV-NH2 | $-\{AEEA\}_2$-gGlu-C(O)$(CH_2)_{16}$COOH |
| 161 | Ac-IVLSLDvPIKLK*QILLEQERQEAibEREQAEKNEQILEQV-NH2 | $-\{AEEA\}_2$-gGlu-C(O)$(CH_2)_{16}$COOH |
| 162 | Ac-IVLSLDvPIELK*QILLEQERQKAibQREQAEKNKQILEQV-NH2 | $-\{AEEA\}_2$-gGlu-C(O)$(CH_2)_{16}$COOH |
| 163 | Ac-IVLSLDvPIHLK*QILLEQERQKAibQREQAEKNKQILEQV-NH2 | $-\{AEEA\}_2$-gGlu-C(O)$(CH_2)_{16}$COOH |
| 164 | Ac-IVLSLDvPIGLK*QILLEQERQKAibQREQAEKNKQILEQV-NH2 | $-\{AEEA\}_2$-gGlu-C(O)$(CH_2)_{16}$COOH |
| 165 | Ac-IVLSLDvPIKLK*QILLEQARQKAibQREQAEKNEQILEQV-NH2 | $-\{AEEA\}_2$-gGlu-C(O)$(CH_2)_{16}$COOH |
| 166 | Ac-IVLSLDvPIKLK*QILLEQERQKAibQREQAEKNEQILEQV-NH2 | $-\{AEEA\}_2$-gGlu-C(O)$(CH_2)_{16}$COOH |
| 167 | Ac-IVLSLDvPIGLK*QILLEQERQKAibQREQAEKNEQILEQV-NH2 | $-\{AEEA\}_2$-gGlu-C(O)$(CH_2)_{16}$COOH |
| 168 | Ac-IVLSLDvPIELK*QILLEQERQKAibQREQAEKNEQILEQV-NH2 | $-\{AEEA\}_2$-gGlu-C(O)$(CH_2)_{16}$COOH |
| 169 | Ac-IVLSLDvPIKLK*QILLEQERQEAibQREQAEKNEQILEQV-NH2 | $-\{AEEA\}_2$-gGlu-C(O)$(CH_2)_{16}$COOH |
| 170 | Ac-IVLSLDvPIELK*QILLEQERQEAibQREQAEKNEQILEQV-NH2 | $-\{AEEA\}_2$-gGlu-C(O)$(CH_2)_{16}$COOH |
| 171 | IVLSLDvPIKLK*QILLKQERQKAibQREQAEKNKQILAQV-NH2 | $-\{AEEA\}_2-\{gGlu\}_2$-C(O)$(CH_2)_{16}$COOH |
| 172 | IVLSLDvPIKLK*QILLKQERQKAibQREQAEKNKQILAQV-NH2 | $-\{AEEA\}_2-\{gGlu\}_2$-C(O)$(CH_2)_{18}$COOH |
| 173 | IVLSLDvPIKLK*QILLKQERQKAibQREQAEKNKQILAQV-NH2 | $-\{AEEA\}_2$-gGlu-C(O)$(CH_2)_{18}$COOH |
| 174 | IVLSLDvPIKLK*QILLKQARQKAibQRAQAEKNKRILERV-NH2 | $-\{AEEA\}_2-\{gGlu\}_2$-C(O)$(CH_2)_{16}$COOH |
| 175 | IVLSLDvPIKLK*QILLKQARQKAibQRAQAEKNKRILERV-NH2 | $-\{AEEA\}_2$-gGlu-C(O)$(CH_2)_{18}$COOH |
| 176 | IVLSLDvPIKLK*QILLKQERQKKQRQQAEKNKQILAQV-NH2 | $-\{AEEA\}_2-\{gGlu\}_2$-C(O)$(CH_2)_{16}$COOH |
| 177 | IVLSLDvPIKLK*QILLKQERQKKQRQQAEKNKQILAQV-NH2 | $-\{AEEA\}_2-\{gGlu\}_2$-C(O)$(CH_2)_{18}$COOH |
| 178 | IVLSLDvPIKLK*QILLKQERQKKQRQQAEKNKQILAQV-NH2 | $-\{AEEA\}_2$-gGlu-C(O)(CH2)$_{18}$COOH |
| 179 | IVLSLDvPIKLK*QILLKQERQKAibQREQAEKNKQILAQV-NH2 | -gGlu-C(O)$(CH_2)_{16}$COOH |
| 180 | IVLSLDvPIKLK*QILLKQARQKAibQRAQAEKNKRILERV-NH2 | -gGlu-C(O)$(CH_2)_{16}$COOH |
| 181 | IVLSLDvPIKLK*QILLKQERQKKQRQQAEKNKQILAQV-NH2 | -gGlu-C(O)$(CH_2)_{16}$COOH |
| 182 | IVLSLDvPIKLK*QILLKQERQKAibQREQAEKNKQILAQV-NH2 | -C(O)$(CH_2)_{16}$COOH |
| 183 | IVLSLDvPIKLK*QILLKQARQKAibQRAQAEKNKRILERV-NH2 | -C(O)$(CH_2)_{16}$COOH |
| 184 | IVLSLDvPIKLK*QILLKQERQKKQRQQAEKNKQILAQV-NH2 | -C(O)$(CH_2)_{16}$COOH |
| 185 | IVLSLDVPIKLK*QILLKQERQKKAibRQKAETNKQILAQV-NH2 | $-\{AEEA\}_2$-gGlu-C(O)$(CH_2)_{16}$COOH |
| 223 | IVLSLDvPTKLK*QKLLKQERQRKEREQAEKNKRILERV-NH2 | -gGlu-C(O)$(CH_2)_{14}CH_3$ |
| 224 | IVLSLDvPTKLK*KKLLKQERKRAibEREKAEKAARILERV-NH2 | $-\{AEEA\}_2$-gGlu-C(O)$(CH_2)_{18}$COOH |
| 225 | IVLSLDvPTKLK*QKLLKQERQRKEREAibAEKNKRILERV-NH2 | -gGlu-C(O)$(CH_2)_{14}CH_3$ |
| 226 | IVLSLDvPIGLK*QKLLKQQRQRKERQQAEKNKRILERV-NH2 | -gGlu-C(O)$(CH_2)_{14}CH_3$ |
| 227 | IVLSLDvPIKLK*QKLLKQQRQRKERQQAEKNKRILERV-NH2 | -gGlu-C(O)$(CH_2)_{14}CH_3$ |

In an embodiment, the compound is a peptide of the following amino acid sequence (SEQ ID NO: 7):

IVLSLDvPTKLK*QKLLKQERQRKEREQAEKNARILARV-NH2 wherein the K residue at position 12 (denoted as K*) is chemically modified such that the epsilon-amino group of its side chain is covalently bound to -gGlu-C(O)$(CH_2)_{14}$COOH; and —$NH_2$ denotes that the C-terminal amino acid residue is amidated as a primary amide;

or a pharmaceutically acceptable salt thereof.

In an embodiment, the compound is a peptide of the following amino acid sequence (SEQ ID NO: 32):

IVLSLDvPTKLK*QKLLKQERQRKEREQAEKNVRILERV-NH2 wherein the K residue at position 12 (denoted as K*) is chemically modified such that the epsilon-amino group of its side chain is covalently bound to -gGlu-C(O)$(CH_2)_{14}$COOH; and —$NH_2$ denotes that the C-terminal amino acid residue is amidated as a primary amide;

or a pharmaceutically acceptable salt thereof.

In an embodiment, the compound is a peptide of the following amino acid sequence (SEQ ID NO: 35):

IVLSLDVPIKLK*KILLEQEKQKKQREQAETNKQILAQV-NH2 wherein the K residue at position 12 (denoted as K*) is chemically modified such that the epsilon-amino group of its side chain is covalently bound to -{AEEA}$_2$-gGlu-C(O)$(CH_2)_{16}$COOH; and —$NH_2$ denotes that the C-terminal amino acid residue is amidated as a primary amide;

or a pharmaceutically acceptable salt thereof.

In an embodiment, the compound is a peptide of the following amino acid sequence (SEQ ID NO: 83):

IVLSLDvPIGLK*QILLKQERQKKAibREQAETNKRILERV-NH2 wherein the K residue at position 12 (denoted as K*) is chemically modified such that the epsilon-amino group of its side chain is covalently bound to an albumin-binding moiety selected from -gGlu-C(O)$(CH_2)_{14}$COOH; and -gGlu-C(O)$(CH_2)_{14}CH_3$, and —$NH_2$ denotes that the C-terminal amino acid residue is amidated as a primary amide;

or a pharmaceutically acceptable salt thereof.

In an embodiment, the compound is a peptide of the following amino acid sequence (SEQ ID NO: 130):

IVLSLDvPIKLK*QILLKQERQKAibQREQAEKNKQILAQV-NH2 wherein the K residue at position 12 (denoted as K*) is chemically modified such that the epsilon-amino group of its side chain is covalently bound to an albumin-binding moiety selected from -{AEEA}$_2$-gGlu-C(O)$(CH_2)_{16}$COOH; -gGlu-C(O)$(CH_2)_{14}$COOH; -{AEEA}$_2$-gGlu-C(O)$(CH_2)_{14}$COOH; -{AEEA}$_2$-{gGlu}$_2$-C(O)$(CH_2)_{14}$COOH; -gGlu-C(O)$(CH_2)_{14}CH_3$; -{AEEA}$_2$-gGlu-C(O)$(CH_2)_{14}CH_3$; and -{AEEA}$_2$-{gGlu}$_2$-C(O)$(CH_2)_{14}CH_3$; in particular-{AEEA}$_2$-gGlu-C(O)$(CH_2)_{16}$COOH; and —$NH_2$ denotes that the C-terminal amino acid residue is amidated as a primary amide;

or a pharmaceutically acceptable salt thereof.

In an embodiment, the compound is a peptide of the following amino acid sequence (SEQ ID NO: 135):

IVLSLDvPIKLK*QILLKQERQKAibQRQQAEKNKQILAQV-NH2 wherein the K residue at position 12 (denoted as K*) is chemically modified such that the epsilon-amino group of its side chain is covalently bound to an albumin-binding moiety selected from -{AEEA}$_2$-gGlu-C(O)$(CH_2)_{16}$COOH; and -gGlu-C(O)$(CH_2)_{14}$COOH; in particular-{AEEA}$_2$-gGlu-C(O)$(CH_2)_{16}$COOH; and —$NH_2$ denotes that the C-terminal amino acid residue is amidated as a primary amide;

or a pharmaceutically acceptable salt thereof.

In an embodiment, the compound is a peptide of the following amino acid sequence (SEQ ID NO: 136):

IVLSLDvPIKLK*QILLKQERQKKAibRQKAEKNKQILAQV-NH2 wherein the K residue at position 12 (denoted as K*) is chemically modified such that the epsilon-amino group of its side chain is covalently bound to an albumin-binding moiety selected from -gGlu-C(O)$(CH_2)_{14}$COOH; -{AEEA}$_2$-gGlu-C(O)$(CH_2)_{14}$COOH; -{AEEA}$_2$-{gGlu}$_2$-C(O)$(CH_2)_{14}$COOH; -gGlu-C(O)$(CH_2)_{14}CH_3$; -{AEEA}$_2$-gGlu-C(O)$(CH_2)_{14}CH_3$; and -{AEEA}$_2$-{gGlu}$_2$-C(O)$(CH_2)_{14}CH_3$; and —$NH_2$ denotes that the C-terminal amino acid residue is amidated as a primary amide;

or a pharmaceutically acceptable salt thereof.

In an embodiment, the compound is a peptide of the following amino acid sequence (SEQ ID NO: 137):

IVLSLDvPIKLK*QILLKQERQKKQREQAEKNKQILEQV-NH2 wherein the K residue at position 12 (denoted as K*) is chemically modified such that the epsilon-amino group of its side chain is covalently bound to an albumin-binding moiety selected from -gGlu-C(O)$(CH_2)_{14}$COOH; -gGlu-C(O)$(CH_2)_{14}CH_3$; and -{AEEA}$_2$-gGlu-C(O)$(CH_2)_{16}$COOH; in particular-{AEEA}$_2$-gGlu-C(O)$(CH_2)_{16}$COOH; and —$NH_2$ denotes that the C-terminal amino acid residue is amidated as a primary amide;

or a pharmaceutically acceptable salt thereof.

In an embodiment, the compound is a peptide of the following amino acid sequence (SEQ ID NO: 138):

IVLSLDvPIKLK*QILLKQERQKKQREQAEKNKQILEQV-NH2 wherein the K residue at position 12 (denoted as K*) is chemically modified such that the epsilon-amino group of its side chain is covalently bound to an albumin-binding moiety selected from -gGlu-C(O)$(CH_2)_{14}$COOH; and -gGlu-C(O)$(CH_2)_{14}CH_3$; and —$NH_2$ denotes that the C-terminal amino acid residue is amidated as a primary amide;

or a pharmaceutically acceptable salt thereof.

In an embodiment, the compound is a peptide of the following amino acid sequence (SEQ ID NO: 139):

IVLSLDvPIKLK*QILLKQERQKKQRQQAEKNKQILAQV-NH2 wherein the K residue at position 12 (denoted as K*) is chemically modified such that the epsilon-amino group of its side chain is covalently bound to an albumin-binding moiety selected from -gGlu-C(O)$(CH_2)_{14}$COOH; and -gGlu-C(O)$(CH_2)_{14}CH_3$; and —$NH_2$ denotes that the C-terminal amino acid residue is amidated as a primary amide;

or a pharmaceutically acceptable salt thereof.

In an embodiment, the compound is a peptide of the following amino acid sequence (SEQ ID NO: 140):

IVLSLDvPIKLK*QILLEQARQKAibQRAQAEKNKRILERV-NH2 wherein the K residue at position 12 (denoted as K*) is chemically modified such that the epsilon-amino group of its side chain is covalently bound to -{AEEA}$_2$-gGlu-C(O)$(CH_2)_{16}$COOH; and —$NH_2$ denotes that the C-terminal amino acid residue is amidated as a primary amide;

or a pharmaceutically acceptable salt thereof.

In an embodiment, the compound is a peptide of the following amino acid sequence (SEQ ID NO: 141):

IVLSLDvPIKLK*QILLKQARQKAibQRAQAEKNKRILERV-NH2 wherein the K residue at position 12 (denoted as K*) is chemically modified such that the epsilon-amino group of its side chain is covalently bound to -{AEEA}$_2$-gGlu-C(O)$(CH_2)_{16}$COOH; and —$NH_2$ denotes that the C-terminal amino acid residue is amidated as a primary amide;

or a pharmaceutically acceptable salt thereof.

In an embodiment, the compound is a peptide of the following amino acid sequence (SEQ ID NO: 142):

IVLSLDvPIKLK*QILLEQARQKAibQREQAEKNKRILERV-NH2 wherein the K residue at position 12 (denoted as K*) is chemically modified such that the epsilon-amino group of its side chain is covalently bound to -{AEEA}$_2$-gGlu-C(O)$(CH_2)_{16}$COOH; and —$NH_2$ denotes that the C-terminal amino acid residue is amidated as a primary amide;

or a pharmaceutically acceptable salt thereof.

In an embodiment, the compound is a peptide of the following amino acid sequence (SEQ ID NO: 147):

IVLSLDvPIGLK*QILLKQERQKKAibREQAETNKQILAQV-NH2 wherein the K residue at position 12 (denoted as K*) is chemically modified such that the epsilon-amino group of its side chain is covalently bound to an albumin-binding moiety selected from -gGlu-C(O)$(CH_2)_{14}$COOH; -{AEEA}$_2$-gGlu-C(O)$(CH_2)_{14}$COOH; -{AEEA}$_2$-{gGlu}$_2$-C(O)$(CH_2)_{14}$COOH; -gGlu-C(O)$(CH_2)_{14}CH_3$; -{AEEA}$_2$-gGlu-C(O)$(CH_2)_{14}CH_3$; and -{AEEA}$_2$-{gGlu}$_2$-C(O)$(CH_2)_{14}CH_3$ and —$NH_2$ denotes that the C-terminal amino acid residue is amidated as a primary amide; or a pharmaceutically acceptable salt thereof.

In an embodiment, the compound is a peptide of the following amino acid sequence (SEQ ID NO: 149):

IVLSLDvPIKLK*QILLKQERQKKAibREQAETNKRILERV-NH2 wherein the K residue at position 12 (denoted as K*) is chemically modified such that the epsilon-amino group of its side chain is covalently bound to -{AEEA}$_2$-gGlu-C(O)$(CH_2)_{16}$COOH; and —$NH_2$ denotes that the C-terminal amino acid residue is amidated as a primary amide;

or a pharmaceutically acceptable salt thereof.

In an embodiment, the compound is a peptide of the following amino acid sequence (SEQ ID NO: 150):

IVLSLDvPIGLK*QILLKQERQKKAibRQQAETNKRILERV-NH2 wherein the K residue at position 12 (denoted as K*) is chemically modified such that the epsilon-amino group of its side chain is covalently bound to an albumin-binding moiety selected from -gGlu-C(O)$(CH_2)_{14}$COOH; and -gGlu-C(O)$(CH_2)_{14}CH_3$; and —$NH_2$ denotes that the C-terminal amino acid residue is amidated as a primary amide;

or a pharmaceutically acceptable salt thereof.

In an embodiment, the compound is a peptide of the following amino acid sequence (SEQ ID NO: 151):

IVLSLDvPIGLK*QILLKQERQKKAibREQAEKNKRILERV-NH2 wherein the K residue at position 12 (denoted as K*) is chemically modified such that the epsilon-amino group of its side chain is covalently bound to an albumin-binding moiety selected from gGlu-C(O)$(CH_2)_{14}$COOH; -gGlu-C(O)$(CH_2)_{14}CH_3$ and -{AEEA}$_2$-gGlu-C(O)$(CH_2)_{16}$COOH; in particular-{AEEA}$_2$-gGlu-C(O)$(CH_2)_{16}$COOH; and —$NH_2$ denotes that the C-terminal amino acid residue is amidated as a primary amide;

or a pharmaceutically acceptable salt thereof.

In an embodiment, the compound is a peptide of the following amino acid sequence (SEQ ID NO: 152):

IVLSLDVPIKLK*QILLKQERQKKAibREQAETNKRILERV-NH2 wherein the K residue at position 12 (denoted as K*) is chemically modified such that the epsilon-amino group of its side chain is covalently bound to -{AEEA}$_2$-gGlu-C(O)$(CH_2)_{16}$COOH; and —$NH_2$ denotes that the C-terminal amino acid residue is amidated as a primary amide;

or a pharmaceutically acceptable salt thereof.

In an embodiment, the compound is a peptide of the following amino acid sequence (SEQ ID NO: 174):

```
IVLSLDvPIKLK*QILLKQARQKAibQRAQAEKNKRILERV-NH2
```

wherein the K residue at position 12 (denoted as K*) is chemically modified such that the epsilon-amino group of its side chain is covalently bound an albumin-binding moiety selected from -gGlu-C(O)$(CH_2)_{14}$COOH; and -gGlu-C(O)$(CH_2)_{14}CH_3$; and —$NH_2$ denotes that the C-terminal amino acid residue is amidated as a primary amide;

or a pharmaceutically acceptable salt thereof.

The compounds of the disclosure may be prepared and utilised in the form of pharmaceutically acceptable salts. Pharmaceutically acceptable salts and methods for their preparation are well known in the art (see, e.g., Stahl, et al. "Handbook of Pharmaceutical Salts: Properties, Selection and Use", Second Revised Edition, Wiley-VCH, 2011; and Berge, et al., "Pharmaceutical Salts," Journal of Pharmaceutical Sciences, 1977, 66, 1). Examples of pharmaceutically acceptable salts include trifluoroacetate salts, acetate salts and hydrochloride salts.

Compound Synthesis

A variety of methods can be used to prepare the compounds of the disclosure. The compounds may be prepared by synthesis in solution or on a solid support, with subsequent isolation and purification. Alternatively, the peptides can be prepared by gene expression in a host cell in which a DNA sequence encoding the peptide has been introduced. Gene expression can also be achieved without utilising a cell system. Combinations of methods may also be used.

In particular, the compounds may be prepared by solid phase synthesis on a suitable resin. Solid phase peptide synthesis is a well-established methodology (see, e.g., Stewart and Young, "Solid Phase Peptide Synthesis", Pierce Chemical Co., Rockford, Ill., 1984; and Atherton and Sheppard, "Solid Phase Peptide Synthesis: A Practical Approach", Oxford-IRL Press, New York, 1989).

Standard manual or automated solid phase synthesis procedures can be used to prepare the compounds. Automated peptide synthesisers are commercially available from, e.g., Applied Biosystems (Foster City, CA) and Protein Technologies Inc. (Tucson, AZ). Reagents for solid phase synthesis are readily available from commercial sources. Solid phase synthesisers can be used according to the manufacturer's instructions for blocking interfering groups, protecting amino acids during reaction, coupling, deprotecting, and capping of unreacted amino acids.

Solid phase synthesis may be initiated by attaching an N-terminally protected amino acid with its carboxy terminus to an inert solid support carrying a cleavable linker. The solid support can be any polymer that allows coupling of the initial amino acid, e.g. a trityl resin, a chlorotrityl resin, a Wang resin or a Rink resin in which the linkage of the carboxy group (or carboxamide group for a Rink resin) to the resin is sensitive to acid (when a Fmoc strategy is used). The support must be one which is stable under the conditions used to deprotect the α-amino group during the peptide synthesis.

After the N-terminally protected first amino acid has been coupled to the solid support, the α-amino protecting group of this amino acid is removed using a reagent such as trifluoroacetic acid (TFA) or piperidine, for example. The remaining protected amino acids are then coupled one after the other or added as a preformed dipeptide, tripeptide or tetrapeptide in the order represented by the peptide sequence using appropriate amide coupling reagents. Examples of coupling reagents include benzotriazol-1-yloxytris(dimethylamino)phosphonium hexafluorophosphate (BOP), hexafluorophosphate benzotriazole tetramethyl uronium (HBTU), hexafluorophosphate azabenzotriazole tetramethyl uronium (HATU), diisopropyl-carbodiimide (DIC), 1-hydroxybenzotriazole (HOBt) and 1-hydroxy-7-azabenzotriazole, and combinations thereof. Typically, couplings are performed at room temperature in an inert solvent such as dimethylformamide (DMF), N-methylpyrrolidone (NMP) or dichloromethane (DCM).

Usually, reactive side chain groups of the amino acids are protected with suitable blocking groups. These protecting groups are removed after the desired peptides have been assembled and they may be removed concomitantly with cleavage of the desired product from the resin under the same conditions. Protecting groups and procedures for their introduction are well known in the art (see, e.g., Greene and Wuts, "Protective Groups in Organic Synthesis", 3rd ed., 1999, Wiley & Sons). Examples of protecting groups include tert-butyloxycarbonyl (tBoc) and fluorenylmethoxycarbonyl (Fmoc).

The albumin-binding moiety may be introduced by selectively functionalising the lysine (K) residue at the position denoted by X12. Thus, the lysine residue may comprise a side chain protecting group which can be selectively removed while other side chain protecting groups remain intact, such that the deprotected lysine residue can be selectively functionalised by the albumin-binding moiety. Conjugation of the albumin-binding moiety to the epsilon-amino group of the lysine side chain may be achieved through an acylation reaction or other suitable reactions known in the art.

By way of illustration, the lysine residue may be protected with a 1-(4,4-dimethyl-2,6-dioxocyclohex-1-ylidene)-3-methylbutyl ("ivDde") protecting group, which is labile to highly nucleophilic bases such as 4% hydrazine in DMF (see Chhabra et al., Tetrahedron Lett. 1998, 39, 1603). Thus, if the N-terminal amino group and all side chain functionalities are protected with acid labile protecting groups, the ivDde group can be selectively removed using a highly nucleophilic base. The resulting free amino group can then be conjugated to the albumin-binding moiety, for example by acylation. Alternatively, the lysine residue may be protected with a (4-methoxyphenyl) diphenylmethyl ("Mmt") protecting group, which is labile to very mild acids such as acetic acid and trifluoroethanol in dichloromethane (see Dubowchik et al., Tetrahedron Lett., 1997, 38 (30), 5257). Thus, if the N-terminal amino group and all side chain functionalities are protected with protecting groups only labile to strong acids, the Mmt group can be selectively removed using, e.g., a mixture of acetic acid and trifluoroethanol in dichloromethane (e.g., in a 1:2:7 ratio). The resulting free amino group can then be conjugated to the albumin-binding moiety, for example by acylation.

Alternatively, the albumin binding moiety can be introduced together with the lysine during peptide synthesis by using a prefunctionalized building block as a coupling partner. Examples of such prefunctionalized building blocks include Fmoc-L-Lys (Palm-L-Glu-OtBu)-OH and Fmoc-L-Lys [$\{AEEA\}_2$-gGlu(OtBu)-C(O)$(CH_2)_{16}$—C(O)OtBu]-OH.

If desired, the N-terminus of the peptide chain can be modified, for example by acetylation. For the synthesis of C-terminal amide peptides, resins incorporating Rink amide 4-methylbenzhydrylamine (MBHA) or Rink amide AM linkers are typically used with Fmoc synthesis, while MBHA resin is generally used with tBoc synthesis.

After completion of synthesis, peptides are cleaved from the solid-phase support with simultaneous side-chain deprotection using standard treatment methods. This can be achieved by using King's cocktail (King et al., Int. J. Peptide Protein Res., 1990, 36, 255-266) or similar cleavage cocktails known in the art.

The raw material can be purified by chromatography (e.g., by preparative RP-HPLC) if necessary. Crude peptides typically are purified using RP-HPLC on C8 or C18 columns using water-acetonitrile gradients in 0.05 to 0.1% trifluoroacetic acid (TFA). The purity of the peptides can be verified by analytical RP-HPLC. The identity of the peptides can be verified by mass spectrometry. The compounds may be isolated in solid form (e.g., as dry powders) using techniques such as lyophilization.

The present disclosure also relates to intermediate compounds for use in synthesising the present compounds. In particular, there is provided a compound which is a peptide comprising the amino acid sequence of formula (I) disclosed herein, in which residues X1 to X11 and X13 to X38 have the meanings recited in connection with formula (I) and X12 is lysine (K); or a salt thereof. Said compound may be used as an intermediate in the preparation of the compounds of the disclosure, which can be obtained by conjugating the albumin-binding moiety to the epsilon-amino group of the lysine side chain at X12. Addition of the albumin-binding moiety may be performed while the peptide is still attached to the solid phase. After adding the albumin-binding moiety, the peptide may be released from the resin and purified.

Particular processes for preparing the compounds of the disclosure are described in the examples below. The specific synthetic steps for each of the routes described may be combined in different ways to prepare the compounds. The reagents and starting materials are readily available or can be prepared by methods known in the art.

Pharmaceutical Compositions

Also disclosed herein are pharmaceutical compositions comprising a compound of the disclosure and a pharmaceutically acceptable carrier or excipient.

A pharmaceutical composition may contain from about 0.1% to about 99.9% by weight of a compound of the disclosure and from about 99.9% to about 0.1% by weight of one or more pharmaceutically acceptable carriers, excipients or diluents. In one example, a pharmaceutical composition comprises from about 5% and about 75% by weight of the compound of the disclosure, with the rest being suitable pharmaceutical carriers, diluents or excipients. Methods of preparing pharmaceutical compositions are known, or will be apparent, to those skilled in this art, e.g., from literature such as Remington: The Science and Practice of Pharmacy, 22$^{nd}$ Edition, Pharmaceutical Press.

In an embodiment, the pharmaceutical composition further comprises one or more additional therapeutic agents.

The pharmaceutical composition may be suitable for administration by a parenteral route, e.g., oral, subcutaneous, intravenous, intraperitoneal, intramuscular, pulmonary or transdermal administration. In particular, the pharmaceutical composition may be suitable for subcutaneous administration. In an embodiment, the pharmaceutical composition is a ready-to-use composition suitable for administration by a pen or autoinjector device.

The compounds may exhibit desirable solubility, chemical stability and/or physical stability, especially in solvents at physiological pH values and solvents containing antimicrobial preservatives such as phenol or meta-cresol. As a consequence, the compounds may be particularly suitable for use in pharmaceutical compositions in solution form.

In a particular embodiment, the pharmaceutical composition is a solution comprising a solvent and, dissolved therein, a compound of the disclosure and an antimicrobial preservative selected from phenol and meta-cresol; wherein the compound of the disclosure is present in an amount of at least 1 mg/ml, at least 5 mg/ml, at least 10 mg/ml or at least 20 mg/ml; and wherein the solution has a pH of from pH 6 to 8 (e.g., pH 7.0 or pH 7.4) measured at 25° C.

Use in Therapy

The compounds of the disclosure are useful in therapy and may be used to treat or prevent a variety of diseases. Thus, in other aspects, the disclosure is directed to the use of the compounds in therapy and to therapeutic methods in which an effective amount of a compound of the disclosure is administered to a patient. The disclosure is also directed to the use of the compounds for the manufacture of medicaments for use in therapy. The compounds are especially useful in the therapy of diseases which can be treated or prevented by agonism of the CRF2 receptor.

The term "therapy" as used herein refers to the treatment or prevention of a disease in a patient.

The term "treat" or "treating" as used herein includes prohibiting, restraining, slowing, stopping, or reversing the progression or severity of an existing disease in a patient. Treatment may eliminate a disease; arrest or slow a disease in a patient; inhibit or slow the development of a new disease in a patient; decrease the frequency or severity of symptoms and/or recurrences in a patient who currently has or who previously has had a disease; and/or prolong, i.e., increase, the lifespan of the patient. In particular, treatment of a disease may result in curing, shortening the duration, ameliorating, slowing down or inhibiting progression or worsening of a disease or the symptoms thereof.

The term "prevent" or "preventing" as used herein refers to inhibiting or delaying the onset of a disease or disease in a patient.

The term "disease" as used herein refers to any condition or disorder that damages or interferes with the normal function of a cell, tissue or organ.

The term "patient" as used herein refers to a mammal, such as a human, mouse, guinea pig, rat, dog or cat. In a particular embodiment, the patient is a human patient.

The term "effective amount" as used herein refers to the amount or dose of compound of the disclosure which, upon single or multiple dose administration to the patient, provides the desired effect in the patient. An effective amount can be readily determined by the attending diagnostician by the use of known techniques and by observing results obtained under analogous circumstances. In determining the effective amount for a patient, a number of factors are considered by the attending diagnostician, including, but not limited to: the species of mammal; its size, age, and general health; the specific disease or disease involved; the degree of or involvement or the severity of the disease or disease; the response of the individual patient; the particular compound administered; the mode of administration; the bioavailability characteristics of the preparation administered; the dose regimen selected; the use of concomitant medication; and other relevant circumstances.

The compounds of the disclosure may be effective over a wide dosage range. For example, dosages per day may fall within the range of about 0.01 to about 50 mg/kg of body weight.

It has been observed that the compounds of the disclosure have excellent stability in the different environments tested. Consequently, the compounds of the disclosure are particularly suitable, in embodiments, wherein the compounds are administered by once daily administration, once weekly, bi-monthly or monthly administration. This is in particular the case for the compounds of the disclosure with a D-Valine at 7, Lysine derivatized with a fatty acid as herein provided for half-life extension at position 12, with an excellent potency on CRF2 and fair selectivity profile over CRF1.

The compounds may be administered in combination with one or more additional therapeutic agents. The term "in combination with" as used herein means administration of the compound of the disclosure either simultaneously, sequentially or in a single combined formulation with the one or more additional therapeutic agents.

The compounds of the disclosure may be administered by a parenteral route, e.g., by inhalation, subcutaneous, intravenous, intraperitoneal, intramuscular, pulmonary or transdermal administration.

In a particular embodiment, the compounds are administered by subcutaneous administration. The compounds may be administered by a physician or self-administered using an injection device. It is understood the gauge size and amount of injection volume is determined by the skilled practitioner. In one embodiment, the amount of injection volume is less than or equal to 2 ml, e.g., less than or equal to 1 ml. In another embodiment, a needle gauge of greater than or equal to 27, e.g., greater than or equal to 29, is used. Administration may be accomplished using an autoinjector or multidose delivery device.

The compounds of the disclosure may be useful in the therapy of diseases which can be treated or prevented by agonism of the CRF2 receptor.

The compounds are particularly useful in the treatment or prevention of sarcopenia, pulmonary hypertension, muscular dystrophy, kidney disease, Peripheral Artery Disease (PAD), cardiovascular diseases including especially heart failure, obesity and diabetes. Thus, embodiments of the disclosure relate to the use of the compounds in the treatment or prevention of sarcopenia, pulmonary hypertension, muscular dystrophy, kidney disease, Peripheral Artery Disease (PAD), cardiovascular disease including especially heart failure, obesity or diabetes in a patient. The disclosure also relates to methods of treating or preventing sarcopenia, pulmonary hypertension, muscular dystrophy, kidney disease Peripheral Artery Disease (PAD), cardiovascular disease including especially heart failure, obesity or diabetes in a patient which comprises administering an effective amount of a compound of the disclosure to the patient. In addition, the disclosure relates to the use of the compounds in the manufacture of a medicament for the treatment or prevention of a cardiovascular disease including especially heart failure, obesity or diabetes in a patient.

Examples of cardiovascular diseases which may be treated or prevented using the present compounds include heart failure, hypertension, dyslipidemia, atherosclerosis, arteriosclerosis, coronary heart disease and stroke. The effect of the compounds in these conditions may be as a result of or associated with their effect on body weight or may be independent thereof. In a particular embodiment, the compounds are used to treat or prevent heart failure. The compound may be administered in combination with one or more additional therapeutic agents useful in the treatment of heart failure, such as angiotensin converting enzyme inhibitor (ACEi), angiotensin II receptor blockers (ARBs), diuretics, sodium glucose co-transporters inhibitors (SGLTi), beta-blockers, mineralocorticoid antagonists or neprilysin inhibitor.

The compounds may also be useful in the treatment or prevention of obesity and other diseases caused or characterised by excess body weight, such as obesity-linked inflammation, obesity-linked gallbladder disease and obesity-induced sleep apnoea. In terms of a human adult patient, obesity can be defined as a body mass index (BMI) greater than or equal to 30 $kg/m^2$. The BMI is a simple index of weight-for-height that is commonly used to classify overweight and obesity in adults. It is defined as a person's weight in kilograms divided by the square of his/her height in meters and hence is expressed in units of $kg/m^2$. The compound may be administered in combination with one or more additional therapeutic agents useful in the treatment of obesity. Alternatively or additionally, the treatment may be combined with diet and exercise.

The compounds may also be used in the treatment or prevention of diabetes, especially type II diabetes. The compounds may be administered alone or in combination with one or more additional therapeutic agents useful in the treatment of diabetes, for example one or more agents selected from metformin, thiazolidinediones (TZDs), sulfonylureas (SUs), dipeptidyl peptidase-IV (DPP-IV) inhibitors, glucagon-like peptide-1 (GLP1) agonists, and sodium glucose co-transporters (SGLTs). Alternatively or additionally, treatment may be combined with diet and exercise. The compounds may also be used to treat or prevent hyperglycemia, type I diabetes and impaired glucose tolerance. The compounds may also be useful in the treatment or prevention of diabetes.

The compounds may also be useful in the treatment or prevention of other diseases such as sarcopenia, pulmonary hypertension, kidney disease, Peripheral Artery Disease (PAD), metabolic syndrome, chronic kidney disease, degenerative diseases (e.g., neurodegenerative diseases) or diseases accompanied by nausea or vomiting.

The present invention is further illustrated by the following examples, which are provided for illustrative purposes only. The examples are not to be construed as limiting the scope or content of the disclosure in any way.

EXAMPLES

Abbreviations

Certain abbreviations are used in the examples and elsewhere herein:

"AA" refers to amino acid;

"AEEA" refers to [2-(2-aminoethoxy) ethoxy]acetyl;

"Aib" refers to 2-amino-isobutyric acid;

"AUC" refers to area under the curve;

"CAMP" refers to cyclic adenosine monophosphate;

"Boc" refers to tert-butyloxycarbonyl;

"BOP" refers to (benzotriazol-1-yloxy)tris(dimethylamino)phosphonium hexafluorophosphate;

"BSA" refers to bovine serum albumin;

"tBu" refers to tertiary butyl;

"DCM" refers to dichloromethane;

"Dde" refers to 1-(4,4-dimethyl-2,6-dioxocyclohexylidene)-ethyl;

"IvDde" refers to 1-(4,4-dimethyl-2,6-dioxocyclohexylidene)-3-methyl-butyl;

"DIC" refers to N,N'-diisopropylcarbodiimide;
"DIPEA" refers to N,N-diisopropylethylamine;
"DMEM" refers to Dulbecco's modified Eagle's medium;
"DMF" refers to dimethyl formamide;
"DMSO" refers to dimethyl sulfoxide;
"EDT" refers to ethane dithiol;
"FA" refers to formic acid;
"FBS" refers to fetal bovine serum;
"Fmoc" refers to fluorenylmethyloxycarbonyl;
"gGlu" refers to gamma-glutamate (yE);
"HATU" refers to O-(7-azabenzotriazol-1-yl)-N,N,N',N'-tetramethyluronium hexafluorophosphate;
"HBSS" refers to Hanks' Balanced Salt Solution;
"HBTU" refers to 2-(1H-benzotriazol-1-yl)-1,1,3,3-tetramethyluronium hexafluorophosphate;
"HEPES" refers to 2-[4-(2-hydroxyethyl) piperazin-1-yl] ethanesulfonic acid;
"HOAt" refers to 1-hydroxy-7-azabenzotriazole;
"HOBt" refers to 1-hydroxybenzotriazole;
"HOSu" refers to N-hydroxysuccinimide;
"HPLC" refers to High Performance Liquid Chromatography;
"hr" refers to hour;
"HTRF" refers to Homogenous Time Resolved Fluorescence;
"IBMX" refers to 3-isobutyl-1-methylxanthine;
"i.v." refers to intravenous;
"kDa" refers to kilodaltons;
"LC/MS" refers to Liquid Chromatography/Mass Spectrometry;
"Mmt" refers to monomethoxy-trityl;
"MS" refers to mass spectrometry;
"OtBu" refers to O-tert-butyl;
"Palm" refers to palmitoyl;
"Pbf" refers to 2,2,4,6,7-pentamethyldihydrobenzofuran-5-sulfonyl;
"PBS" refers to phosphate buffered saline;
"PK" refers to pharmacokinetic;
"RP-HPLC" refers to reversed-phase high performance liquid chromatography;
"s.c." refers to subcutaneous;
"SEM" refers to standard error of the mean;
"Stea" refers to stearyl;
"TIPS" refers to triisopropylsilane;
"TFA" refers to trifluoroacetic acid;
"Trt" refers to trityl; and
"UV" refers to ultraviolet.

Materials and Methods

The following starting materials and methods were employed in the synthetic procedures described in the examples.

Rink-Amide resins (e.g., 4-(2',4'-dimethoxyphenyl-Fmoc-aminomethyl)-phenoxy acetamido-norleucylaminomethyl resin, Merck Biosciences; 4-[(2,4-dimethoxyphenyl) (Fmoc-amino)methyl]phenoxy acetamido methyl resin, Agilent Technologies) were used for the synthesis of peptide amides with loadings in the range of 0.2-0.7 mmol/g. Alternatively, preloaded Wang resins (e.g. ((S)-(9H-fluoren-9-yl)methyl(1-(tert-butoxy)-3-oxopropan-2-yl)carbamate resin, Fmoc-Ser(tBu)-Wang resin, Bachem) were used for the synthesis of peptide acids with loadings in the range of 0.2-0.7 mmol/g.

Fmoc-protected natural amino acids were purchased from Protein Technologies Inc., Senn Chemicals, Merck Biosciences, Novabiochem, Iris Biotech, Bachem, Chem-Impex International or MATRIX Innovation. The following standard amino acids were used in the syntheses: Fmoc-L-Ala-OH, Fmoc-Arg(Pbf)-OH, Fmoc-L-Asn(Trt)-OH, Fmoc-L-Asp(OtBu)-OH, Fmoc-L-Cys(Trt)-OH, Fmoc-L-Gln(Trt)-OH, Fmoc-L-Glu(OtBu)-OH, Fmoc-Gly-OH, Fmoc-L-His(Trt)-OH, Fmoc-L-Ile-OH, Fmoc-L-Leu-OH, Fmoc-L-Lys(Boc)-OH, Fmoc-L-Met-OH, Fmoc-L-Phe-OH, Fmoc-L-Pro-OH, Fmoc-L-Ser(tBu)-OH, Fmoc-L-Thr(tBu)-OH, Fmoc-L-Trp(Boc)-OH, Fmoc-L-Tyr(tBu)-OH, Fmoc-L-Val-OH. In addition, the following amino acids were purchased from the same suppliers as above: Fmoc-L-Lys(ivDde)-OH, Fmoc-L-Lys(Dde)-OH, Fmoc-L-Lys(Mmt)-OH, Fmoc-Aib-OH, Fmoc-D-Ser(tBu)-OH, Fmoc-D-Ala-OH, and Boc-L-Tyr(tBu)-OH.

The following side chain building blocks were either acquired from commercial sources or synthesized via stepwise synthesis or solid phase synthesis as described for example in CN104356224 (Liu; Hangzhou Adlai Nortye Pharmaceutical Technology Co. Ltd.): Fmoc-L-Lys (Palm-L-Glu-OtBu)-OH; Fmoc-L-Lys [{AEEA}$_2$-gGlu(OtBu)-C(O)$(CH_2)_{16}$C(O)OtBu]-OH; Fmoc-AEEA-OH; Fmoc-AEEA-AEEA-OH; Fmoc-L-Ile-Aib-OH; and Boc-L-Tyr-Aib-OH.

The following side chain building blocks were either acquired from commercial sources (e.g. Chengdu Pukang) or synthesized via a stepwise synthesis or solid phase synthesis as described in WO2009022006 (Madsen; Novo Nordisk A/S), WO2009115469 (Madsen; Novo Nordisk A/S) or WO2015028966 (Barlos; Chemical & Biopharmaceutical Laboratories of Patras S.A.): HO-{AEEA}$_2$-gGlu(OtBu)-C(O)$(CH_2)_{16}$C(O)OtBu; HO-{AEEA}$_2$-gGlu(OtBu)-C(O)—$(CH_2)_{18}$C(O)OtBu; HO-{AEEA}$_2$-{gGlu(OtBu)}$_2$C(O)$(CH_2)_{16}$C(O)OtBu; HO-{AEEA}$_2$-{gGlu(OtBu)}$_2$-C(O)$(CH_2)_{18}$—C(O)OtBu; HO—C(O)$(CH_2)_{18}$C(O)OtBu; HO—C(O)$(CH_2)_{16}$C(O)OtBu; and HO-gGlu(OtBu)-C(O)$(CH_2)_{18}$C(O)OtBu.

Crude peptides were purified either on an Äkta Purifier System, a Jasco semiprep HPLC System, an Agilent 1100 HPLC system or a similar HPLC system. Preparative RP-C18-HPLC columns of different sizes and with different flow rates were used depending on the amount of crude peptide to be purified. Specifically, the following columns were used: Waters XSelect CSH C18 OBD Prep 5 μm 30×250 mm, Waters SunFire C18 OBD Prep 5 μm 30×250 mm, Waters SunFire C18 OBD Prep 5 μm 50×150 mm, and Phenomenex Luna Prep C18 5 μm 21.2×250 mm. Acetonitrile (B) and water+0.1% TFA (A) or water+0.1% FA (A) were employed as eluents. Product-containing fractions were collected and lyophilized to obtain the purified product, typically as a TFA salt.

Alternatively, the compounds were isolated as acetate salts via the following procedure: The compound was dissolved in water and the solution adjusted to pH 7.05 with $NaHCO_3$. Then, the dissolved compound was purified with a RP Kinetex 21.2×250 mm (Column Volume CV 88 ml, 5 μm, C18, 100A, Äkta avant 25). The column was equilibrated with solvent A (3×CV), the compound was injected and then washed with a mixture of solvent A (95%) and solvent B (5%) with 3 CV. Then, a gradient solvent A:B (95:5) to A:B (20:80) was run with 15 CV. The purified peptide was collected and lyophilized. Column: Kinetex AXIA 5 μm C18 21.2×250 mm; solvent: A ($H_2O$+0.5% acetic acid):B(ACN+$H_2O$+0.5% acetic acid) (flow 7 ml/min); gradient: 95:5 (0 min) to 95:5 (37 min) to 20:80 (180 min) to 0:100 (6 min)

Analytical HPLC/UHPLC was performed according to one of the following methods:

Method A:

detection at 214 nm column: Waters ACQUITY UPLC® CSH™ C18 1.7 μm (150×2.1 mm) at 50° C.

solvent: $H_2O$+0.05% TFA:ACN+0.045% TFA (flow 0.5 ml/min)

gradient: 80:20 (0 min) to 80:20 (3 min) to 25:75 (23 min) to 5:95 (23.5 min) to 5:95 (26.5 min) to 80:20 (27 min) to 80:20 (33 min)

optionally with mass analyzer: LCT Premier, electrospray positive ion mode

Method B:

detection at 214 nm column: Waters ACQUITY UPLC® CSH™ C18 1.7 μm (150×2.1 mm) at 50° C.

solvent: $H_2O$+0.05% TFA:ACN+0.035% TFA (flow 0.5 ml/min)

gradient: 80:20 (0 min) to 80:20 (3 min) to 25:75 (23 min) to 2:98 (23.5 min) to 2:98 (30.5 min) to 80:20 (31 min) to 80:20 (37 min)

mass analyzer: Agilent 6230 Accurate-Mass TOF or Agilent 6550 iFunnel Q-TOF; both equipped with a Dual Agilent Jet Stream ESI ion source.

Method C:

detection at 214 nm column: Waters ACQUITY UPLC® CSH™ C18 1.7 μm (150×2.1 mm) at 70° C.

solvent: $H_2O$+0.05% TFA:ACN+0.035% TFA (flow 0.5 ml/min)

gradient: 63:37 (0 min) to 63:37 (3 min) to 45:55 (23 min) to 2:98 (23.5 min) to 2:98 (30.5 min) to 63:37 (31 min) to 63:37 (38 min)

mass analyzer: Agilent 6230 Accurate-Mass TOF, Agilent Jet Stream ESI

Example 1: Synthesis of Compounds by Automated Solid Phase Peptide Procedure

Compounds were prepared by solid phase synthesis using a Prelude Peptide Synthesizer (Mesa Laboratories/Gyros Protein Technologies) or a CS Bio automated synthesizer using standard Fmoc chemistry and HBTU/DIPEA or HATU/DIPEA activation. DMF was used as the solvent.

The following conditions were employed:

Deprotection: 20% piperidine/DMF for 2×2.5 min.

Washes: 7×DMF.

Coupling 2:5:10 200 mM AA/500 mM HBTU/2M DIPEA in DMF 2× for 20 min.

Washes: 5×DMF.

HBTU/DIPEA activation was used for all standard couplings. HATU/DIPEA activation was used for the following couplings: Ile-Aib, Aib-Lys [{AEEA}$_2$-gGlu(OtBu)-C(O)$(CH_2)_{16}$C(O)OtBu], Lys [{AEEA}$_2$-gGlu(OtBu)-C(O)$(CH_2)_{16}$C(O)OtBu]-Asp, Gln-Aib, and Leu-Leu. HATU couplings were left reacting in general 2× for 40 min, sometimes 2× for 1 h, and also up to 12 h.

For the modified lysine side chain, Fmoc-L-Lys(Mmt)-OH was used at the position denoted as X12 in formula (I). After completion of the synthesis, the Mmt group was removed by repeated treatment with AcOH/TFE/DCM (1/2/7) for 15 minutes at room temperature, following which the resin was repeatedly washed with DCM, 5% DIPEA in DCM and 5% DIPEA in DCM/DMF.

After removal of the Mmt group, the resin was treated with a solution of the albumin-binding moiety in protected form. By way of illustration, peptides comprising an -{AEEA}$_2$-gGlu-C(O)$(CH_2)_{16}$COOH moiety were prepared by treating the resin with a solution of HO-{AEEA}$_2$-gGlu(OtBu)-C(O)$(CH_2)_{16}$C(O)OtBu (1 eq) in DMF preactivated with HATU (3 eq), HOAt (3 eq), and DIPEA (4 eq). The resin was then washed as above. The OtBu protecting groups were cleaved in the final peptide cleavage from the resin.

Cleavage of the peptides from the resin was performed using King's cleavage cocktail consisting of 82.5% TFA, 5% phenol, 5% water, 5% thioanisole, and 2.5% EDT or a modified cleavage cocktail consisting of 82.5% TFA, 5% phenol, 5% water, 5% thioanisole, and 2.5% DODT. The resins employed in the synthesis were such that the C-terminal was cleaved from the resin as a primary amide.

The crude peptides were then precipitated in diethyl or diisopropyl ether, centrifuged, and lyophilized. Peptides were analysed by analytical HPLC and verified by ESI mass spectrometry. Crude peptides were purified by a conventional preparative RP-HPLC purification procedure.

Example 2: Synthesis of Compounds by Manual Solid-Phase Synthesis Procedure

Compounds were also prepared by a manual synthesis procedure. An illustrative procedure is described below.

Desiccated Rink amide MBHA Resin (0.3 g; 0.5-0.8 mmol/g) was placed in a polyethylene vessel equipped with a polypropylene filter. The resin was swollen in DCM (15 ml) for 1 h and DMF (15 ml) for 1 hour. The Fmoc group on the resin was deprotected by treating it twice with 20% (v/v) piperidine/DMF solution for 5 and 15 min. The resin was washed with DMF/DCM/DMF (6/6/6 time each). A Kaiser test (a quantitative method; see Kaiser et al., Anal. Biochem., 1970, 34, 595-598) was used for the confirmation of removal of Fmoc from solid support. The C-terminal Fmoc-amino acid (5 equiv. excess corresponding to resin loading) in dry DMF was added to the deprotected resin and coupling of the next Fmoc-amino acid was initiated with 5 equivalent excess of DIC and HOBT in DMF. The concentration of each reactant in the reaction mixture was approximately 0.4 M. The mixture was rotated on a rotor at room temperature for 2 h. The resin was filtered and washed with DMF/DCM/DMF (6/6/6 time each). The Kaiser test on the peptide resin aliquot upon completion of coupling was negative (i.e., no colour on the resin). After the first amino acid attachment, the unreacted amino group, if any, in the resin was capped used acetic anhydride/pyridine/DCM (1/8/8) for 20 min to avoid any deletion of the sequence. After capping, the resin was washed with DCM/DMF/DCM/DMF (6/6/6/6 time each). The Fmoc group on the C-terminal amino acid attached peptidyl resin was deprotected by treating it twice with 20% (v/v) piperidine/DMF solution for 5 and 15 min. The resin was washed with DMF/DCM/DMF (6/6/6 time each). The Kaiser test on the peptide resin aliquot upon completion of Fmoc-deprotection was positive.

The remaining amino acids in target sequence on the Rink amide MBHA Resin were sequentially coupled using a Fmoc AA/DIC/HOBt method using 5 equivalent excess corresponding to resin loading in DMF. The concentration of each reactant in the reaction mixture was approximately 0.4 M. The mixture was rotated on a rotor at room temperature for 2 h. The resin was filtered and washed with DMF/DCM/DMF (6/6/6 time each). After each coupling step and Fmoc deprotection step, a Kaiser test was carried out to confirm the completeness of the reaction.

After the completion of the linear sequence, the epsilon-amino group of lysine (protected with Dde) was deprotected by using 2.5% hydrazine hydrate in DMF for 15 min×2 and washed with DMF/DCM/DMF (6/6/6 time each). The γ-carboxyl end of glutamic acid was attached to the epsilon-amino group of Lys using a Fmoc-Glu (OH)-OtBu with DIC/HOBt method (5 equivalent excess with respect to resin loading) in DMF. The mixture was rotated on a rotor at room temperature for 2 h. The resin was filtered and washed with DMF/DCM/DMF (6/6/6 time each, 30 ml each). The Fmoc group on the glutamic acid was deprotected by treating it twice with 20% (v/v) piperidine/DMF solution for 5 and 15 min (25 ml each). The resin was washed with DMF/DCM/DMF (6/6/6 time each). A Kaiser test on peptide resin aliquot upon completion of Fmoc-deprotection was positive.

For peptides where the side chain branching contained an additional γ-glutamic acid, a second Fmoc-Glu (OH)-OtBu was used for the attachment to the free amino group of γ-glutamic acid with DIC/HOBt method (5 equivalent excess with respect to resin loading) in DMF. The mixture was rotated on a rotor at room temperature for 2 h. The resin was filtered and washed with DMF/DCM/DMF (6/6/6 time each, 30 ml each). The Fmoc group on the γ-glutamic acid was deprotected by treating it twice with 20% (v/v) piperidine/DMF solution for 5 and 15 min (25 ml). The resin was washed with DMF/DCM/DMF (6/6/6 time each). A Kaiser test on the peptide resin aliquot upon completion of Fmoc-deprotection was positive.

Attachment of the albumin-binding moieties was performed as described in Example 1. The t-butylester protecting groups were cleaved in the final peptide cleavage from the resin.

Alternatively, the albumin binding moiety was introduced using a prefunctionalized building block where the moiety was already attached to the lysine as coupling partner in the peptide synthesis. This procedure avoids the need of a selective deprotection step as well as the selective attachment of the side chain building blocks on a very advanced synthesis intermediate. By way of illustration, the following procedure was used to incorporate Fmoc-L-Lys [{AEEA}$_2$-gGlu(OtBu)-C(O)$(CH_2)_{16}$C(O)OtBu]-OH into the peptide. 0.67 mmol of peptide resin bearing an amino-group is washed with 20 ml of dimethylformamide. 2.93 g of Fmoc-L-Lys [{AEEA}$_2$-gGlu(OtBu)-C(O)$(CH_2)_{16}$—C(O)OtBu]-OH is dissolved in 20 ml of dimethylformamide together with 310 mg of hydroxybenzotriazol hydrate and 0.32 ml of diisopropylcarbodiimide. After stirring for 5 min the solution is added to the resin. The resin is agitated for 20 h and then washed 3 times with 20 ml of dimethylformamide each. A small resin sample is taken and subjected to the Kaiser test and the Chloranil test (see Vojkovsky, Peptide Research 1995, 8, 236-237).

After coupling of the albumin-binding moiety, the peptidyl resin was washed with DCM (6×10 ml), MeOH (6×10 ml) and ether (6×10 ml) and dried in vacuum desiccators overnight. Cleavage of the peptide from the solid support was achieved by treating the peptide-resin with a reagent cocktail (92% TFA, 2% thioanisole, 2% phenol, 2% water and 2% TIPS) at room temperature for 3 to 4 hours. The cleavage mixture was collected by filtration and the resin was washed with TFA (2 ml) and DCM (2×5 ml). The excess TFA and DCM was concentrated to small volume under nitrogen and a small amount of DCM (5-10 ml) was added to the residue and evaporated under nitrogen. The process was repeated 3-4 times to remove most of the volatile impurities. The residue was cooled to 0° C. and anhydrous ether was added to precipitate the peptide. The precipitated peptide was centrifuged, the supernatant ether was removed, fresh ether was added to the peptide and re-centrifuged. The crude sample was purified by preparative HPLC and lyophilized. The identity of peptide was confirmed by LCMS.

Example 3: Synthesis of the Peptide of SEQ ID NO: 35

The compound of SEQ ID NO: 35 was prepared following the procedure described in Example 1. A Novabiochem Rink-Amide resin (4-(2',4'-dimethoxyphenyl-Fmoc-aminomethyl)-phenoxyacetamido-norleucyl-aminomethyl resin), 100-200 mesh, loading of 0.36 mmol/g was used. The automated Fmoc-synthesis strategy was applied with HBTU/DIPEA-activation or HATU/DIPEA-activation depending on the amino acid sequence. In position 12, Fmoc-Lys(Mmt)-OH was used in the solid phase synthesis protocol. The Mmt-group was cleaved from the peptide as described in the Example 1. Hereafter HO-{AEEA}$_2$-gGlu (OtBu)-C(O)$(CH_2)_{16}$C(O)OtBu was coupled to the liberated amino group employing DIPEA as base and HATU/HOAt as coupling reagents. The peptide was cleaved from the resin with King's cocktail. The crude product was purified via preparative HPLC on a Waters column (Waters SunFire C18 OBD Prep 5 μm 50×150 mm) using an acetonitrile/water gradient (water with 0.1% TFA). The purified peptide was analysed by LCMS (Method B). Deconvolution of the mass signals found under the peak with retention time 11.19 min revealed the peptide mass 5154.09 which is in line with the expected value of 5154.06.

Example 4: Synthesis of the Peptide of SEQ ID NO: 141

The compound of SEQ ID NO: 141 was prepared following the procedure described in Example 1. A Novabiochem Rink-Amide resin (4-(2',4'-dimethoxyphenyl-Fmoc-aminomethyl)-phenoxyacetamido-norleucyl-aminomethyl resin), 100-200 mesh, loading of 0.34 mmol/g was used. The automated Fmoc-synthesis strategy was applied with HBTU/DIPEA-activation or HATU/DIPEA-activation depending on the amino acid sequence. In position 12, Fmoc-L-Lys [{AEEA}$_2$-gGlu(OtBu)-C(O)$(CH_2)_{16}$—C(O)OtBu] was used in the solid phase synthesis protocol. The peptide was cleaved from the resin with King's cocktail. The crude product was purified via preparative HPLC first on a Waters column (Waters SunFire C18 OBD Prep 5 μm 50×150 mm) using an acetonitrile/water gradient (water with 0.1% TFA) and thereafter via preparative HPLC on a Waters column (Waters Xselect CSH Prep C18 5 μm 30×250 mm) using an acetonitrile/water gradient (water with 0.1% formic acid). The purified peptide was collected and lyophilized. The purified peptide was analysed by LCMS (Method B). Deconvolution of the mass signals found under the peak with retention time 9.97 min revealed the peptide mass 5163.18 which is in line with the expected value of 5163.17.

Example 5: Synthesis of the Peptide of SEQ ID NO: 171

The compound of SEQ ID NO: 171 was prepared following the procedure described in Example 1. A Novabiochem Rink-Amide resin (4-(2',4'-dimethoxyphenyl-Fmoc-aminomethyl)-phenoxyacetamido-norleucyl-aminomethyl resin), 100-200 mesh, loading of 0.35 mmol/g was used. The automated Fmoc-synthesis strategy was applied with HBTU/DIPEA-activation or HATU/DIPEA-activation depending on the amino acid sequence. In position 12, Fmoc-Lys(Mmt)-OH was used in the solid phase synthesis protocol. The Mmt-group was cleaved from the peptide as described in Example 1. Hereafter HO-{AEEA}$_2$-{gGlu(OtBu)}$_2$-C(O)$(CH_2)_{16}$C(O)OtBu was coupled to the liberated amino-group employing DIPEA as base and HATU/HOAt as coupling reagents. The peptide was cleaved from the resin with King's cocktail. The crude product was purified via preparative HPLC on a Waters column (Waters SunFire C18 OBD Prep 5 μm 50×150 mm) using an acetonitrile/water gradient (water with 0.1% TFA). The purified peptide was analysed by LCMS (Method B). Deconvolution of the mass signals found under the peak with retention time 9.94 min revealed the peptide mass 5294.21 which is in line with the expected value of 5294.13.

Example 6: Synthesis of Further Peptides

The following peptides were synthesized following the procedures described in Examples 1-5. The calculated and found masses and retention times of these peptides are indicated in Table 3 below, along with those of the compounds of Examples 3-5:

TABLE 3

| SEQ ID NO. | Calc. mass | Found mass | Retention time [min] |
|---|---|---|---|
| 1 | 4650.68 | 4650.64 | 13.55 |
| 2 | 4721.75 | 4721.79 | 12.18 |
| 3 | 4748.80 | 4748.84 | 11.69 |
| 4 | 4664.78 | 4664.80 | 11.26 |
| 5 | 4802.92 | 4802.91 | 10.44 |
| 6 | 4829.96 | 4829.99 | 10.26 |
| 7 | 1224.49 | 1224.92 (M/4 + H)+ | 13.50 |
| 8 | 4741.90 | 4741.93 | 10.13 |
| 9 | 1216.2 | 1216.33 (M/4 + H)+ | 11.40 |
| 10 | 4899.97 | 4899.99 | 9.77 |
| 11 | 4784.91 | 4784.91 | 9.97 |
| 12 | 4812.95 | 4812.92 | 9.52 |
| 13 | 5309.07 | 5309.09 | 9.60 |
| 14 | 4812.99 | 4812.95 | 9.38 |
| 15 | 4788.93 | 4788.95 | 9.88 |
| 16 | 5280.15 | 5280.18 | 9.28 |
| 17 | 1203.23 | 1202.60 (M/4 + H)+ | 11.96 |
| 18 | 5006.03 | 5006.03 | 9.81 |
| 19 | 1242.51 | 1243.5 (M/4 + H)+ | 11.66 |
| 20 | 1242.28 | 1242.6 (M/4 + H)+ | 11.52 |
| 21 | 1235.51 | 1236.4 (M/4 + H)+ | 11.56 |
| 22 | 1292.84 | 1292.67 (M/4 + H)+ | 10.60 |
| 23 | 1242.28 | 1242.8 (M/4 + H)+ | 11.52 |
| 24 | 5354.19 | 5354.21 | 8.62 |
| 25 | 4949.08 | 4949.10 | 9.36 |
| 26 | 4906.04 | 4906.06 | 9.59 |
| 27 | 4949.05 | 4949.06 | 9.52 |
| 28 | 4906.08 | 4906.09 | 9.407 |
| 29 | 4863.04 | 4863.04 | 9.80 |
| 30 | 4906.04 | 4906.05 | 9.62 |
| 31 | 4962.99 | 4962.99 | 10.11 |
| 32 | 4977.01 | 4977.02 | 10.04 |
| 33 | 4978.99 | 4978.99 | 10.04 |
| 34 | 5248.13 | 5248.15 | 8.39 |
| 35 | 5154.06 | 5154.09 | 11.19 |
| 36 | 1329.36 | 1329.05 (M/4 + H)+ | 9.93 |
| 37 | 5326.16 | 5326.18 | 8.33 |
| 38 | 5283.11 | 5283.16 | 8.54 |
| 39 | 1290.04 | 1289.95 (M/4 + H)+ | 10.82 |
| 40 | 1297.06 | 1296.96 (M/4 + H)+ | 10.87 |
| 41 | 1066.09 | 1065.90 (M/5 + H)+ | 10.56 |
| 42 | 1057.47 | 1057.29 (M/5 + H)+ | 10.76 |
| 43 | 1278.82 | 1278.82 (M/4 + H)+ | 10.81 |
| 44 | 1282.81 | 1282.67 (M/4 + H)+ | 10.77 |
| 45 | 1261.05 | 1260.94 (M/4 + H)+ | 11.14 |
| 46 | 1268.06 | 1267.94 (M/4 + H)+ | 11.08 |
| 47 | 5236.06 | 5236.09 | 11.42 |
| 48 | 5137.97 | 5137.99 | 11.14 |
| 49 | 5252.06 | 5252.12 | 10.37 |
| 50 | 5239.08 | 5239.07 | 9.68 |
| 51 | 5275.09 | 5275.13 | 9.42 |
| 52 | 5289.12 | 5289.15 | 9.11 |
| 53 | 5262.07 | 5262.10 | 9.31 |
| 54 | 5245.08 | 5245.12 | 9.98 |
| 55 | 5233.08 | 5233.07 | 9.31 |
| 56 | 5174.01 | 5174.00 | 10.20 |
| 57 | 5174.04 | 5174.07 | 9.93 |
| 58 | 1336.11 | 1336.00 (M/4 + H)+ | 11.01 |
| 59 | 1327.61 | 1327.45 (M/4 + H)+ | 10.92 |
| 60 | 1331.12 | 1330.92 (M/4 + H)+ | 10.85 |
| 61 | 1324.35 | 1324.15 (M/4 + H)+ | 10.94 |
| 62 | 1320.1 | 1319.91 (M/4 + H)+ | 11.1 |
| 63 | 1320.34 | 1320.17 (M/4 + H)+ | 11.34 |
| 64 | 1755.8 | 1755.58 (M/3 + H)+ | 10.99 |
| 65 | 1736.1 | 1735.83 (M/3 + H)+ | 11.46 |
| 66 | 1302.33 | 1302.18 (M/4 + H)+ | 11.32 |
| 67 | 5154.03 | 5154.01 | 10.11 |
| 68 | 5154.04 | 5154.02 | 10.13 |
| 69 | 5138.99 | 5138.98 | 9.49 |
| 70 | 5111.00 | 5111.04 | 10.68 |
| 71 | 5138.01 | 5138.06 | 9.94 |
| 72 | 5138.01 | 5138.05 | 10.66 |
| 73 | 5138.04 | 5138.02 | 10.31 |
| 74 | 5225.04 | 5224.99 | 10.20 |
| 75 | 5137.06 | 5137.09 | 10.26 |
| 76 | 5066.93 | 5066.97 | 11.09 |
| 77 | 5180.14 | 5180.13 | 9.61 |
| 78 | 5126.95 | 5126.95 | 10.19 |
| 79 | 5110.98 | 5111.01 | 10.46 |
| 80 | 1290.55 | 1290.39 (M/4 + H)+ | 11.28 |
| 81 | 1286.56 | 1286.41 (M/4 + H)+ | 11.52 |
| 82 | 5211.11 | 5211.07 | 9.12 |
| 83 | 5181.10 | 5181.06 | 10.03 |
| 84 | 1294.06 | 1293.90 (M/4 + H)+ | 10.25 |
| 85 | 1297.08 | 1296.90 (M/4 + H)+ | 10.60 |
| 86 | 1296.84 | 1296.70 (M/4 + H)+ | 10.54 |
| 87 | 1296.85 | 1296.68 (M/4 + H)+ | 10.43 |
| 88 | 1286.09 | 1285.89 (M/4 + H)+ | 10.78 |
| 89 | 1286.08 | 1285.90 (M/4 + H)+ | 10.87 |
| 90 | 1289.59 | 1289.43 (M/4 + H)+ | 10.70 |
| 91 | 1289.84 | 1289.63 (M/4 + H)+ | 10.35 |
| 92 | 1290.30 | 1290.14 (M/4 + H)+ | 10.68 |
| 93 | 1293.35 | 1293.21 (M/4 + H)+ | 10.46 |
| 94 | 1297.33 | 1297.16 (M/4 + H)+ | 10.44 |
| 95 | 1301.08 | 1300.85 (M/4 + H)+ | 10.25 |
| 96 | 1297.32 | 1297.16 (M/4 + H)+ | 10.88 |
| 97 | 1300.83 | 1300.70 (M/4 + H)+ | 10.48 |
| 98 | 1290.07 | 1289.91 (M/4 + H)+ | 10.54 |
| 99 | 5165.16 | 5165.20 | 9.71 |
| 100 | 5095.07 | 5095.07 | 9.86 |
| 101 | 5224.16 | 5224.17 | 9.09 |
| 102 | 1297.08 | 1296.92 (M/4 + H)+ | 11.12 |
| 103 | 1286.55 | 1286.34 (M/4 + H)+ | 11.14 |
| 104 | 1286.31 | 1286.13 (M/4 + H)+ | 10.99 |
| 105 | 1286.30 | 1286.12 (M/4 + H)+ | 10.98 |
| 106 | 1308.07 | 1307.85 (M/4 + H)+ | 10.94 |
| 107 | 1307.83 | 1307.65 (M/4 + H)+ | 10.87 |
| 108 | 1286.08 | 1285.86 (M/4 + H)+ | 10.70 |
| 109 | 1286.32 | 1286.09 (M/4 + H)+ | 10.68 |
| 110 | 1286.07 | 1285.87 (M/4 + H)+ | 10.81 |
| 111 | 1350.88 | 1350.70 (M/4 + H)+ | 11.16 |
| 112 | 1336.38 | 1336.15 (M/4 + H)+ | — |
| 113 | 1336.13 | 1335.92 (M/4 + H)+ | 13.15 |
| 114 | 1325.35 | 1325.12 (M/4 + H)+ | 11.49 |
| 115 | 1314.60 | 1314.40 (M/4 + H)+ | 10.73 |
| 116 | 1293.09 | 1292.95 (M/4 + H)+ | 10.63 |
| 117 | 1292.83 | 1292.64 (M/4 + H)+ | 10.78 |
| 118 | 1292.84 | 1292.70 (M/4 + H)+ | 10.86 |
| 119 | 1292.85 | 1292.66 (M/4 + H)+ | 10.62 |
| 120 | 1318.36 | 1318.17 (M/4 + H)+ | — |
| 121 | 1303.86 | 1303.68 (M/4 + H)+ | 10.44 |
| 122 | 1303.60 | 1303.41 (M/4 + H)+ | 10.59 |
| 123 | 1292.83 | 1292.63 (M/4 + H)+ | 10.84 |
| 124 | 1292.59 | 1292.44 (M/4 + H)+ | — |
| 125 | 1046.07 | 1045.90 (M/5 + H)+ | 10.77 |

TABLE 3-continued

| SEQ ID NO. | Calc. mass | Found mass | Retention time [min] |
|---|---|---|---|
| 126 | 1028.86 | 1028.72 (M/5 + H)+ | 11.02 |
| 127 | 1040.47 | 1040.26 (M/5 + H)+ | 11.05 |
| 128 | 1307.10 | 1306.94 (M/4 + H)+ | 11.04 |
| 129 | 1034.85 | 1034.63 (M/5 + H)+ | 11.11 |
| 130 | 5165.09 | 5165.11 | 10.09 |
| 131 | 5165.05 | 5165.07 | 10.50 |
| 132 | 5252.08 | 5252.09 | 10.22 |
| 133 | 5251.14 | 5251.14 | 10.01 |
| 134 | 5165.13 | 5165.11 | 10.13 |
| 135 | 5164.10 | 5164.09 | 10.19 |
| 136 | 5164.18 | 5164.16 | 9.73 |
| 137 | 5266.14 | 5266.15 | 9.95 |
| 138 | 5208.17 | 5208.16 | 9.64 |
| 139 | 5207.15 | 5207.14 | 9.82 |
| 140 | 5164.12 | 5164.11 | 10.36 |
| 141 | 5163.17 | 5163.18 | 9.97 |
| 142 | 5222.12 | 5222.15 | 10.61 |
| 143 | 5261.16 | 5261.17 | 8.97 |
| 144 | 5289.16 | 5289.21 | 9.43 |
| 145 | 5316.21 | 5316.27 | 9.28 |
| 146 | 5328.25 | 5328.24 | 9.62 |
| 147 | 5067.00 | 5067.01 | 10.82 |
| 148 | 5181.10 | 5181.14 | 10.86 |
| 149 | 5252.17 | 5252.21 | 9.82 |
| 150 | 5180.11 | 5180.10 | 10.37 |
| 151 | 5208.14 | 5208.15 | 10.06 |
| 152 | 5252.17 | 5252.18 | 9.54 |
| 153 | 5040.85 | 5040.82 | 13.61 |
| 154 | 5169.98 | 5170.00 | 10.41 |
| 155 | 5197.03 | 5197.07 | 10.13 |
| 156 | 5009.95 | 5009.91 | 10.67 |
| 157 | 5208.05 | 5208.08 | 12.36 |
| 158 | 5266.05 | 5266.11 | 12.20 |
| 159 | 5267.00 | 5267.07 | 12.93 |
| 160 | 5240.94 | 5240.96 | 13.57 |
| 161 | 5268.93 | 5268.97 | 13.36 |
| 162 | 5224.99 | 5225.02 | 11.31 |
| 163 | 5233.01 | 5233.03 | 10.55 |
| 164 | 5152.97 | 5153.01 | 11.42 |
| 165 | 5166.98 | 5166.98 | 11.06 |
| 166 | 5224.99 | 5224.97 | 10.86 |
| 167 | 5153.92 | 5153.95 | 11.54 |
| 168 | 5225.94 | 5225.96 | 11.53 |
| 169 | 5225.94 | 5225.96 | 11.58 |
| 170 | 5226.88 | 5226.92 | 12.42 |
| 171 | 5294.13 | 5294.21 | 9.94 |
| 172 | 5322.16 | 5322.17 | 10.63 |
| 173 | 5193.12 | 5193.15 | 10.82 |
| 174 | 5292.21 | 5292.24 | 9.71 |
| 175 | 5191.20 | 5191.23 | 10.89 |
| 176 | 5336.19 | 5336.23 | 9.99 |
| 177 | 5364.22 | 5364.22 | 10.70 |
| 178 | 5235.18 | 5235.20 | 10.87 |
| 179 | 4874.94 | 4874.97 | 10.46 |
| 180 | 4873.02 | 4873.01 | 10.51 |
| 181 | 4917.00 | 4916.97 | 10.39 |
| 182 | 4745.90 | 4745.91 | 11.12 |
| 183 | 4743.98 | 4743.99 | 10.89 |
| 184 | 4787.96 | 4787.97 | 10.69 |
| 185 | 1325.38 | 1325.14 (M/4 + H)+ | — |

Example 7: Assessment of Activity at Human CRF2 α Receptor

Agonism of compounds for human corticotropin-releasing factor 2α (CRF2 α receptor) was determined by functional assays measuring CAMP response of a TeloHEAC cell line stably expressing human CRF2 α receptor.

Cells were grown in a T175 culture flask placed at 37° C. to near confluence in medium (DMEM/10% FBS) and collected in 2 ml vials in cell culture medium containing 10% DMSO in a concentration of 10-50 million cells/ml. Each vial contained 1.8 ml cells. The vials were slowly frozen to −80° C. in isopropanol and then transferred in liquid nitrogen for storage. Prior to use, frozen cells were thawed quickly at 37° C. and washed (5 min at 900 rpm) with 20 ml cell buffer (1×HBSS; 20 mM HEPES; 0% or 0.1% HSA). Cells were resuspended in assay buffer (cell buffer plus 2 mM IBMX) and adjusted to a cell density of 1 million cells/ml. For measurement, 5 μl cells (final 2000 cells/well) and 5 μL of test compound were added to a 384-well plate, followed by incubation for 30 minutes at room temperature.

The CAMP content of cells was determined using a kit from Cisbio Corp. (cat. no. 62AM4PEC) based on HTRF (Homogenous Time Resolved Fluorescence). After addition of HTRF reagents diluted in lysis buffer (kit components), the plates were incubated for 1 h, followed by measurement of the fluorescence ratio at 665/620 nm. The percent activity value (E %) was calculated by setting 1000 nM of urocortin 2 (UCN2) as 100%. The in vitro potency of the compounds was quantified by determining the concentrations that caused 50% activation of maximal response (EC50).

Representative EC50 values are provided in Table 4 below:

TABLE 4

| SEQ ID NO. | EC50 [nM], 0% HSA | EC50 [nM], 0.1% HSA |
|---|---|---|
| 1 | 0.01 | — |
| 2 | 0.01 | 0.01 |
| 3 | 0.01 | — |
| 4 | 0.04 | — |
| 5 | 0.04 | — |
| 6 | 0.16 | 0.18 |
| 7 | 0.02 | 0.03 |
| 8 | 0.20 | — |
| 11 | 0.02 | — |
| 12 | 0.09 | — |
| 13 | 0.98 | 64.1 |
| 14 | 0.18 | — |
| 15 | 0.88 | — |
| 16 | 0.30 | — |
| 17 | 0.02 | — |
| 18 | 0.03 | — |
| 19 | 0.01 | — |
| 20 | 0.01 | — |
| 21 | 0.02 | — |
| 22 | 0.12 | — |
| 23 | 0.02 | — |
| 24 | 6.95 | — |
| 25 | 0.09 | — |
| 26 | 0.01 | — |
| 27 | 0.01 | — |
| 28 | 0.14 | — |
| 29 | 0.12 | — |
| 30 | 0.16 | — |
| 31 | 0.01 | — |
| 32 | 0.01 | — |
| 33 | 0.20 | — |
| 34 | 6.88 | — |
| 35 | 0.24 | 3.82 |
| 36 | 1.45 | — |
| 37 | 1.60 | — |
| 38 | 20.90 | — |
| 39 | 0.65 | — |
| 40 | 15.40 | — |
| 41 | 15.60 | — |
| 42 | 15.40 | — |
| 43 | 1.90 | — |
| 44 | 13.70 | — |
| 45 | 3.77 | — |
| 46 | 0.52 | — |
| 47 | 6.85 | — |
| 48 | 2.20 | — |
| 49 | 12.70 | — |
| 50 | 17.20 | — |
| 51 | 0.32 | 21.4 |

TABLE 4-continued

| SEQ ID NO. | EC50 [nM], 0% HSA | EC50 [nM], 0.1% HSA |
|---|---|---|
| 52 | 0.70 | 45.8 |
| 53 | 1.01 | 55.1 |
| 54 | 0.57 | 24.5 |
| 55 | 48.50 | — |
| 56 | 22.90 | — |
| 57 | 38.80 | — |
| 58 | 0.28 | — |
| 59 | 0.15 | 17.4 |
| 60 | 0.48 | — |
| 61 | 0.38 | — |
| 62 | 0.80 | — |
| 63 | 0.63 | — |
| 64 | 13.20 | — |
| 65 | 9.31 | — |
| 66 | 25.40 | — |
| 67 | 0.57 | — |
| 68 | 0.20 | — |
| 69 | 0.61 | — |
| 70 | 0.91 | — |
| 71 | 3.15 | — |
| 72 | 0.65 | — |
| 73 | 2.60 | — |
| 74 | 2.12 | — |
| 75 | 0.48 | — |
| 76 | 13.40 | — |
| 77 | 0.33 | — |
| 78 | 10.60 | — |
| 79 | 0.46 | — |
| 80 | 0.90 | 92.52 |
| 81 | 0.14 | 18.5 |
| 82 | 10.10 | — |
| 83 | 0.07 | 2.99 |
| 84 | 1.85 | 61.7 |
| 85 | 0.10 | 3.58 |
| 86 | 0.11 | 5.7 |
| 87 | 0.23 | 16.2 |
| 88 | 0.68 | 25.7 |
| 89 | 0.30 | 15.6 |
| 90 | 3.91 | 92.6 |
| 91 | 14.30 | — |
| 92 | 9.17 | — |
| 93 | 50.90 | — |
| 94 | 1.73 | 49.1 |
| 95 | 25.00 | — |
| 96 | 0.38 | — |
| 97 | 1.66 | — |
| 98 | 2.36 | — |
| 99 | 0.06 | 1.6 |
| 100 | 0.51 | 20.5 |
| 101 | 0.11 | 4.28 |
| 102 | 0.07 | — |
| 103 | 0.84 | — |
| 104 | 0.32 | — |
| 105 | 0.41 | 15.3 |
| 106 | 0.53 | 13.2 |
| 107 | 0.81 | 16.1 |
| 108 | 0.23 | — |
| 109 | 0.95 | — |
| 110 | 0.18 | — |
| 112 | 0.66 | 68.9 |
| 113 | 0.10 | 11.9 |
| 114 | 0.16 | 12.4 |
| 115 | 2.77 | — |
| 116 | 0.70 | — |
| 117 | 0.11 | — |
| 118 | 0.04 | 2.13 |
| 119 | 0.13 | 4.97 |
| 120 | 1.27 | 61.1 |
| 121 | 0.73 | 41.3 |
| 122 | 0.04 | 1.71 |
| 123 | 0.33 | 9.74 |
| 124 | 0.11 | 4.37 |
| 125 | 0.47 | 19.9 |
| 126 | 0.22 | 5.59 |
| 127 | 0.16 | 5.14 |
| 128 | 0.64 | 20.1 |
| 129 | 0.15 | 3.02 |
| 130 | 0.05 | 2.11 |

TABLE 4-continued

| SEQ ID NO. | EC50 [nM], 0% HSA | EC50 [nM], 0.1% HSA |
|---|---|---|
| 131 | 0.11 | 2.44 |
| 132 | 0.38 | 8.76 |
| 133 | 0.09 | 3.19 |
| 134 | 0.07 | 3.44 |
| 135 | 0.04 | 1.48 |
| 136 | 0.05 | 2.41 |
| 137 | 0.04 | 1.78 |
| 138 | 0.06 | 3.12 |
| 139 | 0.03 | 1.31 |
| 140 | 0.04 | 1.27 |
| 141 | 0.03 | 0.97 |
| 142 | 0.05 | 1.42 |
| 143 | 1.44 | 93.8 |
| 144 | 1.36 | 76.3 |
| 145 | 1.46 | 96.9 |
| 146 | 0.11 | 4.36 |
| 147 | 0.18 | 8.17 |
| 148 | 0.29 | 14.3 |
| 149 | 0.06 | 2.54 |
| 150 | 0.07 | 3.99 |
| 151 | 0.08 | 3.87 |
| 152 | 0.09 | 4.94 |
| 153 | 33.70 | — |
| 154 | 15.00 | 15.28 |
| 155 | 8.87 | — |
| 156 | 1.06 | — |
| 157 | 0.12 | 2.53 |
| 158 | 0.42 | 5.63 |
| 159 | 1.27 | 27.4 |
| 160 | 8.56 | 28.9 |
| 161 | 36.00 | 977 |
| 162 | 2.00 | 30.46 |
| 163 | 0.24 | 3.91 |
| 164 | 0.69 | 10.1 |
| 165 | 0.28 | 5.06 |
| 166 | 0.90 | 14 |
| 167 | 3.95 | 74.4 |
| 168 | 13.90 | — |
| 169 | 4.01 | 98.1 |
| 170 | 62.09 | — |
| 171 | 0.17 | 2.62 |
| 172 | 0.04 | 2.76 |
| 173 | 0.03 | 3.49 |
| 174 | 0.07 | 0.88 |
| 175 | 0.06 | 3.64 |
| 176 | 0.11 | 3.05 |
| 177 | 0.07 | 5.19 |
| 178 | 0.04 | 3.77 |
| 179 | 0.03 | 1.88 |
| 180 | 0.05 | 1.74 |
| 181 | 1.18 | 15.3 |
| 182 | 0.03 | 3.13 |
| 183 | 0.12 | 1.58 |
| 184 | 0.05 | 2.83 |
| 222 | 0.01 | — |
| 224 | 6.85 | — |

Example 8: Assessment of Activity at Rat CRF2 α Receptor

Using the procedure described in Example 7, the activity of the compounds at the rat CRF2R α receptor was assessed. The A7R5 rat aortic smooth muscle cell line was used in this study.

Representative EC50 values are provided in Table 5 below.

TABLE 5

| SEQ ID NO. | EC50 [nM], 0% HSA |
|---|---|
| 8 | 0.11 |
| 11 | 0.01 |
| 13 | 2.5 |
| 15 | 1.38 |
| 18 | 0.02 |
| 24 | 4.94 |
| 35 | 0.81 |
| 36 | 13.3 |
| 39 | 2.04 |
| 43 | 11.5 |
| 45 | 47.3 |
| 46 | 8.97 |
| 51 | 0.87 |
| 52 | 0.76 |
| 53 | 1.32 |
| 54 | 1.51 |
| 58 | 0.72 |
| 59 | 0.34 |
| 60 | 1.35 |
| 61 | 0.94 |
| 62 | 2.9 |
| 63 | 4.73 |
| 67 | 0.66 |
| 68 | 1.74 |
| 69 | 7.33 |
| 70 | 8.72 |
| 72 | 4.31 |
| 75 | 1.71 |
| 77 | 3.26 |
| 79 | 3.99 |
| 80 | 5.2 |
| 81 | 0.94 |
| 83 | 1.83 |
| 85 | 0.73 |
| 86 | 0.69 |
| 87 | 1.49 |
| 99 | 0.62 |
| 100 | 7.52 |
| 101 | 1.02 |
| 130 | 0.13 |
| 131 | 0.39 |
| 132 | 0.79 |
| 135 | 0.13 |
| 136 | 0.38 |
| 137 | 0.14 |
| 138 | 0.26 |
| 139 | 0.1 |
| 140 | 0.1 |
| 141 | 0.05 |
| 142 | 0.2 |
| 146 | 0.22 |
| 147 | 2.53 |
| 151 | 0.49 |
| 157 | 1.14 |
| 158 | 5.29 |
| 159 | 15.6 |
| 162 | 48.57 |
| 163 | 1.5 |
| 164 | 12.6 |
| 165 | 2.41 |
| 166 | 9.99 |
| 167 | 76.9 |
| 173 | 0.83 |
| 174 | 0.42 |
| 182 | 0.59 |
| 183 | 1.12 |
| 184 | 0.42 |
| 225 | 0.12 |
| 226 | 0.04 |
| 227 | 0.61 |

Example 9: Assessment of Activity at Anti-Target CFR1R Receptor

Using the procedure described in Example 7, the activity of the compounds at the anti-target CRF1R receptor was assessed. A CRF1R-overexpression CHO cell line was used in this study.

Representative EC50 and Emax values are provided in Table 6 below:

TABLE 6

| SEQ ID NO. | EC50[nM] 0% HSA | Emax (%) |
|---|---|---|
| 4 | >1000 | 17.45 |
| 5 | >1000 | 37.41 |
| 6 | 830 | 47.16 |
| 7 | 588 | 58.57 |
| 8 | >1000 | 15.96 |
| 9 | >1000 | 14.86 |
| 10 | >1000 | 10.23 |
| 11 | >1000 | 12.74 |
| 12 | >1000 | 41.82 |
| 13 | >1000 | 4.3 |
| 14 | >1000 | 14.08 |
| 15 | >1000 | 7.75 |
| 19 | 571 | 57.4 |
| 21 | 618 | 59.16 |
| 24 | >1000 | 1.48 |
| 32 | >1000 | 27.04 |
| 35 | >1000 | 1.77 |
| 39 | >1000 | 13.28 |
| 46 | >1000 | 5.88 |
| 51 | >1000 | 3.38 |
| 52 | >1000 | 5.3 |
| 53 | >1000 | 4.14 |
| 54 | >1000 | 2.72 |
| 58 | >1000 | 9.12 |
| 59 | >1000 | 11.12 |
| 60 | >1000 | 4.84 |
| 61 | >1000 | 3.31 |
| 62 | >1000 | 2.28 |
| 63 | >1000 | 4.68 |
| 67 | >1000 | 9.18 |
| 68 | >1000 | 12.34 |
| 69 | >1000 | 0.02 |
| 70 | >1000 | 3.03 |
| 72 | >1000 | 2.58 |
| 75 | >1000 | 2.7 |
| 77 | >1000 | 1.56 |
| 79 | >1000 | 8.74 |
| 80 | >1000 | 12.68 |
| 81 | >1000 | 23.34 |
| 83 | >1000 | 7.51 |
| 85 | >1000 | 0.14 |
| 86 | >1000 | 15.9 |
| 87 | >1000 | −0.2 |
| 99 | >1000 | 3.25 |
| 100 | >1000 | 5.06 |
| 101 | >1000 | −0.34 |
| 130 | >1000 | 20.3 |
| 132 | >1000 | 36.94 |
| 135 | >1000 | 28.4 |
| 136 | >1000 | 21.75 |
| 137 | >1000 | 22.5 |
| 138 | >1000 | 4.38 |
| 139 | >1000 | 37.61 |
| 146 | >1000 | 1.03 |
| 147 | >1000 | 4.54 |
| 151 | >1000 | 9.07 |
| 160 | >1000 | 20.76 |
| 161 | >1000 | 3.42 |
| 164 | >1000 | 25.82 |
| 165 | >1000 | 26.95 |
| 166 | >1000 | 5.94 |
| 167 | >1000 | −0.46 |
| 171 | >1000 | 7.54 |
| 172 | >1000 | 25.56 |

Example 10: Assessment of Activity in Cells Expressing Endogenous Human CRF2

The agonist effect of the compounds was assessed in NCI-H82 cells expressing endogenous human CRF2.

NCI-H82 cells in suspension were plated in low-volume 384-well plates at a density of 30000 cells/well in 5 μl of test medium (RPMI+1 mM IBMX). The plates were briefly centrifuged at 800 rpm to allow the cell suspension to move to the bottom of the wells and then incubated for 2 hours at 37° C. in 5% CO2. 5 μl of test compounds at appropriate concentrations (10-11 to 3×10-7) diluted in test medium were then transferred in 384 wells plates. After 5 min of activation, the reaction was stopped by addition of HTRF revelation reagents with a multidrop dispenser. The two reagents were 5 μl/well of Anti-CAMP-cryptate diluted 20-fold in conjugate and lysis buffer and 5 μl/well of cAMP-D2 diluted 20-fold in conjugate and lysis buffer. After one-hour incubation at room temperature in the dark, the plates were read on a Clariostar apparatus. The HTRF signal was read at 620 and 665 nm and was calculated as follows: Ratio HTRF=[(signal 665 nm)/(signal 620 nm)]×104. The CAMP measurement was calculated using a standard cAMP curve (0.17 nM to 712 nM) drawn on each plate, from which the EC50 values were determined.

Representative EC50 values are provided in Table 7 below:

TABLE 7

| SEQ ID NO. | EC50 [nM] |
|---|---|
| 35 | 23 |
| 59 | 6.8 |
| 81 | 110 |
| 101 | 4.1 |
| 130 | 4.3 |
| 135 | 110 |
| 137 | 120 |
| 138 | 8.4 |
| 139 | 18 |
| 141 | 12 |
| 143 | 93 |
| 147 | 13 |
| 151 | 7.4 |

Example 11: Binding Studies in HEK Cells Expressing Recombinant CRF2

Receptor binding of the compounds was assessed using a CRF2a (h) (agonist radioligand) assay.

HEK cells expressing recombinant human CRF2 were used as a source of receptor for membrane preparation. [125]sauvagine was used as the competing ligand for the CRF2 receptor. The test compounds were incubated for one hour at several concentrations in competition with [125] sauvagine (0.1 nM) to determine residual binding. Compound binding was calculated as a % inhibition of the binding of [125]sauvagine specific for CRF2.

IC50 values (concentration causing a half-maximal inhibition of control specific binding) and Hill coefficients (nH) were determined by non-linear regression analysis of the competition curves generated with mean replicate values using Hill equation curve fitting. The inhibition constants (Ki) were calculated using the Cheng Prusoff equation [Ki=IC50/(1+L/KD) where L is the concentration of radioligand in the assay, and KD is the affinity of the radioligand for the receptor). A Scatchard plot was used to determine the KD.

Representative Ki and nH values are provided in Table 8 below:

TABLE 8

| SEQ ID NO. | Ki [nM] | nH |
|---|---|---|
| 17 | 4.4 | 1.5 |
| 35 | 7.9 | 1.7 |
| 51 | 4.3 | 0.8 |
| 59 | 7.2 | 0.6 |
| 68 | 5.4 | 0.8 |

Example 12: Assessment of Chemical Stability

The chemical stability of the compounds was assessed by storing the compounds under various conditions and then determining the loss of purity by UPLC-UV.

Prior to measuring the chemical stability of a batch of test compound, the purity of the compound was determined through UPLC/MS. For stability testing the target concentration was 300 μM pure compound. Therefore, solutions from solid samples were prepared in a pH 4.5, 20 mM acetate buffer system with a concentration of 300 μM compound based on the previously determined % purity:

Solutions of the test compounds were filtered through a filter (0.22 μM pore size) and filled into aliquots under aseptic conditions. At the starting point, UPLC-UV was performed by injection of 2 μl of the undiluted sample. Aliquots were then stored for 28 days at temperatures of 5 and 40° C. After this time period, the samples were centrifuged for 15 min at 2500 RCF. Then 2 μl samples of the undiluted supernatant were analysed with UPLC-UV. The chemical stability was calculated by the equation: [(purity after 28 days at 5° C.)−(purity after 28 days at 40° C.)]/(purity after 28 days at 5° C.)]×100%. The purity was calculated as: [(peak area compound)/(total peak area)]×100%.

Representative stability data are provided in Table 9 below:

TABLE 9

| SEQ ID NO. | Relative purity loss [%] |
|---|---|
| 6 | 1.9 |
| 35 | 4.45 |
| 36 | 3.65 |
| 59 | 2.85 |
| 68 | 6.00 |
| 77 | 3.60 |
| 130 | 4.25 |
| 135 | 3.55 |
| 136 | 3.10 |
| 137 | 4.80 |
| 138 | 2.85 |
| 139 | 3.05 |
| 140 | 4.30 |
| 141 | 2.90 |

Example 13: Assessment of Solubility

The solubility of the compounds was assessed in the following buffer systems: 100 mM acetate buffer, pH 4.5 (Buffer A); 100 mM acetate buffer, pH 4.5, 2.7 mg/ml m-cresol (Buffer B); and 100 mM phosphate buffer, pH 7.4 (Buffer C).

Prior to performing the solubility measurements, the purity of the compounds was determined through UPLC/MS. For solubility testing, the target concentration was 10 mg pure compound/ml. Therefore, solutions from solid samples were prepared in a buffer system with a concentration of 10 mg/mL compound based on the previously determined % purity.

UPLC-UV was performed after 1 hour of gentle agitation from the supernatant, which was obtained after 15 minutes of centrifugation at 2500 RCF (relative centrifugal acceleration). The solubility was determined by the comparison of the UV peak area of a 2 μL-injection of a buffered sample diluted 1:10 with a standard curve of a reference compound with known concentration. The different UV extinction coefficients of sample and reference compound were calculated based on the different amino acid sequences and considered in the concentration calculation.

Representative solubility data are provided in Table 10 below:

TABLE 10

| SEQ ID NO. | Solubility in Buffer A [mg/ml] | Solubility in Buffer B [mg/ml] | Solubility in Buffer C [mg/ml] |
|---|---|---|---|
| 2 | — | >7.6 | — |
| 3 | — | >8.8 | — |
| 4 | — | >9.6 | — |
| 6 | — | >8.5 | >8.1 |
| 7 | — | >8.9 | — |
| 10 | — | — | >10.0 |
| 14 | >9.1 | — | >8.7 |
| 17 | — | — | >10.7 |
| 18 | >10.2 | >9.3 | — |
| 19 | >10.2 | >10.8 | 5.7 |
| 20 | >9.5 | >9.1 | 6.8 |
| 23 | — | — | 9.1 |
| 24 | — | — | >10.1 |
| 32 | — | — | 8.6 |
| 35 | — | >8.7 | >9.8 |
| 36 | — | — | >9.7 |
| 39 | — | — | 10.3 |
| 43 | — | — | >9.8 |
| 51 | — | >8.8 | >7.7 |
| 58 | — | >9.5 | >9.4 |
| 59 | — | >9.4 | >9.1 |
| 60 | — | >11.5 | >11.0 |
| 61 | — | >10.6 | >9.5 |
| 67 | — | 6.8 | 7.5 |
| 68 | — | >9.8 | >8.9 |
| 72 | — | >10.7 | — |
| 75 | — | >9.0 | >7.9 |
| 77 | — | >8.0 | >9.0 |
| 79 | — | 18.9 | >8.8 |
| 81 | — | 20.4 | >9.6 |
| 99 | >10.0 | — | — |
| 135 | >8.4 | >9.2 | 7.5 |
| 136 | >8.4 | >8.6 | 7.8 |
| 137 | >8.6 | >8.4 | >8.7 |
| 138 | >8.6 | >8.7 | 8.2 |
| 139 | >9.1 | >8.6 | >8.8 |
| 141 | — | >8.3 | — |
| 142 | — | >8.7 | — |
| 146 | — | — | >8.8 |

Example 14: Assessment of Physical Stability Using a Thioflavin T Assay

The physical stability of the compounds was assessed using a Thioflavin T (ThT) assay.

Low physical stability of a peptide solution may lead to amyloid fibril formation, which is observed as well-ordered, thread-like macromolecular structures in the sample, which eventually may lead to gel formation. ThT is widely used to visualise and quantify the presence of misfolded protein aggregates (see Biancalana et al., Biochim. Biophys. Acta, 2010, 1804 (7), 1405). When it binds to fibrils, such as those in amyloid aggregates, the dye displays a distinct fluorescence signature (see Naiki et al., Anal. Biochem., 1989, 177, 244; and LeVine et al., Methods. Enzymol., 1999, 309, 274). The time course for fibril formation often follows the characteristic shape of a sigmoidal curve and can be separated into three regions: a lag phase, a fast growth phase, and a plateau phase. The typical fibril formation process starts with the lag phase in which the amount of partially folded peptide turned into fibrils is not significant enough to be detected. The lag-time corresponds to the time the critical mass of the nucleus is built. Afterwards, a drastic elongation phase follows and fibril concentration increases rapidly. Therefore, by measuring the increase in fluorescence intensity attributable to ThT as well as the lag time of the increase, the fibrillation tendency of a peptide can be determined, thereby providing a measure of the physical stability of the peptide.

In the present study, test compounds were diluted in buffer to a final concentration of 3 mg/ml. Subsequently, 20 μL of a 10.1 mM ThT solution in water was added to 2 mL of peptide solution to obtain a final concentration of 100 μM ThT. Experiments were conducted using two buffers: 100 mM acetate buffer, pH 4.5 (Buffer A); and 100 mM acetate buffer, pH 4.5 and 2.7 mg/ml m-cresol (Buffer B).

The fibrillation tendencies of the peptides were determined under stress using a Fluoroskan Ascent FL or Fluoroskan Ascent fluorometer. 200 μL samples were placed into a 96-well microtiter plate PS, flat bottom, Greiner Fluotrac No. 655076. Plates were sealed with Scotch Tape (Quiagen). Samples were stressed by continuous cycles of 10 s shaking at 960 rpm and 50 s rest period at 37° C. Fibril development was monitored by measuring fluorescence intensity every 20 minutes. For each sample, eight replicates were tested.

Representative stability data obtained in Buffer A are provided in Table 11 below, in which "FI" refers to the fluorescence intensity:

TABLE 11

| SEQ ID NO. | Increase in FI | Lag time [h] |
|---|---|---|
| 4 | Yes | 18 |
| 6 | No | >45 |
| 35 | No | >45 |
| 60 | No | >45 |
| 75 | No | >45 |
| 141 | No | >45 |
| 146 | No | >45 |

Representative stability data obtained in Buffer B are provided in Table 12 below:

TABLE 12

| SEQ ID NO. | Increase in FI | Lag time [h] |
|---|---|---|
| 6 | No | >45 |
| 7 | No | >45 |
| 35 | No | >45 |
| 60 | No | >45 |
| 72 | Yes | 34.7-41.0 |
| 75 | No | >45 |
| 77 | Yes | 23.0-29.7 |
| 83 | No | >45 |
| 99 | No | >45 |
| 130 | No | >45 |
| 131 | No | >45 |

TABLE 12-continued

| SEQ ID NO. | Increase in FI | Lag time [h] |
|---|---|---|
| 132 | No | >45 |
| 135 | No | >45 |
| 141 | No | >45 |
| 142 | No | >45 |
| 146 | No | >45 |

Example 15: Assessment of Physical Stability Using a Dynamic Light Scattering Assay The physical stability of the compounds was also assessed using a dynamic light scattering assay.

Dynamic Light Scattering (DLS) measures light scattered from particles (1 nm≤radius≤1 μm) that undergo Brownian motion. This motion is induced by collisions between the particles and solvent molecules, that themselves are moving due to their thermal energy. The diffusional motion of the particles results in temporal fluctuations of the scattered light (Pecora, "Dynamic Light Scattering: Applications of Photon Correlation Spectroscopy", Plenum Press, 1985). The scattered light intensity fluctuations are recorded and transformed into an autocorrelation function. By fitting the autocorrelation curve to an exponential function, the diffusion coefficient D of the particles in solution can be derived. The diffusion coefficient is then used to calculate the hydrodynamic radius Rh (or apparent Stokes radius) through the Stokes-Einstein equation assuming spherical particles. This calculation is defined in International Standard ISO13321, Methods for Determination of Particle Size Distribution Part 8: Photon Correlation Spectroscopy, International Organisation for Standardisation $(ISO)_{1996}$; and International Standard ISO22412 Particle Size Analysis—Dynamic Light Scattering, International Organisation for Standardisation (ISO)2008.

The DLS interaction parameter ($K_D$) is a measure to describe inter-particle interactions, where the particles are folded proteins or peptides (Yadav et al., J. Pharm. Sc. 2010, 99 (3), 1152; and Connolly et al., Biophys. J. 2012, 103, 69). High values indicate strong net-repulsive interactions, while low values indicate net-attractive forces. Therefore, kp can be used for the purposes of relative, qualitative comparison.

In the present study, the physical stability of test compounds was assessed by determining the apparent hydrodynamic radius (Rh), the scattering intensity (I) and mass contribution (M) after synthesis (0 weeks) and after storage for 4 weeks at 40° C.

The stability of the compounds was assessed in five different buffer systems: 100 mM acetate buffer, pH 4.5 (Buffer A); 100 mM acetate buffer, pH 4.5, 2.7 mg/ml m-cresol (Buffer B); 20 mM phosphate buffer, pH 6.2 (Buffer C); 20 mM phosphate buffer, pH 7.4 (Buffer D); and 20 mM acetate buffer, pH 4.5 (Buffer E).

For each solution of test compound, the hydrodynamic radius Rh and the diffusion constant D (related via the Stokes-Einstein equation) were determined as an average over triplicates. Both parameters were determined at different compound concentrations (e.g., $R_{h1}$ and $D_1$: 1 mg/ml and $R_{h5}$ and $D_5$: 5 mg/ml, $R_{h10}$ and $D_{10}$: 10 mg/mL) in the same buffer system. The difference of these parameters between low and high peptide concentration is a surrogate for the DLS interaction parameter $k_D$. Increasing values for D or decreasing values of Rh with increasing peptide concentration correspond to $k_D>0$ and therefore to repulsive interparticle interactions that result in improved physical (or colloidal) stability. In addition, the hydrodynamic radius Rh and the corresponding Scattering Intensity (%) were determined as an average over duplicates. The target concentration was 300 μM. Therefore, solutions from solid samples were prepared in a buffer system with a concentration of 300 μM compound based on the previously determined % purity.

DLS measurements were performed on a DynaPro Plate Reader I (Wyatt Technology, Santa Barbara, CA, US) with an 837 nm laser light source at a scattering angle of 150°. The data were collected and processed with Dynamics V 7.8.1.3 or 7.8.2.18 software provided by Wyatt Technology.

Hydrodynamic radii were determined with non-negatively constrained least squares (NNLS) methods using DYNALS algorithms with regularization fit. For comparative reasons, the refractive index n=1.330 and η=0.89 cP of water were used for all samples. Samples were tempered over 1 hour at +25° C. and visually inspected before analysis.

Samples were mixed with the aid of a pipet tip. Measurements were performed in 5 replicates. Therefore 5 aliquots of 15 μL were pipetted on the polystyrene 384 assay plate with clear bottom (Greiner Bio-One, Germany) and sealed. The plate was centrifuged for 2 minutes at 600 rcf. After removing the sealing, the samples were measured at +25° C.

Representative stability data are provided in Table 13 below:

TABLE 13

| SEQ ID | Apparent $R_h$ [nm] | | Scattering Intensity (I) [%] | | Mass Contribution (M) [%] | | |
|---|---|---|---|---|---|---|---|
| NO. | 0 weeks | 4 weeks | 0 weeks | 4 weeks | 0 weeks | 4 weeks | Buffer |
| 36 | 1.42 ± 0.08 | 1.48 ± 0.11 | 88 ± 8 | 98 ± 2 | 1.42 ± 0.08 | 1.48 ± 0.11 | A |
| 59 | 3.66 ± 0.05 | 3.75 ± 0.08 | 100 ± 0 | 100 ± 0 | 3.66 ± 0.05 | 3.75 ± 0.08 | C |
| 99 | 3.32 ± 0.18 | 3.42 ± 0.04 | 100 ± 1 | 99 ± 1 | 3.32 ± 0.18 | 3.42 ± 0.04 | A |
| 135 | 2.83 ± 0.12 | 3.01 ± 0.03 | 99 ± 1 | 99 ± 1 | 2.83 ± 0.12 | 3.01 ± 0.03 | A |
| 135 | 2.54 ± 0.16 | 2.63 ± 0.15 | 100 ± 0 | 100 ± 0 | 2.54 ± 0.16 | 2.63 ± 0.15 | D |
| 136 | 2.75 ± 0.14 | 2.70 ± 0.28 | 98 ± 3 | 97 ± 2 | 2.75 ± 0.14 | 2.70 ± 0.28 | A |
| 136 | 2.40 ± 0.15 | 2.48 ± 0.07 | 98 ± 3 | 98 ± 2 | 2.40 ± 0.15 | 2.48 ± 0.07 | D |
| 137 | 3.31 ± 0.15 | 3.34 ± 0.25 | 94 ± 1 | 100 ± 0 | 3.31 ± 0.15 | 3.34 ± 0.25 | A |
| 137 | 3.50 ± 0.03 | 3.60 ± 0.10 | 100 ± 0 | 100 ± 0 | 3.50 ± 0.03 | 3.60 ± 0.10 | B |
| 137 | 2.66 ± 0.13 | 2.65 ± 0.11 | 84 ± 6 | 88 ± 9 | 2.66 ± 0.13 | 2.65 ± 0.11 | D |
| 137 | 2.38 ± 0.13 | 2.59 ± 0.07 | 98 ± 2 | 100 ± 0 | 2.38 ± 0.13 | 2.59 ± 0.07 | E |
| 138 | 2.75 ± 0.19 | 2.82 ± 0.11 | 86 ± 4 | 84 ± 1 | 2.75 ± 0.19 | 2.82 ± 0.11 | A |
| 139 | 3.04 ± 0.08 | 3.13 ± 0.22 | 98 ± 1 | 95 ± 4 | 3.04 ± 0.08 | 3.13 ± 0.22 | A |
| 139 | 2.94 ± 0.32 | 3.11 ± 0.14 | 96 ± 5 | 93 ± 3 | 2.94 ± 0.32 | 3.11 ± 0.14 | B |
| 139 | 2.38 ± 0.23 | 2.56 ± 0.29 | 96 ± 3 | 100 ± 0 | 2.38 ± 0.23 | 2.56 ± 0.29 | D |

TABLE 13-continued

| SEQ ID | Apparent $R_h$ [nm] | | Scattering Intensity (I) [%] | | Mass Contribution (M) [%] | | |
|---|---|---|---|---|---|---|---|
| NO. | 0 weeks | 4 weeks | 0 weeks | 4 weeks | 0 weeks | 4 weeks | Buffer |
| 141 | 2.19 ± 0.18 | 2.34 ± 0.22 | 100 ± 1 | 98 ± 2 | 2.19 ± 0.18 | 2.34 ± 0.22 | D |
| 142 | 3.63 ± 0.14 | 3.59 ± 0.04 | 100 ± 0 | 100 ± 0 | 3.63 ± 0.14 | 3.59 ± 0.04 | B |

Example 16: Assessment of Pharmacokinetic Properties

The pharmacokinetic properties of exemplary peptides SEQ ID NO: 35 and SEQ ID NO: 24 were assessed in mice and rats.

The test compound was administered in a suitable buffer system (PBS buffer solution at pH 7.4, or DPBS solution) at concentrations of 0.05, 0.1, 0.5 or 1 mg/ml depending on the dose, species and administration volume. Female C57Bl/6 mice and male SD rate were dosed 0.1 mg/kg or 0.3 mg/kg intravenously or subcutaneously. The animals were sacrificed, and blood samples were collected after 0.08, 0.25, 0.5, 1, 2, 4, 8, 24, 32, and 48 hours post-intravenous administration and 0.25, 0.5, 1, 2, 4, 8, 24, 32, and 48 hours post-subcutaneous administration, respectively. Plasma samples were analysed after protein precipitation via liquid chromatography mass spectrometry (LC/MS). Pharmacokinetic parameters and half-life were calculated using Phoenix-WinNonlin 8.1 using a non-compartmental model and linear trapezoidal interpolation calculation.

The results of this study for these peptides are presented in Table 14 below:

TABLE 14

| SEQ ID NO: | Species | Treatment | $T_{1/2}$ [h] | Cmax [ng/ml] | AUClast [h*ng/ml] | CI [L/h/kg] | F [%] |
|---|---|---|---|---|---|---|---|
| 35 | Mouse | 0.3 mg/kg i.v. | 6.4 | 4150 | 23700 | 0.0126 | — |
| 35 | Mouse | 0.1 mg/kg s.c. | 5.5 | 1410 | 18500 | — | — |
| 35 | Rat | 0.1 mg/kg i.v. | 3.0 | 1900 | 2790 | 0.0358 | — |
| 35 | Rat | 0.1 mg/kg s.c. | 6.1 | 131 | 1200 | — | 45.8 |
| 24 | Rat | 0.1 mg/kg i.v. | 4.81 | 1480 | 3790 | 0.0258 | — |
| 24 | Rat | 0.3 mg/kg s.c. | 5.51 | 171 | 2610 | — | 24.0 |

Example 17: Assessment of Effect on Blood Pressure

The effect of the compounds on blood pressure was determined in telemetry studies in Sprague Dawley rats at a dosage of 0.1 mg/kg SC.

The rats were previously implanted with a telemetry device (DSI, Saint-Paul, USA, HD-S10, HD-S11 or HD S21) and allowed to recover for a minimum period of 2 weeks before treatment with vehicle or the different peptides. Blood pressure (BP) was recorded through a catheter inserted into the abdominal aorta. The device body was placed in the abdomen. At the end of surgery, animals were placed in individual cages until the end of the study.

Pressure signals were recorded for one hour before the treatment (basal period). Thereafter, the subcutaneous administration of the test compound or its vehicle was performed, under continuous recording of the signal over a 48-hour period. Data acquisition was performed using Hem 4.3 acquisition software (Notocord®, Le Pecq, France) connected to the telemetry device. Hemodynamic parameters were recorded during a 2-hour period before treatment and every 4-hour period following subcutaneous administration over 48 hours.

Investigated parameters (calculated from BP signal) were Heart Rate (HR) in beats per minute (bpm), Diastolic and Systolic Blood Pressure (DBP) in mmHg, and Mean Blood Pressure (MBP) in mmHg.

Data from Hem were manipulated using Microsoft Excel®. For each parameter, a basal value was determined as the average calculated over a 1-hour period during the pre-treatment sequence, and the values post treatment were calculated over 4-hour periods ([0-4], [4-8], [8-12], [12-16], [16-20], [20-24], [24-28], [32-36], [36-40], [40-44] and [44-48] hours) covering the 48-hour period following administration.

Representative data are presented in Table 15 below, in which "n" represents the number of animals for which individual values were obtained and "Duration" indicates the last time point for which a significant effect on BP was still seen: Table 15

TABLE 15

| | | Effect on Systolic Pressure % change from baseline | | |
|---|---|---|---|---|
| Compound | n | 8 h | 24 h | Duration (h) |
| Vehicle | 29 | 1.3 | 1.0 | — |
| SEQ ID NO: 35 | 8 | −14.1 | −5.0 | 30 |
| SEQ ID NO: 130 | 4 | −15.2 | −9.9 | 30 |
| SEQ ID NO: 135 | 4 | −8.8 | −4.8 | 30 |
| SEQ ID NO: 137 | 4 | −15.9 | −6.5 | 28 |
| SEQ ID NO: 140 | 4 | −19.9 | −3.0 | 32 |
| SEQ ID NO: 142 | 4 | −22.2 | −6.5 | 30 |
| SEQ ID NO: 149 | 3 | −11.5 | −2.5 | 30 |
| SEQ ID NO: 151 | 3 | −12.3 | −3.8 | 28 |
| SEQ ID NO: 152 | 3 | −8.6 | −6.0 | 20 |
| SEQ ID NO: 141 | 5 | −5.2 | −4.2 | 24 |
| SEQ ID NO: 138 | 4 | −6.1 | −3.6 | 30 |

Example 18: Assessment of Effect on Body Mass and Body Fat Content

The peptide of SEQ ID NO: 35 was assessed for its ability to reduce body mass and body fat content in mice. Its efficacy was compared with that of a reference compound, namely the compound of Example 4 of WO2018013803 (Alsina-Fernandez; Eli Lilly and Company), referred to herein as "Compound A".

Female C57BL/6N Crl mice were group housed under vivarium conditions that included a 12 h light/dark cycle and a room temperature of 23±1° C. All animals had free access to water and diet (Ssniff adjusted high fat diet: TD.97366, Soest, Germany) for 18 weeks prior to pharmacological intervention (dosing phase). After the pre-feeding period, mice were single housed and randomized according to body weight to treatment groups with n=8, so that each group has similar mean body weight. At the start of the study, mice were between 25-26 weeks old with body weight of 42-50 g. Mice were treated every second day during late afternoon hours prior lights off with a subcutaneous injection of 8 nmol/kg of the test compounds or their vehicle (phosphate-buffered saline (PBS). Body weight and food intake were measured daily throughout the dosing phase while body fat content was measured at day 0 prior to the start of treatment and at day 15. The study was terminated on day 15.

For statistical analyses a One-Way Analysis of Variance (ANOVA) was performed with SigmaStat 3.5. The test was performed with a risk alpha of 0.050 and a comparison versus the high fat diet-Vehicle group was performed with Dunnett's tests.

Figure 2:
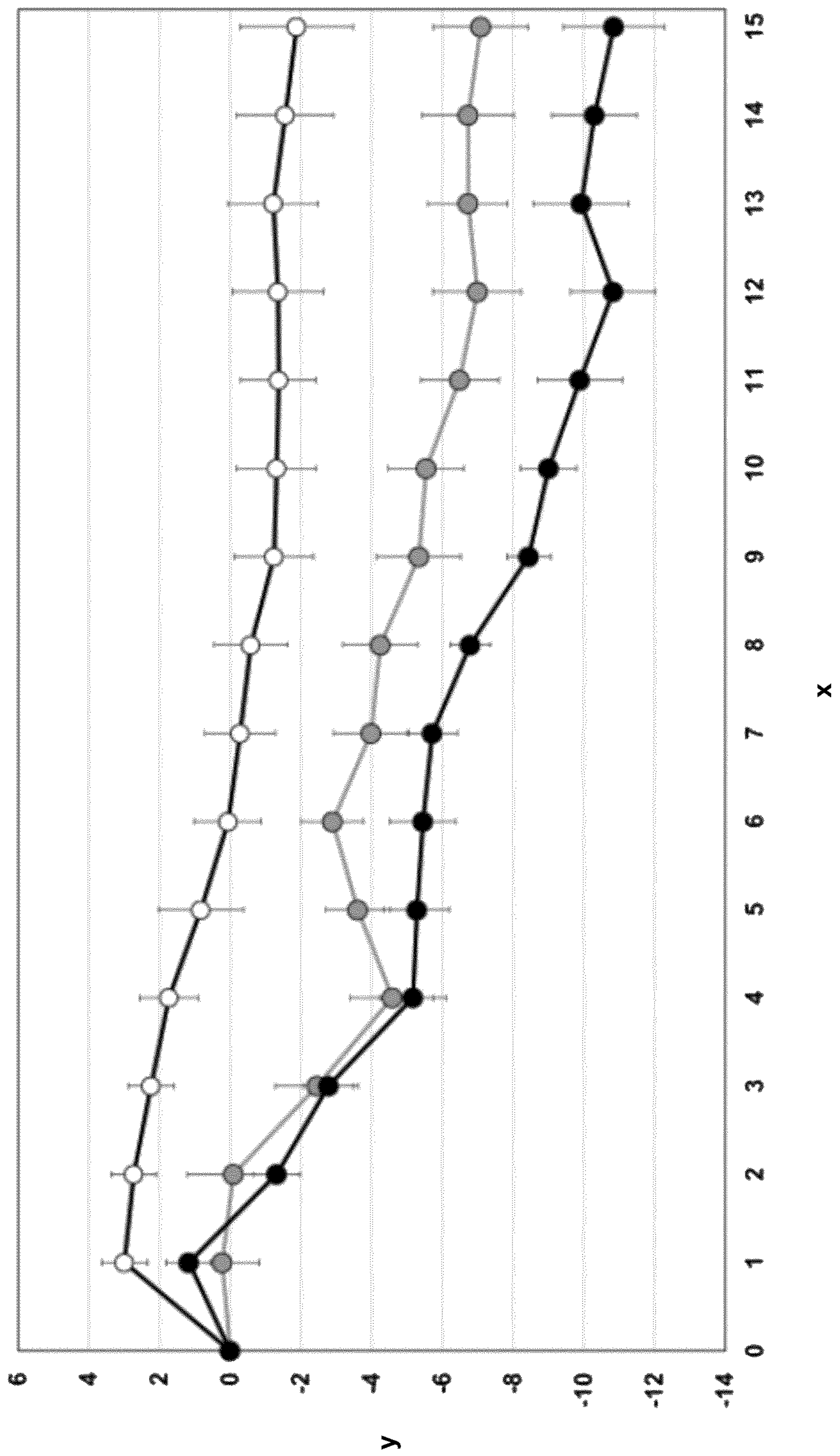
FIG. 2 is a graph depicting the relative body weight change throughout the dosing period of high fat, diet fed C57BL/6N mice (DIO), treated subcutaneously with the compound of SEQ ID NO: 35 (black circles), a reference compound (grey circles) or vehicle (white circles). The x-axis indicates the study day and the y-axis indicates the relative body weight change (in %). Values are expressed as mean±SEM.

The results of this study are presented in FIGS. 1 and 2. It can be seen from FIG. 1 that the first administration of SEQ ID NO:35 and Compound A elicited a meaningful reduction of food intake which normalized after second treatment, parallel to mice treated with vehicle. Body weight was significantly reduced after a 15-day treatment period in mice treated with SEQ ID NO: 35 or Compound A compared to the vehicle control (P<0.001). Mice treated with vehicle had a near constant body weight over the 15 days (−1.9±1.6% over the two weeks), whereas mice treated with SEQ ID NO: 35 lost −10.8±1.4% of body weight and mice treated with Compound A lost −7.1±1.3% and (see FIG. 2). The reduction of body weight corresponds to a significant reduction in body fat content: −34.2±2.9% for SEQ ID NO: 35 and −27.5±1.9% for Compound A. In addition when compared in the same study to semaglutide administered subcutaneously at 10 nmol/kg every second day, SEQ ID NO.35 reduced obesity to a similar extend but with a lower incidence on food intake (cumulative food intake over 15 days: 39.3±2.5 g for SEQ ID NO: 35 and 29.6±0.9 g for semaglutide versus 43.7±1.3 g for vehicle) and with a better preservation of lean mass: −6.3±1.7% for SEQ ID NO: 35 and −14.8±0.7% for semaglutide versus −8.6±1.1% for vehicle.

Example 19: Fatty Acid Modifications

The effect of fatty acid modifications has been assessed for those peptides of table 2 herein disclosed having $EC_{50}$ on hCRF2<0.2 nM, a selectivity profile hCRF1/hCRF2>500 and the absence of known metabolic and chemical liabilities. Preferential sequences feature the presence of a D-Valine at position 7, and preferentially bulky amino acids flanking N31.

Ten optimized sequences, having the forementioned profile, were selected from the list of table 2 and are shown in FIG. 3. For said peptides the following additional peptides (Table 16) were synthesized. These compounds share the same amino acid sequences of formerly disclosed compounds in the patent application from FIG. 3, but differ in the linker/fatty acid derivatization. In table 16 below, for each newly proposed compounds it is also indicated the original Seq ID #, of the filed patent application, with which they share the same amino acid sequence.

Peptide Synthesis: Materials and Methods

The following starting materials and methods were employed in the synthetic procedures described in the examples. Rink Amide AM resin LL 0.29 mmol/g (4-(2',4'-Dimethoxyphenyl-Fmoc-aminomethyl)-phenoxyacetamido-norleucylaminomethyl resin, Novabiochem), 100-200 mesh was used for the synthesis of all peptide amides. Fmoc-protected natural amino acids were purchased from Novabiochem, Iris Biotech, Bachem or Chem-Impex International. The following standard amino acids were used in the syntheses: Fmoc-L-Ala-OH, Fmoc-L-Arg (Pbf)-OH, Fmoc-L-Asn (Trt)-OH, Fmoc-L-Asp (OMpe)-OH, Fmoc-L-Gln (Trt)-OH, Fmoc-L-Glu (OtBu)-OH, Fmoc-L-Gly-OH, Fmoc-L-Ile-OH, Fmoc-L-Leu-OH, Fmoc-L-Lys (Boc)-OH, Fmoc-L-Pro-OH, Fmoc-L-Ser(tBu)-OH, Fmoc-L-Thr (tBu)-OH, Fmoc-L-Tyr (tBu)-OH, Fmoc-L-Val-OH.

In addition, the following amino acids were purchased from the same suppliers as above: Fmoc-L-Lys (Dde)-OH, Fmoc-Aib-OH, Fmoc-D-Val-OH.

TABLE 16

| SEQ ID NO. | Amino acid sequence | Same AA sequence of former Seq ID# | $R^a$ |
|---|---|---|---|
| 187 | IVLSLDvPIKLK*QILLKQERQKAibQREQAEKNKQILAQV-NH2 | Seq ID 130 | -gGlu-C(O)$(CH_2)_{14}$COOH |
| 188 | IVLSLDvPIKLK*QILLKQERQKAibQRQQAEKNKQILAQV-NH2 | Seq ID 135 | -gGlu-C(O)$(CH_2)_{14}$COOH |
| 189 | IVLSLDvPIKLK*QILLKQERQKKAibRQKAEKNKQILAQV-NH2 | Seq ID 136 | -gGlu-C(O)$(CH_2)_{14}$COOH |
| 190 | IVLSLDvPIKLK*QILLKQERQKKQREQAEKNKQILEQV-NH2 | Seq ID 137 | -gGlu-C(O)$(CH_2)_{14}$COOH |
| 191 | IVLSLDvPIKLK*QILLKQERQKKQREKAEKNKQILAQV-NH2 | Seq ID 138 | -gGlu-C(O)$(CH_2)_{14}$COOH |
| 192 | IVLSLDvPIKLK*QILLKQERQKKQRQQAEKNKQILAQV-NH2 | Seq ID 139 | -gGlu-C(O)$(CH_2)_{14}$COOH |
| 193 | IVLSLDvPIGLK*QILLKQERQKKAibREQAETNKRILERV-NH2 | Seq ID 83 | -gGlu-C(O)$(CH_2)_{14}$COOH |
| 194 | IVLSLDvPIGLK*QILLKQERQKKAibREQAETNKQILAQV-NH2 | Seq ID 147 | -gGlu-C(O)$(CH_2)_{14}$COOH |
| 195 | IVLSLDvPIGLK*QILLKQERQKKAibRQQAETNKRILERV-NH2 | Seq ID 150 | -gGlu-C(O)$(CH_2)_{14}$COOH |

TABLE 16-continued

| SEQ ID NO. | Amino acid sequence | Same AA sequence of former Seq ID# | R[a] |
|---|---|---|---|
| 196 | IVLSLDvPIGLK*QILLKQERQKKAibREQAEKNKRILERV-NH2 | Seq ID 151 | -gGlu-C(O)$(CH_2)_{14}$COOH |
| 197 | IVLSLDvPIKLK*QILLKQARQKAibQRAQAEKNKRILERV-NH2 | Seq ID 174 | -gGlu-C(O)$(CH_2)_{14}$COOH |
| 198 | IVLSLDvPIKLK*QILLKQERQKAibQREQAEKNKQILAQV-NH2 | Seq ID 130 | -$(AEEA)_2$-gGlu-C(O)$(CH_2)_{14}$COOH |
| 199 | IVLSLDvPIKLK*QILLKQERQKAibQREQAEKNKQILAQV-NH2 | Seq ID 130 | -$\{AEEA\}_2$-$\{gGlu\}_2$-C(O)$(CH_2)_{14}$COOH |
| 200 | IVLSLDvPIKLK*QILLKQERQKKAibRQKAEKNKQILAQV-NH2 | Seq ID 136 | -$\{AEEA\}_2$-gGlu-C(O)$(CH_2)_{14}$COOH |
| 201 | IVLSLDvPIKLK*QILLKQERQKKAibRQKAEKNKQILAQV-NH2 | Seq ID 136 | -$\{AEEA\}_2$-$\{gGlu\}_2$-C(O)$(CH_2)_{14}$COOH |
| 202 | IVLSLDvPIGLK*QILLKQERQKKAibREQAETNKQILAQV-NH2 | Seq ID 147 | -$\{AEEA\}_2$-gGlu-C(O)$(CH_2)_{14}$COOH |
| 203 | IVLSLDvPIGLK*QILLKQERQKKAibREQAETNKQILAQV-NH2 | Seq ID 147 | -$\{AEEA\}_2$-$\{gGlu\}_2$ C(O)$(CH_2)_{14}$COOH |
| 204 | IVLSLDvPIKLK*QILLKQERQKAibQREQAEKNKQILAQV-NH2 | Seq ID 130 | -gGlu-C(O)$(CH_2)_{14}CH_3$ |
| 205 | IVLSLDvPIKLK*QILLKQERQKAibQREQAEKNKQILAQV-NH2 | Seq ID 130 | -$\{AEEA\}_2$-gGlu-C(O)$(CH_2)_{14}CH_3$ |
| 206 | IVLSLDvPIKLK*QILLKQERQKAibQREQAEKNKQILAQV-NH2 | Seq ID 130 | -$\{AEEA\}_2$-$\{gGlu\}_2$-C(O)$(CH_2)_{14}CH_3$ |
| 207 | IVLSLDvPIGLK*QILLKQERQKKAibREQAETNKRILERV-NH2 | Seq ID 83 | -gGlu-C(O)$(CH_2)_{14}CH_3$ |
| 208 | IVLSLDvPIKLK*QILLKQERQKAibQRQQAEKNKQILAQV-NH2 | Seq ID 135 | -gGlu-C(O)$(CH_2)_{14}CH_3$ |
| 209 | IVLSLDvPIKLK*QILLKQERQKKAibRQKAEKNKQILAQV-NH2 | Seq ID 136 | -gGlu-C(O)$(CH_2)_{14}CH_3$ |
| 210 | IVLSLDvPIKLK*QILLKQERQKKAibRQKAEKNKQILAQV-NH2 | Seq ID 136 | -$\{AEEA\}_2$-gGlu-C(O)$(CH_2)_{14}CH_3$ |
| 211 | IVLSLDvPIKLK*QILLKQERQKKAibRQKAEKNKQILAQV-NH2 | Seq ID 136 | -$\{AEEA\}_2$-$\{gGlu\}_2$-C(O)$(CH_2)_{14}CH_3$ |
| 212 | IVLSLDvPIKLK*QILLKQERQKKQREQAEKNKQILEQV-NH2 | Seq ID 137 | -gGlu-C(O)$(CH_2)_{14}CH_3$ |
| 213 | IVLSLDvPIKLK*QILLKQERQKKQREKAEKNKQILAQV-NH2 | Seq ID 138 | -gGlu-C(O)$(CH_2)_{14}CH_3$ |
| 214 | IVLSLDvPIKLK*QILLKQERQKKQRQQAEKNKQILAQV-NH2 | Seq ID 139 | -gGlu-C(O)$(CH_2)_{14}CH_3$ |
| 215 | IVLSLDvPIGLK*QILLKQERQKKAibREQAETNKQILAQV-NH2 | Seq ID 147 | -gGlu-C(O)$(CH_2)_{14}CH_3$ |
| 216 | IVLSLDvPIGLK*QILLKQERQKKAibREQAETNKQILAQV-NH2 | Seq ID 147 | -$\{AEEA\}_2$-gGlu-C(O)$(CH_2)_{14}CH_3$ |
| 217 | IVLSLDvPIGLK*QILLKQERQKKAibREQAETNKQILAQV-NH2 | Seq ID 147 | -$\{AEEA\}_2$-$\{gGlu\}_2$-C(O)$(CH_2)_{14}CH_3$ |
| 218 | IVLSLDvPIGLK*QILLKQERQKKAibREQAEKNKRILERV-NH2 | Seq ID 151 | -gGlu-C(O)$(CH_2)_{14}CH_3$ |
| 219 | IVLSLDvPIKLK*QILLKQARQKAibQRAQAEKNKRILERV-NH2 | Seq ID 174 | -gGlu-C(O)$(CH_2)_{14}CH_3$ |
| 220 | IVLSLDvPIGLK*QILLKQERQKKAibRQQAETNKRILERV-NH2 | Seq ID 150 | -gGlu-C(O)$(CH_2)_{14}CH_3$ |
| 221 | IVLSLDvPTKLK*QKLLKQERQRKEREQAEKNARILARV-NH2 | Seq ID 7 | -gGlu-C(O)$(CH_2)_{14}$COOH |
| 222 | IVLSLDvPTKLK*QKLLKQERQRKEREQAEKNVRILERV-NH2 | Seq ID 32 | -gGlu-C(O)$(CH_2)_{14}$COOH |

Peptide Synthesis: Materials and Methods—Continued

The following side chain building blocks were acquired from Iris Biotech, TCI, Merck: Fmoc-AEEA-OH, Fmoc-L-Glu-OtBu, Palmitic acid (HO—C(O)$(CH_2)_{14}CH_3$), Hexadecanedioic acid (HO—C(O)$(CH_2)_{14}$COOH).

Crude peptides were purified on a preparative HPLC Waters system with a C4 column. Specifically, the following column was used: Reprosil Gold C4 Prep (Dr Maisch), 250×40 cm, 120 Å, 5 μm. Acetonitrile+0.1% TFA and water+0.1% TFA were employed as eluents. Product containing fractions were collected and lyophilized to obtain the purified product, typically as a TFA salt.

Alternatively, the compounds were isolated as acetate salts via the following procedure. The ion exchange was performed using a HiTrap™ Q HP column (GE Healthcare). The pure peptides were dissolved in a 0.16M acetic acid solution at 2 mg/ml, slowly loaded on the column and eluted with 0.16M solution of acetic acid. The collected solution was freeze-dried.

Crude and purified peptides were analyzed by Ultra-high performance liquid chromatography with UV and mass spectrometry detection (UPLC-UV-MS). Analytical UPLC was performed according to one of the following methods:

Method A:

- Detection at 214 nm
- Column: Acquity Waters BEH130 C4, 1.7 μm (2.1×100 mm) at 45° C.
- Solvent: $H_2O$+0.1% TFA:ACN+0.1% TFA (flow 0.4 ml/min)
- Gradient: 70:30 (0 min) to 70:30 (1 min) to 50:50 (5 min) to 10:90 (5.2 min) to 10:90 (5.5 min) to 70:30 (5.7 min) to 70:30 (6 min)
- Mass analyzer: Waters SQ Detector with electrospray ionization in positive ion detection mode Method B:

- Detection at 214 nm
- Column: Acquity Waters BEH130 C4, 1.7 μm (2.1×100 mm) at 45° C.
- Solvent: $H_2O$+0.1% TFA:ACN+0.1% TFA (flow 0.4 ml/min)
- Gradient: 65:35 (0 min) to 65:35 (1 min) to 45:55 (5 min) to 10:90 (5.2 min) to 10:90 (5.5 min) to 65:35 (5.7 min) to 65:35 (6 min)
- Mass analyzer: Waters SQ Detector with electrospray ionization in positive ion detection mode

Example 19.1: General Synthesis Procedure SEQ ID NO: 187-222

The synthesis of all the peptides (SEQ ID NO: 187-222) was performed by standard Fmoc stepwise solid phase synthesis (SPPS) on a Liberty Blue microwave synthesizer (CEM corp.). The assembly was performed using a Rink amide AM Resin LL 0.29 mmol/g on a 0.1 mmol scale, with DIC/Oxyma activation. DMF was used as the solvent. For the modified lysine side chain, Fmoc-L-Lys (Dde)-OH was used at position 12.

The following conditions were employed:

- Standard deprotection: 20% piperidine in DMF for 2×120 s, 90° C.
- Washes: 4×DMF.
- Standard Single coupling: 5 eq. AA 0.4 M/5 eq. DIC 1M/5 eq. Oxyma 1M, 120 s, 90° C.
- Washes: 4×DMF.

At the end of the assembly, N-terminus of the peptide was protected using tert-butoxycarbonyl tert-butyl carbonate (10 equivalent excess with respect to resin loading, Fluoro-Chem) in DMF; the mixture was shaken at room temperature for 30 minutes and the reaction was monitored by Kaiser Test.

The removal of Dde group on Lys12 was achieved by dropping 2% hydrazine monohydrate and washing the resins with DMF/DCM/DMF (6/6/6 time each).

After the removal of the Dde group, the resins were treated as reported in Examples 2-7 according to the peptide sequence side chain derivatization.

Cleavage of the peptides from the resin was performed using the following cleavage cocktail: 87.5% TFA, 5% phenol, 5% water, 2.5% TIPS for 2 to 2.5 hours. The resin employed in the synthesis was such that the C-terminal was cleaved from the resin as a primary amide.

The cleavage mixture was collected by filtration, the crude peptides were precipitated in methyl tert-butyl ether, centrifuged, the supernatant was removed, fresh diethyl ether was added to the peptides and re-centrifuged, twice; the crude peptides were then lyophilized.

Peptides were analyzed by analytical UPLC and verified by $ESI^+$ mass spectrometry. Crude peptides were purified by a conventional preparative RP-HPLC purification procedure.

Example 19.2: Synthesis of the Peptide of SEQ ID NO: 187

The compound of SEQ ID NO: 186 was prepared following the procedure described in Example 19.1. A Novabiochem Rink amide AM Resin LL 0.29 mmol/g (4-(2',4'-Dimethoxyphenyl-Fmoc-aminomethyl)-phenoxyacetamido-norleucylaminomethyl resin), 100-200 mesh was used. The automated Fmoc-synthesis strategy was applied with DIC/Oxyma-activation. In position 12, Fmoc-L-Lys (Dde)-OH was used in the solid phase synthesis protocol.

At the end of the assembly, N-terminus of the peptide was protected and Dde protecting group on Lys12 was removed as reported in Example 19.1.

The γ-carboxyl end of glutamic acid was attached to the epsilon-amino group of Lys using a Fmoc-L-Glu-OtBu with DIC/HOAt method (4 equivalent excess with respect to resin loading) in DMF. The mixture was shaken at room temperature for 1 h and the reaction was monitored by Kaiser Test. The resin was filtered and washed with DMF/DCM/DMF (6/6/6 time each). The Fmoc group on the glutamic acid was removed by treating it twice with 20% (v/v) piperidine/DMF solution for 5 minutes (25 ml each). The resin was washed with NMP/DCM/NMP (6/6/6 time each). A Kaiser test on peptide resin aliquot upon completion of Fmoc-deprotection was positive.

Attachment of the albumin-binding moiety was performed using Hexadecanedioic acid ($HO—C(O)(CH_2)_{14}COOH$) with DIC/HOAt method (5 equivalent excess with respect to resin loading) in NMP. The mixture was shaken at room temperature for 1 h and the reaction was monitored by Kaiser Test. The resin was filtered and washed with NMP/DCM/NMP (6/6/6 time each).

The peptide was cleaved from the resin as described in the Example 19.1. The crude product was purified via preparative RP-HPLC on a Reprosil Gold C4 Prep (Dr Maisch), 250×40 cm, 120 Å, 5 μm using an acetonitrile/water gradient (with 0.1% TFA). The purified peptide was analyzed by LC/MS (Method A). $(M/4+H)^+$ mass signal found under the peak with retention time 3.84 min revealed the peptide mass 1213.97 which is in line with the expected value of 1213.47.

Example 19.3: Synthesis of the Peptide of SEQ ID NO: 198

The compound of SEQ ID NO: 197 was prepared following the procedure described in Example 19.1. A Novabiochem Rink amide AM Resin LL 0.29 mmol/g (4-(2',4'-Dimethoxyphenyl-Fmoc-aminomethyl)-phenoxyacetamido-norleucylaminomethyl resin), 100-200 mesh was used. The automated Fmoc-synthesis strategy was applied with DIC/Oxyma-activation. In position 12, Fmoc-L-Lys (Dde)-OH was used in the solid phase synthesis protocol.

At the end of the assembly, N-terminus of the peptide was protected and Dde protecting group on Lys12 was removed as reported in Example 19.1.

Fmoc-AEEA-OH was attached to the epsilon-amino group of Lys with DIC/HOAt method (4 equivalent excess with respect to resin loading) in DMF. The mixture was shaken at room temperature for 1 h and the reaction was monitored by Kaiser Test. The resin was filtered and washed with DMF/DCM/DMF (6/6/6 time each). The Fmoc group on AEEA was removed by treating the resin twice with 20% (v/v) piperidine/DMF solution for 5 minutes (25 ml each). The resin was washed with DMF/DCM/DMF (6/6/6 time each). A Kaiser test on peptide resin aliquot upon completion of Fmoc-deprotection was positive.

A second Fmoc-AEEA-OH was attached to the deprotected amino group with DIC/HOAt method in DMF and then deprotected from Fmoc as reported above.

The γ-carboxyl end of glutamic acid was attached to the deprotected amino group using a Fmoc-L-Glu-OtBu with DIC/HOAt method (4 equivalent excess with respect to resin loading) in DMF. The mixture was shaken at room temperature for 1 h and the reaction was monitored by Kaiser Test. The resin was filtered and washed with DMF/DCM/DMF (6/6/6 time each). The Fmoc group on the glutamic acid was removed by treating it twice with 20% (v/v) piperidine/DMF solution for 5 minutes (25 ml each). The resin was washed with NMP/DCM/NMP (6/6/6 time each). A Kaiser test on peptide resin aliquot upon completion of Fmoc-deprotection was positive.

Attachment of the albumin-binding moiety was performed using Hexadecanedioic acid (HO—C(O)$(CH_2)_{14}$COOH) with DIC/HOAt method (5 equivalent excess with respect to resin loading) in NMP. The mixture was shaken at room temperature for 1 h and the reaction was monitored by Kaiser Test. The resin was filtered and washed with NMP/DCM/NMP (6/6/6 time each).

The peptide was cleaved from the resin as described in the Example 19.1. The crude product was purified via preparative RP-HPLC on a Reprosil Gold C4 Prep (Dr Maisch), 250×40 cm, 120 Å, 5 μm using an acetonitrile/water gradient (with 0.1% TFA). The purified peptide was analyzed by LC/MS (Method A). $(M/4+H)^+$ mass signal found under the peak with retention time 3.66 min revealed the peptide mass 1286.7 which is in line with the expected value of 1286.05.

Example 19.4: Synthesis of the Peptide of SEQ ID NO: 199

The compound of SEQ ID NO: 198 was prepared following the procedure described in Example 19.1. A Novabiochem Rink amide AM Resin LL 0.29 mmol/g (4-(2',4'-Dimethoxyphenyl-Fmoc-aminomethyl)-phenoxyacetamido-norleucylaminomethyl resin), 100-200 mesh was used. The automated Fmoc-synthesis strategy was applied with DIC/Oxyma-activation. In position 12, Fmoc-L-Lys (Dde)-OH was used in the solid phase synthesis protocol.

At the end of the assembly, N-terminus of the peptide was protected and Dde protecting group on Lys12 was removed as reported in Example 19.1.

Fmoc-AEEA-OH was attached to the epsilon-amino group of Lys with DIC/HOAt method (4 equivalent excess with respect to resin loading) in DMF. The mixture was shaken at room temperature for 1 h and the reaction was monitored by Kaiser Test. The resin was filtered and washed with DMF/DCM/DMF (6/6/6 time each). The Fmoc group on AEEA was removed by treating the resin twice with 20% (v/v) piperidine/DMF solution for 5 minutes (25 ml each). The resin was washed with DMF/DCM/DMF (6/6/6 time each). A Kaiser test on peptide resin aliquot upon completion of Fmoc-deprotection was positive.

A second Fmoc-AEEA-OH was attached to the deprotected amino group with DIC/HOAt method in DMF and then deprotected from Fmoc as reported above.

The γ-carboxyl end of glutamic acid was attached to the deprotected amino group using a Fmoc-L-Glu-OtBu with DIC/HOAt method (4 equivalent excess with respect to resin loading) in DMF. The mixture was shaken at room temperature for 1 h and the reaction was monitored by Kaiser Test. The resin was filtered and washed with DMF/DCM/DMF (6/6/6 time each). The Fmoc group on the glutamic acid was removed by treating it twice with 20% (v/v) piperidine/DMF solution for 5 minutes (25 ml each). The resin was washed with DMF/DCM/DMF (6/6/6 time each). A Kaiser test on peptide resin aliquot upon completion of Fmoc-deprotection was positive.

A second Fmoc-L-Glu-OtBu was attached to the deprotected amino group with DIC/HOAt method in DMF and then deprotected from Fmoc as reported above. The resin was washed with NMP/DCM/NMP (6/6/6 time each).

Attachment of the albumin-binding moiety was performed using Hexadecanedioic acid (HO—C(O)$(CH_2)_{14}$COOH) with DIC/HOAt method (5 equivalent excess with respect to resin loading) in NMP. The mixture was shaken at room temperature for 1 h and the reaction was monitored by Kaiser Test. The resin was filtered and washed with NMP/DCM/NMP (6/6/6 time each).

The peptide was cleaved from the resin as described in the Example 19.1. The crude product was purified via preparative RP-HPLC on a Reprosil Gold C4 Prep (Dr Maisch), 250×40 cm, 120 Å, 5 μm using an acetonitrile/water gradient (with 0.1% TFA). The purified peptide was analyzed by LC/MS (Method A). $(M/4+H)^+$ mass signal found under the peak with retention time 3.50 min revealed the peptide mass 1318.70 which is in line with the expected value of 1318.33.

Example 19.5: Synthesis of the Peptide of SEQ ID NO: 204

The compound of SEQ ID NO: 203 was prepared following the procedure described in Example 19.1. A Novabiochem Rink amide AM Resin LL 0.29 mmol/g (4-(2',4'-Dimethoxyphenyl-Fmoc-aminomethyl)-phenoxyacetamido-norleucylaminomethyl resin), 100-200 mesh was used. The automated Fmoc-synthesis strategy was applied with DIC/Oxyma-activation. In position 12, Fmoc-L-Lys (Dde)-OH was used in the solid phase synthesis protocol.

At the end of the assembly, N-terminus of the peptide was protected and Dde protecting group on Lys12 was removed as reported in Example 19.1.

The γ-carboxyl end of glutamic acid was attached to the epsilon-amino group of Lys using a Fmoc-L-Glu-OtBu with DIC/HOAt method (4 equivalent excess with respect to resin loading) in DMF. The mixture was shaken at room temperature for 1 h and the reaction was monitored by Kaiser Test. The resin was filtered and washed with DMF/DCM/DMF (6/6/6 time each). The Fmoc group on the glutamic acid was removed by treating it twice with 20% (v/v) piperidine/DMF solution for 5 minutes (25 ml each). The resin was washed with DMF/DCM/DMF (6/6/6 time each). A Kaiser test on peptide resin aliquot upon completion of Fmoc-deprotection was positive.

Attachment of the albumin-binding moiety was performed using palmitic acid (HO—C(O)$(CH_2)_{14}CH_3$) with DIC/HOAt method (5 equivalent excess with respect to resin loading) in DMF. The mixture was shaken at room temperature for 1 h and the reaction was monitored by Kaiser Test. The resin was filtered and washed with DMF/DCM/DMF (6/6/6 time each).

The peptide was cleaved from the resin as described in the Example 19.1. The crude product was purified via preparative RP-HPLC on a Reprosil Gold C4 Prep (Dr Maisch), 250×40 cm, 120 Å, 5 μm using an acetonitrile/water gradient (with 0.1% TFA). The purified peptide was analyzed by LC/MS (Method B). $(M/4+H)^+$ mass signal found under the peak with retention time 3.84 min revealed the peptide mass 1206.50 which is in line with the expected value of 1205.98.

Example 19.6: Synthesis of the Peptide of SEQ ID NO: 205

The compound of SEQ ID NO: 204 was prepared following the procedure described in Example 1. A Novabiochem Rink amide AM Resin LL 0.29 mmol/g (4-(2',4'-Dimethoxyphenyl-Fmoc-aminomethyl)-phenoxyacetamido-norleucylaminomethyl resin), 100-200 mesh was used. The automated Fmoc-synthesis strategy was applied with DIC/Oxyma-activation. In position 12, Fmoc-L-Lys (Dde)-OH was used in the solid phase synthesis protocol.

At the end of the assembly, N-terminus of the peptide was protected and Dde protecting group on Lys12 was removed as reported in Example 19.1.

Fmoc-AEEA-OH was attached to the epsilon-amino group of Lys with DIC/HOAt method (4 equivalent excess with respect to resin loading) in DMF. The mixture was shaken at room temperature for 1 h and the reaction was monitored by Kaiser Test. The resin was filtered and washed with DMF/DCM/DMF (6/6/6 time each). The Fmoc group on AEEA was removed by treating the resin twice with 20% (v/v) piperidine/DMF solution for 5 minutes (25 ml each). The resin was washed with DMF/DCM/DMF (6/6/6 time each). A Kaiser test on peptide resin aliquot upon completion of Fmoc-deprotection was positive.

A second Fmoc-AEEA-OH was attached to the deprotected amino group with DIC/HOAt method in DMF and then deprotected from Fmoc as reported above.

The γ-carboxyl end of glutamic acid was attached to the epsilon-amino group of Lys using a Fmoc-L-Glu-OtBu with DIC/HOAt method (4 equivalent excess with respect to resin loading) in DMF. The mixture was shaken at room temperature for 1 h and the reaction was monitored by Kaiser Test. The resin was filtered and washed with DMF/DCM/DMF (6/6/6 time each). The Fmoc group on the glutamic acid was removed by treating it twice with 20% (v/v) piperidine/DMF solution for 5 minutes (25 ml each). The resin was washed with DMF/DCM/DMF (6/6/6 time each). A Kaiser test on peptide resin aliquot upon completion of Fmoc-deprotection was positive.

Attachment of the albumin-binding moiety was performed using palmitic acid ($HO—C(O)(CH_2)_{14}CH_3$) with DIC/HOAt method (5 equivalent excess with respect to resin loading) in DMF. The mixture was shaken at room temperature for 1 h and the reaction was monitored by Kaiser Test. The resin was filtered and washed with DMF/DCM/DMF (6/6/6 time each).

The peptide was cleaved from the resin as described in the Example 19.1. The crude product was purified via preparative RP-HPLC on a Reprosil Gold C4 Prep (Dr Maisch), 250×40 cm, 120 Å, 5 μm using an acetonitrile/water gradient (with 0.1% TFA). The purified peptide was analyzed by LC/MS (Method B). $(M/4+H)^+$ mass signal found under the peak with retention time 3.45 min revealed the peptide mass 1279.0 which is in line with the expected value of 1278.56.

Example 19.7: Synthesis of the Peptide of SEQ ID NO: 206

The compound of SEQ ID NO: 205 was prepared following the procedure described in Example 19.1. A Novabiochem Rink amide AM Resin LL 0.29 mmol/g (4-(2',4'-Dimethoxyphenyl-Fmoc-aminomethyl)-phenoxyacetamido-norleucylaminomethyl resin), 100-200 mesh was used. The automated Fmoc-synthesis strategy was applied with DIC/Oxyma-activation. In position 12, Fmoc-L-Lys (Dde)-OH was used in the solid phase synthesis protocol.

At the end of the assembly, N-terminus of the peptide was protected and Dde protecting group on Lys12 was removed as reported in Example 19.1.

Fmoc-AEEA-OH was attached to the epsilon-amino group of Lys with DIC/HOAt method (4 equivalent excess with respect to resin loading) in DMF. The mixture was shaken at room temperature for 1 h and the reaction was monitored by Kaiser Test. The resin was filtered and washed with DMF/DCM/DMF (6/6/6 time each). The Fmoc group on AEEA was removed by treating the resin twice with 20% (v/v) piperidine/DMF solution for 5 minutes (25 ml each). The resin was washed with DMF/DCM/DMF (6/6/6 time each). A Kaiser test on peptide resin aliquot upon completion of Fmoc-deprotection was positive.

A second Fmoc-AEEA-OH was attached to the deprotected amino group with DIC/HOAt method in DMF and then deprotected from Fmoc as reported above.

The γ-carboxyl end of glutamic acid was attached to the deprotected amino group using a Fmoc-L-Glu-OtBu with DIC/HOAt method (4 equivalent excess with respect to resin loading) in DMF. The mixture was shaken at room temperature for 1 h and the reaction was monitored by Kaiser Test. The resin was filtered and washed with DMF/DCM/DMF (6/6/6 time each). The Fmoc group on the glutamic acid was removed by treating it twice with 20% (v/v) piperidine/DMF solution for 5 minutes (25 ml each). The resin was washed with DMF/DCM/DMF (6/6/6 time each). A Kaiser test on peptide resin aliquot upon completion of Fmoc-deprotection was positive.

A second Fmoc-L-Glu-OtBu was attached to the deprotected amino group with DIC/HOAt method in DMF and then deprotected from Fmoc as reported above.

Attachment of the albumin-binding moiety was performed using palmitic acid ($HO—C(O)(CH_2)_{14}CH_3$) with DIC/HOAt method (5 equivalent excess with respect to resin loading) in DMF. The mixture was shaken at room temperature for 1 h and the reaction was monitored by Kaiser Test. The resin was filtered and washed with DMF/DCM/DMF (6/6/6 time each).

The peptide was cleaved from the resin as described in the Example 19.1. The crude product was purified via preparative RP-HPLC on a Reprosil Gold C4 Prep (Dr Maisch), 250×40 cm, 120 Å, 5 μm using an acetonitrile/water gradient (with 0.1% TFA). The purified peptide was analyzed by LC/MS (Method B). $(M/4+H)^+$ mass signal found under the peak with retention time 3.30 min revealed the peptide mass 1311.35 which is in line with the expected value of 1310.83.

Example 19.8: Synthesis of Further Peptides

The following peptides were synthesized following the procedures described in Examples 19.1-7. The calculated and found masses and retention times of these peptides are indicated in Table 3 below, along with those of the compounds of Examples 19.2-7:

TABLE 17

| SEQ ID NO. | Calc. mass (M/4 + H)+ | Found mass (M/4 + H)+ | Retention Time (min) | Method |
|---|---|---|---|---|
| 187 | 1213.47 | 1213.97 | 3.84 | A |
| 188 | 1213.23 | 1213.69 | 3.82 | A |
| 189 | 1213.25 | 1213.60 | 3.61 | A |
| 190 | 1238.75 | 1239.24 | 3.71 | A |
| 191 | 1224.25 | 1224.70 | 3.63 | A |
| 192 | 1223.99 | 1224.54 | 3.7 | A |
| 193 | 1217.47 | 1217.89 | 3.99 | A |
| 194 | 1188.93 | 1189.40 | 4.08 | A |
| 195 | 1217.23 | 1217.70 | 3.91 | A |
| 196 | 1224.24 | 1224.70 | 3.87 | A |
| 197 | 1212.99 | 1213.4 | 3.89 | A |
| 198 | 1286.05 | 1286.7 | 3.66 | A |
| 199 | 1318.33 | 1318.7 | 3.50 | A |
| 200 | 1285.83 | 1286.4 | 3.49 | A |
| 201 | 1318.11 | 1318.6 | 3.35 | A |
| 202 | 1261.51 | 1261.9 | 3.87 | A |
| 203 | 1293.79 | 1294.2 | 3.74 | A |
| 204 | 1205.98 | 1206.5 | 3.67 | B |
| 205 | 1278.56 | 1279.0 | 3.45 | B |
| 206 | 1310.83 | 1311.35 | 3.30 | B |
| 207 | 1209.98 | 1210.5 | 3.87 | B |
| 208 | 1205.73 | 1206.3 | 3.63 | B |
| 209 | 1205.75 | 1206.3 | 3.44 | B |
| 210 | 1278.33 | 1278.87 | 3.22 | B |
| 211 | 1310.61 | 1311.07 | 3.12 | B |
| 212 | 1231.25 | 1231.8 | 3.52 | B |
| 213 | 1216.75 | 1217.2 | 3.51 | B |
| 214 | 1216.50 | 1217.0 | 3.52 | B |
| 215 | 1181.44 | 1181.9 | 3.98 | B |
| 216 | 1254.02 | 1254.5 | 3.76 | B |
| 217 | 1286.30 | 1286.8 | 3.62 | B |
| 218 | 1216.74 | 1217.3 | 3.76 | B |
| 219 | 1205.50 | 1205.9 | 3.63 | B |
| 220 | 1209.73 | 1210.3 | 3.82 | B |
| 221 | 1231.98 | 1232.2 | 3.09 | A |
| 222 | 1253.51 | 1253.9 | 3.11 | A |

Abbreviations

Certain abbreviations are used in the examples and elsewhere herein:

"AA" refers to amino acid;

"AEEA" refers to [2-(2-aminoethoxy) ethoxy]acetyl;

"Aib" refers to 2-amino-isobutyric acid;

"Boc" refers to tert-butyloxycarbonyl;

"tBu" refers to tertiary butyl;

"DCM" refers to dichloromethane;

"Dde" refers to 1-(4,4-dimethyl-2,6-dioxocyclohexylidene)-ethyl;

"DIC" refers to N,N'-diisopropylcarbodiimide;

"DMF" refers to dimethyl formamide;

"Fmoc" refers to fluorenylmethyloxycarbonyl;

"gGlu" refers to gamma-glutamate (yE);

"HOAt" refers to 1-hydroxy-7-azabenzotriazole;

"HPLC" refers to High Performance Liquid Chromatography;

"LC/MS" refers to Liquid Chromatography/Mass Spectrometry;

"MS" refers to mass spectrometry;

"NMP" refers to N-Methyl-2-pyrrolidone;

"OtBu" refers to O-tert-butyl;

"Oxyma" refers to ethyl cyanohydroxyiminoacetate;

"Pbf" refers to 2,2,4,6,7-pentamethyldihydrobenzofuran-5-sulfonyl;

"RP-HPLC" refers to reversed-phase high performance liquid chromatography;

"TIPS" refers to triisopropylsilane;

"TFA" refers to trifluoroacetic acid;

"Trt" refers to trityl;

Example 19.9: Assessment of Activity at Human CRF2 α Receptor of these FA Modified Peptides Agonism of compounds for human corticotropin-releasing factor 2α (CRF2α receptor) was determined by a functional assay measuring cAMP modulation upon treatment of TeloHEAC cells stably expressing human CRF2α receptor.

Compounds were dissolved at 0.5 mM in 100% DMSO and serially diluted (1:2) in 100% DMSO for 16 dilutions. 20 nL of each dilution was then transferred to 384-well assay plate using an acoustic droplet ejection instrument. 5 μL of compound buffer (1×HBSS; 20 mM HEPES, 2 mM IBMX, 0% or 0.2% HSA) were then added to each well.

Prior to use, frozen cells were thawed quickly at 37° C. and washed (5 min at 900 rpm) with 20 mL cell buffer (1×HBSS; 20 mM HEPES). Cells were resuspended in cell buffer and adjusted to a cell density of 800.000 cells/ml.

5 μL cells (final dell density: 4000 cells/well) were dispensed in the compound-containing 384-well assay plate and incubated for 30 minutes 37° C.

The CAMP level in treated cells was determined using the Cisbio 62AM4PEC kit according to manufacturer's instruction. Finally, plates were incubated for 1 h at room temperature before measuring the fluorescence ratio between 665/620 nm.

The percent activity value (E %) was calculated by setting 100 nM of urocortin 2 (UCN2) as 100%. The in vitro potency of the compounds was quantified by determining the concentrations that caused 50% activation of maximal response (EC50) relative to urocortin 2.

Representative EC50 values are provided in Table 18 below:

TABLE 18

| SEQ ID NO. | EC50 [nM], 0% HSA |
|---|---|
| 187 | 0.44 |
| 188 | 0.46 |
| 189 | 3.49 |
| 190 | 2.47 |
| 191 | 2.68 |
| 192 | 0.83 |
| 193 | 0.82 |
| 194 | 0.11 |
| 195 | 0.34 |
| 196 | 1.08 |
| 197 | 2.27 |
| 198 | 0.49 |
| 199 | 1.39 |
| 200 | 8.70 |
| 201 | 4.66 |
| 202 | 0.87 |
| 203 | 4.70 |
| 204 | 0.14 |
| 205 | 0.32 |
| 206 | 0.09 |
| 207 | 0.68 |
| 208 | 0.90 |
| 209 | 8.62 |
| 210 | 2.98 |
| 211 | 0.94 |
| 212 | 1.23 |
| 213 | 4.48 |
| 214 | 4.15 |
| 215 | 0.15 |
| 216 | 0.19 |
| 217 | 0.16 |

TABLE 18-continued

| SEQ ID NO. | EC50 [nM], 0% HSA |
|---|---|
| 218 | 1.58 |
| 219 | 5.98 |
| 220 | 1.48 |
| 221 | 2.71 |
| 222 | 7.38 |

Example 19.10: Assessment of Activity at Anti-Target CFR1R Receptor of the Compounds According to the Invention The CRF1R-overexpression CHO-K1 cell line clone 2 was purchased from PerkinElmer.

Cells were grown in a 10 cm dish at 37° C./5% CO2 in medium (F12 (Hams)/10% FBS/400 μg/ml G418) to near confluence. At that stage, cells were harvested, resuspended to 10 million/mL in culture medium without G418 and with 10% DMSO. 1 mL vial aliquots were slowly frozen to -80° C. in isopropanol and then transferred in liquid nitrogen for storage. These vials were used to run the experiment following the procedure reported 10 in the previous paragraph, except for the compound used in the control well to define the 100% activation (Sauvagine at 100 nM)

Representative EC50 and Emax values are provided in Table 19 below:

TABLE 19

| SEQ ID NO. | EC50 [nM] 0% HSA | Emax (%) |
|---|---|---|
| 16 | >100 | 0.4 |
| 22 | >100 | 1.2 |
| 25 | >100 | 0.1 |
| 26 | >100 | 0.6 |
| 27 | >100 | 34.2 |
| 28 | >100 | 8.4 |
| 29 | >100 | 18.4 |
| 30 | >100 | 14.5 |
| 88 | >100 | 2.3 |
| 89 | >100 | 3.7 |
| 96 | >100 | 2.3 |
| 102 | >100 | 9.0 |
| 103 | >100 | 14.0 |
| 104 | >100 | 3.7 |
| 105 | >100 | 15.4 |
| 106 | >100 | 5.1 |
| 108 | >100 | −2.0 |
| 109 | >100 | 1.1 |
| 110 | >100 | 5.4 |
| 116 | >100 | 0.8 |
| 117 | >100 | −6.0 |
| 118 | >100 | 1.5 |
| 119 | >100 | 0.4 |
| 121 | >100 | −1.1 |
| 122 | >100 | 6.9 |
| 123 | >100 | 9.0 |
| 124 | >100 | −2.5 |
| 125 | >100 | 17.7 |
| 126 | >100 | 36.5 |
| 134 | >100 | −8.6 |
| 148 | >100 | 2.6 |
| 149 | >100 | 6.6 |
| 150 | >100 | 7.2 |
| 152 | >100 | 4.9 |
| 156 | >100 | 4.0 |
| 187 | >100 | 43.79 |
| 189 | >100 | 14.97 |
| 190 | >100 | 11.96 |
| 191 | >100 | 12.51 |
| 193 | >100 | 8.77 |
| 194 | >100 | 21.63 |
| 195 | >100 | 17.15 |
| 196 | >100 | 16.95 |
| 197 | >100 | 24.40 |
| 198 | >100 | 1.40 |
| 199 | >100 | −2.90 |
| 200 | >100 | 1.90 |
| 201 | >100 | −2.80 |
| 202 | >100 | 5.40 |
| 203 | >100 | 4.70 |
| 221 | >100 | 3.20 |
| 222 | >100 | 6.20 |
| 223 | 82.81 | 57.3 |
| 224 | >100 | 52.59 |
| 225 | 24.2 | 58.92 |
| 226 | 96.2 | 83.98 |

Notable in this table is an apparent effect on the presence of a free carboxylic acid in the FA modification of K12. See for example on how peptides 223, 225, and 226 all comprising the albumin binding moiety-gGlu-C(O)$(CH_2)_{14}CH_3$, compare to for examples peptides 222 and 224, comprising as albumin binding moieties respectively-gGlu-C(O)$(CH_2)_{14}COOH$ and -$\{AEEA\}_2$-gGlu-C(O)$(CH_2)_{18}COOH$. This is even more apparent for the side-to-side comparison (Table 20) of peptides only differing from one another in the presence of said free carboxylic acid.

TABLE 20

| Seq ID | CRF2 EC50 | CRF1 EC50 | CRF1/CRF2 ratio | Peptide seq id | RA |
|---|---|---|---|---|---|
| 219 | 5.98 | 13.48 | 2 | 174 | -gGlu-C(O)$(CH_2)_{14}CH_3$ |
| 197 | 2.27 | >100 | >500 | 174 | -gGlu-C(O)$(CH_2)_{14}COOH$ |
| 208 | 0.9 | 1.43 | 2 | 135 | -gGlu-C(O)$(CH_2)_{14}CH_3$ |
| 188 | 0.46 | 69.09 | 134 | 135 | -gGlu-C(O)$(CH_2)_{14}COOH$ |
| 214 | 4.15 | 4.27 | 1 | 139 | -gGlu-C(O)$(CH_2)_{14}CH_3$ |
| 192 | 0.83 | 56.56 | 68 | 139 | -gGlu-C(O)$(CH_2)_{14}COOH$ |
| 212 | 1.23 | 0.9 | 1 | 137 | -gGlu-C(O)$(CH_2)_{14}CH_3$ |
| 190 | 2.47 | >100 | >500 | 137 | -gGlu-C(O)$(CH_2)_{14}COOH$ |
| 218 | 1.58 | 6.97 | 4 | 151 | -gGlu-C(O)$(CH_2)_{14}CH_3$ |
| 196 | 1.08 | >100 | >500 | 151 | -gGlu-C(O)$(CH_2)_{14}COOH$ |
| 207 | 0.68 | 4.18 | 6 | 83 | -gGlu-C(O)$(CH_2)_{14}CH_3$ |
| 193 | 0.82 | >100 | >500 | 83 | -gGlu-C(O)$(CH_2)_{14}COOH$ |
| 220 | 1.48 | 8.91 | 6 | 150 | -gGlu-C(O)$(CH_2)_{14}CH_3$ |
| 195 | 0.34 | >100 | >500 | 150 | -gGlu-C(O)$(CH_2)_{14}COOH$ |
| 209 | 8.62 | 21.73 | 3 | 136 | -gGlu-C(O)$(CH_2)_{14}CH_3$ |
| 189 | 3.49 | >100 | >500 | 136 | -gGlu-C(O)$(CH_2)_{14}COOH$ |

TABLE 20-continued

| Seq ID | CRF2 EC50 | CRF1 EC50 | CRF1/CRF2 ratio | Peptide seq id | RA |
|---|---|---|---|---|---|
| 204 | 0.14 | 0.44 | 3 | 130 | -gGlu-C(O)$(CH_2)_{14}CH_3$ |
| 187 | 0.44 | >100 | >500 | 130 | -gGlu-C(O)$(CH_2)_{14}$COOH |

It has also been observed (data not shown) that extending the linker, such as -$\{AEEA\}_2$-gGlu- and -$\{AEEA\}_2$-$(gGlu)_2$-, of said albumin binding moieties, comprising a free carboxylic acid even further improves the CRF2 selectivity of the peptides.

Example 19.11: DMPK Protocols and Results of these FA Modified Peptides In Vitro Plasma Stability In vitro plasma metabolic stability was studied in male Sprague Dawley rats and human. Test compound were incubated at 3 mM for 2 hours at 37° C. At each time point (0, 0.25, 1 and 2 h), samples were prepared for analysis by means of a single step protein precipitation technique by adding 150 μL of ethanol, 0.1% formic acid to 50 μL aliquots of plasma. Samples were mixed by vortex for homogeneity and then subjected to centrifugation at 14000 rpm for 15 min. The supernatant (100 μL) was collected, diluted with 100 μL of water, 0.1% formic acid and analyzed by LC-HRMS (TripleTOF 6600+, AB Sciex). For each test compound, the area ratios at each time point were compared to the 0 h area ratio and converted to a percentage remaining.

Representative plasma stability data are provided in Table 21 below:

TABLE 21

| Seq ID | Species | % remaining at 2 hours |
|---|---|---|
| 187 | Human | 97 |
| | Rat | 102 |
| | Rat | 92 |
| 189 | Human | 97 |
| | Rat | 101 |
| 190 | Human | 100 |
| | Rat | 92 |
| 191 | Human | 96 |
| | Rat | 85 |
| 192 | Human | 95 |
| | Rat | 109 |
| 193 | Human | 80 |
| | Rat | 84 |
| 194 | Human | 101 |
| | Rat | 85 |

Solubility and Chemical Stability

As for example 15 above, also the chemical stability of representative examples of these FA modified peptides has been assessed, using LC-UV instead of light scattering. Solubility and chemical stability were studied in 100 mM phosphate buffer (pH 7.4) and 100 mM acetate buffer (pH 4.5). Test compound powders were dissolved in both buffers at a target concentration of 10 mg/mL and incubated for 1 hour at room temperature. After centrifugation at 2500 rcf for 15 minutes, 10 mL of supernatant was diluted with 190 mL of the incubation buffer and analyzed by LC-UV (Acquity UPLC-DAD, Waters). Solubility was calculated by comparing the peak area of the test compound in the buffer sample with the peak area of the same compound dissolved at 0.5 mg/ml in water:acetonitrile 1:1, 0.1% formic acid.

From the centrifuged supernatant, two additional 80 mL aliquots were collected and diluted with 160 mL of incubation buffer. One aliquot was stored at 5° C., while the other was stored at 40° C. After 28 days, the samples were analyzed by LC-UV. Chemical stability was calculated as % loss using the following equations:

Chemical stability (as % loss)=[(purity after 28 days at 5° C.)−(purity after 28 days at 40° C.)]×100/(purity after 28 days at 5° C.)

% purity=[(peak area compound)×100/(total peak area)]

Representative buffer solubility data are provided in Table 22 below:

TABLE 22

| Seq ID | pH | Solubility (mg/mL) |
|---|---|---|
| 187 | 7.4 | 8.8 |
| | 4.5 | 8.2 |
| 188 | 7.4 | 7.9 |
| | 4.5 | 8.3 |
| 189 | 7.4 | 6.3 |
| | 4.5 | 9.0 |
| 190 | 7.4 | 8.5 |
| | 4.5 | 8.5 |
| 191 | 7.4 | 9.0 |
| | 4.5 | 8.5 |
| 192 | 7.4 | 7.9 |
| | 4.5 | 8.4 |
| 193 | 7.4 | 0.1 |
| | 4.5 | 8.6 |
| 194 | 7.4 | 0.7 |
| | 4.5 | 7.3 |

Representative chemical stability data are provided in Table 23 below:

TABLE 23

| Seq ID | pH | % loss |
|---|---|---|
| 187 | 7.4 | 31 |
| | 4.5 | 0 |
| 188 | 7.4 | 40 |
| | 4.5 | 0 |
| 189 | 7.4 | 48 |
| | 4.5 | 0 |
| 190 | 7.4 | 35 |
| | 4.5 | 0 |
| 191 | 7.4 | 54 |
| | 4.5 | 0 |
| 192 | 7.4 | 49 |
| | 4.5 | 0 |

All sequences disclosed herein are listed in the appended sequence listing, the entire content of which forms a part of this specification.

All publications, patent applications, patents, and other references mentioned herein are incorporated by reference in their entirety. In addition, the materials, methods, and examples given are illustrative only and not intended to be limiting. Unless otherwise defined, all technical and scientific terms used herein have the same meaning as commonly understood by one of ordinary skill in the art to which this invention belongs. It is to be understood that while the disclosure has been described in conjunction with the detailed description thereof, the foregoing description is intended to illustrate and not limit the scope of the invention, which is defined by the scope of the appended claims. Other aspects, advantages, and modifications are within the scope of the claims.

The invention claimed is:

1. A compound which is a peptide, the peptide comprising the amino acid sequence of formula (I):

X1-X2-L-S-L-D-X7-P-X9-X10-X11-X12-X13-X14-L-X16-X17-Q-X19-X20-X21-X22-X23-X24-X25-X26-X27-A-X29-X30-X31-X32-X33-X34-L-X36-X37-X38 Formula (I)

or a pharmaceutically acceptable salt thereof, wherein:

X1 is isoleucine (I) or phenylalanine (F);

X2 is valine (V) or threonine (T);

X7 is valine (V) or D-valine (v);

X9 is isoleucine (I) or threonine (T);

X10 is lysine (K), glutamate (E), histidine (H), or glycine (G);

X11 is isoleucine (I) or leucine (L);

X12 is lysine (K), wherein the epsilon-amino group of the lysine side chain is covalently bound to an albumin-binding moiety;

X13 is glutamine (Q) or lysine (K);

X14 is isoleucine (I), lysine (K), or 2-aminoisobutyric acid (Aib);

X16 is leucine (L) or phenylalanine (F);

X17 is glutamate (E) or lysine (K);

X19 is alanine (A), glutamate (E), or glutamine (Q);

X20 is lysine (K) or arginine (R);

X21 is glutamine (Q) or lysine (K);

X22 is lysine (K), arginine (R), or glutamate (E);

X23 is lysine (K) or 2-aminoisobutyric acid (Aib);

X24 is glutamine (Q), 2-aminoisobutyric acid (Aib), leucine (L), or glutamate (E);

X25 is arginine (R), lysine (K), or 2-aminoisobutyric acid (Aib);

X26 is alanine (A), glutamate (E), 2-aminoisobutyric acid (Aib), or glutamine (Q);

X27 is glutamine (Q), 2-aminoisobutyric acid (Aib), or lysine (K);

X29 is glutamate (E) or lysine (K);

X30 is lysine (K) or threonine (T);

X31 is asparagine (N) or alanine (A);

X32 is lysine (K), alanine (A), valine (V), threonine (T), glutamate (E), or 2-aminoisobutyric acid (Aib);

X33 is arginine (R), lysine (K), or glutamine (Q);

X34 is isoleucine (I) or leucine (L);

X36 is alanine (A) or glutamate (E);

X37 is glutamine (Q) or arginine (R); and

X38 is isoleucine (I) or valine (V); and wherein the albumin-binding moiety is a group of the formula (II):

$$—Z^1—Y—Z^2—C(O)R^1 \quad (II)$$

wherein:

Y is AEEA, {AEEA}$_2$, {AEEA}$_3$, Gly, {Gly}$_2$, {Gly}$_3$, N-MeGly, {N-MeGly}$_2$, {N-MeGly}$_3$ or absent, wherein Y is absent when $Z^2$ is gGlu, or {gGlu}$_2$, and wherein AEEA denotes [2-(2-amino-ethoxy)ethoxy]-acetyl;

$Z^1$ and $Z^2$ are each independently selected from gGlu, {gGlu}$_2$, {gGlu}$_3$, {gGlu}$_4$ or absent, wherein $Z^1$ is absent when Y is {AEEA}$_2$ and $Z^2$ is gGlu or {gGlu}$_2$; and $R^1$ is —$(CH_2)_x$COOH or —$(CH_2)_x CH_3$, wherein x is an integer from 12 to 22.

2. The compound of claim 1, wherein the albumin-binding moiety is selected from the following groups:

-(gGlu)$_{n=1-4}$-C(O)$(CH_2)_{14}CH_3$;

-(gGlu)$_{n=1-4}$-C(O)$(CH_2)_{14}$COOH;

-(gGlu)$_{n=1-4}$-C(O)$(CH_2)_{16}CH_3$;

-(gGlu)$_{n=1-4}$-C(O)$(CH_2)_{16}$COOH;

-(gGlu)$_{n=1-4}$-C(O)$(CH_2)_{18}CH_3$;

-(gGlu)$_{n=1-4}$-C(O)$(CH_2)_{18}$COOH;

-(AEEA)$_{n=1,2}$-(gGlu)$_{n=1-4}$-C(O)$(CH_2)_{14}CH_3$;

-(AEEA)$_{n=1,2}$-(gGlu)$_{n=1-4}$-C(O)$(CH_2)_{14}$COOH;

-(AEEA)$_{n=1,2}$-(gGlu)$_{n=1-4}$-C(O)$(CH_2)_{16}CH_3$;

-(AEEA)$_{n=1,2}$-(gGlu)$_{n=1-4}$-C(O)$(CH_2)_{16}$COOH;

-(AEEA)$_{n=1,2}$-(gGlu)$_{n=1-4}$-C(O)$(CH_2)_{18}CH_3$;

-(AEEA)$_{n=1,2}$-(gGlu)$_{n=1-4}$-C(O)$(CH_2)_{18}$COOH;

-(gGlu)$_{n=1-4}$-(AEEA)$_{n=1,2}$-(gGlu)$_{n=1-4}$-C(O)$(CH_2)_{14}CH_3$;

-(gGlu)$_{n=1-4}$-(AEEA)$_{n=1,2}$-(gGlu)$_{n=1-4}$-C(O)$(CH_2)_{14}$COOH;

-(gGlu) n=1-4 (AEEA)$_{n=1,2}$-(gGlu)$_{n=1-4}$-C(O)$(CH_2)_{16}CH_3$;

-(gGlu)$_{n=1-4}$-(AEEA)$_{n=1,2}$-(gGlu)$_{n=1-4}$-C(O)$(CH_2)_{16}$COOH;

-(gGlu)$_{n=1-4}$-(AEEA)$_{n=1,2}$-(gGlu)$_{n=1-4}$-C(O)$(CH_2)_{18}CH_3$; and

-(gGlu)$_{n=1-4}$-(AEEA)$_{n=1,2}$-(gGlu)$_{n=1-4}$-C(O)$(CH_2)_{18}$COOH.

3. The compound of claim 1, wherein:

X1 is isoleucine (I);

X2 is valine (V);

X7 is valine (V) or D-valine (v);

X9 is isoleucine (I) or threonine (T);

X10 is lysine (K) or glycine (G);

X11 is leucine (L);

X13 is lysine (K) or glutamine (Q);

X14 is lysine (K) or isoleucine (I);

X16 is leucine (L);

X19 is alanine (A) or glutamate (E);

X21 is glutamine (Q);

X22 is glutamate (E), arginine (R) or lysine (K);

X23 is lysine (K) or 2-aminoisobutyric acid (Aib);

X24 is glutamate (E) or glutamine (Q) or 2-aminoisobutyric acid (Aib);

X25 is lysine (K) or arginine (R);

X26 is alanine (A), glutamate (E) or glutamine (Q);

X27 is 2-aminoisobutyric acid (Aib); lysine (K) or glutamine (Q);

X29 is glutamate (E);

X30 is lysine (K) or threonine (T);

X31 is asparagine (N);

X32 is lysine (K) or alanine (A);

X33 is arginine (R) or glutamine (Q);

X34 is isoleucine (I);

X36 is alanine (A) or glutamate (E);

X37 is arginine (R) or glutamine (Q); and

X38 is valine (V).

4. The compound of claim 1, wherein:

X7 is D-valine (v);

X10 is lysine (K) or glycine (G);

X19 is alanine (A) or glutamate (E);

X23 is 2-aminoisobutyric acid (Aib), or lysine (K);

X24 is 2-aminoisobutyric acid (Aib), or glutamine (Q);

X25 is arginine (R);

X26 is glutamine (Q), alanine (A) or glutamate (E);

X27 is glutamine (Q) or lysine (K);

X30 is threonine (T) or lysine (K);

X33 is arginine (R) or glutamine (Q);

X36 is alanine (A) or glutamate (E); and

X37 is arginine (R) or glutamine (Q).

5. The compound of claim 1, wherein:

X10 is lysine;

X19 is glutamate (E);

X24 is glutamine (Q);

X25 is arginine (R);

X26 is glutamate (E);

X27 is glutamine (Q);

X30 is lysine (K);

X33 is glutamine (Q);

X36 is alanine (A); and

X37 is glutamine (Q).

6. The compound of claim 1, wherein the compound is a peptide of the amino acid sequence of formula (I) or a pharmaceutically acceptable salt thereof, optionally wherein the amino acid residue at X1 is acetylated, and optionally wherein the amino acid residue at X38 is amidated.

7. The compound of claim 6, wherein the amino acid residue at X38 is amidated as a C-terminal primary amide.

8. The compound of claim 1, wherein the albumin-binding moiety is selected from the following groups:

-(gGlu)$_{n=1-4}$-C(O)$(CH_2)_{14}$COOH;

-(gGlu)$_{n=1-4}$-C(O)$(CH_2)_{16}$COOH;

-(gGlu)$_{n=1-4}$-C(O)$(CH_2)_{18}$COOH;

-(AEEA)$_{n=1,2}$-(gGlu)$_{n=1-4}$-C(O)$(CH_2)_{14}$COOH;

-(AEEA)$_{n=1,2}$-(gGlu)$_{n=1-4}$-C(O)$(CH_2)_{16}$COOH;

-(AEEA)$_{n=1,2}$-(gGlu)$_{n=1-4}$-C(O)$(CH_2)_{18}$COOH;

-(gGlu)$_{n=1-4}$-(AEEA)$_{n=1,2}$-(gGlu)$_{n=1-4}$-C(O)$(CH_2)_{14}$COOH;

-(gGlu)$_{n=1-4}$-(AEEA)$_{n=1,2}$-(gGlu)$_{n=1-4}$-C(O)$(CH_2)_{16}$COOH; and

-(gGlu)$_{n=1-4}$-(AEEA)$_{n=1,2}$-(gGlu)$_{n=1-4}$-C(O)$(CH_2)_{18}$COOH.

9. The compound of claim 1, wherein the albumin-binding moiety is -{AEEA}$_2$-gGlu-C(O)$(CH_2)_{14}$COOH or -{AEEA}$_2$gGlu-C(O)$(CH_2)_{16}$COOH.

10. The compound of claim 1, wherein the compound is a peptide of any one of SEQ ID NOs: 1 to 227 or a pharmaceutically acceptable salt thereof.

11. The compound of claim 1, wherein the compound is a peptide of any one of SEQ ID NOs: 3, 7, 35, 83, 130, 135, 136, 137, 138, 139, 140, 141, 142, 147, 149, 151, 152, 171, 172, 173, and 174, or a pharmaceutically acceptable salt thereof.

12. A pharmaceutical composition comprising a compound of claim 1 and a pharmaceutically acceptable excipient, diluent, or carrier.

* * * * *

SEQUENCE LISTING

```
<160> NUMBER OF SEQ ID NOS: 227

<210> SEQ ID NO 1
<211> LENGTH: 38
<212> TYPE: PRT
<213> ORGANISM: Artificial Sequence
<220> FEATURE:
<223> OTHER INFORMATION: compound Seq_1
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 1

Ile Val Leu Ser Leu Asp Val Pro Ile Gly Leu Lys Gln Ile Leu Leu
1               5                   10                  15

Glu Gln Glu Lys Gln Glu Lys Glu Lys Gln Gln Ala Glu Thr Asn Ala
            20                  25                  30

Gln Ile Leu Ala Gln Val
        35


<210> SEQ ID NO 2
<211> LENGTH: 38
<212> TYPE: PRT
<213> ORGANISM: Artificial Sequence
<220> FEATURE:
<223> OTHER INFORMATION: compound Seq_2
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 2

Ile Val Leu Ser Leu Asp Val Pro Ile Lys Leu Lys Lys Ile Leu Leu
1               5                   10                  15

Glu Gln Glu Lys Gln Glu Lys Glu Lys Gln Gln Ala Glu Thr Asn Ala
            20                  25                  30

Gln Ile Leu Ala Gln Val
        35


<210> SEQ ID NO 3
<211> LENGTH: 38
<212> TYPE: PRT
<213> ORGANISM: Artificial Sequence
<220> FEATURE:
<223> OTHER INFORMATION: compound Seq_3
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-gGlu-C(O)(CH2)14CH3
<220> FEATURE:
```

-continued

<221> NAME/KEY: MOD_RES
<222> LOCATION: 38
<223> OTHER INFORMATION: C-terminal amino acid residue is amidated as a
      primary amide

<400> SEQUENCE: 3

Ile Val Leu Ser Leu Asp Val Pro Ile Lys Leu Lys Lys Ile Leu Leu
1               5                   10                  15

Glu Gln Glu Lys Gln Glu Lys Glu Lys Gln Gln Ala Glu Lys Asn Ala
            20                  25                  30

Gln Ile Leu Ala Gln Val
        35

<210> SEQ ID NO 4
<211> LENGTH: 38
<212> TYPE: PRT
<213> ORGANISM: Artificial Sequence
<220> FEATURE:
<223> OTHER INFORMATION: compound Seq_4
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is ”-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 4

Ile Val Leu Ser Leu Asp Val Pro Ile Gly Leu Lys Gln Lys Leu Leu
1               5                   10                  15

Lys Gln Glu Lys Gln Glu Lys Glu Lys Gln Gln Ala Glu Thr Asn Ala
            20                  25                  30

Lys Ile Leu Ala Gln Val
        35

<210> SEQ ID NO 5
<211> LENGTH: 38
<212> TYPE: PRT
<213> ORGANISM: Artificial Sequence
<220> FEATURE:
<223> OTHER INFORMATION: compound Seq_5
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is “-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 5

Ile Val Leu Ser Leu Asp Val Pro Ile Gly Leu Lys Gln Lys Leu Leu
1               5                   10                  15

Lys Gln Gln Arg Gln Arg Lys Glu Arg Gln Gln Ala Glu Thr Asn Ala
            20                  25                  30

Arg Ile Leu Ala Arg Val
        35

<210> SEQ ID NO 6
<211> LENGTH: 38
<212> TYPE: PRT
<213> ORGANISM: Artificial Sequence
<220> FEATURE:
<223> OTHER INFORMATION: compound Seq_6
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a primary amide

<400> SEQUENCE: 6

```
Ile Val Leu Ser Leu Asp Val Pro Ile Gly Leu Lys Gln Lys Leu Leu
1               5                   10                  15

Lys Gln Gln Arg Gln Arg Lys Glu Arg Gln Gln Ala Glu Lys Asn Ala
            20                  25                  30

Arg Ile Leu Ala Arg Val
        35
```

<210> SEQ ID NO 7
<211> LENGTH: 38
<212> TYPE: PRT
<213> ORGANISM: Artificial Sequence
<220> FEATURE:
<223> OTHER INFORMATION: compound Seq_7
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a primary amide

<400> SEQUENCE: 7

```
Ile Val Leu Ser Leu Asp Xaa Pro Thr Lys Leu Lys Gln Lys Leu Leu
1               5                   10                  15

Lys Gln Glu Arg Gln Arg Lys Glu Arg Glu Gln Ala Glu Lys Asn Ala
            20                  25                  30

Arg Ile Leu Ala Arg Val
        35
```

<210> SEQ ID NO 8
<211> LENGTH: 38
<212> TYPE: PRT
<213> ORGANISM: Artificial Sequence
<220> FEATURE:
<223> OTHER INFORMATION: compound Seq_8
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a primary amide

<400> SEQUENCE: 8

```
Phe Thr Leu Ser Leu Asp Val Pro Thr Lys Ile Lys Gln Lys Leu Leu
1               5                   10                  15
```

-continued

```
Lys Gln Glu Lys Gln Lys Lys Gln Arg Gln Lys Ala Lys Thr Ala Ala
            20                  25                  30

Gln Ile Leu Ala Gln Val
        35


<210> SEQ ID NO 9
<211> LENGTH: 38
<212> TYPE: PRT
<213> ORGANISM: Artificial Sequence
<220> FEATURE:
<223> OTHER INFORMATION: compound Seq_9
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 9

Phe Thr Leu Ser Leu Asp Val Pro Thr Lys Ile Lys Gln Lys Leu Leu
1               5                   10                  15

Lys Gln Glu Lys Gln Lys Lys Gln Arg Gln Lys Ala Lys Thr Ala Lys
            20                  25                  30

Gln Ile Leu Glu Gln Val
        35


<210> SEQ ID NO 10
<211> LENGTH: 38
<212> TYPE: PRT
<213> ORGANISM: Artificial Sequence
<220> FEATURE:
<223> OTHER INFORMATION: compound Seq_10
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 10

Phe Thr Leu Ser Leu Asp Val Pro Thr Lys Ile Lys Gln Lys Leu Leu
1               5                   10                  15

Lys Gln Glu Lys Gln Lys Lys Gln Arg Gln Lys Ala Lys Thr Asn Lys
            20                  25                  30

Gln Ile Leu Glu Gln Val
        35


<210> SEQ ID NO 11
<211> LENGTH: 38
<212> TYPE: PRT
<213> ORGANISM: Artificial Sequence
<220> FEATURE:
<223> OTHER INFORMATION: compound Seq_11
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-gGlu-C(O)(CH2)14CH3
<220> FEATURE:
<221> NAME/KEY: MOD_RES
```

<222> LOCATION: 38
<223> OTHER INFORMATION: C-terminal amino acid residue is amidated as a
      primary amide

<400> SEQUENCE: 11

```
Phe Thr Leu Ser Leu Asp Val Pro Thr Lys Ile Lys Gln Lys Leu Leu
1               5                   10                  15

Lys Gln Glu Lys Gln Lys Lys Gln Arg Gln Lys Ala Lys Thr Asn Ala
            20                  25                  30

Gln Ile Leu Ala Gln Val
        35
```

<210> SEQ ID NO 12
<211> LENGTH: 38
<212> TYPE: PRT
<213> ORGANISM: Artificial Sequence
<220> FEATURE:
<223> OTHER INFORMATION: compound Seq_12
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 12

```
Phe Thr Leu Ser Leu Asp Val Pro Thr Lys Ile Lys Gln Lys Leu Leu
1               5                   10                  15

Lys Gln Glu Lys Gln Arg Lys Gln Lys Gln Gln Ala Lys Thr Asn Ala
            20                  25                  30

Lys Ile Leu Ala Arg Val
        35
```

<210> SEQ ID NO 13
<211> LENGTH: 38
<212> TYPE: PRT
<213> ORGANISM: Artificial Sequence
<220> FEATURE:
<223> OTHER INFORMATION: compound Seq_13
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is
      "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 13

```
Phe Thr Leu Ser Leu Asp Val Pro Thr Lys Ile Lys Gln Ile Leu Phe
1               5                   10                  15

Lys Gln Gln Lys Gln Lys Lys Glu Arg Gln Gln Ala Glu Lys Asn Lys
            20                  25                  30

Gln Leu Leu Glu Gln Ile
        35
```

<210> SEQ ID NO 14
<211> LENGTH: 38
<212> TYPE: PRT
<213> ORGANISM: Artificial Sequence

```
<220> FEATURE:
<223> OTHER INFORMATION: compound Seq_14
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 14

Phe Thr Leu Ser Leu Asp Val Pro Thr Lys Ile Lys Gln Lys Leu Leu
1               5                   10                  15

Lys Gln Glu Lys Gln Arg Lys Gln Lys Gln Lys Ala Lys Thr Asn Ala
            20                  25                  30

Lys Ile Leu Ala Arg Val
        35


<210> SEQ ID NO 15
<211> LENGTH: 38
<212> TYPE: PRT
<213> ORGANISM: Artificial Sequence
<220> FEATURE:
<223> OTHER INFORMATION: compound Seq_15
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 15

Phe Thr Leu Ser Leu Asp Val Pro Thr Lys Ile Lys Gln Lys Leu Phe
1               5                   10                  15

Lys Gln Ala Lys Gln Lys Lys Gln Arg Gln Lys Ala Lys Thr Asn Ala
            20                  25                  30

Gln Ile Leu Ala Arg Val
        35


<210> SEQ ID NO 16
<211> LENGTH: 38
<212> TYPE: PRT
<213> ORGANISM: Artificial Sequence
<220> FEATURE:
<223> OTHER INFORMATION: compound Seq_16
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is
      "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 16

Ile Val Leu Ser Leu Asp Val Pro Ile Gly Leu Lys Gln Lys Leu Leu
1               5                   10                  15

Lys Gln Gln Arg Gln Arg Lys Glu Arg Gln Gln Ala Glu Lys Asn Ala
            20                  25                  30
```

Arg Ile Leu Ala Arg Val
35

<210> SEQ ID NO 17
<211> LENGTH: 38
<212> TYPE: PRT
<213> ORGANISM: Artificial Sequence
<220> FEATURE:
<223> OTHER INFORMATION: compound Seq_17
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a primary amide

<400> SEQUENCE: 17

Ile Val Leu Ser Leu Asp Val Pro Ile Lys Leu Lys Lys Ile Leu Leu
1 5 10 15

Glu Gln Glu Lys Gln Lys Lys Gln Arg Glu Gln Ala Glu Thr Asn Lys
20 25 30

Gln Ile Leu Ala Gln Val
35

<210> SEQ ID NO 18
<211> LENGTH: 38
<212> TYPE: PRT
<213> ORGANISM: Artificial Sequence
<220> FEATURE:
<223> OTHER INFORMATION: compound Seq_18
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a primary amide

<400> SEQUENCE: 18

Ile Val Leu Ser Leu Asp Xaa Pro Thr Lys Leu Lys Gln Lys Leu Leu
1 5 10 15

Lys Gln Glu Arg Gln Arg Lys Glu Arg Glu Gln Ala Glu Lys Asn Lys
20 25 30

Arg Ile Leu Glu Arg Val
35

<210> SEQ ID NO 19
<211> LENGTH: 38
<212> TYPE: PRT
<213> ORGANISM: Artificial Sequence
<220> FEATURE:
<223> OTHER INFORMATION: compound Seq_19
<220> FEATURE:
<221> NAME/KEY: VARIANT
<222> LOCATION: 7
<223> OTHER INFORMATION: D-valine (v)
<220> FEATURE:
<221> NAME/KEY: VARIANT -continued

```
<222> LOCATION: 12
<223> OTHER INFORMATION: K* denotes the modified lysine residue at X12,
      Ra denotes the albumin-binding moiety, Ra is "-gGlu-C(O)(CH2)14CH3
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 19

Ile Val Leu Ser Leu Asp Xaa Pro Thr Lys Leu Lys Gln Lys Leu Leu
1               5                   10                  15

Lys Gln Glu Arg Gln Arg Xaa Glu Arg Glu Gln Ala Glu Lys Asn Lys
            20                  25                  30

Arg Ile Leu Glu Arg Val
        35


<210> SEQ ID NO 20
<211> LENGTH: 38
<212> TYPE: PRT
<213> ORGANISM: Artificial Sequence
<220> FEATURE:
<223> OTHER INFORMATION: compound Seq_20
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-gGlu-C(O)(CH2)14CH3
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 20

Ile Val Leu Ser Leu Asp Xaa Pro Thr Lys Leu Lys Gln Lys Leu Leu
1               5                   10                  15

Lys Gln Glu Arg Gln Arg Lys Xaa Arg Glu Gln Ala Glu Lys Asn Lys
            20                  25                  30

Arg Ile Leu Glu Arg Val
        35


<210> SEQ ID NO 21
<211> LENGTH: 38
<212> TYPE: PRT
<213> ORGANISM: Artificial Sequence
<220> FEATURE:
<223> OTHER INFORMATION: compound Seq_21
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-gGlu-C(O)(CH2)14CH3
<220> FEATURE:
<221> NAME/KEY: VARIANT
```

<222> LOCATION: 25
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 21

```
Ile Val Leu Ser Leu Asp Xaa Pro Thr Lys Leu Lys Gln Lys Leu Leu
1               5                   10                  15

Lys Gln Glu Arg Gln Arg Lys Glu Xaa Glu Gln Ala Glu Lys Asn Lys
            20                  25                  30

Arg Ile Leu Glu Arg Val
        35
```

<210> SEQ ID NO 22
<211> LENGTH: 38
<212> TYPE: PRT
<213> ORGANISM: Artificial Sequence
<220> FEATURE:
<223> OTHER INFORMATION: compound Seq_22
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 22

```
Ile Val Leu Ser Leu Asp Val Pro Ile Lys Leu Lys Gln Ile Leu Leu
1               5                   10                  15

Lys Gln Glu Arg Gln Lys Xaa Gln Arg Gln Lys Ala Glu Lys Asn Lys
            20                  25                  30

Gln Ile Leu Ala Gln Val
        35
```

<210> SEQ ID NO 23
<211> LENGTH: 38
<212> TYPE: PRT
<213> ORGANISM: Artificial Sequence
<220> FEATURE:
<223> OTHER INFORMATION: compound Seq_23
<220> FEATURE:
<221> NAME/KEY: VARIANT
<222> LOCATION: 7
<223> OTHER INFORMATION: D-valine (D)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-gGlu-C(O)(CH2)14CH3
<220> FEATURE:
<221> NAME/KEY: VARIANT
<222> LOCATION: 26
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 23

Ile Val Leu Ser Leu Asp Xaa Pro Thr Lys Leu Lys Gln Lys Leu Leu
1 5 10 15

Lys Gln Glu Arg Gln Arg Lys Glu Arg Xaa Gln Ala Glu Lys Asn Lys
20 25 30

Arg Ile Leu Glu Arg Val
35

<210> SEQ ID NO 24
<211> LENGTH: 38
<212> TYPE: PRT
<213> ORGANISM: Artificial Sequence
<220> FEATURE:
<223> OTHER INFORMATION: compound Seq_24
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 24

Ile Val Leu Ser Leu Asp Xaa Pro Thr Lys Leu Lys Gln Lys Leu Leu
1 5 10 15

Lys Gln Glu Arg Gln Arg Lys Glu Arg Glu Gln Ala Glu Lys Asn Lys
20 25 30

Arg Ile Leu Glu Arg Val
35

<210> SEQ ID NO 25
<211> LENGTH: 38
<212> TYPE: PRT
<213> ORGANISM: Artificial Sequence
<220> FEATURE:
<223> OTHER INFORMATION: compound Seq_25
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a primary amide

<400> SEQUENCE: 25

Ile Val Leu Ser Leu Asp Xaa Pro Thr Lys Leu Lys Lys Lys Leu Leu
1 5 10 15

Lys Gln Glu Arg Lys Arg Lys Glu Arg Glu Lys Ala Glu Lys Asn Ala
20 25 30

Arg Ile Leu Glu Arg Val
35

-continued

<210> SEQ ID NO 26
<211> LENGTH: 38
<212> TYPE: PRT
<213> ORGANISM: Artificial Sequence
<220> FEATURE:
<223> OTHER INFORMATION: compound Seq_26
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-gGlu-C(O)(CH2)14CH3
<220> FEATURE:
<221> NAME/KEY: VARIANT
<222> LOCATION: 27
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 26

```
Ile Val Leu Ser Leu Asp Xaa Pro Thr Lys Leu Lys Lys Lys Leu Leu
1               5                   10                  15

Lys Gln Glu Arg Lys Arg Lys Glu Arg Glu Xaa Ala Glu Lys Asn Ala
            20                  25                  30

Arg Ile Leu Glu Arg Val
        35
```

<210> SEQ ID NO 27
<211> LENGTH: 38
<212> TYPE: PRT
<213> ORGANISM: Artificial Sequence
<220> FEATURE:
<223> OTHER INFORMATION: compound Seq_27
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 27

```
Ile Val Leu Ser Leu Asp Xaa Pro Thr Lys Leu Lys Lys Lys Leu Leu
1               5                   10                  15

Lys Gln Glu Arg Lys Arg Lys Glu Arg Glu Gln Ala Glu Lys Asn Ala
            20                  25                  30

Arg Ile Leu Glu Arg Val
        35
```

<210> SEQ ID NO 28
<211> LENGTH: 38
<212> TYPE: PRT
<213> ORGANISM: Artificial Sequence
<220> FEATURE:
<223> OTHER INFORMATION: compound Seq_28
<220> FEATURE:
<221> NAME/KEY: VARIANT
<222> LOCATION: 7

-continued

<223> OTHER INFORMATION: D-valine (d)
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is ″-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 28

```
Ile Val Leu Ser Leu Asp Xaa Pro Thr Lys Leu Lys Lys Lys Leu Leu
1               5                   10                  15

Lys Gln Glu Arg Lys Arg Lys Glu Arg Glu Lys Ala Glu Lys Ala Ala
            20                  25                  30

Arg Ile Leu Glu Arg Val
        35
```

<210> SEQ ID NO 29
<211> LENGTH: 38
<212> TYPE: PRT
<213> ORGANISM: Artificial Sequence
<220> FEATURE:
<223> OTHER INFORMATION: compound Seq_29
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is ‶-gGlu-C(O)(CH2)14CH3
<220> FEATURE:
<221> NAME/KEY: VARIANT
<222> LOCATION: 27
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 29

```
Ile Val Leu Ser Leu Asp Xaa Pro Thr Lys Leu Lys Lys Lys Leu Leu
1               5                   10                  15

Lys Gln Glu Arg Lys Arg Lys Glu Arg Glu Xaa Ala Glu Lys Ala Ala
            20                  25                  30

Arg Ile Leu Glu Arg Val
        35
```

<210> SEQ ID NO 30
<211> LENGTH: 38
<212> TYPE: PRT
<213> ORGANISM: Artificial Sequence
<220> FEATURE:
<223> OTHER INFORMATION: compound Seq_30
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is ″-gGlu-C(O)(CH2)14CH3
<220> FEATURE:
<221> NAME/KEY: MOD_RES
<222> LOCATION: 38

<223> OTHER INFORMATION: C-terminal amino acid residue is amidated as a primary amide

<400> SEQUENCE: 30

```
Ile Val Leu Ser Leu Asp Xaa Pro Thr Lys Leu Lys Lys Lys Leu Leu
1               5                   10                  15

Lys Gln Glu Arg Lys Arg Lys Glu Arg Glu Gln Ala Glu Lys Ala Ala
            20                  25                  30

Arg Ile Leu Glu Arg Val
        35
```

<210> SEQ ID NO 31
<211> LENGTH: 38
<212> TYPE: PRT
<213> ORGANISM: Artificial Sequence
<220> FEATURE:
<223> OTHER INFORMATION: compound Seq_31
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-gGlu-C(O)(CH2)14CH3
<220> FEATURE:
<221> NAME/KEY: VARIANT
<222> LOCATION: 32
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 31

```
Ile Val Leu Ser Leu Asp Xaa Pro Thr Lys Leu Lys Gln Lys Leu Leu
1               5                   10                  15

Lys Gln Glu Arg Gln Arg Lys Glu Arg Glu Gln Ala Glu Lys Asn Xaa
            20                  25                  30

Arg Ile Leu Glu Arg Val
        35
```

<210> SEQ ID NO 32
<211> LENGTH: 38
<212> TYPE: PRT
<213> ORGANISM: Artificial Sequence
<220> FEATURE:
<223> OTHER INFORMATION: compound Seq_32
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a primary amide

<400> SEQUENCE: 32

```
Ile Val Leu Ser Leu Asp Xaa Pro Thr Lys Leu Lys Gln Lys Leu Leu
1               5                   10                  15

Lys Gln Glu Arg Gln Arg Lys Glu Arg Glu Gln Ala Glu Lys Asn Val
```

```
            20                  25                  30

Arg Ile Leu Glu Arg Val
        35


<210> SEQ ID NO 33
<211> LENGTH: 38
<212> TYPE: PRT
<213> ORGANISM: Artificial Sequence
<220> FEATURE:
<223> OTHER INFORMATION: compound Seq_33
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is “-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 33

Ile Val Leu Ser Leu Asp Xaa Pro Thr Lys Leu Lys Gln Lys Leu Leu
1               5                   10                  15

Lys Gln Glu Arg Gln Arg Lys Glu Arg Glu Gln Ala Glu Lys Asn Thr
            20                  25                  30

Arg Ile Leu Glu Arg Val
        35


<210> SEQ ID NO 34
<211> LENGTH: 38
<212> TYPE: PRT
<213> ORGANISM: Artificial Sequence
<220> FEATURE:
<223> OTHER INFORMATION: compound Seq_34
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is ”-{AEEA}2-gGlu-
      C(O)(CH2)16COOH
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 34

Phe Thr Leu Ser Leu Asp Val Pro Thr Lys Ile Lys Gln Lys Leu Leu
1               5                   10                  15

Lys Gln Glu Lys Gln Lys Lys Gln Arg Gln Lys Ala Lys Thr Asn Lys
            20                  25                  30

Gln Ile Leu Glu Gln Val
        35


<210> SEQ ID NO 35
<211> LENGTH: 38
<212> TYPE: PRT
<213> ORGANISM: Artificial Sequence
<220> FEATURE:
<223> OTHER INFORMATION: compound Seq_35
<220> FEATURE:
<221> NAME/KEY: VARIANT
<222> LOCATION: 12
<223> OTHER INFORMATION: K* denotes the modified lysine residue at X12,
```

Ra denotes the albumin-binding moiety, Ra is "-{AEEA}2-gGlu-
C(O)(CH2)16COOH
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 35

Ile Val Leu Ser Leu Asp Val Pro Ile Lys Leu Lys Lys Ile Leu Leu
1 5 10 15

Glu Gln Glu Lys Gln Lys Lys Gln Arg Glu Gln Ala Glu Thr Asn Lys
20 25 30

Gln Ile Leu Ala Gln Val
35

<210> SEQ ID NO 36
<211> LENGTH: 38
<212> TYPE: PRT
<213> ORGANISM: Artificial Sequence
<220> FEATURE:
<223> OTHER INFORMATION: compound Seq_36
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-{AEEA}2-gGlu-
C(O)(CH2)16COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 36

Ile Val Leu Ser Leu Asp Xaa Pro Thr Lys Leu Lys Gln Lys Leu Leu
1 5 10 15

Lys Gln Glu Arg Gln Arg Lys Xaa Arg Glu Gln Ala Glu Lys Asn Lys
20 25 30

Arg Ile Leu Glu Arg Val
35

<210> SEQ ID NO 37
<211> LENGTH: 38
<212> TYPE: PRT
<213> ORGANISM: Artificial Sequence
<220> FEATURE:
<223> OTHER INFORMATION: compound Seq_37
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-{AEEA}2-gGlu-
C(O)(CH2)16COOH
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 37

Ile Val Leu Ser Leu Asp Val Pro Thr Lys Leu Lys Gln Lys Leu Leu 1 5 10 15

Lys Gln Glu Arg Gln Arg Lys Glu Arg Gln Gln Ala Glu Thr Asn Lys
20 25 30

Arg Ile Leu Glu Arg Val
35

<210> SEQ ID NO 38
<211> LENGTH: 38
<212> TYPE: PRT
<213> ORGANISM: Artificial Sequence
<220> FEATURE:
<223> OTHER INFORMATION: compound Seq_38
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is ”-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 38

Ile Val Leu Ser Leu Asp Val Pro Thr Lys Leu Lys Gln Lys Leu Leu
1 5 10 15

Lys Gln Glu Arg Gln Arg Xaa Glu Arg Gln Gln Ala Glu Thr Asn Lys
20 25 30

Arg Ile Leu Glu Arg Val
35

<210> SEQ ID NO 39
<211> LENGTH: 38
<212> TYPE: PRT
<213> ORGANISM: Artificial Sequence
<220> FEATURE:
<223> OTHER INFORMATION: compound Seq_39
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is “-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 39

Ile Val Leu Ser Leu Asp Val Pro Ile Lys Leu Lys Gln Ile Leu Leu
1 5 10 15

Glu Gln Glu Arg Gln Arg Lys Glu Arg Gln Gln Ala Glu Thr Asn Ala
20 25 30

Gln Ile Leu Ala Gln Val
35

<210> SEQ ID NO 40
<211> LENGTH: 38
<212> TYPE: PRT
<213> ORGANISM: Artificial Sequence
<220> FEATURE:
<223> OTHER INFORMATION: compound Seq_40

<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 40

Ile Val Leu Ser Leu Asp Val Pro Ile Lys Leu Lys Gln Ile Leu Leu
1 5 10 15

Glu Gln Glu Arg Gln Arg Lys Glu Arg Gln Gln Ala Glu Thr Asn Val
20 25 30

Gln Ile Leu Ala Gln Val
35

<210> SEQ ID NO 41
<211> LENGTH: 38
<212> TYPE: PRT
<213> ORGANISM: Artificial Sequence
<220> FEATURE:
<223> OTHER INFORMATION: compound Seq_41
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 41

Ile Val Leu Ser Leu Asp Val Pro Ile Lys Leu Lys Gln Ile Leu Leu
1 5 10 15

Glu Gln Glu Arg Gln Arg Lys Glu Arg Gln Gln Ala Glu Lys Asn Val
20 25 30

Arg Ile Leu Glu Arg Val
35

<210> SEQ ID NO 42
<211> LENGTH: 38
<212> TYPE: PRT
<213> ORGANISM: Artificial Sequence
<220> FEATURE:
<223> OTHER INFORMATION: compound Seq_42
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 42

Ile Val Leu Ser Leu Asp Val Pro Ile Lys Leu Lys Gln Ile Leu Leu

```
1               5                   10                  15

Glu Gln Glu Arg Gln Arg Xaa Glu Arg Gln Gln Ala Glu Lys Asn Val
            20                  25                  30

Arg Ile Leu Glu Arg Val
        35


<210> SEQ ID NO 43
<211> LENGTH: 38
<212> TYPE: PRT
<213> ORGANISM: Artificial Sequence
<220> FEATURE:
<223> OTHER INFORMATION: compound Seq_43
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 43

Ile Val Leu Ser Leu Asp Val Pro Ile Lys Leu Lys Gln Ile Leu Leu
1               5                   10                  15

Glu Gln Ala Lys Gln Lys Lys Leu Arg Ala Gln Ala Glu Thr Asn Val
            20                  25                  30

Arg Ile Leu Glu Arg Val
        35


<210> SEQ ID NO 44
<211> LENGTH: 38
<212> TYPE: PRT
<213> ORGANISM: Artificial Sequence
<220> FEATURE:
<223> OTHER INFORMATION: compound Seq_44
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 44

Ile Val Leu Ser Leu Asp Val Pro Ile Lys Leu Lys Gln Ile Leu Leu
1               5                   10                  15

Glu Gln Ala Lys Gln Lys Lys Glu Arg Ala Gln Ala Glu Thr Asn Val
            20                  25                  30

Arg Ile Leu Glu Arg Val
        35


<210> SEQ ID NO 45
<211> LENGTH: 38
<212> TYPE: PRT
<213> ORGANISM: Artificial Sequence
<220> FEATURE:
<223> OTHER INFORMATION: compound Seq_45
<220> FEATURE:
<221> NAME/KEY: VARIANT
<222> LOCATION: 12
<223> OTHER INFORMATION: K* denotes the modified lysine residue at X12,
```

-continued

Ra denotes the albumin-binding moiety, Ra is "-{AEEA}2-gGlu-
C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 45

```
Ile Val Leu Ser Leu Asp Val Pro Ile Lys Leu Lys Gln Ile Leu Leu
1               5                   10                  15

Glu Gln Ala Lys Gln Lys Xaa Leu Lys Ala Gln Ala Glu Thr Asn Val
            20                  25                  30

Arg Ile Leu Glu Arg Val
        35
```

<210> SEQ ID NO 46
<211> LENGTH: 38
<212> TYPE: PRT
<213> ORGANISM: Artificial Sequence
<220> FEATURE:
<223> OTHER INFORMATION: compound Seq_46
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-{AEEA}2-gGlu-
C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 46

```
Ile Val Leu Ser Leu Asp Val Pro Ile Lys Leu Lys Gln Ile Leu Leu
1               5                   10                  15

Glu Gln Ala Lys Gln Lys Xaa Leu Arg Ala Gln Ala Glu Thr Asn Val
            20                  25                  30

Arg Ile Leu Glu Arg Val
        35
```

<210> SEQ ID NO 47
<211> LENGTH: 38
<212> TYPE: PRT
<213> ORGANISM: Artificial Sequence
<220> FEATURE:
<223> OTHER INFORMATION: compound Seq_47
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-{AEEA}2-gGlu-
C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:

<221> NAME/KEY: MOD_RES
<222> LOCATION: 38
<223> OTHER INFORMATION: C-terminal amino acid residue is amidated as a
primary amide

<400> SEQUENCE: 47

Ile Val Leu Ser Leu Asp Xaa Pro Thr Lys Leu Lys Lys Lys Leu Leu
1 5 10 15

Lys Gln Glu Arg Lys Arg Xaa Glu Arg Glu Lys Ala Glu Lys Ala Ala
20 25 30

Arg Ile Leu Glu Arg Val
35

<210> SEQ ID NO 48
<211> LENGTH: 38
<212> TYPE: PRT
<213> ORGANISM: Artificial Sequence
<220> FEATURE:
<223> OTHER INFORMATION: compound Seq_48
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-{AEEA}2-gGlu-
C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 48

Ile Val Leu Ser Leu Asp Val Pro Ile Lys Leu Lys Gln Ile Leu Leu
1 5 10 15

Glu Gln Glu Arg Gln Arg Xaa Glu Arg Gln Gln Ala Glu Thr Asn Val
20 25 30

Gln Ile Leu Ala Gln Val
35

<210> SEQ ID NO 49
<211> LENGTH: 38
<212> TYPE: PRT
<213> ORGANISM: Artificial Sequence
<220> FEATURE:
<223> OTHER INFORMATION: compound Seq_49
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-{AEEA}2-gGlu-
C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 49

Ile Val Leu Ser Leu Asp Val Pro Ile Lys Leu Lys Gln Ile Leu Leu
1 5 10 15

Glu Gln Glu Arg Gln Arg Xaa Glu Arg Gln Gln Ala Glu Thr Asn Val 20 25 30

Arg Ile Leu Glu Arg Val
35

<210> SEQ ID NO 50
<211> LENGTH: 38
<212> TYPE: PRT
<213> ORGANISM: Artificial Sequence
<220> FEATURE:
<223> OTHER INFORMATION: compound Seq_50
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 50

Ile Val Leu Ser Leu Asp Val Pro Thr Lys Leu Lys Gln Ile Leu Leu
1 5 10 15

Lys Gln Glu Arg Gln Arg Xaa Glu Arg Gln Gln Ala Glu Thr Asn Val
20 25 30

Arg Ile Leu Glu Arg Val
35

<210> SEQ ID NO 51
<211> LENGTH: 38
<212> TYPE: PRT
<213> ORGANISM: Artificial Sequence
<220> FEATURE:
<223> OTHER INFORMATION: compound Seq_51
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 51

Phe Thr Leu Ser Leu Asp Val Pro Thr Lys Ile Lys Gln Ile Leu Leu
1 5 10 15

Lys Gln Gln Lys Gln Lys Lys Glu Arg Gln Gln Ala Glu Lys Asn Lys
20 25 30

Gln Leu Leu Glu Gln Ile
35

<210> SEQ ID NO 52
<211> LENGTH: 38
<212> TYPE: PRT
<213> ORGANISM: Artificial Sequence
<220> FEATURE:
<223> OTHER INFORMATION: compound Seq_52
<220> FEATURE:
<221> NAME/KEY: VARIANT
<222> LOCATION: 12

<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 52

```
Phe Thr Leu Ser Leu Asp Val Pro Thr Lys Ile Lys Gln Ile Leu Leu
1               5                   10                  15

Lys Gln Gln Lys Gln Lys Lys Glu Arg Gln Gln Ala Glu Lys Asn Lys
            20                  25                  30

Gln Leu Leu Glu Arg Val
        35
```

<210> SEQ ID NO 53
<211> LENGTH: 38
<212> TYPE: PRT
<213> ORGANISM: Artificial Sequence
<220> FEATURE:
<223> OTHER INFORMATION: compound Seq_53
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 53

```
Phe Thr Leu Ser Leu Asp Val Pro Thr Lys Ile Lys Gln Ile Leu Leu
1               5                   10                  15

Lys Gln Gln Lys Gln Lys Lys Glu Arg Gln Gln Ala Glu Thr Asn Lys
            20                  25                  30

Gln Leu Leu Glu Arg Val
        35
```

<210> SEQ ID NO 54
<211> LENGTH: 38
<212> TYPE: PRT
<213> ORGANISM: Artificial Sequence
<220> FEATURE:
<223> OTHER INFORMATION: compound Seq_54
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 54

```
Phe Thr Leu Ser Leu Asp Val Pro Ile Lys Leu Lys Gln Ile Leu Leu
1               5                   10                  15

Lys Gln Gln Lys Gln Lys Lys Glu Arg Gln Gln Ala Glu Thr Asn Val
            20                  25                  30

Gln Leu Leu Glu Arg Val
        35
```

<210> SEQ ID NO 55
<211> LENGTH: 38
<212> TYPE: PRT
<213> ORGANISM: Artificial Sequence
<220> FEATURE:
<223> OTHER INFORMATION: compound Seq_55
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 55

```
Phe Thr Leu Ser Leu Asp Val Pro Thr Lys Ile Lys Gln Ile Leu Leu
1               5                   10                  15

Lys Gln Gln Lys Gln Lys Lys Glu Arg Gln Lys Ala Glu Thr Asn Val
            20                  25                  30

Gln Leu Leu Glu Arg Val
        35
```

<210> SEQ ID NO 56
<211> LENGTH: 38
<212> TYPE: PRT
<213> ORGANISM: Artificial Sequence
<220> FEATURE:
<223> OTHER INFORMATION: compound Seq_56
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 56

```
Phe Thr Leu Ser Leu Asp Val Pro Ile Gly Leu Lys Gln Ile Leu Leu
1               5                   10                  15

Lys Gln Gln Lys Gln Lys Lys Glu Arg Gln Gln Ala Glu Thr Asn Val
            20                  25                  30

Gln Leu Leu Glu Arg Val
        35
```

<210> SEQ ID NO 57
<211> LENGTH: 38
<212> TYPE: PRT
<213> ORGANISM: Artificial Sequence
<220> FEATURE:
<223> OTHER INFORMATION: compound Seq_57
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 57

Phe Thr Leu Ser Leu Asp Val Pro Ile Gly Leu Lys Gln Ile Leu Leu
1 5 10 15

Lys Gln Gln Lys Gln Lys Lys Glu Arg Gln Lys Ala Glu Thr Asn Val
20 25 30

Gln Leu Leu Glu Arg Val
35

<210> SEQ ID NO 58
<211> LENGTH: 38
<212> TYPE: PRT
<213> ORGANISM: Artificial Sequence
<220> FEATURE:
<223> OTHER INFORMATION: compound Seq_58
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 58

Phe Thr Leu Ser Leu Asp Val Pro Thr Lys Ile Lys Gln Ile Leu Phe
1 5 10 15

Lys Gln Gln Lys Gln Lys Lys Glu Arg Gln Gln Ala Glu Lys Asn Lys
20 25 30

Gln Leu Leu Glu Gln Ile
35

<210> SEQ ID NO 59
<211> LENGTH: 38
<212> TYPE: PRT
<213> ORGANISM: Artificial Sequence
<220> FEATURE:
<223> OTHER INFORMATION: compound Seq_59
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 59

Phe Thr Leu Ser Leu Asp Val Pro Thr Lys Ile Lys Gln Ile Leu Leu
1 5 10 15

Lys Gln Gln Lys Gln Lys Lys Glu Arg Gln Gln Ala Glu Lys Asn Lys
20 25 30

Gln Leu Leu Glu Gln Ile
35

<210> SEQ ID NO 60
<211> LENGTH: 38
<212> TYPE: PRT
<213> ORGANISM: Artificial Sequence
<220> FEATURE:
<223> OTHER INFORMATION: compound Seq_60

<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 60

```
Phe Thr Leu Ser Leu Asp Val Pro Thr Lys Ile Lys Gln Ile Leu Leu
1               5                   10                  15

Lys Gln Gln Lys Gln Lys Lys Glu Arg Gln Gln Ala Glu Lys Asn Lys
            20                  25                  30

Gln Leu Leu Glu Arg Val
        35
```

<210> SEQ ID NO 61
<211> LENGTH: 38
<212> TYPE: PRT
<213> ORGANISM: Artificial Sequence
<220> FEATURE:
<223> OTHER INFORMATION: compound Seq_61
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 61

```
Phe Thr Leu Ser Leu Asp Val Pro Thr Lys Ile Lys Gln Ile Leu Leu
1               5                   10                  15

Lys Gln Gln Lys Gln Lys Lys Glu Arg Gln Gln Ala Glu Thr Asn Lys
            20                  25                  30

Gln Leu Leu Glu Arg Val
        35
```

<210> SEQ ID NO 62
<211> LENGTH: 38
<212> TYPE: PRT
<213> ORGANISM: Artificial Sequence
<220> FEATURE:
<223> OTHER INFORMATION: compound Seq_62
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 62

```
Phe Thr Leu Ser Leu Asp Val Pro Ile Lys Leu Lys Gln Ile Leu Leu
1               5                   10                  15

Lys Gln Gln Lys Gln Lys Lys Glu Arg Gln Gln Ala Glu Thr Asn Val
            20                  25                  30
```

Gln Leu Leu Glu Arg Val
35

<210> SEQ ID NO 63
<211> LENGTH: 38
<212> TYPE: PRT
<213> ORGANISM: Artificial Sequence
<220> FEATURE:
<223> OTHER INFORMATION: compound Seq_63
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 63

Phe Thr Leu Ser Leu Asp Val Pro Ile Lys Leu Lys Gln Ile Leu Leu
1 5 10 15

Glu Gln Gln Lys Gln Lys Lys Glu Arg Gln Gln Ala Glu Thr Asn Val
20 25 30

Gln Leu Leu Glu Arg Val
35

<210> SEQ ID NO 64
<211> LENGTH: 38
<212> TYPE: PRT
<213> ORGANISM: Artificial Sequence
<220> FEATURE:
<223> OTHER INFORMATION: compound Seq_64
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 64

Phe Thr Leu Ser Leu Asp Val Pro Thr Lys Ile Lys Gln Ile Leu Leu
1 5 10 15

Lys Gln Gln Lys Gln Lys Lys Glu Arg Gln Lys Ala Glu Thr Asn Val
20 25 30

Gln Leu Leu Glu Arg Val
35

<210> SEQ ID NO 65
<211> LENGTH: 38
<212> TYPE: PRT
<213> ORGANISM: Artificial Sequence
<220> FEATURE:
<223> OTHER INFORMATION: compound Seq_65
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 65

Phe Thr Leu Ser Leu Asp Val Pro Ile Gly Leu Lys Gln Ile Leu Leu
1 5 10 15

Lys Gln Gln Lys Gln Lys Lys Glu Arg Gln Gln Ala Glu Thr Asn Val
20 25 30

Gln Leu Leu Glu Arg Val
35

<210> SEQ ID NO 66
<211> LENGTH: 38
<212> TYPE: PRT
<213> ORGANISM: Artificial Sequence
<220> FEATURE:
<223> OTHER INFORMATION: compound Seq_66
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 66

Phe Thr Leu Ser Leu Asp Val Pro Ile Gly Leu Lys Gln Ile Leu Leu
1 5 10 15

Lys Gln Gln Lys Gln Lys Lys Glu Arg Gln Lys Ala Glu Thr Asn Val
20 25 30

Gln Leu Leu Glu Arg Val
35

<210> SEQ ID NO 67
<211> LENGTH: 38
<212> TYPE: PRT
<213> ORGANISM: Artificial Sequence
<220> FEATURE:
<223> OTHER INFORMATION: compound Seq_67
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 67

Ile Val Leu Ser Leu Asp Val Pro Ile Lys Leu Lys Gln Ile Leu Leu
1 5 10 15

Glu Gln Glu Lys Gln Lys Lys Gln Arg Glu Gln Ala Glu Thr Asn Lys
20 25 30

Gln Ile Leu Ala Gln Val
35

<210> SEQ ID NO 68
<211> LENGTH: 38
<212> TYPE: PRT

<213> ORGANISM: Artificial Sequence
<220> FEATURE:
<223> OTHER INFORMATION: compound Seq_68
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 68

```
Ile Val Leu Ser Leu Asp Val Pro Ile Lys Leu Lys Gln Ile Leu Leu
1               5                   10                  15

Glu Gln Glu Arg Gln Lys Lys Gln Arg Glu Gln Ala Glu Thr Asn Lys
            20                  25                  30

Gln Ile Leu Ala Gln Val
        35
```

<210> SEQ ID NO 69
<211> LENGTH: 38
<212> TYPE: PRT
<213> ORGANISM: Artificial Sequence
<220> FEATURE:
<223> OTHER INFORMATION: compound Seq_69
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 14
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 69

```
Ile Val Leu Ser Leu Asp Val Pro Ile Lys Leu Lys Lys Xaa Leu Leu
1               5                   10                  15

Glu Gln Glu Arg Gln Lys Lys Gln Arg Glu Gln Ala Glu Thr Asn Lys
            20                  25                  30

Gln Ile Leu Ala Gln Val
        35
```

<210> SEQ ID NO 70
<211> LENGTH: 38
<212> TYPE: PRT
<213> ORGANISM: Artificial Sequence
<220> FEATURE:
<223> OTHER INFORMATION: compound Seq_70
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 32
<223> OTHER INFORMATION: 2-aminoisobutyric acid (Aib)
<220> FEATURE:
<221> NAME/KEY: MOD_RES -continued
<222> LOCATION: 38
<223> OTHER INFORMATION: C-terminal amino acid residue is amidated as a primary amide

<400> SEQUENCE: 70

```
Ile Val Leu Ser Leu Asp Val Pro Ile Lys Leu Lys Gln Ile Leu Leu
1               5                   10                  15

Glu Gln Glu Arg Gln Lys Lys Gln Arg Glu Gln Ala Glu Thr Asn Xaa
            20                  25                  30

Gln Ile Leu Ala Gln Val
        35
```

<210> SEQ ID NO 71
<211> LENGTH: 38
<212> TYPE: PRT
<213> ORGANISM: Artificial Sequence
<220> FEATURE:
<223> OTHER INFORMATION: compound Seq_71
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 14
<223> OTHER INFORMATION: 2-aminoisobutyric acid (Aib)
<220> FEATURE:
<221> NAME/KEY: VARIANT
<222> LOCATION: 32
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 71

```
Ile Val Leu Ser Leu Asp Val Pro Ile Lys Leu Lys Lys Xaa Leu Leu
1               5                   10                  15

Glu Gln Glu Arg Gln Lys Lys Gln Arg Glu Gln Ala Glu Thr Asn Xaa
            20                  25                  30

Gln Ile Leu Ala Gln Val
        35
```

<210> SEQ ID NO 72
<211> LENGTH: 38
<212> TYPE: PRT
<213> ORGANISM: Artificial Sequence
<220> FEATURE:
<223> OTHER INFORMATION: compound Seq_72
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 32
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 72

```
Ile Val Leu Ser Leu Asp Val Pro Ile Lys Leu Lys Gln Ile Leu Leu
```

```
1               5                   10                  15

Glu Gln Glu Arg Gln Lys Lys Gln Arg Gln Gln Ala Glu Thr Asn Xaa
            20                  25                  30

Gln Ile Leu Ala Gln Val
        35


<210> SEQ ID NO 73
<211> LENGTH: 38
<212> TYPE: PRT
<213> ORGANISM: Artificial Sequence
<220> FEATURE:
<223> OTHER INFORMATION: compound Seq_73
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 32
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 73

Ile Val Leu Ser Leu Asp Val Pro Ile Lys Leu Lys Gln Ile Leu Leu
1               5                   10                  15

Glu Gln Glu Arg Gln Lys Lys Gln Arg Gln Lys Ala Glu Thr Asn Xaa
            20                  25                  30

Gln Ile Leu Ala Gln Val
        35


<210> SEQ ID NO 74
<211> LENGTH: 38
<212> TYPE: PRT
<213> ORGANISM: Artificial Sequence
<220> FEATURE:
<223> OTHER INFORMATION: compound Seq_74
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 32
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 74

Ile Val Leu Ser Leu Asp Val Pro Ile Lys Leu Lys Gln Ile Leu Leu
1               5                   10                  15

Glu Gln Glu Arg Gln Lys Lys Gln Arg Glu Gln Ala Glu Thr Asn Xaa
            20                  25                  30

Gln Ile Leu Glu Arg Val
        35


<210> SEQ ID NO 75
<211> LENGTH: 38
```

-continued

<212> TYPE: PRT
<213> ORGANISM: Artificial Sequence
<220> FEATURE:
<223> OTHER INFORMATION: compound Seq_75
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 32
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 75

Ile Val Leu Ser Leu Asp Val Pro Ile Lys Leu Lys Gln Ile Leu Leu
1 5 10 15

Lys Gln Glu Arg Gln Lys Lys Gln Arg Gln Gln Ala Glu Thr Asn Xaa
20 25 30

Gln Ile Leu Ala Gln Val
35

<210> SEQ ID NO 76
<211> LENGTH: 38
<212> TYPE: PRT
<213> ORGANISM: Artificial Sequence
<220> FEATURE:
<223> OTHER INFORMATION: compound Seq_76
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 32
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 76

Ile Val Leu Ser Leu Asp Val Pro Ile Gly Leu Lys Gln Ile Leu Leu
1 5 10 15

Glu Gln Glu Arg Gln Lys Lys Gln Arg Gln Gln Ala Glu Thr Asn Xaa
20 25 30

Gln Ile Leu Ala Gln Val
35

<210> SEQ ID NO 77
<211> LENGTH: 38
<212> TYPE: PRT
<213> ORGANISM: Artificial Sequence
<220> FEATURE:
<223> OTHER INFORMATION: compound Seq_77
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:

<221> NAME/KEY: MOD_RES
<222> LOCATION: 38
<223> OTHER INFORMATION: C-terminal amino acid residue is amidated as a primary amide

<400> SEQUENCE: 77

```
Ile Val Leu Ser Leu Asp Val Pro Ile Lys Leu Lys Gln Ile Leu Leu
1               5                   10                  15

Lys Gln Glu Arg Gln Lys Lys Gln Arg Gln Lys Ala Glu Thr Asn Lys
            20                  25                  30

Gln Ile Leu Ala Gln Val
        35
```

<210> SEQ ID NO 78
<211> LENGTH: 38
<212> TYPE: PRT
<213> ORGANISM: Artificial Sequence
<220> FEATURE:
<223> OTHER INFORMATION: compound Seq_78
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 32
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 78

```
Ile Val Leu Ser Leu Asp Val Pro Thr Lys Leu Lys Gln Ile Leu Leu
1               5                   10                  15

Glu Gln Glu Arg Gln Lys Lys Gln Arg Glu Gln Ala Glu Thr Asn Xaa
            20                  25                  30

Gln Ile Leu Ala Gln Val
        35
```

<210> SEQ ID NO 79
<211> LENGTH: 38
<212> TYPE: PRT
<213> ORGANISM: Artificial Sequence
<220> FEATURE:
<223> OTHER INFORMATION: compound Seq_79
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 79

```
Ile Val Leu Ser Leu Asp Val Pro Ile Lys Leu Lys Gln Ile Leu Leu
1               5                   10                  15

Glu Gln Glu Lys Gln Lys Xaa Gln Arg Glu Gln Ala Glu Thr Asn Lys
```

```
            20                  25                  30

Gln Ile Leu Ala Gln Val
        35


<210> SEQ ID NO 80
<211> LENGTH: 38
<212> TYPE: PRT
<213> ORGANISM: Artificial Sequence
<220> FEATURE:
<223> OTHER INFORMATION: compound Seq_80
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 32
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 80

Ile Val Leu Ser Leu Asp Val Pro Thr Lys Leu Lys Gln Ile Leu Leu
1               5                   10                  15

Glu Gln Glu Arg Gln Lys Lys Gln Arg Glu Gln Ala Glu Thr Asn Xaa
            20                  25                  30

Gln Ile Leu Ala Gln Val
        35


<210> SEQ ID NO 81
<211> LENGTH: 38
<212> TYPE: PRT
<213> ORGANISM: Artificial Sequence
<220> FEATURE:
<223> OTHER INFORMATION: compound Seq_81
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 81

Ile Val Leu Ser Leu Asp Val Pro Ile Lys Leu Lys Gln Ile Leu Leu
1               5                   10                  15

Glu Gln Glu Lys Gln Lys Xaa Gln Arg Glu Gln Ala Glu Thr Asn Lys
            20                  25                  30

Gln Ile Leu Ala Gln Val
        35


<210> SEQ ID NO 82
<211> LENGTH: 38
<212> TYPE: PRT
<213> ORGANISM: Artificial Sequence
<220> FEATURE:
```

<223> OTHER INFORMATION: compound Seq_82
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-{AEEA}2-gGlu-
C(O)(CH2)16COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 82

```
Ile Val Leu Ser Leu Asp Val Pro Thr Lys Leu Lys Gln Ile Leu Leu
1               5                   10                  15

Lys Gln Glu Arg Gln Lys Lys Xaa Arg Glu Gln Ala Glu Thr Asn Val
            20                  25                  30

Arg Ile Leu Glu Arg Val
        35
```

<210> SEQ ID NO 83
<211> LENGTH: 38
<212> TYPE: PRT
<213> ORGANISM: Artificial Sequence
<220> FEATURE:
<223> OTHER INFORMATION: compound Seq_83
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-{AEEA}2-gGlu-
C(O)(CH2)16COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 83

```
Ile Val Leu Ser Leu Asp Xaa Pro Ile Gly Leu Lys Gln Ile Leu Leu
1               5                   10                  15

Lys Gln Glu Arg Gln Lys Lys Xaa Arg Glu Gln Ala Glu Thr Asn Lys
            20                  25                  30

Arg Ile Leu Glu Arg Val
        35
```

<210> SEQ ID NO 84
<211> LENGTH: 38
<212> TYPE: PRT
<213> ORGANISM: Artificial Sequence
<220> FEATURE:
<223> OTHER INFORMATION: compound Seq_84
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-{AEEA}2-gGlu-
C(O)(CH2)16COOH -continued <220> FEATURE:
<221> NAME/KEY: MOD_RES
<222> LOCATION: 38
<223> OTHER INFORMATION: C-terminal amino acid residue is amidated as a primary amide

<400> SEQUENCE: 84

Ile Val Leu Ser Leu Asp Val Pro Ile Lys Leu Lys Gln Lys Leu Leu
1 5 10 15

Glu Gln Glu Lys Gln Lys Lys Gln Arg Glu Gln Ala Glu Thr Asn Lys
20 25 30

Gln Ile Leu Ala Gln Val
35

<210> SEQ ID NO 85
<211> LENGTH: 38
<212> TYPE: PRT
<213> ORGANISM: Artificial Sequence
<220> FEATURE:
<223> OTHER INFORMATION: compound Seq_85
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 85

Ile Val Leu Ser Leu Asp Val Pro Ile Lys Leu Lys Gln Ile Leu Leu
1 5 10 15

Lys Gln Glu Arg Gln Lys Lys Gln Arg Glu Gln Ala Glu Thr Asn Lys
20 25 30

Gln Ile Leu Ala Gln Val
35

<210> SEQ ID NO 86
<211> LENGTH: 38
<212> TYPE: PRT
<213> ORGANISM: Artificial Sequence
<220> FEATURE:
<223> OTHER INFORMATION: compound Seq_86
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 86

Ile Val Leu Ser Leu Asp Val Pro Ile Lys Leu Lys Gln Ile Leu Leu
1 5 10 15

Lys Gln Glu Arg Gln Lys Lys Gln Arg Glu Gln Ala Lys Thr Asn Lys
20 25 30

Gln Ile Leu Ala Gln Val
35

<210> SEQ ID NO 87

<211> LENGTH: 38
<212> TYPE: PRT
<213> ORGANISM: Artificial Sequence
<220> FEATURE:
<223> OTHER INFORMATION: compound Seq_87
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 87

Ile Val Leu Ser Leu Asp Val Pro Ile Lys Leu Lys Gln Ile Leu Leu
1               5                   10                  15

Lys Gln Glu Arg Gln Lys Lys Gln Arg Glu Lys Ala Lys Thr Asn Lys
            20                  25                  30

Gln Ile Leu Ala Gln Val
        35

<210> SEQ ID NO 88
<211> LENGTH: 38
<212> TYPE: PRT
<213> ORGANISM: Artificial Sequence
<220> FEATURE:
<223> OTHER INFORMATION: compound Seq_88
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 32
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 88

Ile Val Leu Ser Leu Asp Val Pro Ile Lys Leu Lys Gln Ile Leu Leu
1               5                   10                  15

Lys Gln Glu Arg Gln Lys Lys Gln Arg Glu Lys Ala Lys Thr Asn Xaa
            20                  25                  30

Gln Ile Leu Ala Gln Val
        35

<210> SEQ ID NO 89
<211> LENGTH: 38
<212> TYPE: PRT
<213> ORGANISM: Artificial Sequence
<220> FEATURE:
<223> OTHER INFORMATION: compound Seq_89
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 32
<223> OTHER INFORMATION: 2-aminoisobutyric acid (Aib)

```
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 89

Ile Val Leu Ser Leu Asp Val Pro Ile Lys Leu Lys Gln Ile Leu Leu
1               5                   10                  15

Lys Gln Glu Arg Gln Lys Lys Gln Arg Glu Gln Ala Lys Thr Asn Xaa
            20                  25                  30

Gln Ile Leu Ala Gln Val
        35


<210> SEQ ID NO 90
<211> LENGTH: 38
<212> TYPE: PRT
<213> ORGANISM: Artificial Sequence
<220> FEATURE:
<223> OTHER INFORMATION: compound Seq_90
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 90

Ile Val Leu Ser Leu Asp Val Pro Ile Lys Leu Lys Gln Ile Leu Leu
1               5                   10                  15

Lys Gln Glu Arg Gln Lys Lys Gln Arg Glu Lys Ala Lys Thr Asn Val
            20                  25                  30

Gln Ile Leu Ala Gln Val
        35


<210> SEQ ID NO 91
<211> LENGTH: 38
<212> TYPE: PRT
<213> ORGANISM: Artificial Sequence
<220> FEATURE:
<223> OTHER INFORMATION: compound Seq_91
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 32
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 91

Ile Val Leu Ser Leu Asp Val Pro Ile Lys Leu Lys Gln Lys Leu Leu
1               5                   10                  15

Lys Gln Glu Arg Gln Lys Lys Gln Arg Glu Lys Ala Lys Thr Asn Xaa
            20                  25                  30

Gln Ile Leu Ala Gln Val
```

35

<210> SEQ ID NO 92
<211> LENGTH: 38
<212> TYPE: PRT
<213> ORGANISM: Artificial Sequence
<220> FEATURE:
<223> OTHER INFORMATION: compound Seq_92
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 32
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 92

Ile Val Leu Ser Leu Asp Val Pro Ile Lys Leu Lys Gln Lys Leu Leu
1 5 10 15

Glu Gln Glu Arg Gln Lys Lys Gln Arg Glu Gln Ala Glu Thr Asn Xaa
20 25 30

Gln Ile Leu Ala Gln Val
35

<210> SEQ ID NO 93
<211> LENGTH: 38
<212> TYPE: PRT
<213> ORGANISM: Artificial Sequence
<220> FEATURE:
<223> OTHER INFORMATION: compound Seq_93
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 93

Ile Val Leu Ser Leu Asp Val Pro Ile Lys Leu Lys Gln Lys Leu Leu
1 5 10 15

Lys Gln Glu Arg Gln Lys Lys Gln Arg Glu Lys Ala Lys Thr Asn Val
20 25 30

Gln Ile Leu Ala Gln Val
35

<210> SEQ ID NO 94
<211> LENGTH: 38
<212> TYPE: PRT
<213> ORGANISM: Artificial Sequence
<220> FEATURE:
<223> OTHER INFORMATION: compound Seq_94
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH -continued
<220> FEATURE:
<221> NAME/KEY: MOD_RES
<222> LOCATION: 38
<223> OTHER INFORMATION: C-terminal amino acid residue is amidated as a primary amide

<400> SEQUENCE: 94

```
Ile Val Leu Ser Leu Asp Val Pro Ile Lys Leu Lys Lys Ile Leu Leu
1               5                   10                  15

Lys Gln Glu Arg Gln Lys Lys Glu Arg Glu Gln Ala Glu Thr Asn Lys
            20                  25                  30

Gln Ile Leu Ala Gln Val
        35
```

<210> SEQ ID NO 95
<211> LENGTH: 38
<212> TYPE: PRT
<213> ORGANISM: Artificial Sequence
<220> FEATURE:
<223> OTHER INFORMATION: compound Seq_95
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 95

```
Ile Val Leu Ser Leu Asp Val Pro Ile Lys Leu Lys Gln Lys Leu Leu
1               5                   10                  15

Lys Gln Glu Arg Gln Lys Lys Glu Arg Glu Gln Ala Glu Thr Asn Lys
            20                  25                  30

Gln Ile Leu Ala Gln Val
        35
```

<210> SEQ ID NO 96
<211> LENGTH: 38
<212> TYPE: PRT
<213> ORGANISM: Artificial Sequence
<220> FEATURE:
<223> OTHER INFORMATION: compound Seq_96
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 96

```
Ile Val Leu Ser Leu Asp Val Pro Ile Lys Leu Lys Gln Ile Leu Leu
1               5                   10                  15

Lys Gln Glu Arg Gln Lys Lys Glu Arg Glu Gln Ala Glu Thr Asn Lys
            20                  25                  30

Gln Ile Leu Ala Gln Val
        35
```

<210> SEQ ID NO 97

-continued

<211> LENGTH: 38
<212> TYPE: PRT
<213> ORGANISM: Artificial Sequence
<220> FEATURE:
<223> OTHER INFORMATION: compound Seq_97
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 97

```
Ile Val Leu Ser Leu Asp Val Pro Ile Lys Leu Lys Gln Lys Leu Leu
1               5                   10                  15

Lys Gln Glu Arg Gln Lys Lys Gln Arg Glu Gln Ala Glu Thr Asn Lys
            20                  25                  30

Gln Ile Leu Ala Gln Val
        35
```

<210> SEQ ID NO 98
<211> LENGTH: 38
<212> TYPE: PRT
<213> ORGANISM: Artificial Sequence
<220> FEATURE:
<223> OTHER INFORMATION: compound Seq_98
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 98

```
Ile Val Leu Ser Leu Asp Val Pro Ile Lys Leu Lys Gln Lys Leu Leu
1               5                   10                  15

Lys Gln Glu Arg Gln Lys Lys Xaa Arg Glu Gln Ala Glu Thr Asn Lys
            20                  25                  30

Gln Ile Leu Ala Gln Val
        35
```

<210> SEQ ID NO 99
<211> LENGTH: 38
<212> TYPE: PRT
<213> ORGANISM: Artificial Sequence
<220> FEATURE:
<223> OTHER INFORMATION: compound Seq_99
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 24
<223> OTHER INFORMATION: 2-aminoisobutyric acid (Aib)

<220> FEATURE:
<221> NAME/KEY: MOD_RES
<222> LOCATION: 38
<223> OTHER INFORMATION: C-terminal amino acid residue is amidated as a primary amide

<400> SEQUENCE: 99

```
Ile Val Leu Ser Leu Asp Val Pro Ile Lys Leu Lys Lys Ile Leu Leu
1               5                   10                  15

Lys Gln Glu Arg Gln Lys Lys Xaa Arg Glu Gln Ala Glu Lys Asn Lys
            20                  25                  30

Gln Ile Leu Ala Gln Val
        35
```

<210> SEQ ID NO 100
<211> LENGTH: 38
<212> TYPE: PRT
<213> ORGANISM: Artificial Sequence
<220> FEATURE:
<223> OTHER INFORMATION: compound Seq_100
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: VARIANT
<222> LOCATION: 32
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 100

```
Ile Val Leu Ser Leu Asp Val Pro Ile Lys Leu Lys Lys Ile Leu Leu
1               5                   10                  15

Lys Gln Glu Arg Gln Lys Lys Xaa Arg Glu Gln Ala Glu Thr Asn Xaa
            20                  25                  30

Gln Ile Leu Ala Gln Val
        35
```

<210> SEQ ID NO 101
<211> LENGTH: 38
<212> TYPE: PRT
<213> ORGANISM: Artificial Sequence
<220> FEATURE:
<223> OTHER INFORMATION: compound Seq_101
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 101

```
Ile Val Leu Ser Leu Asp Val Pro Ile Lys Leu Lys Lys Ile Leu Leu
1               5                   10                  15

Lys Gln Glu Arg Gln Lys Lys Xaa Arg Glu Gln Ala Glu Thr Asn Lys
            20                  25                  30

Gln Ile Leu Glu Arg Val
        35


<210> SEQ ID NO 102
<211> LENGTH: 38
<212> TYPE: PRT
<213> ORGANISM: Artificial Sequence
<220> FEATURE:
<223> OTHER INFORMATION: compound Seq_102
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 102

Ile Val Leu Ser Leu Asp Xaa Pro Ile Lys Leu Lys Gln Ile Leu Leu
1               5                   10                  15

Lys Gln Glu Arg Gln Lys Lys Gln Arg Glu Gln Ala Glu Thr Asn Lys
            20                  25                  30

Gln Ile Leu Ala Gln Val
        35


<210> SEQ ID NO 103
<211> LENGTH: 38
<212> TYPE: PRT
<213> ORGANISM: Artificial Sequence
<220> FEATURE:
<223> OTHER INFORMATION: compound Seq_103
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 103

Ile Val Leu Ser Leu Asp Val Pro Ile Lys Leu Lys Gln Ile Leu Leu
1               5                   10                  15

Glu Gln Glu Arg Gln Lys Xaa Gln Arg Glu Gln Ala Glu Thr Asn Lys
            20                  25                  30

Gln Ile Leu Ala Gln Val
        35
```

<210> SEQ ID NO 104
<211> LENGTH: 38
<212> TYPE: PRT
<213> ORGANISM: Artificial Sequence
<220> FEATURE:
<223> OTHER INFORMATION: compound Seq_104
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-{AEEA}2-gGlu-
C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 104

```
Ile Val Leu Ser Leu Asp Val Pro Ile Lys Leu Lys Gln Ile Leu Leu
1               5                   10                  15

Lys Gln Glu Arg Gln Lys Xaa Gln Arg Glu Gln Ala Glu Thr Asn Lys
            20                  25                  30

Gln Ile Leu Ala Gln Val
        35
```

<210> SEQ ID NO 105
<211> LENGTH: 38
<212> TYPE: PRT
<213> ORGANISM: Artificial Sequence
<220> FEATURE:
<223> OTHER INFORMATION: compound Seq_105
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-{AEEA}2-gGlu-
C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 105

```
Ile Val Leu Ser Leu Asp Val Pro Ile Lys Leu Lys Gln Ile Leu Leu
1               5                   10                  15

Glu Gln Glu Arg Gln Lys Xaa Gln Arg Gln Gln Ala Glu Thr Asn Lys
            20                  25                  30

Gln Ile Leu Ala Gln Val
        35
```

<210> SEQ ID NO 106
<211> LENGTH: 38
<212> TYPE: PRT
<213> ORGANISM: Artificial Sequence
<220> FEATURE:
<223> OTHER INFORMATION: compound Seq_106
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-{AEEA}2-gGlu- C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 106

```
Ile Val Leu Ser Leu Asp Val Pro Ile Lys Leu Lys Gln Ile Leu Leu
1               5                   10                  15

Glu Gln Glu Arg Gln Lys Xaa Gln Arg Glu Gln Ala Glu Thr Asn Lys
            20                  25                  30

Gln Ile Leu Glu Arg Val
        35
```

<210> SEQ ID NO 107
<211> LENGTH: 38
<212> TYPE: PRT
<213> ORGANISM: Artificial Sequence
<220> FEATURE:
<223> OTHER INFORMATION: compound Seq_107
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 107

```
Ile Val Leu Ser Leu Asp Val Pro Ile Lys Leu Lys Gln Ile Leu Leu
1               5                   10                  15

Lys Gln Glu Arg Gln Lys Xaa Gln Arg Glu Gln Ala Glu Thr Asn Lys
            20                  25                  30

Gln Ile Leu Glu Arg Val
        35
```

<210> SEQ ID NO 108
<211> LENGTH: 38
<212> TYPE: PRT
<213> ORGANISM: Artificial Sequence
<220> FEATURE:
<223> OTHER INFORMATION: compound Seq_108
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 108

Ile Val Leu Ser Leu Asp Val Pro Ile Lys Leu Lys Gln Ile Leu Leu
1 5 10 15

Lys Gln Glu Arg Gln Lys Xaa Gln Arg Gln Lys Ala Glu Thr Asn Lys
20 25 30

Gln Ile Leu Ala Gln Val
35

<210> SEQ ID NO 109
<211> LENGTH: 38
<212> TYPE: PRT
<213> ORGANISM: Artificial Sequence
<220> FEATURE:
<223> OTHER INFORMATION: compound Seq_109
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 109

Ile Val Leu Ser Leu Asp Val Pro Ile Lys Leu Lys Gln Ile Leu Leu
1 5 10 15

Lys Gln Glu Arg Gln Lys Xaa Gln Arg Glu Lys Ala Glu Thr Asn Lys
20 25 30

Gln Ile Leu Ala Gln Val
35

<210> SEQ ID NO 110
<211> LENGTH: 38
<212> TYPE: PRT
<213> ORGANISM: Artificial Sequence
<220> FEATURE:
<223> OTHER INFORMATION: compound Seq_110
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 110

Ile Val Leu Ser Leu Asp Val Pro Ile Lys Leu Lys Gln Ile Leu Leu
1 5 10 15

Lys Gln Glu Arg Gln Lys Xaa Gln Arg Gln Gln Ala Glu Thr Asn Lys
20 25 30

Gln Ile Leu Ala Gln Val
35

-continued

<210> SEQ ID NO 111
<211> LENGTH: 38
<212> TYPE: PRT
<213> ORGANISM: Artificial Sequence
<220> FEATURE:
<223> OTHER INFORMATION: compound Seq_111
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 111

```
Ile Val Leu Ser Leu Asp Val Pro Ile Lys Leu Lys Gln Ile Leu Leu
1               5                   10                  15

Lys Gln Glu Arg Gln Lys Lys Gln Arg Glu Gln Ala Glu Thr Asn Lys
            20                  25                  30

Gln Ile Leu Glu Gln Val
        35
```

<210> SEQ ID NO 112
<211> LENGTH: 38
<212> TYPE: PRT
<213> ORGANISM: Artificial Sequence
<220> FEATURE:
<223> OTHER INFORMATION: compound Seq_112
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 112

```
Ile Val Leu Ser Leu Asp Val Pro Ile Lys Leu Lys Gln Ile Leu Leu
1               5                   10                  15

Lys Gln Glu Arg Gln Lys Lys Gln Arg Glu Lys Ala Glu Thr Asn Lys
            20                  25                  30

Gln Ile Leu Ala Gln Val
        35
```

<210> SEQ ID NO 113
<211> LENGTH: 38
<212> TYPE: PRT
<213> ORGANISM: Artificial Sequence
<220> FEATURE:
<223> OTHER INFORMATION: compound Seq_113
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 113

Ile Val Leu Ser Leu Asp Val Pro Ile Lys Leu Lys Gln Ile Leu Leu
1               5                   10                  15

Lys Gln Glu Arg Gln Lys Lys Gln Arg Gln Gln Ala Glu Thr Asn Lys
            20                  25                  30

Gln Ile Leu Ala Gln Val
        35

<210> SEQ ID NO 114
<211> LENGTH: 38
<212> TYPE: PRT
<213> ORGANISM: Artificial Sequence
<220> FEATURE:
<223> OTHER INFORMATION: compound Seq_114
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 114

Ile Val Leu Ser Leu Asp Val Pro Ile Lys Leu Lys Gln Ile Leu Leu
1               5                   10                  15

Glu Gln Ala Arg Gln Lys Xaa Gln Arg Ala Gln Ala Glu Thr Asn Lys
            20                  25                  30

Arg Ile Leu Glu Arg Val
        35

<210> SEQ ID NO 115
<211> LENGTH: 38
<212> TYPE: PRT
<213> ORGANISM: Artificial Sequence
<220> FEATURE:
<223> OTHER INFORMATION: compound Seq_115
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 115

Ile Val Leu Ser Leu Asp Val Pro Ile Lys Leu Lys Gln Ile Leu Leu
1               5                   10                  15

Lys Gln Glu Arg Gln Lys Xaa Gln Arg Glu Gln Ala Glu Lys Asn Lys
            20                  25                  30

Gln Ile Leu Glu Arg Val
        35

<210> SEQ ID NO 116
<211> LENGTH: 38
<212> TYPE: PRT
<213> ORGANISM: Artificial Sequence
<220> FEATURE:
<223> OTHER INFORMATION: compound Seq_116
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-{AEEA}2-gGlu-
C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 116

```
Ile Val Leu Ser Leu Asp Val Pro Ile Lys Leu Lys Gln Ile Leu Leu
1               5                   10                  15

Lys Gln Glu Arg Gln Lys Xaa Gln Arg Glu Lys Ala Glu Lys Asn Lys
            20                  25                  30

Gln Ile Leu Ala Gln Val
        35
```

<210> SEQ ID NO 117
<211> LENGTH: 38
<212> TYPE: PRT
<213> ORGANISM: Artificial Sequence
<220> FEATURE:
<223> OTHER INFORMATION: compound Seq_117
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-{AEEA}2-gGlu-
C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 117

```
Ile Val Leu Ser Leu Asp Val Pro Ile Lys Leu Lys Gln Ile Leu Leu
1               5                   10                  15

Lys Gln Glu Arg Gln Lys Xaa Gln Arg Gln Gln Ala Glu Lys Asn Lys
            20                  25                  30

Gln Ile Leu Ala Gln Val
        35
```

<210> SEQ ID NO 118
<211> LENGTH: 38
<212> TYPE: PRT
<213> ORGANISM: Artificial Sequence
<220> FEATURE:
<223> OTHER INFORMATION: compound Seq_118
<220> FEATURE:
<221> NAME/KEY: VARIANT
<222> LOCATION: 7
<223> OTHER INFORMATION: D-valine (v)

<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 118

```
Ile Val Leu Ser Leu Asp Xaa Pro Ile Lys Leu Lys Gln Ile Leu Leu
1               5                   10                  15

Lys Gln Glu Arg Gln Lys Xaa Gln Arg Gln Lys Ala Glu Lys Asn Lys
            20                  25                  30

Gln Ile Leu Ala Gln Val
        35
```

<210> SEQ ID NO 119
<211> LENGTH: 38
<212> TYPE: PRT
<213> ORGANISM: Artificial Sequence
<220> FEATURE:
<223> OTHER INFORMATION: compound Seq_119
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 119

```
Ile Val Leu Ser Leu Asp Val Pro Ile Lys Leu Lys Gln Ile Leu Leu
1               5                   10                  15

Lys Gln Glu Arg Gln Lys Lys Xaa Arg Gln Lys Ala Glu Lys Asn Lys
            20                  25                  30

Gln Ile Leu Ala Gln Val
        35
```

<210> SEQ ID NO 120
<211> LENGTH: 38
<212> TYPE: PRT
<213> ORGANISM: Artificial Sequence
<220> FEATURE:
<223> OTHER INFORMATION: compound Seq_120
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 120

Ile Val Leu Ser Leu Asp Val Pro Ile Lys Leu Lys Gln Ile Leu Leu
1 5 10 15

Lys Gln Glu Arg Gln Lys Lys Gln Arg Glu Gln Ala Glu Lys Asn Lys
20 25 30

Gln Ile Leu Glu Gln Val
35

<210> SEQ ID NO 121
<211> LENGTH: 38
<212> TYPE: PRT
<213> ORGANISM: Artificial Sequence
<220> FEATURE:
<223> OTHER INFORMATION: compound Seq_121
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 121

Ile Val Leu Ser Leu Asp Val Pro Ile Lys Leu Lys Gln Ile Leu Leu
1 5 10 15

Lys Gln Glu Arg Gln Lys Lys Gln Arg Glu Lys Ala Glu Lys Asn Lys
20 25 30

Gln Ile Leu Ala Gln Val
35

<210> SEQ ID NO 122
<211> LENGTH: 38
<212> TYPE: PRT
<213> ORGANISM: Artificial Sequence
<220> FEATURE:
<223> OTHER INFORMATION: compound Seq_122
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 122

Ile Val Leu Ser Leu Asp Val Pro Ile Lys Leu Lys Gln Ile Leu Leu
1 5 10 15

Lys Gln Glu Arg Gln Lys Lys Gln Arg Gln Gln Ala Glu Lys Asn Lys
20 25 30

Gln Ile Leu Ala Gln Val
35

<210> SEQ ID NO 123
<211> LENGTH: 38
<212> TYPE: PRT
<213> ORGANISM: Artificial Sequence
<220> FEATURE:
<223> OTHER INFORMATION: compound Seq_123

-continued

<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is “-{AEEA}2-gGlu-
      C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 123

Ile Val Leu Ser Leu Asp Val Pro Ile Lys Leu Lys Gln Ile Leu Leu
1               5                   10                  15

Glu Gln Ala Arg Gln Lys Xaa Gln Arg Ala Gln Ala Glu Lys Asn Lys
            20                  25                  30

Arg Ile Leu Glu Arg Val
        35

<210> SEQ ID NO 124
<211> LENGTH: 38
<212> TYPE: PRT
<213> ORGANISM: Artificial Sequence
<220> FEATURE:
<223> OTHER INFORMATION: compound Seq_124
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is ″-{AEEA}2-gGlu-
      C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 124

Ile Val Leu Ser Leu Asp Val Pro Ile Lys Leu Lys Gln Ile Leu Leu
1               5                   10                  15

Lys Gln Ala Arg Gln Lys Xaa Gln Arg Ala Gln Ala Glu Lys Asn Lys
            20                  25                  30

Arg Ile Leu Glu Arg Val
        35

<210> SEQ ID NO 125
<211> LENGTH: 38
<212> TYPE: PRT
<213> ORGANISM: Artificial Sequence
<220> FEATURE:
<223> OTHER INFORMATION: compound Seq_125
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is “-{AEEA}2-gGlu-
      C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:

-continued

<221> NAME/KEY: MOD_RES
<222> LOCATION: 38
<223> OTHER INFORMATION: C-terminal amino acid residue is amidated as a
primary amide

<400> SEQUENCE: 125

Ile Val Leu Ser Leu Asp Val Pro Ile Lys Leu Lys Gln Ile Leu Leu
1 5 10 15

Glu Gln Ala Arg Gln Lys Xaa Gln Arg Glu Gln Ala Glu Lys Asn Lys
20 25 30

Arg Ile Leu Glu Arg Val
35

<210> SEQ ID NO 126
<211> LENGTH: 38
<212> TYPE: PRT
<213> ORGANISM: Artificial Sequence
<220> FEATURE:
<223> OTHER INFORMATION: compound Seq_126
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is ″-{AEEA}2-gGlu-
C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 126

Ile Val Leu Ser Leu Asp Xaa Pro Ile Lys Leu Lys Gln Ile Leu Leu
1 5 10 15

Glu Gln Ala Lys Gln Lys Xaa Gln Arg Ala Gln Ala Glu Lys Asn Lys
20 25 30

Arg Ile Leu Glu Arg Val
35

<210> SEQ ID NO 127
<211> LENGTH: 38
<212> TYPE: PRT
<213> ORGANISM: Artificial Sequence
<220> FEATURE:
<223> OTHER INFORMATION: compound Seq_127
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is “-{AEEA}2-gGlu-
C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 127

Ile Val Leu Ser Leu Asp Xaa Pro Ile Lys Leu Lys Gln Ile Leu Leu
1 5 10 15

Glu Gln Ala Lys Gln Lys Xaa Gln Arg Glu Gln Ala Glu Lys Asn Lys
20 25 30

Arg Ile Leu Glu Arg Val
35

<210> SEQ ID NO 128
<211> LENGTH: 38
<212> TYPE: PRT
<213> ORGANISM: Artificial Sequence
<220> FEATURE:
<223> OTHER INFORMATION: compound Seq_128
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 128

Ile Val Leu Ser Leu Asp Xaa Pro Ile Lys Leu Lys Gln Ile Leu Leu
1 5 10 15

Lys Gln Ala Arg Gln Lys Xaa Gln Arg Glu Gln Ala Glu Lys Asn Lys
20 25 30

Arg Ile Leu Glu Arg Val
35

<210> SEQ ID NO 129
<211> LENGTH: 38
<212> TYPE: PRT
<213> ORGANISM: Artificial Sequence
<220> FEATURE:
<223> OTHER INFORMATION: compound Seq_129
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 129

```
Ile Val Leu Ser Leu Asp Xaa Pro Ile Lys Leu Lys Gln Ile Leu Leu
1               5                   10                  15

Glu Gln Glu Arg Gln Lys Xaa Gln Arg Glu Gln Ala Glu Lys Asn Lys
            20                  25                  30

Gln Ile Leu Ala Gln Val
        35


<210> SEQ ID NO 130
<211> LENGTH: 38
<212> TYPE: PRT
<213> ORGANISM: Artificial Sequence
<220> FEATURE:
<223> OTHER INFORMATION: compound Seq_130
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 130

Ile Val Leu Ser Leu Asp Xaa Pro Ile Lys Leu Lys Gln Ile Leu Leu
1               5                   10                  15

Lys Gln Glu Arg Gln Lys Xaa Gln Arg Glu Gln Ala Glu Lys Asn Lys
            20                  25                  30

Gln Ile Leu Ala Gln Val
        35


<210> SEQ ID NO 131
<211> LENGTH: 38
<212> TYPE: PRT
<213> ORGANISM: Artificial Sequence
<220> FEATURE:
<223> OTHER INFORMATION: compound Seq_131
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 131

Ile Val Leu Ser Leu Asp Xaa Pro Ile Lys Leu Lys Gln Ile Leu Leu
1               5                   10                  15
```

```
Glu Gln Glu Arg Gln Lys Xaa Gln Arg Gln Gln Ala Glu Lys Asn Lys
            20                  25                  30

Gln Ile Leu Ala Gln Val
        35


<210> SEQ ID NO 132
<211> LENGTH: 38
<212> TYPE: PRT
<213> ORGANISM: Artificial Sequence
<220> FEATURE:
<223> OTHER INFORMATION: compound Seq_132
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 132

Ile Val Leu Ser Leu Asp Xaa Pro Ile Lys Leu Lys Gln Ile Leu Leu
1               5                   10                  15

Glu Gln Glu Arg Gln Lys Xaa Gln Arg Glu Gln Ala Glu Lys Asn Lys
            20                  25                  30

Gln Ile Leu Glu Arg Val
        35


<210> SEQ ID NO 133
<211> LENGTH: 38
<212> TYPE: PRT
<213> ORGANISM: Artificial Sequence
<220> FEATURE:
<223> OTHER INFORMATION: compound Seq_133
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 133

Ile Val Leu Ser Leu Asp Xaa Pro Ile Lys Leu Lys Gln Ile Leu Leu
1               5                   10                  15

Lys Gln Glu Arg Gln Lys Xaa Gln Arg Glu Gln Ala Glu Lys Asn Lys
            20                  25                  30
```

Gln Ile Leu Glu Arg Val
35

<210> SEQ ID NO 134
<211> LENGTH: 38
<212> TYPE: PRT
<213> ORGANISM: Artificial Sequence
<220> FEATURE:
<223> OTHER INFORMATION: compound Seq_134
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 134

Ile Val Leu Ser Leu Asp Xaa Pro Ile Lys Leu Lys Gln Ile Leu Leu
1 5 10 15

Lys Gln Glu Arg Gln Lys Xaa Gln Arg Glu Lys Ala Glu Lys Asn Lys
20 25 30

Gln Ile Leu Ala Gln Val
35

<210> SEQ ID NO 135
<211> LENGTH: 38
<212> TYPE: PRT
<213> ORGANISM: Artificial Sequence
<220> FEATURE:
<223> OTHER INFORMATION: compound Seq_135
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 135

Ile Val Leu Ser Leu Asp Xaa Pro Ile Lys Leu Lys Gln Ile Leu Leu
1 5 10 15

Lys Gln Glu Arg Gln Lys Xaa Gln Arg Gln Gln Ala Glu Lys Asn Lys
20 25 30

Gln Ile Leu Ala Gln Val
35

<210> SEQ ID NO 136
<211> LENGTH: 38
<212> TYPE: PRT
<213> ORGANISM: Artificial Sequence
<220> FEATURE:
<223> OTHER INFORMATION: compound Seq_136
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 136

```
Ile Val Leu Ser Leu Asp Xaa Pro Ile Lys Leu Lys Gln Ile Leu Leu
1               5                   10                  15

Lys Gln Glu Arg Gln Lys Lys Xaa Arg Gln Lys Ala Glu Lys Asn Lys
            20                  25                  30

Gln Ile Leu Ala Gln Val
        35
```

<210> SEQ ID NO 137
<211> LENGTH: 38
<212> TYPE: PRT
<213> ORGANISM: Artificial Sequence
<220> FEATURE:
<223> OTHER INFORMATION: compound Seq_137
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 137

```
Ile Val Leu Ser Leu Asp Xaa Pro Ile Lys Leu Lys Gln Ile Leu Leu
1               5                   10                  15

Lys Gln Glu Arg Gln Lys Lys Gln Arg Glu Gln Ala Glu Lys Asn Lys
            20                  25                  30

Gln Ile Leu Glu Gln Val
        35
```

<210> SEQ ID NO 138
<211> LENGTH: 38
<212> TYPE: PRT
<213> ORGANISM: Artificial Sequence
<220> FEATURE:

```
<223> OTHER INFORMATION: compound Seq_138
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 138

Ile Val Leu Ser Leu Asp Xaa Pro Ile Lys Leu Lys Gln Ile Leu Leu
1               5                   10                  15

Lys Gln Glu Arg Gln Lys Lys Gln Arg Glu Lys Ala Glu Lys Asn Lys
            20                  25                  30

Gln Ile Leu Ala Gln Val
        35


<210> SEQ ID NO 139
<211> LENGTH: 38
<212> TYPE: PRT
<213> ORGANISM: Artificial Sequence
<220> FEATURE:
<223> OTHER INFORMATION: compound Seq_139
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 139

Ile Val Leu Ser Leu Asp Xaa Pro Ile Lys Leu Lys Gln Ile Leu Leu
1               5                   10                  15

Lys Gln Glu Arg Gln Lys Lys Gln Arg Gln Gln Ala Glu Lys Asn Lys
            20                  25                  30

Gln Ile Leu Ala Gln Val
        35


<210> SEQ ID NO 140
<211> LENGTH: 38
<212> TYPE: PRT
<213> ORGANISM: Artificial Sequence
<220> FEATURE:
<223> OTHER INFORMATION: compound Seq_140
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
```

<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 140

```
Ile Val Leu Ser Leu Asp Xaa Pro Ile Lys Leu Lys Gln Ile Leu Leu
1               5                   10                  15

Glu Gln Ala Arg Gln Lys Xaa Gln Arg Ala Gln Ala Glu Lys Asn Lys
            20                  25                  30

Arg Ile Leu Glu Arg Val
        35
```

<210> SEQ ID NO 141
<211> LENGTH: 38
<212> TYPE: PRT
<213> ORGANISM: Artificial Sequence
<220> FEATURE:
<223> OTHER INFORMATION: compound Seq_141
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 141

```
Ile Val Leu Ser Leu Asp Xaa Pro Ile Lys Leu Lys Gln Ile Leu Leu
1               5                   10                  15

Lys Gln Ala Arg Gln Lys Xaa Gln Arg Ala Gln Ala Glu Lys Asn Lys
            20                  25                  30

Arg Ile Leu Glu Arg Val
        35
```

<210> SEQ ID NO 142
<211> LENGTH: 38
<212> TYPE: PRT
<213> ORGANISM: Artificial Sequence
<220> FEATURE:
<223> OTHER INFORMATION: compound Seq_142
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23

<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 142

```
Ile Val Leu Ser Leu Asp Xaa Pro Ile Lys Leu Lys Gln Ile Leu Leu
1               5                   10                  15

Glu Gln Ala Arg Gln Lys Xaa Gln Arg Glu Gln Ala Glu Lys Asn Lys
            20                  25                  30

Arg Ile Leu Glu Arg Val
        35
```

<210> SEQ ID NO 143
<211> LENGTH: 38
<212> TYPE: PRT
<213> ORGANISM: Artificial Sequence
<220> FEATURE:
<223> OTHER INFORMATION: compound Seq_143
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 143

```
Phe Thr Leu Ser Leu Asp Val Pro Thr Lys Ile Lys Gln Ile Leu Leu
1               5                   10                  15

Lys Gln Glu Lys Gln Lys Lys Gln Arg Gln Lys Ala Lys Thr Asn Lys
            20                  25                  30

Gln Ile Leu Glu Arg Val
        35
```

<210> SEQ ID NO 144
<211> LENGTH: 38
<212> TYPE: PRT
<213> ORGANISM: Artificial Sequence
<220> FEATURE:
<223> OTHER INFORMATION: compound Seq_144
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 144

```
Phe Thr Leu Ser Leu Asp Val Pro Thr Lys Ile Lys Gln Ile Leu Leu
1               5                   10                  15

Lys Gln Glu Arg Gln Lys Lys Gln Arg Gln Lys Ala Lys Thr Asn Lys
            20                  25                  30

Gln Ile Leu Glu Arg Val
        35
```

```
<210> SEQ ID NO 145
<211> LENGTH: 38
<212> TYPE: PRT
<213> ORGANISM: Artificial Sequence
<220> FEATURE:
<223> OTHER INFORMATION: compound Seq_145
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 145

Phe Thr Leu Ser Leu Asp Val Pro Thr Lys Ile Lys Gln Ile Leu Leu
1               5                   10                  15

Lys Gln Glu Arg Gln Lys Lys Gln Arg Gln Lys Ala Lys Lys Asn Lys
            20                  25                  30

Gln Ile Leu Glu Arg Val
        35


<210> SEQ ID NO 146
<211> LENGTH: 38
<212> TYPE: PRT
<213> ORGANISM: Artificial Sequence
<220> FEATURE:
<223> OTHER INFORMATION: compound Seq_146
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 146

Phe Thr Leu Ser Leu Asp Val Pro Ile Lys Leu Lys Gln Ile Leu Leu
1               5                   10                  15

Lys Gln Glu Arg Gln Lys Lys Gln Arg Gln Lys Ala Lys Lys Asn Lys
            20                  25                  30

Gln Ile Leu Glu Arg Val
        35


<210> SEQ ID NO 147
<211> LENGTH: 38
<212> TYPE: PRT
<213> ORGANISM: Artificial Sequence
<220> FEATURE:
<223> OTHER INFORMATION: compound Seq_147
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 24
```

```
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 147

Ile Val Leu Ser Leu Asp Xaa Pro Ile Gly Leu Lys Gln Ile Leu Leu
1               5                   10                  15

Lys Gln Glu Arg Gln Lys Lys Xaa Arg Glu Gln Ala Glu Thr Asn Lys
            20                  25                  30

Gln Ile Leu Ala Gln Val
        35


<210> SEQ ID NO 148
<211> LENGTH: 38
<212> TYPE: PRT
<213> ORGANISM: Artificial Sequence
<220> FEATURE:
<223> OTHER INFORMATION: compound Seq_148
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 148

Ile Val Leu Ser Leu Asp Val Pro Ile Gly Leu Lys Gln Ile Leu Leu
1               5                   10                  15

Lys Gln Glu Arg Gln Lys Lys Xaa Arg Glu Gln Ala Glu Thr Asn Lys
            20                  25                  30

Arg Ile Leu Glu Arg Val
        35


<210> SEQ ID NO 149
<211> LENGTH: 38
<212> TYPE: PRT
<213> ORGANISM: Artificial Sequence
<220> FEATURE:
<223> OTHER INFORMATION: compound Seq_149
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide
```

<400> SEQUENCE: 149

Ile Val Leu Ser Leu Asp Xaa Pro Ile Lys Leu Lys Gln Ile Leu Leu
1 5 10 15

Lys Gln Glu Arg Gln Lys Lys Xaa Arg Glu Gln Ala Glu Thr Asn Lys
20 25 30

Arg Ile Leu Glu Arg Val
35

<210> SEQ ID NO 150
<211> LENGTH: 38
<212> TYPE: PRT
<213> ORGANISM: Artificial Sequence
<220> FEATURE:
<223> OTHER INFORMATION: compound Seq_150
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 150

Ile Val Leu Ser Leu Asp Xaa Pro Ile Gly Leu Lys Gln Ile Leu Leu
1 5 10 15

Lys Gln Glu Arg Gln Lys Lys Xaa Arg Gln Gln Ala Glu Thr Asn Lys
20 25 30

Arg Ile Leu Glu Arg Val
35

<210> SEQ ID NO 151
<211> LENGTH: 38
<212> TYPE: PRT
<213> ORGANISM: Artificial Sequence
<220> FEATURE:
<223> OTHER INFORMATION: compound Seq_151
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 151

Ile Val Leu Ser Leu Asp Xaa Pro Ile Gly Leu Lys Gln Ile Leu Leu

-continued 1 5 10 15

Lys Gln Glu Arg Gln Lys Lys Xaa Arg Glu Gln Ala Glu Lys Asn Lys
20 25 30

Arg Ile Leu Glu Arg Val
35

<210> SEQ ID NO 152
<211> LENGTH: 38
<212> TYPE: PRT
<213> ORGANISM: Artificial Sequence
<220> FEATURE:
<223> OTHER INFORMATION: compound Seq_152
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 152

Ile Val Leu Ser Leu Asp Val Pro Ile Lys Leu Lys Gln Ile Leu Leu
1 5 10 15

Lys Gln Glu Arg Gln Lys Lys Xaa Arg Glu Gln Ala Glu Thr Asn Lys
20 25 30

Arg Ile Leu Glu Arg Val
35

<210> SEQ ID NO 153
<211> LENGTH: 38
<212> TYPE: PRT
<213> ORGANISM: Artificial Sequence
<220> FEATURE:
<221> NAME/KEY: MOD_RES
<222> LOCATION: 1
<223> OTHER INFORMATION: Acetylation
<220> FEATURE:
<223> OTHER INFORMATION: compound Seq_153
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 153

Ile Val Leu Ser Leu Asp Val Pro Ile Gly Leu Lys Gln Ile Leu Leu
1 5 10 15

Glu Gln Glu Lys Gln Glu Lys Glu Lys Gln Gln Ala Glu Thr Asn Ala
20 25 30

Gln Ile Leu Ala Gln Val
35

<210> SEQ ID NO 154
<211> LENGTH: 38

-continued

```
<212> TYPE: PRT
<213> ORGANISM: Artificial Sequence
<220> FEATURE:
<223> OTHER INFORMATION: compound Seq_154
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 154

Ile Val Leu Ser Leu Asp Val Pro Ile Gly Leu Lys Gln Ile Leu Leu
1               5                   10                  15

Glu Gln Glu Lys Gln Glu Lys Glu Lys Gln Gln Ala Glu Thr Asn Lys
            20                  25                  30

Arg Ile Leu Glu Arg Val
        35


<210> SEQ ID NO 155
<211> LENGTH: 38
<212> TYPE: PRT
<213> ORGANISM: Artificial Sequence
<220> FEATURE:
<223> OTHER INFORMATION: compound Seq_155
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 155

Ile Val Leu Ser Leu Asp Val Pro Ile Gly Leu Lys Gln Ile Leu Leu
1               5                   10                  15

Glu Gln Glu Lys Gln Glu Lys Glu Lys Gln Gln Ala Glu Lys Asn Lys
            20                  25                  30

Arg Ile Leu Glu Arg Val
        35


<210> SEQ ID NO 156
<211> LENGTH: 38
<212> TYPE: PRT
<213> ORGANISM: Artificial Sequence
<220> FEATURE:
<223> OTHER INFORMATION: compound Seq_156
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide
```

<400> SEQUENCE: 156

Ile Val Leu Ser Leu Asp Val Pro Ile Gly Leu Lys Gln Ile Leu Leu
1 5 10 15

Lys Gln Glu Arg Gln Lys Lys Xaa Arg Glu Gln Ala Glu Thr Asn Ala
20 25 30

Gln Ile Leu Ala Gln Val
35

<210> SEQ ID NO 157
<211> LENGTH: 38
<212> TYPE: PRT
<213> ORGANISM: Artificial Sequence
<220> FEATURE:
<221> NAME/KEY: MOD_RES
<222> LOCATION: 1
<223> OTHER INFORMATION: Acetylation
<220> FEATURE:
<223> OTHER INFORMATION: compound Seq_157
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 157

Ile Val Leu Ser Leu Asp Xaa Pro Ile Lys Leu Lys Gln Ile Leu Leu
1 5 10 15

Glu Gln Ala Arg Gln Lys Xaa Gln Arg Glu Gln Ala Glu Lys Asn Lys
20 25 30

Gln Ile Leu Glu Gln Val
35

<210> SEQ ID NO 158
<211> LENGTH: 38
<212> TYPE: PRT
<213> ORGANISM: Artificial Sequence
<220> FEATURE:
<221> NAME/KEY: MOD_RES
<222> LOCATION: 1
<223> OTHER INFORMATION: Acetylation
<220> FEATURE:
<223> OTHER INFORMATION: compound Seq_158
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)

<220> FEATURE:
<221> NAME/KEY: MOD_RES
<222> LOCATION: 38
<223> OTHER INFORMATION: C-terminal amino acid residue is amidated as a primary amide

<400> SEQUENCE: 158

```
Ile Val Leu Ser Leu Asp Xaa Pro Ile Lys Leu Lys Gln Ile Leu Leu
1               5                   10                  15

Glu Gln Glu Arg Gln Lys Xaa Gln Arg Glu Gln Ala Glu Lys Asn Lys
            20                  25                  30

Gln Ile Leu Glu Gln Val
        35
```

<210> SEQ ID NO 159
<211> LENGTH: 38
<212> TYPE: PRT
<213> ORGANISM: Artificial Sequence
<220> FEATURE:
<221> NAME/KEY: MOD_RES
<222> LOCATION: 1
<223> OTHER INFORMATION: Acetylation
<220> FEATURE:
<223> OTHER INFORMATION: compound Seq_159
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 159

```
Ile Val Leu Ser Leu Asp Xaa Pro Ile Lys Leu Lys Gln Ile Leu Leu
1               5                   10                  15

Glu Gln Glu Arg Gln Glu Xaa Gln Arg Glu Gln Ala Glu Lys Asn Lys
            20                  25                  30

Gln Ile Leu Glu Gln Val
        35
```

<210> SEQ ID NO 160
<211> LENGTH: 38
<212> TYPE: PRT
<213> ORGANISM: Artificial Sequence
<220> FEATURE:
<221> NAME/KEY: MOD_RES
<222> LOCATION: 1
<223> OTHER INFORMATION: Acetylation
<220> FEATURE:
<223> OTHER INFORMATION: compound Seq_160
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu- C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 160

```
Ile Val Leu Ser Leu Asp Xaa Pro Ile Lys Leu Lys Gln Ile Leu Leu
1               5                   10                  15

Glu Gln Glu Arg Gln Glu Xaa Glu Arg Glu Gln Ala Glu Thr Asn Lys
            20                  25                  30

Gln Ile Leu Glu Gln Val
        35
```

<210> SEQ ID NO 161
<211> LENGTH: 38
<212> TYPE: PRT
<213> ORGANISM: Artificial Sequence
<220> FEATURE:
<221> NAME/KEY: MOD_RES
<222> LOCATION: 1
<223> OTHER INFORMATION: Acetylation
<220> FEATURE:
<223> OTHER INFORMATION: compound Seq_161
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 161

```
Ile Val Leu Ser Leu Asp Xaa Pro Ile Lys Leu Lys Gln Ile Leu Leu
1               5                   10                  15

Glu Gln Glu Arg Gln Glu Xaa Glu Arg Glu Gln Ala Glu Lys Asn Glu
            20                  25                  30

Gln Ile Leu Glu Gln Val
        35
```

<210> SEQ ID NO 162
<211> LENGTH: 38
<212> TYPE: PRT
<213> ORGANISM: Artificial Sequence
<220> FEATURE:
<221> NAME/KEY: MOD_RES
<222> LOCATION: 1
<223> OTHER INFORMATION: Acetylation
<220> FEATURE:
<223> OTHER INFORMATION: compound Seq_162
<220> FEATURE:
<221> NAME/KEY: VARIANT
<222> LOCATION: 7
<223> OTHER INFORMATION: D-valine (v)

<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 162

```
Ile Val Leu Ser Leu Asp Xaa Pro Ile Glu Leu Lys Gln Ile Leu Leu
1               5                   10                  15

Glu Gln Glu Arg Gln Lys Xaa Gln Arg Glu Gln Ala Glu Lys Asn Lys
            20                  25                  30

Gln Ile Leu Glu Gln Val
        35
```

<210> SEQ ID NO 163
<211> LENGTH: 38
<212> TYPE: PRT
<213> ORGANISM: Artificial Sequence
<220> FEATURE:
<221> NAME/KEY: MOD_RES
<222> LOCATION: 1
<223> OTHER INFORMATION: Acetylation
<220> FEATURE:
<223> OTHER INFORMATION: compound Seq_163
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 163

```
Ile Val Leu Ser Leu Asp Xaa Pro Ile His Leu Lys Gln Ile Leu Leu
1               5                   10                  15

Glu Gln Glu Arg Gln Lys Xaa Gln Arg Glu Gln Ala Glu Lys Asn Lys
            20                  25                  30

Gln Ile Leu Glu Gln Val
        35
```

<210> SEQ ID NO 164
<211> LENGTH: 38
<212> TYPE: PRT
<213> ORGANISM: Artificial Sequence
<220> FEATURE:
<221> NAME/KEY: MOD_RES
<222> LOCATION: 1
<223> OTHER INFORMATION: Acetylation
<220> FEATURE:

<223> OTHER INFORMATION: compound Seq_164
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is ”-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 164

```
Ile Val Leu Ser Leu Asp Xaa Pro Ile Gly Leu Lys Gln Ile Leu Leu
1               5                   10                  15

Glu Gln Glu Arg Gln Lys Xaa Gln Arg Glu Gln Ala Glu Lys Asn Lys
            20                  25                  30

Gln Ile Leu Glu Gln Val
        35
```

<210> SEQ ID NO 165
<211> LENGTH: 38
<212> TYPE: PRT
<213> ORGANISM: Artificial Sequence
<220> FEATURE:
<221> NAME/KEY: MOD_RES
<222> LOCATION: 1
<223> OTHER INFORMATION: Acetylation
<220> FEATURE:
<223> OTHER INFORMATION: compound Seq_165
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is “-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 165

```
Ile Val Leu Ser Leu Asp Xaa Pro Ile Lys Leu Lys Gln Ile Leu Leu
1               5                   10                  15

Glu Gln Ala Arg Gln Lys Xaa Gln Arg Glu Gln Ala Glu Lys Asn Glu
            20                  25                  30

Gln Ile Leu Glu Gln Val
        35
```

<210> SEQ ID NO 166
<211> LENGTH: 38
<212> TYPE: PRT
<213> ORGANISM: Artificial Sequence
<220> FEATURE:
<221> NAME/KEY: MOD_RES
<222> LOCATION: 1
<223> OTHER INFORMATION: Acetylation
<220> FEATURE:
<223> OTHER INFORMATION: compound Seq_166
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 166

```
Ile Val Leu Ser Leu Asp Xaa Pro Ile Lys Leu Lys Gln Ile Leu Leu
1               5                   10                  15

Glu Gln Glu Arg Gln Lys Xaa Gln Arg Glu Gln Ala Glu Lys Asn Glu
            20                  25                  30

Gln Ile Leu Glu Gln Val
        35
```

<210> SEQ ID NO 167
<211> LENGTH: 38
<212> TYPE: PRT
<213> ORGANISM: Artificial Sequence
<220> FEATURE:
<221> NAME/KEY: MOD_RES
<222> LOCATION: 1
<223> OTHER INFORMATION: Acetylation
<220> FEATURE:
<223> OTHER INFORMATION: compound Seq_167
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 167

```
Ile Val Leu Ser Leu Asp Xaa Pro Ile Gly Leu Lys Gln Ile Leu Leu
1               5                   10                  15

Glu Gln Glu Arg Gln Lys Xaa Gln Arg Glu Gln Ala Glu Lys Asn Glu
            20                  25                  30

Gln Ile Leu Glu Gln Val
        35
```

<210> SEQ ID NO 168
<211> LENGTH: 38
<212> TYPE: PRT
<213> ORGANISM: Artificial Sequence
<220> FEATURE:
<221> NAME/KEY: MOD_RES
<222> LOCATION: 1
<223> OTHER INFORMATION: Acetylation
<220> FEATURE:
<223> OTHER INFORMATION: compound Seq_168
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 168

```
Ile Val Leu Ser Leu Asp Xaa Pro Ile Glu Leu Lys Gln Ile Leu Leu
1               5                   10                  15

Glu Gln Glu Arg Gln Lys Xaa Gln Arg Glu Gln Ala Glu Lys Asn Glu
            20                  25                  30

Gln Ile Leu Glu Gln Val
        35
```

<210> SEQ ID NO 169
<211> LENGTH: 38
<212> TYPE: PRT
<213> ORGANISM: Artificial Sequence
<220> FEATURE:
<221> NAME/KEY: MOD_RES
<222> LOCATION: 1
<223> OTHER INFORMATION: Acetylation
<220> FEATURE:
<223> OTHER INFORMATION: compound Seq_169
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 169

```
Ile Val Leu Ser Leu Asp Xaa Pro Ile Lys Leu Lys Gln Ile Leu Leu
1               5                   10                  15

Glu Gln Glu Arg Gln Glu Xaa Gln Arg Glu Gln Ala Glu Lys Asn Glu
```

```
            20                  25                  30

Gln Ile Leu Glu Gln Val
        35


<210> SEQ ID NO 170
<211> LENGTH: 38
<212> TYPE: PRT
<213> ORGANISM: Artificial Sequence
<220> FEATURE:
<221> NAME/KEY: MOD_RES
<222> LOCATION: 1
<223> OTHER INFORMATION: Acetylation
<220> FEATURE:
<223> OTHER INFORMATION: compound Seq_170
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 170

Ile Val Leu Ser Leu Asp Xaa Pro Ile Glu Leu Lys Gln Ile Leu Leu
1               5                   10                  15

Glu Gln Glu Arg Gln Glu Xaa Gln Arg Glu Gln Ala Glu Lys Asn Glu
            20                  25                  30

Gln Ile Leu Glu Gln Val
        35


<210> SEQ ID NO 171
<211> LENGTH: 38
<212> TYPE: PRT
<213> ORGANISM: Artificial Sequence
<220> FEATURE:
<223> OTHER INFORMATION: compound Seq_171
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-{gGlu}2-
      C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 171

Ile Val Leu Ser Leu Asp Xaa Pro Ile Lys Leu Lys Gln Ile Leu Leu
1               5                   10                  15
```

```
Lys Gln Glu Arg Gln Lys Xaa Gln Arg Glu Gln Ala Glu Lys Asn Lys
            20                  25                  30

Gln Ile Leu Ala Gln Val
        35


<210> SEQ ID NO 172
<211> LENGTH: 38
<212> TYPE: PRT
<213> ORGANISM: Artificial Sequence
<220> FEATURE:
<223> OTHER INFORMATION: compound Seq_172
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-{gGlu}2-
      C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 172

Ile Val Leu Ser Leu Asp Xaa Pro Ile Lys Leu Lys Gln Ile Leu Leu
1               5                   10                  15

Lys Gln Glu Arg Gln Lys Xaa Gln Arg Glu Gln Ala Glu Lys Asn Lys
            20                  25                  30

Gln Ile Leu Ala Gln Val
        35


<210> SEQ ID NO 173
<211> LENGTH: 38
<212> TYPE: PRT
<213> ORGANISM: Artificial Sequence
<220> FEATURE:
<223> OTHER INFORMATION: compound Seq_173
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)18COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 173

Ile Val Leu Ser Leu Asp Xaa Pro Ile Lys Leu Lys Gln Ile Leu Leu
1               5                   10                  15

Lys Gln Glu Arg Gln Lys Xaa Gln Arg Glu Gln Ala Glu Lys Asn Lys
            20                  25                  30
```

```
Gln Ile Leu Ala Gln Val
        35


<210> SEQ ID NO 174
<211> LENGTH: 38
<212> TYPE: PRT
<213> ORGANISM: Artificial Sequence
<220> FEATURE:
<223> OTHER INFORMATION: compound Seq_174
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-{gGlu}2-
      C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 174

Ile Val Leu Ser Leu Asp Xaa Pro Ile Lys Leu Lys Gln Ile Leu Leu
1               5                   10                  15

Lys Gln Ala Arg Gln Lys Xaa Gln Arg Ala Gln Ala Glu Lys Asn Lys
            20                  25                  30

Arg Ile Leu Glu Arg Val
        35


<210> SEQ ID NO 175
<211> LENGTH: 38
<212> TYPE: PRT
<213> ORGANISM: Artificial Sequence
<220> FEATURE:
<223> OTHER INFORMATION: compound Seq_175
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)18COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 175

Ile Val Leu Ser Leu Asp Xaa Pro Ile Lys Leu Lys Gln Ile Leu Leu
1               5                   10                  15

Lys Gln Ala Arg Gln Lys Xaa Gln Arg Ala Gln Ala Glu Lys Asn Lys
            20                  25                  30

Arg Ile Leu Glu Arg Val
        35
```

-continued

<210> SEQ ID NO 176
<211> LENGTH: 38
<212> TYPE: PRT
<213> ORGANISM: Artificial Sequence
<220> FEATURE:
<223> OTHER INFORMATION: compound Seq_176
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is ”-{AEEA}2-{gGlu}2-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 176

Ile Val Leu Ser Leu Asp Xaa Pro Ile Lys Leu Lys Gln Ile Leu Leu
1 5 10 15

Lys Gln Glu Arg Gln Lys Lys Gln Arg Gln Gln Ala Glu Lys Asn Lys
20 25 30

Gln Ile Leu Ala Gln Val
35

<210> SEQ ID NO 177
<211> LENGTH: 38
<212> TYPE: PRT
<213> ORGANISM: Artificial Sequence
<220> FEATURE:
<223> OTHER INFORMATION: compound Seq_177
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is “-{AEEA}2-{gGlu}2-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 177

Ile Val Leu Ser Leu Asp Xaa Pro Ile Lys Leu Lys Gln Ile Leu Leu
1 5 10 15

Lys Gln Glu Arg Gln Lys Lys Gln Arg Gln Gln Ala Glu Lys Asn Lys
20 25 30

Gln Ile Leu Ala Gln Val
35

<210> SEQ ID NO 178
<211> LENGTH: 38
<212> TYPE: PRT
<213> ORGANISM: Artificial Sequence
<220> FEATURE:
<223> OTHER INFORMATION: compound Seq_178
<220> FEATURE:
<221> NAME/KEY: VARIANT
<222> LOCATION: 7
<223> OTHER INFORMATION: D-valine (v)

<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-{AEEA}2-gGlu-
C(O)(CH2)18COOH
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 178

Ile Val Leu Ser Leu Asp Xaa Pro Ile Lys Leu Lys Gln Ile Leu Leu
1 5 10 15

Lys Gln Glu Arg Gln Lys Lys Gln Arg Gln Gln Ala Glu Lys Asn Lys
20 25 30

Gln Ile Leu Ala Gln Val
35

<210> SEQ ID NO 179
<211> LENGTH: 38
<212> TYPE: PRT
<213> ORGANISM: Artificial Sequence
<220> FEATURE:
<223> OTHER INFORMATION: compound Seq_179
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-gGlu-
C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 179

Ile Val Leu Ser Leu Asp Xaa Pro Ile Lys Leu Lys Gln Ile Leu Leu
1 5 10 15

Lys Gln Glu Arg Gln Lys Xaa Gln Arg Glu Gln Ala Glu Lys Asn Lys
20 25 30

Gln Ile Leu Ala Gln Val
35

<210> SEQ ID NO 180
<211> LENGTH: 38
<212> TYPE: PRT
<213> ORGANISM: Artificial Sequence
<220> FEATURE:
<223> OTHER INFORMATION: compound Seq_180
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-gGlu-
C(O)(CH2)16COOH
<220> FEATURE:

-continued

<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 180

```
Ile Val Leu Ser Leu Asp Xaa Pro Ile Lys Leu Lys Gln Ile Leu Leu
1               5                   10                  15

Lys Gln Ala Arg Gln Lys Xaa Gln Arg Ala Gln Ala Glu Lys Asn Lys
            20                  25                  30

Arg Ile Leu Glu Arg Val
        35
```

<210> SEQ ID NO 181
<211> LENGTH: 38
<212> TYPE: PRT
<213> ORGANISM: Artificial Sequence
<220> FEATURE:
<223> OTHER INFORMATION: compound Seq_181
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-gGlu-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 181

```
Ile Val Leu Ser Leu Asp Xaa Pro Ile Lys Leu Lys Gln Ile Leu Leu
1               5                   10                  15

Lys Gln Glu Arg Gln Lys Lys Gln Arg Gln Gln Ala Glu Lys Asn Lys
            20                  25                  30

Gln Ile Leu Ala Gln Val
        35
```

<210> SEQ ID NO 182
<211> LENGTH: 38
<212> TYPE: PRT
<213> ORGANISM: Artificial Sequence
<220> FEATURE:
<223> OTHER INFORMATION: compound Seq_182
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 182

Ile Val Leu Ser Leu Asp Xaa Pro Ile Lys Leu Lys Gln Ile Leu Leu
1 5 10 15

Lys Gln Glu Arg Gln Lys Xaa Gln Arg Glu Gln Ala Glu Lys Asn Lys
20 25 30

Gln Ile Leu Ala Gln Val
35

<210> SEQ ID NO 183
<211> LENGTH: 38
<212> TYPE: PRT
<213> ORGANISM: Artificial Sequence
<220> FEATURE:
<223> OTHER INFORMATION: compound Seq_183
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-C(O)(CH2)16COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 183

Ile Val Leu Ser Leu Asp Xaa Pro Ile Lys Leu Lys Gln Ile Leu Leu
1 5 10 15

Lys Gln Ala Arg Gln Lys Xaa Gln Arg Ala Gln Ala Glu Lys Asn Lys
20 25 30

Arg Ile Leu Glu Arg Val
35

<210> SEQ ID NO 184
<211> LENGTH: 38
<212> TYPE: PRT
<213> ORGANISM: Artificial Sequence
<220> FEATURE:
<223> OTHER INFORMATION: compound Seq_184
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-C(O)(CH2)16COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 184

Ile Val Leu Ser Leu Asp Xaa Pro Ile Lys Leu Lys Gln Ile Leu Leu
1 5 10 15

Lys Gln Glu Arg Gln Lys Lys Gln Arg Gln Gln Ala Glu Lys Asn Lys
20 25 30

Gln Ile Leu Ala Gln Val
35

<210> SEQ ID NO 185
<211> LENGTH: 38
<212> TYPE: PRT
<213> ORGANISM: Artificial Sequence
<220> FEATURE:
<223> OTHER INFORMATION: compound Seq_185
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)16COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 185

Ile Val Leu Ser Leu Asp Val Pro Ile Lys Leu Lys Gln Ile Leu Leu
1 5 10 15

Lys Gln Glu Arg Gln Lys Lys Xaa Arg Gln Lys Ala Glu Thr Asn Lys
20 25 30

Gln Ile Leu Ala Gln Val
35

<210> SEQ ID NO 186
<211> LENGTH: 38
<212> TYPE: PRT
<213> ORGANISM: Artificial Sequence
<220> FEATURE:
<223> OTHER INFORMATION: compound Seq_186
<220> FEATURE:
<221> NAME/KEY: VARIANT
<222> LOCATION: 1
<223> OTHER INFORMATION: isoleucine (I) or phenylalanine (F)
<220> FEATURE:
<221> NAME/KEY: VARIANT
<222> LOCATION: 2
<223> OTHER INFORMATION: valine (V) or threonine (T)
<220> FEATURE:
<221> NAME/KEY: VARIANT
<222> LOCATION: 7
<223> OTHER INFORMATION: valine (V) or D-valine (v)
<220> FEATURE:
<221> NAME/KEY: VARIANT
<222> LOCATION: 9
<223> OTHER INFORMATION: isoleucine (I) or threonine (T)
<220> FEATURE:
<221> NAME/KEY: VARIANT
<222> LOCATION: 10
<223> OTHER INFORMATION: lysine (K), glutamate (E), histidine (H) or glycine (G)
<220> FEATURE:
<221> NAME/KEY: VARIANT
<222> LOCATION: 11
<223> OTHER INFORMATION: isoleucine (I) or leucine (L)
<220> FEATURE:
<221> NAME/KEY: VARIANT
<222> LOCATION: 12
<223> OTHER INFORMATION: lysine (K), wherein the epsilon-amino group of the lysine side chain is covalently bound to an albumin-binding moiety
<220> FEATURE:
<221> NAME/KEY: VARIANT
<222> LOCATION: 13
<223> OTHER INFORMATION: glutamine (Q) or lysine (K)

```
<220> FEATURE:
<221> NAME/KEY: VARIANT
<222> LOCATION: 14
<223> OTHER INFORMATION: isoleucine (I), lysine (K) or 2-aminoisobutyric
      acid (Aib)
<220> FEATURE:
<221> NAME/KEY: VARIANT
<222> LOCATION: 16
<223> OTHER INFORMATION: leucine (L) or phenylalanine (F)
<220> FEATURE:
<221> NAME/KEY: VARIANT
<222> LOCATION: 17
<223> OTHER INFORMATION: glutamate (E) or lysine (K)
<220> FEATURE:
<221> NAME/KEY: VARIANT
<222> LOCATION: 19
<223> OTHER INFORMATION: alanine (A), glutamate (E) or glutamine (Q)
<220> FEATURE:
<221> NAME/KEY: VARIANT
<222> LOCATION: 20
<223> OTHER INFORMATION: lysine (K) or arginine (R)
<220> FEATURE:
<221> NAME/KEY: VARIANT
<222> LOCATION: 21
<223> OTHER INFORMATION: glutamine (Q) or lysine (K)
<220> FEATURE:
<221> NAME/KEY: VARIANT
<222> LOCATION: 22
<223> OTHER INFORMATION: lysine (K), arginine (R) or glutamate (E)
<220> FEATURE:
<221> NAME/KEY: VARIANT
<222> LOCATION: 23
<223> OTHER INFORMATION: lysine (K) or 2-aminoisobutyric acid (Aib)
<220> FEATURE:
<221> NAME/KEY: VARIANT
<222> LOCATION: 24
<223> OTHER INFORMATION: glutamine (Q), 2-aminoisobutyric acid (Aib),
      leucine (L) or glutamate (E)
<220> FEATURE:
<221> NAME/KEY: VARIANT
<222> LOCATION: 25
<223> OTHER INFORMATION: arginine (R), lysine (K) or 2-aminoisobutyric
      acid (Aib)
<220> FEATURE:
<221> NAME/KEY: VARIANT
<222> LOCATION: 26
<223> OTHER INFORMATION: alanine (A), glutamate (E), 2-aminoisobutyric
      acid (Aib) or glutamine (Q)
<220> FEATURE:
<221> NAME/KEY: VARIANT
<222> LOCATION: 27
<223> OTHER INFORMATION: glutamine (Q), 2-aminoisobutyric acid (Aib) or
      lysine (K)
<220> FEATURE:
<221> NAME/KEY: VARIANT
<222> LOCATION: 29
<223> OTHER INFORMATION: glutamate (E) or lysine (K)
<220> FEATURE:
<221> NAME/KEY: VARIANT
<222> LOCATION: 30
<223> OTHER INFORMATION: lysine (K) or threonine (T)
<220> FEATURE:
<221> NAME/KEY: VARIANT
<222> LOCATION: 31
<223> OTHER INFORMATION: asparagine (N) or alanine (A)
<220> FEATURE:
<221> NAME/KEY: VARIANT
<222> LOCATION: 32
<223> OTHER INFORMATION: lysine (K), alanine (A), valine (V), threonine
      (T), glutamate (E) or 2-aminoisobutyric acid (Aib)
<220> FEATURE:
<221> NAME/KEY: VARIANT
<222> LOCATION: 33
<223> OTHER INFORMATION: arginine (R), lysine (K) or glutamine (Q)
<220> FEATURE:
<221> NAME/KEY: VARIANT
<222> LOCATION: 34
<223> OTHER INFORMATION: isoleucine (I) or leucine (L)
<220> FEATURE:
```

<221> NAME/KEY: VARIANT
<222> LOCATION: 36
<223> OTHER INFORMATION: alanine (A) or glutamate (E)
<220> FEATURE:
<221> NAME/KEY: VARIANT
<222> LOCATION: 37
<223> OTHER INFORMATION: glutamine (Q) or arginine (R)
<220> FEATURE:
<221> NAME/KEY: VARIANT
<222> LOCATION: 38
<223> OTHER INFORMATION: isoleucine (I) or valine (V)

<400> SEQUENCE: 186

```
Xaa Xaa Leu Ser Leu Asp Xaa Pro Xaa Xaa Xaa Xaa Xaa Xaa Leu Xaa
1               5                   10                  15

Xaa Gln Xaa Xaa Xaa Xaa Xaa Xaa Xaa Xaa Xaa Ala Xaa Xaa Xaa Xaa
            20                  25                  30

Xaa Xaa Leu Xaa Xaa Xaa
        35
```

<210> SEQ ID NO 187
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_187; AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "--gGlu-C(O)(CH2)14COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 187

```
Ile Val Leu Ser Leu Asp Val Pro Ile Lys Leu Lys Gln Ile Leu Leu
1               5                   10                  15

Lys Gln Glu Arg Gln Lys Xaa Gln Arg Glu Gln Ala Glu Lys Asn Lys
            20                  25                  30

Gln Ile Leu Ala Gln Val
        35
```

<210> SEQ ID NO 188
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_188; AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "--gGlu- C(O)(CH2)14COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 188

```
Ile Val Leu Ser Leu Asp Val Pro Ile Lys Leu Lys Gln Ile Leu Leu
1               5                   10                  15

Lys Gln Glu Arg Gln Lys Xaa Gln Arg Gln Gln Ala Glu Lys Asn Lys
            20                  25                  30

Gln Ile Leu Ala Gln Val
        35
```

<210> SEQ ID NO 189
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_189; AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-gGlu-C(O)(CH2)14COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 189

```
Ile Val Leu Ser Leu Asp Val Pro Ile Lys Leu Lys Gln Ile Leu Leu
1               5                   10                  15

Lys Gln Glu Arg Gln Lys Lys Xaa Arg Gln Lys Ala Glu Lys Asn Lys
            20                  25                  30

Gln Ile Leu Ala Gln Val
        35
```

<210> SEQ ID NO 190
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_190; AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-gGlu-C(O)(CH2)14COOH
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 190

Ile Val Leu Ser Leu Asp Val Pro Ile Lys Leu Lys Gln Ile Leu Leu
1 5 10 15

Lys Gln Glu Arg Gln Lys Lys Gln Arg Glu Gln Ala Glu Lys Asn Lys
20 25 30

Gln Ile Leu Glu Gln Val
35

<210> SEQ ID NO 191
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_191;
AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-gGlu-
C(O)(CH2)14COOH
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 191

Ile Val Leu Ser Leu Asp Val Pro Ile Lys Leu Lys Gln Ile Leu Leu
1 5 10 15

Lys Gln Glu Arg Gln Lys Lys Gln Arg Glu Lys Ala Glu Lys Asn Lys
20 25 30

Gln Ile Leu Ala Gln Val
35

<210> SEQ ID NO 192
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_192;
AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-gGlu-
C(O)(CH2)14COOH
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 192

Ile Val Leu Ser Leu Asp Val Pro Ile Lys Leu Lys Gln Ile Leu Leu

```
1               5                   10                  15

Lys Gln Glu Arg Gln Lys Lys Gln Arg Gln Gln Ala Glu Lys Asn Lys
            20                  25                  30

Gln Ile Leu Ala Gln Val
        35


<210> SEQ ID NO 193
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_193;
      AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-gGlu-
      C(O)(CH2)14COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 193

Ile Val Leu Ser Leu Asp Val Pro Ile Gly Leu Lys Gln Ile Leu Leu
1               5                   10                  15

Lys Gln Glu Arg Gln Lys Lys Xaa Arg Glu Gln Ala Glu Thr Asn Lys
            20                  25                  30

Arg Ile Leu Glu Arg Val
        35


<210> SEQ ID NO 194
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_194;
      AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-gGlu-
      C(O)(CH2)14COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 194

Ile Val Leu Ser Leu Asp Val Pro Ile Gly Leu Lys Gln Ile Leu Leu
1               5                   10                  15
```

Lys Gln Glu Arg Gln Lys Lys Xaa Arg Glu Gln Ala Glu Thr Asn Lys
20 25 30

Gln Ile Leu Ala Gln Val
35

<210> SEQ ID NO 195
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_195; AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is ”-gGlu-C(O)(CH2)14COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 195

Ile Val Leu Ser Leu Asp Val Pro Ile Gly Leu Lys Gln Ile Leu Leu
1 5 10 15

Lys Gln Glu Arg Gln Lys Lys Xaa Arg Gln Gln Ala Glu Thr Asn Lys
20 25 30

Arg Ile Leu Glu Arg Val
35

<210> SEQ ID NO 196
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_196; AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is “-gGlu-C(O)(CH2)14COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 196

Ile Val Leu Ser Leu Asp Val Pro Ile Gly Leu Lys Gln Ile Leu Leu
1 5 10 15

```
Lys Gln Glu Arg Gln Lys Lys Xaa Arg Glu Gln Ala Glu Lys Asn Lys
            20                  25                  30

Arg Ile Leu Glu Arg Val
        35
```

<210> SEQ ID NO 197
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_197; AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-gGlu-C(O)(CH2)14COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 197

```
Ile Val Leu Ser Leu Asp Val Pro Ile Lys Leu Lys Gln Ile Leu Leu
1               5                   10                  15

Lys Gln Ala Arg Gln Lys Xaa Gln Arg Ala Gln Ala Glu Lys Asn Lys
            20                  25                  30

Arg Ile Leu Glu Arg Val
        35
```

<210> SEQ ID NO 198
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_198; AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)14COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 198

```
Ile Val Leu Ser Leu Asp Val Pro Ile Lys Leu Lys Gln Ile Leu Leu
1               5                   10                  15

Lys Gln Glu Arg Gln Lys Xaa Gln Arg Glu Gln Ala Glu Lys Asn Lys
```

```
            20                  25                  30

Gln Ile Leu Ala Gln Val
        35


<210> SEQ ID NO 199
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_199;
      AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-{gGLU}2-
      C(O)(CH2)14COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 199

Ile Val Leu Ser Leu Asp Val Pro Ile Lys Leu Lys Gln Ile Leu Leu
1               5                   10                  15

Lys Gln Glu Arg Gln Lys Xaa Gln Arg Glu Gln Ala Glu Lys Asn Lys
            20                  25                  30

Gln Ile Leu Ala Gln Val
        35


<210> SEQ ID NO 200
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_200;
      AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)14COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 200

Ile Val Leu Ser Leu Asp Val Pro Ile Lys Leu Lys Gln Ile Leu Leu
1               5                   10                  15

Lys Gln Glu Arg Gln Lys Lys Xaa Arg Gln Lys Ala Glu Lys Asn Lys
            20                  25                  30
```

```
Gln Ile Leu Ala Gln Val
        35


<210> SEQ ID NO 201
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_201;
      AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-{gGLU}2-
      C(O)(CH2)14COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 201

Ile Val Leu Ser Leu Asp Val Pro Ile Lys Leu Lys Gln Ile Leu Leu
1               5                   10                  15

Lys Gln Glu Arg Gln Lys Lys Xaa Arg Gln Lys Ala Glu Lys Asn Lys
            20                  25                  30

Gln Ile Leu Ala Gln Val
        35


<210> SEQ ID NO 202
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_202;
      AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)14COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 202

Ile Val Leu Ser Leu Asp Val Pro Ile Gly Leu Lys Gln Ile Leu Leu
1               5                   10                  15

Lys Gln Glu Arg Gln Lys Lys Xaa Arg Glu Gln Ala Glu Thr Asn Lys
            20                  25                  30
```

Gln Ile Leu Ala Gln Val
35

<210> SEQ ID NO 203
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_203; AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-{AEEA}2-gGlu-C(O)(CH2)14COOH
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 203

Ile Val Leu Ser Leu Asp Val Pro Ile Gly Leu Lys Gln Ile Leu Leu
1 5 10 15

Lys Gln Glu Arg Gln Lys Lys Xaa Arg Glu Gln Ala Glu Thr Asn Lys
20 25 30

Gln Ile Leu Ala Gln Val
35

<210> SEQ ID NO 204
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_204; AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-gGlu-C(O)(CH2)14CH3
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 204

Ile Val Leu Ser Leu Asp Val Pro Ile Lys Leu Lys Gln Ile Leu Leu
1 5 10 15

Lys Gln Glu Arg Gln Lys Xaa Gln Arg Glu Gln Ala Glu Lys Asn Lys
20 25 30

Gln Ile Leu Ala Gln Val
35

```
<210> SEQ ID NO 205
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_205;
      AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-gGlu-
      C(O)(CH2)14CH3
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 205

Ile Val Leu Ser Leu Asp Val Pro Ile Lys Leu Lys Gln Ile Leu Leu
1               5                   10                  15

Lys Gln Glu Arg Gln Lys Xaa Gln Arg Glu Gln Ala Glu Lys Asn Lys
            20                  25                  30

Gln Ile Leu Ala Gln Val
        35


<210> SEQ ID NO 206
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_206;
      AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-{gGLU}2-
      C(O)(CH2)14CH3
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 206

Ile Val Leu Ser Leu Asp Val Pro Ile Lys Leu Lys Gln Ile Leu Leu
1               5                   10                  15

Lys Gln Glu Arg Gln Lys Xaa Gln Arg Glu Gln Ala Glu Lys Asn Lys
            20                  25                  30

Gln Ile Leu Ala Gln Val
        35
```

```
<210> SEQ ID NO 207
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_207;
      AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-gGlu-C(O)(CH2)14CH3
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 207

Ile Val Leu Ser Leu Asp Val Pro Ile Gly Leu Lys Gln Ile Leu Leu
1               5                   10                  15

Lys Gln Glu Arg Gln Lys Lys Xaa Arg Glu Gln Ala Glu Thr Asn Lys
            20                  25                  30

Arg Ile Leu Glu Arg Val
        35


<210> SEQ ID NO 208
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_208;
      AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-gGlu-C(O)(CH2)14CH3
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 208

Ile Val Leu Ser Leu Asp Val Pro Ile Lys Leu Lys Gln Ile Leu Leu
1               5                   10                  15

Lys Gln Glu Arg Gln Lys Xaa Gln Arg Gln Gln Ala Glu Lys Asn Lys
            20                  25                  30

Gln Ile Leu Ala Gln Val
        35


<210> SEQ ID NO 209
<211> LENGTH: 38
```

<212> TYPE: PRT
<213> ORGANISM: Artificial Sequence
<220> FEATURE:
<223> OTHER INFORMATION: >CRP-001 210819 Sequence Listing final_seq_209;
AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-gGlu-C(O)(CH2)14CH3
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 209

```
Ile Val Leu Ser Leu Asp Val Pro Ile Lys Leu Lys Gln Ile Leu Leu
1               5                   10                  15

Lys Gln Glu Arg Gln Lys Lys Xaa Arg Gln Lys Ala Glu Lys Asn Lys
            20                  25                  30

Gln Ile Leu Ala Gln Val
        35
```

<210> SEQ ID NO 210
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_210;
AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-{AEEA}2-gGlu-
C(O)(CH2)14CH3
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 210

```
Ile Val Leu Ser Leu Asp Val Pro Ile Lys Leu Lys Gln Ile Leu Leu
1               5                   10                  15

Lys Gln Glu Arg Gln Lys Lys Xaa Arg Gln Lys Ala Glu Lys Asn Lys
            20                  25                  30

Gln Ile Leu Ala Gln Val
        35
```

<210> SEQ ID NO 211
<211> LENGTH: 38
<212> TYPE: PRT
<213> ORGANISM: Artificial Sequence

```
<220> FEATURE:
<223> OTHER INFORMATION: >CRP-001 210819 Sequence Listing final_seq_211;
      AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-{AEEA}2-{gGLU}2-
      C(O)(CH2)14CH3
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 211

Ile Val Leu Ser Leu Asp Val Pro Ile Lys Leu Lys Gln Ile Leu Leu
1               5                   10                  15

Lys Gln Glu Arg Gln Lys Lys Xaa Arg Gln Lys Ala Glu Lys Asn Lys
            20                  25                  30

Gln Ile Leu Ala Gln Val
        35


<210> SEQ ID NO 212
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_212;
      AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 212

Ile Val Leu Ser Leu Asp Val Pro Ile Lys Leu Lys Gln Ile Leu Leu
1               5                   10                  15

Lys Gln Glu Arg Gln Lys Lys Gln Arg Glu Gln Ala Glu Lys Asn Lys
            20                  25                  30

Gln Ile Leu Glu Gln Val
        35


<210> SEQ ID NO 213
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_213;
      AA; synthetic construct>
<220> FEATURE:
<221> NAME/KEY: VARIANT
<222> LOCATION: 7
```

<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 213

Ile Val Leu Ser Leu Asp Val Pro Ile Lys Leu Lys Gln Ile Leu Leu
1 5 10 15

Lys Gln Glu Arg Gln Lys Lys Gln Arg Glu Lys Ala Glu Lys Asn Lys
20 25 30

Gln Ile Leu Ala Gln Val
35

<210> SEQ ID NO 214
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_214;
AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 214

Ile Val Leu Ser Leu Asp Val Pro Ile Lys Leu Lys Gln Ile Leu Leu
1 5 10 15

Lys Gln Glu Arg Gln Lys Lys Gln Arg Gln Gln Ala Glu Lys Asn Lys
20 25 30

Gln Ile Leu Ala Gln Val
35

<210> SEQ ID NO 215
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_215;
AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-gGlu-C(O)(CH2)14CH3
<220> FEATURE:
<221> NAME/KEY: VARIANT
<222> LOCATION: 24
<223> OTHER INFORMATION: 2-aminoisobutyric acid (Aib)
<220> FEATURE:

```
<221> NAME/KEY: MOD_RES
<222> LOCATION: 38
<223> OTHER INFORMATION: C-terminal amino acid residue is amidated as a
      primary amide

<400> SEQUENCE: 215

Ile Val Leu Ser Leu Asp Val Pro Ile Gly Leu Lys Gln Ile Leu Leu
1               5                   10                  15

Lys Gln Glu Arg Gln Lys Lys Xaa Arg Glu Gln Ala Glu Thr Asn Lys
            20                  25                  30

Gln Ile Leu Ala Gln Val
        35


<210> SEQ ID NO 216
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_216;
      AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is “-gGlu-C(O)(CH2)14CH3
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 216

Ile Val Leu Ser Leu Asp Val Pro Ile Gly Leu Lys Gln Ile Leu Leu
1               5                   10                  15

Lys Gln Glu Arg Gln Lys Lys Xaa Arg Glu Gln Ala Glu Thr Asn Lys
            20                  25                  30

Gln Ile Leu Ala Gln Val
        35


<210> SEQ ID NO 217
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_217;
      AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is ″-gGlu-C(O)(CH2)14CH3
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
```

primary amide

<400> SEQUENCE: 217

Ile Val Leu Ser Leu Asp Val Pro Ile Gly Leu Lys Gln Ile Leu Leu
1 5 10 15

Lys Gln Glu Arg Gln Lys Lys Xaa Arg Glu Gln Ala Glu Thr Asn Lys
20 25 30

Gln Ile Leu Ala Gln Val
35

<210> SEQ ID NO 218
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_218; AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-gGlu-C(O)(CH2)14CH3
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 218

Ile Val Leu Ser Leu Asp Val Pro Ile Gly Leu Lys Gln Ile Leu Leu
1 5 10 15

Lys Gln Glu Arg Gln Lys Lys Xaa Arg Glu Gln Ala Glu Lys Asn Lys
20 25 30

Arg Ile Leu Glu Arg Val
35

<210> SEQ ID NO 219
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_219; AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-gGlu-C(O)(CH2)14CH3
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a primary amide

<400> SEQUENCE: 219

```
Ile Val Leu Ser Leu Asp Val Pro Ile Lys Leu Lys Gln Ile Leu Leu
1               5                   10                  15

Lys Gln Ala Arg Gln Lys Xaa Gln Arg Ala Gln Ala Glu Lys Asn Lys
            20                  25                  30

Arg Ile Leu Glu Arg Val
        35


<210> SEQ ID NO 220
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_220;
      AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is “-gGlu-C(O)(CH2)14CH3
<220> FEATURE:
<221> NAME/KEY: VARIANT
<222> LOCATION: 24
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 220

Ile Val Leu Ser Leu Asp Val Pro Ile Gly Leu Lys Gln Ile Leu Leu
1               5                   10                  15

Lys Gln Glu Arg Gln Lys Lys Xaa Arg Gln Gln Ala Glu Thr Asn Lys
            20                  25                  30

Arg Ile Leu Glu Arg Val
        35


<210> SEQ ID NO 221
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_221;
      AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is ”-gGlu-
      C(O)(CH2)14COOH
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 221

Ile Val Leu Ser Leu Asp Val Pro Thr Lys Leu Lys Gln Lys Leu Leu
1               5                   10                  15

Lys Gln Glu Arg Gln Arg Lys Glu Arg Glu Gln Ala Glu Lys Asn Ala
            20                  25                  30
```

Arg Ile Leu Ala Arg Val
35

<210> SEQ ID NO 222
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_222; AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-gGlu-C(O)(CH2)14COOH
<220> FEATURE:
<221> NAME/KEY: MOD_RES
<222> LOCATION: 38
<223> OTHER INFORMATION: C-terminal amino acid residue is amidated as a primary amide

<400> SEQUENCE: 222

Ile Val Leu Ser Leu Asp Val Pro Thr Lys Leu Lys Gln Lys Leu Leu
1 5 10 15

Lys Gln Glu Arg Gln Arg Lys Glu Arg Glu Gln Ala Glu Lys Asn Val
20 25 30

Arg Ile Leu Glu Arg Val
35

<210> SEQ ID NO 223
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_223; AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12, Ra denotes the albumin-binding moiety, Ra is "-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a primary amide

<400> SEQUENCE: 223

Ile Val Leu Ser Leu Asp Val Pro Thr Lys Leu Lys Gln Lys Leu Leu
1 5 10 15

Lys Gln Glu Arg Gln Arg Lys Glu Arg Glu Gln Ala Glu Lys Asn Lys
20 25 30

Arg Ile Leu Glu Arg Val
35

<210> SEQ ID NO 224
<211> LENGTH: 38
<212> TYPE: PRT
<213> ORGANISM: Artificial Sequence
<220> FEATURE:

<223> OTHER INFORMATION: >CRP-001 210819 Sequence Listing final_seq_224;
AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-{AEEA}2-gGlu-
C(O)(CH2)18COOH
<220> FEATURE:
<221> NAME/KEY: VARIANT
<222> LOCATION: 23
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 224

```
Ile Val Leu Ser Leu Asp Xaa Pro Thr Lys Leu Lys Lys Lys Leu Leu
1               5                   10                  15

Lys Gln Glu Arg Lys Arg Xaa Glu Arg Glu Lys Ala Glu Lys Ala Ala
            20                  25                  30

Arg Ile Leu Glu Arg Val
        35
```

<210> SEQ ID NO 225
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_225;
AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
Ra denotes the albumin-binding moiety, Ra is "-gGlu-C(O)(CH2)14CH3
<220> FEATURE:
<221> NAME/KEY: VARIANT
<222> LOCATION: 27
<223> OTHER INFORMATION: 2-aminoisobutyric acid (Aib)
<220> FEATURE:
<221> NAME/KEY: MOD_RES
<222> LOCATION: 38
<223> OTHER INFORMATION: C-terminal amino acid residue is amidated as a
primary amide

<400> SEQUENCE: 225

```
Ile Val Leu Ser Leu Asp Val Pro Thr Lys Leu Lys Gln Lys Leu Leu
1               5                   10                  15

Lys Gln Glu Arg Gln Arg Lys Glu Arg Glu Xaa Ala Glu Lys Asn Lys
            20                  25                  30

Arg Ile Leu Glu Arg Val
        35
```

<210> SEQ ID NO 226
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_226;
AA; synthetic construct>

-continued

```
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 226

Ile Val Leu Ser Leu Asp Val Pro Ile Gly Leu Lys Gln Lys Leu Leu
1               5                   10                  15

Lys Gln Gln Arg Gln Arg Lys Glu Arg Gln Gln Ala Glu Lys Asn Lys
            20                  25                  30

Arg Ile Leu Glu Arg Val
        35


<210> SEQ ID NO 227
<211> LENGTH: 38
<212> TYPE: PRT
<213> ORGANISM: Artificial Sequence
<220> FEATURE:
<223> OTHER INFORMATION: >CRP-001 210819 Sequence Listing final_seq_227;
      AA; synthetic construct>
<220> FEATURE:
<221> NAME/KEY: VARIANT
<222> LOCATION: 7
<223> OTHER INFORMATION: D-valine (v)
<220> FEATURE:
<221> NAME/KEY: VARIANT
<222> LOCATION: 12
<223> OTHER INFORMATION: K* denotes the modified lysine residue at X12,
      Ra denotes the albumin-binding moiety, Ra is "-gGlu-C(O)(CH2)14CH3
<220> FEATURE:
<221> NAME/KEY: MOD_RES
<222> LOCATION: 38
<223> OTHER INFORMATION: C-terminal amino acid residue is amidated as a
      primary amide

<400> SEQUENCE: 227

Ile Val Leu Ser Leu Asp Val Pro Ile Lys Leu Lys Gln Lys Leu Leu
1               5                   10                  15

Lys Gln Gln Arg Gln Arg Lys Glu Arg Gln Gln Ala Glu Lys Asn Lys
            20                  25                  30

Arg Ile Leu Glu Arg Val
        35
```